United States Patent
Wallace

(10) Patent No.: US 12,201,683 B2
(45) Date of Patent: *Jan. 21, 2025

(54) METHODS FOR PREVENTING DENGUE AND HEPATITIS A

(71) Applicant: Takeda Vaccines, Inc., Cambridge, MA (US)

(72) Inventor: Derek Wallace, Brookline, MA (US)

(73) Assignee: Takeda Vaccines, Inc., Cambridge, MA (US)

( * ) Notice: Subject to any disclaimer, the term of this patent is extended or adjusted under 35 U.S.C. 154(b) by 13 days.

This patent is subject to a terminal disclaimer.

(21) Appl. No.: 17/869,776

(22) Filed: Jul. 20, 2022

(65) Prior Publication Data

US 2023/0149538 A1 May 18, 2023

Related U.S. Application Data

(63) Continuation of application No. 16/809,268, filed on Mar. 4, 2020, now Pat. No. 11,426,461, which is a continuation-in-part of application No. 16/561,953, filed on Sep. 5, 2019, now Pat. No. 11,590,221.

(30) Foreign Application Priority Data

| Sep. 5, 2018 | (EP) | 18192701 |
| Sep. 5, 2018 | (EP) | 18192711 |
| Sep. 5, 2018 | (EP) | 18192717 |
| Sep. 5, 2018 | (EP) | 18192776 |
| Sep. 5, 2018 | (EP) | 18192787 |
| Sep. 5, 2018 | (EP) | 18192793 |
| Sep. 5, 2018 | (EP) | 18192800 |
| Sep. 5, 2018 | (EP) | 18192814 |
| Jan. 29, 2019 | (EP) | 19154334 |
| Mar. 7, 2019 | (EP) | 19161184 |

(51) Int. Cl.
| A61K 39/29 | (2006.01) |
| A61K 9/00 | (2006.01) |
| A61K 39/295 | (2006.01) |
| A61K 39/39 | (2006.01) |
| A61P 31/14 | (2006.01) |

(52) U.S. Cl.
CPC .......... *A61K 39/295* (2013.01); *A61K 9/0019* (2013.01); *A61K 39/29* (2013.01); *A61K 39/39* (2013.01); *A61P 31/14* (2018.01)

(58) Field of Classification Search
None
See application file for complete search history.

(56) References Cited

U.S. PATENT DOCUMENTS

| 4,810,092 A | 3/1989 | Auth |
| 5,021,347 A | 6/1991 | Yasui et al. |
| 5,229,293 A | 7/1993 | Matsuura et al. |
| 5,494,671 A | 2/1996 | Lai et al. |
| 5,514,375 A | 5/1996 | Paoletti et al. |
| 6,165,477 A | 12/2000 | Ivy et al. |
| 6,184,024 B1 | 2/2001 | Lai et al. |
| 6,660,273 B2 | 12/2003 | Pletnev et al. |
| 7,094,411 B2 | 8/2006 | Kinney et al. |
| 8,673,316 B2 | 3/2014 | Kinney et al. |
| 2006/0062803 A1 | 3/2006 | Kinney et al. |
| 2010/0303860 A1 | 12/2010 | Stinchcomb et al. |
| 2011/0150771 A1 | 6/2011 | Kinney et al. |
| 2011/0311579 A1 | 12/2011 | Mason et al. |
| 2014/0302088 A1 | 10/2014 | Stinchcomb et al. |
| 2015/0150961 A1 | 6/2015 | Stinchcomb et al. |
| 2015/0265695 A1 | 9/2015 | Yao et al. |
| 2017/0304426 A1 | 10/2017 | Tornieporth et al. |
| 2019/0381163 A1 | 12/2019 | Wallace et al. |
| 2020/0069751 A1 | 3/2020 | Wallace |

FOREIGN PATENT DOCUMENTS

| CN | 10123809 A | 8/2008 |
| CN | 101238209 A | 8/2008 |
| CN | 1012385144 A | 8/2008 |
| CN | 101560520 A | 10/2009 |
| CN | 102711817 A | 10/2012 |
| CN | 1006999564 A | 8/2017 |
| EP | 1159968 A1 | 12/2001 |
| EP | 2353609 A1 | 8/2011 |
| JP | H05276941 A | 10/1993 |
| JP | 2003-523189 A | 8/2003 |
| JP | 2016-513970 A | 5/2016 |
| KR | 10-2008-0018271 A | 2/2008 |
| TW | 1726312 B | 3/2014 |
| WO | 1990001946 A1 | 3/1990 |

(Continued)

OTHER PUBLICATIONS

Kelly, E. et al., "Evolution of attenuating mutations in dengue-2 strain S16803 PDK50 vaccine and comparison of growth kinetics with parent virus," Virus Genes, 2011, vol. 43, pp. 18-26.

Khin, M. et al., "Infection, Dissemination, Transmission, and Biological Attributes of Dengue-2 PDK53 Candidate Vaccine Virus after Oral Infection in Aedes Aegypti," Am. J. Trop. Med. Hyg., 1994, vol. 51, No. 6, pp. 864-869.

Kimura-Kuroda, J. et al., "Topographical Analysis of Antigenic Determinants on Envelope Glycoprotein V3 (E) of Japanese Encephalitis Virus, Using Monoclonal Antibodies" Journal of Virology, Jan. 1983, vol. 45, No. 1, pp. 124-132.

(Continued)

*Primary Examiner* — Benjamin P Blumel
(74) *Attorney, Agent, or Firm* — Honigman LLP

(57) ABSTRACT

The invention relates to a method for preventing dengue disease and hepatitis A in a subject or subject population by simultaneously administering a unit dose of a dengue vaccine composition and a hepatitis A vaccine on the same day. The unit dose of a dengue vaccine composition includes constructs of each dengue serotype, such as TDV-1, TDV-2, TDV-3 and TDV-4, at various concentrations in order to improve protection from dengue infection.

40 Claims, 6 Drawing Sheets

Specification includes a Sequence Listing.

(56) References Cited

FOREIGN PATENT DOCUMENTS

| WO | 1992003545 A1 | 3/1992 |
|---|---|---|
| WO | 1993006214 A1 | 4/1993 |
| WO | 1996040933 A1 | 12/1996 |
| WO | 1998037911 A1 | 9/1998 |
| WO | 1999063095 A1 | 12/1999 |
| WO | 0139802 A1 | 6/2001 |
| WO | 2001060847 A2 | 8/2001 |
| WO | 2001060847 A3 | 4/2002 |
| WO | 2002072036 A2 | 9/2002 |
| WO | 2002072036 A3 | 5/2003 |
| WO | 2006134443 A1 | 12/2006 |
| WO | 2009048658 A9 | 6/2009 |
| WO | 2009139725 A1 | 11/2009 |
| WO | 2010141386 A1 | 12/2010 |
| WO | 2011038473 A1 | 4/2011 |
| WO | 2013188315 A1 | 12/2013 |
| WO | 2014016360 A1 | 1/2014 |
| WO | 2014016362 A1 | 1/2014 |
| WO | 2014074912 A1 | 5/2014 |
| WO | 2014093182 A1 | 6/2014 |
| WO | 2014150939 A2 | 9/2014 |
| WO | 2016034629 A1 | 3/2016 |
| WO | 2017005652 A1 | 1/2017 |
| WO | 2017005654 A1 | 1/2017 |
| WO | 2017041156 A1 | 3/2017 |
| WO | 2017179017 A1 | 10/2017 |
| WO | 2018052375 A1 | 3/2018 |
| WO | 2019077622 A1 | 4/2019 |

OTHER PUBLICATIONS

Kimura-Kuroda, J. et al., "Antigenic Comparison of Envelope Protein E between Japanese Encephalitis Virus and Some Other Flaviviruses Using Monoclonal Antibodies," J. Gen. Virol., 1986, vol. 67, pp. 2663-1672.

Kinney, R. et al. "Construction of Infectious cDNA Clones for Dengue 2 Virus: Strain 16681 and Its Attenuated Vaccine Derivative, Strain PDK-531" Virology, 1997, vol. 230, No. 2, pp. 300-308.

Kinney, R. et al., "Development of New Vaccines against Dengue Fever and Japanese Encephalitis," Intervirology, 2001, vol. 44, pp. 176-197.

Klinman, D. et al., "CpG motifs as immune adjuvants," Vaccine, 1999, vol. 17, pp. 19-25.

Kochel, T. et al., "Inoculation of plasmids expressing the dengue-2 envelope gene elicit neutralizing antibodies in mice," Vaccine. 1997, vol. 15, No. 5, pp. 547-552.

Köhler, G. et al., "Continuous cultures of fused cells secreting antibody of predefined specificity," Nature, Aug. 7, 1975, vol. 256, pp. 495-497.

Konishi, E. et al., "Avipox virus-vectored Japanese encephalitis virus vaccines: use as vaccine candidates in combination with purified subunit immunogens," Vaccine, 1994, vol. 12, No. 7, pp. 633-638.

Konishi, E. et al., "Comparison of Protective Immunity Elicited by Recombinant Vaccinia Viruses That Synthesize E or NS1 of Japanese Encephalitis Virus," Virology, 1991, vol. 185, pp. 401-410.

Konishi, E. et al., "Generation and Characterization of a Mammalian Cell Line Continuously Expressing Japanese Encephalitis Virus Subviral Particles," Journal of Virology, Mar. 2001, vol. 75, No. 5, pp. 2204-2212.

Konishi, E. et al., "Induction of Protective Immunity against Japanese Encephalitis in Mice by Immunization with a Plasmid Encoding Japanese Encephalitis Virus Premembrane and Envelope Genes," Journal of Virology, Jun. 1998, vol. 72, No. 6, pp. 4925-4930.

Konishi, E. et al., "Mice Immunized with a Subviral Particle Containing the Japanese Encephalitis Virus prM/M and E Proteins Are Protected from Lethal JEV Infection," Virology, 1992, vol. 188, pp. 714-720.

Kozak, M. "Circumstances and Mechanisms of Inhibition of Translation by Secondary Structure in Eucaryotic mRNAs," Molecular and Cellular Biology, Nov. 1989, vol. 9, No. 11, pp. 5134-5142.

Kuno, G. et al., "Phylogeny of the Genus Flavivirus," Journal of Virology, Jan. 1998, vol. 72, No. 1, pp. 73-83.

Laemmli, U., "Cleavage of Structural Proteins during the Assembly of the Head of Bacteriophage T4," Nature, Aug. 15, 1970, vol. 227, pp. 680-685.

Lai, C. et al., "Evaluation of molecular strategies to develop a live dengue vaccine," Clinical and Diagnostic Virology, 1998, vol. 10, pp. 173-179.

Lai, C. et al., "Immunization of Monkeys with Baculovirus Recombinant-expressed Dengue Envelope and NS1 Glycoproteins Induces Partial Resistance to Challenge with Homotypic Dengue Virus," Vaccines 90: Modern approaches to New Vaccines including Prevention of AIDS, Cold Spring Harbor, NY, 1990, pp. 119-124.

Liljeström, P. et al., "In Vitro Mutagenesis of a Full-Length eDNA Clone of Semliki Forest Virus: the Small 6,000 Molecular-Weight Membrane Protein Modulates Virus Release," Journal of Virology, Aug. 1991, vol. 65, No. 8, pp. 4107-4113.

Lin, Y. et al., "DNA Immunization with Japanese Encephalitis Virus Nonstructural Protein NS1 Elicits Protective Immunity in Mice," Journal of Virology, Jan. 1998, vol. 72, No. 1, pp. 191-200.

Mackow, E. et al., "The Nucleotide Sequence of Dengue Type 4 Virus: Analysis of Genes Coding for Nonstructural Proteins," Virology, 1987, vol. 159, pp. 217-228.

Mandl, C. et al., "Complete Genomic Sequence of Powassan Virus: Evaluation of Genetic Elements in Tick-Borne versus Mosquito-Borne Flaviviruses," Virology, 1993, vol. 194, pp. 173-184.

Martin, D. et al., "Standardization of Immunoglobulin M Capture Enzyme-Linked Immunosorbent Assays for Routine Diagnosis of Arboviral Infections," Journal of Clinical Microbiology, May 2000, vol. 38, No. 5, pp. 1823-1826.

Mason, P. et al., "Japanese Encephalitis Virus-Vaccinia Recombinants Produce Particulate Forms of the Structural Membrane Proteins and Induce High Levels of Protection against Lethal JEV infection," Virology, 1991, vol. 180, pp. 294-305.

Mason, P. et al., "Sequence of the Dengue-1 Virus Genome in the Region Encoding the Three Structural Proteins and the Major Nonstructural Protein NS1," Virology, 1987, vol. 161, pp. 262-267.

Men, R. et al., "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys," Journal of Virology, Jun. 1996, vol. 70, No. 6, pp. 3930-3937.

Midgley, C.M., et al., Men, R. et al., "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys," Journal of Virology, Jun. 1996, vol. 70, No. 6, pp. 3930-3937. Structural analysis of a dengue cross-reactive antibody complexed with envelope domain III reveals the molecular basis of cross-reactivity. J Immunol. May 15, 2012; 188(10): 4971-4979.

Mir, L. et al., "High-efficiency gene transfer into skeletal muscle mediated by electric pulses," Applied Biological Sciences, Proc. Natl. Acad. Sci. USA, Apr. 1999, vol. 96, pp. 4262-4267.

Monath, T. et al., "Recombinant, chimeric live, attenuated vaccine (ChimeriVax) incorporating the envelope genes of Japanese encephalitis (SA14-14-2) virus and the capsid and nonstructural genes of yellow fever (17D) virus is safe, immunogenic and protective in non-human primates," Vaccine, 1999, vol. 17pp. 1869-1882.

NCT02993757 "Immunogenicity and Safety of a Tetravalent Dengue Vaccine Administered Concomitantly or Sequentially With Gardasil," ClinicalTrials.gov, Apr. 5, 2018, Retrieved from the Internet Oct. 25, 2018, 10 pages.

NCT03525119 "Immunogenicity and Safety of Tetravalent Dengue Vaccine (TDV) Co-administered With an Hepatitis A Virus Vaccine," ClinicalTrials.gov, May 15, 2018, Retrieved from the Internet Oct. 26, 2018, 12 pages.

Nitayaphan, S. et al., "Nucleotide Sequence of the Virulent SA-14 Strain of Japanese Encephalitis Virus and Its Attenuated Vaccine Derivative, SA-14-14-2," Virology, 1990, vol. 177, pp. 541-552.

(56) References Cited

OTHER PUBLICATIONS

Nowak, T. et al., "Analysis of the Terminal 4 Sequences of West Nile Virus Structural Proteins and of the in Vitro Translation of these Proteins Allow the Proposal of a Complete Scheme of the Proteolytic Cleavages Involved in Their Synthesis," Virology, Academic Press. Orlando, Apr. 1, 1989, vol. 169, No. 2, pp. 365-376.
Osatomi, K. et al., "Complete Nucleotide Sequence of Dengue Type 3 Virus Genome RNA," Virology, 1990, vol. 176, pp. 643-647.
Osorio, J. et al "Efficacy of a Tetravalent Chimeric Dengue Vaccine (DENVax) in Cynomolgus Macaques," Am. J. Trop. Med. Hyg., 2011, vol. 84, No. 6, pp. 978-987.
Osorio, J. et al., "Development of DENVax: A chimeric dengue-2 PDK-53-based tetravalent vaccine for protection against dengue fever," Vaccine, Jul. 11, 2011, vol. 29, No. 42, pp. 7251-7260.
Phillpotts, R. et al., "Immunisation with DNA polynucleotides protects mice against lethal challenge with St. Louis encephalitis virus." Arch Virol., 1996, vol. 141, pp. 743-749.
Pletnev, A. et al., "Chimeric Tick-Borne Encephalitis and Dengue Type 4 Viruses: Effects of Mutations on Neurovirulence in Mice." J. Virol., Aug. 1993, vol. 67, No. 8, pp. 4956-4963.
Pletnev, A. et al., "Construction and characterization of chimeric tick-borne encephalitis/ dengue type 4 viruses." Proc. Nat. Acad. Sci. USA, Medical Sciences, Nov. 1992, vol. 89: pp. 10532-10536.
Press Release: "Takeda's Dengue Vaccine Candidate Meets Primary Endpoint in Pivotal Phase 3 Efficacy Trial," Jan. 29, 2019, 4 pages.
Puri, B. et al., "Molecular analysis of dengue virus attenuation after serial passage in primary in dog kidney cells." J. Gen Virol., 1997, vol. 78, pp. 2287-2291.
Putnak, et al., "Comparative Evaluation of Three Assays for Measurement of Dengue Virus Neutralizing Antibodies," The American Journal of Tropical Medicine and Hygiene, 2008, vol. 79, No. 1, pp. 115-122.
Rice, C. et al., "Nucleotide Sequence of Yellow Fever Virus: Implications for Flavivirus Gene Expression and Evolution," Science, 1985, vol. 229, pp. 726-733.
Rice, C. et al., "Transcription of Infectious Yellow Fever RNA From Full-Length eDNA Templates Produced by In Vitro Ligation," The New Biologist, Dec. 1989, vol. 1, No. 3, pp. 285-296.
Roehrig, J. et al., "Identification of Epitopes on the E Glycoprotein of Saint Louis Encephalitis Virus Using Monoclonal Antibodies." Virology, 1983, vol. 128, pp. 118-126.
Roehrig, J. et al., "Synthetic Peptides Derived from the Deduced Amino Acid Sequence of the E-Glycoprotein of Murray Valley Encephalitis Virus Elicit Antiviral Antibody," Virology, 1989, vol. 171, pp. 49-60.
Sabchareon, A. et al., "Safety and Immunogenicity of Tetravalent Live-Attenuated Dengue Vaccines in Thai Adult Volunteers: Role of Serotype Concentration, Ratio, and Multiple Doses," Am. J. Trop. Med. Hyg., 2002, vol. 66, No. 3, pp. 264-272.
Sabchareon, et al., "Protective efficacy of the recombinant, live-attenuated, CYD tetravalent dengue vaccine in Thai schoolchildren: a randomised, controlled phase 2b trial," The Lancet, Nov. 3, 2012, vol. 380, pp. 1559-1567.
Saez-Llorens et al., "Safety and immunogenicity of one versus two doses of Takeda's tetravalent dengue vaccine in chil-dren in Asia and Latin America: interim results from a phase 2, randomized, placebo-controlled study," Lancet Infectious Disease, Elsevier Ltd, US, Mar. 30, 2017, vol. 17, No. 6, pp. 615-625.
CN Office Action + English translation for CN application 202080071928.2 dated Aug. 22, 2023.
Glasner, D.R., et al., Magnitude and functionality of NS1-specific antibody response elicited by Takeda's Tetravalent Dengue Vaccine Candidate, Poster No. 1618 presented at the American Society of Tropical Medicine & Hygiene Conference on Oct. 28 to Nov. 1, 2018.
Abstract, "There will be epidemics . . . ," American Society of Tropical Medicine & Hygiene 67th Annual Meeting, Abstract Book, vol. 99, No. 4, Oct. 2018.
Butrapet, S. et al., "Determining genetic stabilities of chimeric dengue vaccine candidates based on dengue 2 PDK-53 virus by sequencing and quantitative TaqMAMA," Journal of Virological Methods, 2005, vol. 131, No. 1, pp. 1-9.
Cahour, A. et al., "Growth-Restricted Dengue Virus Mutants Containing Deletions in the 5' Noncoding Region of the RNA Genome," Virology, 1995, vol. 207, pp. 68-76.
Calvert, A. et al., "Non-structural proteins of dengue 2 virus offer limited protection to interferon-deficient mice after dengue 2 virus challenge,", Journal of General Virology, vol. 87, 2006, pp. 339-346.
Caufour, A. et al., "Construction, characterization and immunogenicity of recombinant yellow fever 17D-dengue type 2 viruses," Virus Research, 2001, vol. 79, pp. 1-14.
Chambers, T. et al., "Flavivirus Genome Organization, Expression, and Replication," Annu. Rev. Microbiol. 1990, vol. 44, pp. 649-688.
Chambers, T. et al., "Yellow Fever Virus/Dengue-2 Virus and Yellow Fever Virus/Dengue-4 Virus Chimeras: Biological Characterization, Immunogenicity, and Protection against Dengue Encephalitis in the Mouse Model," Journal of Virology, Mar. 2003. Vol. 77, No. 6, pp. 3655-3668.
Chambers, T. et al., "Yellow Fever/Japanese Encephalitis Chimeric Viruses: Construction and Biological Properties," Journal of Virology, Apr. 1999, vol. 73, No. 4, pp. 3095-3101.
Chang, G. et al., "A Single Intramuscular Injection of Recombinant Plasmid DNA Induces Protective Immunity and Prevents Japanese Encephalitis in Mice," Journal of Virology, May 2000, vol. 74, No. 9, pp. 4244-4252.
Chen, W. et al., "Construction of Intertypic Chimeric Dengue Viruses Exhibiting Type 3 Antigenicity and Neurovirulence for Mice," Journal of Virology, Aug. 1995, vol. 69, No. 8, pp. 5186-5190.
Chokephaibulkit K., "Combination Vaccines," Chot Mai Het Thang Phaet, Journal of the Medical Association of Thai, Medical Association of Thailand, Aug. 1, 2002, vol. 85, No. Suppl. 2, pp. S694-S699.
Clarke, D. et al., "Techniques for Hemagglutination and Hemagglutination-Inhibition with Arthropod-Borne Viruses," The Rockefeller Foundation Virus Laboratories, New York, N.Y., Am. J. Trop. Med. Hyg., 1958, p. 561-573.
Cooper, J. et al., "Update: Surveillance for West Nile Virus in Overwintering Mosquitoes—New York, 2000," 3 pages.
Davis, B. et al., "West Nile Virus Recombinant DNA Vaccine Protects Mouse and Horse from Virus Challenge and Expresses In Vitro a Noninfectious Recombinant Antigen That Can Be Used in Enzyme-Linked Immunosorbent Assays," Journal of Virology, May 2001, vol. 75, No. 9, pp. 4040-4047.
Deubel, V. et al., "Nucleotide Sequence and Deduced Amino Acid Sequence of the Nonstructural Proteins of Dengue Type 2 Virus, Jamaica Genotype: Comparative Analysis of the Full-Length Genome" Virology, 1988, vol. 165, pp. 234-244.
Deubel, V. et al., "Nucleotide Sequence and Deduced Amino Acid Sequence of the Structural Proteins of Dengue Type 2 Virus, Jamaica Genotype," Virology, 1986, vol. 155, pp. 365-377.
Dharakul, T. et al., "Dengue Virus-Specific Memory T Cell Responses in Human Volunteers Receiving a Live Attenuated Dengue Virus Type 2 Candidate Vaccine," JID Jul. 1994, vol. 170, pp. 27-33.
Dmitriev, I. et al., "Immunization with recombinant vaccinia viruses expressing structural and part of the nonstructural region of tick-borne encephalitis virus eDNA protect mice against lethal encephalitis," Journal of Biotechnology, 1996, vol. 44, pp. 97-103.
Duarte Dos Santos, C. et al., "Complete nucleotide sequence of yellow fever virus vaccine strains 17DD and 17D-213," Virus Research 1995, vol. 35, pp. 35-41.
Durbin, A. et al., "Attenuation and Immunogenicity in Humans of a Live Dengue Virus Type-4 Vaccine Candidate with a 30 Nucleotide Deletion in its 3'—Untranslated Region," Am. J. Trop. Med. Hyg. 2001, vol. 65(5), pp. 405-413.
Falgout, B. et al., "Immunization of Mice with Recombinant Vaccinia Virus Expressing Authentic Dengue Virus Nonstructural Protein NS1 Protects against Lethal Dengue Virus Encephalitis," Journal of Virology, Sep. 1990, vol. 64, No. 9, pp. 4356-4363.
Falgout, B. et al., "Proper Processing of Dengue Virus Nonstructural Glycoprotein NS1 Requires the N-Terminal Hydrophobic Signal

(56) References Cited

OTHER PUBLICATIONS

Sequence and the Downstream Nonstructural Protein NS2a," Journal of Virology, May 1989, vol. 63, No. 5, pp. 1852-1860.
Garmendia, A. et al., "Recovery and Identification of West Nile Virus from a Hawk in Winter," Journal of Clinical Microbiology, Aug. 2000, vol. 38, No. 8, pp. 3110-3111.
George et al., "Safety and immunogenicity of a Live Attenuated Tetravalent Dengue Vaccine Candidate in Flavivirus-Naïve Adults: A Randomized, Double-Blinded Phase 1 Clinical Trial," Journal of Infectious Diseases, Mar. 19, 2015, vol. 212, No. 7, pp. 1032-1041.
Gruenberg, A. et al., "Partial Nucleotide Sequence and Deduced Amino Acid Sequence of the Structural Proteins of Dengue Virus Type 2, New Guinea C and PUO-218 Strains" J. gen. Virol., 1988, vol. 69, pp. 1391-1398.
Guirakhoo, F. et al., "Construction, Safety, and Immunogenicity in Nonhuman Primates of a Chimeric Yellow Fever-Dengue Virus Tetravalent Vaccine" Journal of Virology, Aug. 2001, vol. 75, No. 16, pp. 7290-7304.
Guirakhoo, F. et al., "Immunogenicity, Genetic Stability, and Protective Efficacy of a Recombinant, Chimeric Yellow Fever-Japanese Encephalitis Virus (ChimeriVax-JE) as a Live, Attenuated Vaccine Candidate against Japanese Encephalitis," Virology, 1999, vol. 257, pp. 363-372.
Guirakhoo, F. et al., "Recombinant Chimeric Yellow Fever-Dengue Type 2 Virus Is Immunogenic and Protective in Nonhuman Primates" Journal of Virology, The American Society for Microbiology, Jun. 1, 2000, vol. 74, No. 12, pp. 5477-5485.
Guirakhoo, F. et al., "Viremia and Immunogenicity in Nonhuman Primates of a Tetravalent Yellow Fever-Dengue Chimeric Vaccine: Genetic Reconstructions, Dose Adjustment, and Antibody Responses against Wild-type Dengue Virus Isolates" Virology, 2002, vol. 298, pp. 146-159.
Hahn, Y. et al., "Nucleotide Sequence of Dengue 2 RNA and Comparison of the Encoded Proteins with Those of Other Flaviviruses," Virology, 1988, vol. 162, pp. 167-180.
Halstead, S. et al., Observations related to the pathogenesis of dengue hemorrhagic fever. II. Antigenic and Biologic Properties of Dengue Viruses and their Association with disease in the host; Yale Journal of Biology and Medicine, Apr. 1970, vol. 42, pp. 276-292.
Hashimoto, H. et al., "Molecular Cloning and Complete Nucleotide Sequence of the Genome of Japanese Encephalitis Virus Beijing-1 Strain," Virus Genes, 1988, vol. 1, No. 3, pp. 305-317.
Heinz, F. et al., "Flaviviruses" Immunochemistry of viruses II, The basis for serodiagnosis and vaccines, (edited by von Regenmortel and Neurath), Elsevier Science Publishers B.V., Chapter 14, 1990 pp. 289-305.
Henchal E. et al., "Dengue Virus-Specific and Flavivirus Group Determinants Identified with Monoclonal Antibodies by Indirect Immunofluorescence," Flavivirus-Specific and Group Determinants, Am. J. Trop Med. Hyg., 1982, vol. 31, No. 4, pp. 830-836.
Hennessy, S. et al., "Effectiv ness of live-attenuated Japanese encephalitis vaccine (SA14-14-2): a case-control study" The Lancet, vol. 347, Jun. 8, 1996, pp. 1583-1586.
Ho, T. et al., "DNA vaccination induces a long-term antibody response and protective immunity against pseudorabies virus in mice" Archives of Virology, 1998, vol. 143, pp. 115-125.
Hsiang-Chi, L. et al., "Dengue Type 4 Live-Attenuated Vaccine Viruses Passaged in Vero Cells Affect Genetic Stability and Dengue-Induced Hemorrhaging in Mice," PLOS One, Oct. 28, 2011 (Oct. 28, 2011), vol. 6, No. 10, p. e25800.
Huang, C. et al., "Chimeric Dengue 2 PDK-53/West Nile NY99 Viruses Retain the Phenotypic Attenuation Markers of the Candidate PDK-53 Vaccine Virus and Protect Mice against Lethal Challenge with West Nile Virus" Journal of Virology, vol. 79, No. 12, Jun. 2005, pp. 7300-7310.
Huang, C. et al., "Chimeric Dengue Type 2 (Vaccine Strain PDK-53)/Dengue Type 1 Virus as a Potential Candidate Dengue Type 1 Virus Vaccine" Journal Of Virology, Apr. 2000, vol. 74, No. 7, pp. 3020-3028.

Huang, C. et al., "Concomitant administration of live attenuated Japanese encephalitis chimeric virus vaccine (JE-CV) and measles, mumps, rubella (MMR) vaccine: Randomized study in toddlers in Taiwan," Vaccine, Sep. 1, 2014, vol. 32, No. 41, pp. 5363-5369.
Huang, C. et al., "Dengue 2 PDK-53 virus as a chimeric carrier for tetravalent dengue vaccine development," J. Virology, Nov. 2003, vol. 77, No. 21, pp. 11436-11447.
Huang, C. et al., "Genetic and Phenotypic Characterization of Manufacturing Seeds for a Tetravalent Dengue Vaccine (DENVax)," PLOS Neglected Dis, May 2013, vol. 7, No. 5, e2243, 11 pages.
Hubálek, Z. et al., "West Nile Fever—a Reemerging Mosquito-Borne Viral Disease in Europe" Emerging Infectious Diseases, Sep.-Oct. 1999, vol. 5, No. 5, pp. 643-650.
Hunt, A. et al., "Relationships of Bunyamwera Group Viruses by Neutralization" Am. J. Trop. Med. Hyg. 1979, vol. 28, No. 4, pp. 740-749.
Jia, X. et al., "Genetic analysis of West Nile New York 1999 encephalitis virus" The Lancet, Dec. 4, 1999, vol. 354, pp. 1971-1972.
Jirakanjanakit, N. et al., "Dynamics of Susceptibility and Transmissibility of the Live Attenuated, Candidate Vaccines Dengue-1 PDK-13, Dengue-3 PGMK30F3, and Dengue-4 PDK-48 after Oral Infection in Aedes Aegypti," Am. J. Trop. Med. Hyg. 1999, vol. 61, No. 4, pp. 672-676.
Johnson, A. et al., "Detection of Anti-Arboviral Immunoglobulin G by Using a Monoclonal Antibody-Based Capture Enzyme-Linked Immunosorbent Assay," Journal of Clinical Microbiology, May 2000, vol. 38, No. 5, pp. 1827-1831.
Johnson, B. et al., "Growth Characteristics of ChimeriVax-DEN2 Vaccine Virus in Aedes Aegypti and Aedes Albopictus Mosquitoes," Am. J. Trop Med. Hyg., 2002, vol. 67, No. 3, pp. 260-265.
JP 19920043682 19920228 "Non-infective structure particle prepn., useful as vaccine—by infecting preliminarily flavivirus infected cell with cDNA integrated recombinant vaccinia virus, and then sepg. non-infective structure particles contg. E-protein of flavivirus" XP-00211903; Abtract Only.; (Cited as JP H05276941A).
Kanesa-Thasan, N. et al., "Safety and immunogenicity of attenuated dengue virus vaccines (Aventis Pasteur) in human volunteers," Vaccine, 2001 vol. 19 pp. 3179-3188.
Kawano, H. et al., "Genetic Determinants of Dengue Type 4 Virus Neurovirulence for Mice," Journal of Virology, Nov. 1993, vol. 67, No. 11, pp. 6567-6575.
Press Release: "Takeda Completes Enrollment of More Than 20,000 Children and Adolescents in Global Phase 3 Trial of Dengue Vaccine Candidate" Apr. 5, 2017—DEN-301, 4 pages.
Press Release: "Takeda's Pipeline Has Potential to Contribute Signi?cantly to Revenue Growth Over Next Decade," Dec. 9, 2020, 4 pages.
Puerta-Guardo et al., "Dengue Virus NS1 Disrupts the Endothelial Glycocalyx, Leading to Hyperpermeability," PloS Pathog, Jul. 14, 2016, vol. 12, No. 7, pp. 1-29.
Rinderknecht et al., "Immunogenicity and Safety of an Inactivated Hepatitis A Vaccine When Coadministered With Mea-sles-mumps-rubella and Varicella Vaccines in Children Less Than 2 Years of Age," Pediatric Infectious Disease Journal, Oct. 1, 2011, vol. 30, No. 10, pages e179-e185.
Roehrig et al., "Guidelines for Plaque-Reduction Neutralization Testing of Human Antibodies to Dengue Viruses," Viral Immunology, Jun. 1, 2008, vol. 21, No. 2, pp. 123-132.
Rupp et al., "Safety and immunogenicity of different doses and schedules of a live attenuated tetravalent dengue vaccine (TDV) in healthy adults: A Phase 1b randomized study," Vaccine, Nov. 1, 2015, vol. 33, No. 46, pp. 6351-6359.
Saez-Llorens et al., "Immunogenicity and safety of one versus two doses of tetravalent dengue vaccine in healthy chil-dren aged 2-17 years in Asia and Latin America: 18-month interim data from a phase 2, randomised, placebo-controlled study," Lancet Infect Dis, Nov. 6, 2017, vol. 18, pp. 162-170.
Schilling et al., "Coadministration of a 9-Valent Human Papillomavirus Vaccine With Meningococcal and Tdap Vaccines," Pediatrics, Sep. 1, 2015, vol. 136, No. 3, pp. e563-e572.

(56) References Cited

OTHER PUBLICATIONS

Sela, Michael, "The Choice of Carrier." In Synthetic Vaccines vol. I, R. Amon, (ed) CRC Press Inc., Boca Raton, FL. Chapter 6, 1987, pp. 83-92.
Sirivichayakul et al., "Safety and immunogenicity of a Tetravalent Dengue Vaccine Candidate in Healthy Children and Adults in Dengue-Endemic Regions: A Randomized, Placebo-Controlled Phase 2 Study," Journal of Infectious Diseases, Dec. 23, 2015, vol. 213, No. 10, pp. 1562-1572.
Sridhar et al., "Effect of Dengue Serostatus on Dengue Vaccine Safety and Efficacy," New England Journal of Medicine, Jul. 26, 2018, vol. 379, No. 4, pp. 327-340.
Stanaway et al., "The global burden of dengue: an analysis from the Global Burden of Disease Study 2013," Lancet Infect Dis., Jun. 16, 2016, vol. 16, No. 6, pp. 712-723.
Stocks et al: "Signal Peptidase Cleavage at the Flavivirus C-prM Junction: Dependence on the Viral NS2B-3 Protease for Efficient Processing Requires Determinants in C, the Signal Peptide, and prM," Journal of Virology, LNKDPUBMED: 9499070, Mar. 1998, Mar. 1998 (Mar. 1998), vol. 72, No. 3, pp. 2141-2149.
Timiryasova et al., "Optimization and Validation of a Plaque Reduction Neutralization Test for the Detection of Neutraliz-ing Antibodies to Four Serotypes of Dengue Virus Used in Support of Dengue Vaccine Development," American Journal Of Tropical Medicine & Hygiene, May 1, 2013, vol. 88, No. 5, pp. 962-970.
Trent Dennis W. et al., "Partial Nucleotide Sequence of St. Louis Encephalitis Virus RNA: Structural Proteins, NS1, ns2a, and ns2b," Virology, 1987, vol. 156, pp. 293-304.
Trent Dennis W. et al., "Recombinant dengue virus vaccines." In: Dengue and Dengue Hemorrhagic Fever. D.J. Gubler and G. Kuno (eds.). CAB International, New York, NY Chapter 18, 1997, pp. 379-403.
Tsai et al "Japanese Encephalitis Vaccines," In Vaccines, (3rd edition) Plotkin and Orenstein (eds), W.B. Saunders Company, Philadelphia, PA. Chapter 27, 1999, pp. 672-710.
Update: "Surveillance for Weste Nile Virus in Overwintering Mosquitoes—New York, 2000," Morb. Mortal. Wkly. Rep., Mar. 10, 2000, vol. 49, No. 09, pp. 178-179.
Update: "West Nile Virus Activity—Northeastern United States, 2000," Morb. Mortal. Wkly. Rep., Sep. 15, 2000, vol. 49, No. 36, pp. 820-822.
Vesikari et al., "Safety and Immunogenicity of a Booster Dose of the 10-Valent Pneumococcal Nontypeable Haemophilus influenza Protein D Conjugate Vaccine Coadministered With Measles-Mumps-Rubella-Varicella Vaccine in Children Aged 12to 16 Months," Pediatric Infectious Disease Journal, Jun. 1, 2010, vol. 29, No. 6, pp. e47-e56.
Villar et al., "Safety and immunogenicity of a recombinant tetravalent dengue vaccine in 9-16 year olds: a randomized, controlled, phase II trial in Latin America," Pediatr Infect Dis J, Oct. 2013, vol. 32, No. 10, pp. 1102-1109.
Wang et al., "Immune Response to Neonatal Genetic Immunization," Virology, 1997, vol. 228, pp. 278-284.
Wichmann et al., "Live-attenuated tetravalent dengue vaccines: The needs and challenges of post-licensure evaluation of vaccine safety and effectiveness," Vaccine, Oct. 1, 2017, vol. 35, No. 42, pp. 5535-5542.
Wilder-Smith et al., "Age specific differences in efficacy and safety for the CYD-tetravalent dengue vaccine," Expert Re-view of Vaccines, Apr. 2, 2016, vol. 15, No. 4, pp. 437-441.
World Health Organization, "Dengue vaccine research: Immunization, Vaccines and Biologicals" www.who.int/immunization/research/development/dengue_vaccines/en/, Sep. 12, 2018, 3 pages.
World Health Organization, "Guidelines for plaque reduction neutralization testing of human antibodies to dengue viruses," Immunization, Vaccines and Biologicals, Sep. 21, 2007 pp. 1-36, Retrieved from the internet [retrieved on Oct. 29, 2018].
World Health Organization, "Table 3: Recommendations for Interrupted or Delayed Routine Immunization—Sum-mary of WHO position papers," Aug. 2018, 10 pages.
World Health Organization, Dengue Vaccine Research, website page at www.who.int/immunuzation/research/development/dengue_vaccines/en, last updated Dec. 5, 2017, 3 pages.
World Health Organization, Recommendations for all immunization programmes, Aug. 1, 2018, Retrieved from the Internet, 10 pages.
World Health Organization, Updated Questions and Answers related to the dengue vaccine Dengvaxia and its use, website page at www.who.int/immunization/diseases/dengue/q_and_a_dengue_vaccine_dengvaxia_use/en/ published Dec. 22, 2017, 7 pages.
Butrapet, S. et al., "Chimeric Dengue Type 2/Type 1 Viruses Induce Immune Responses in Cynomolgus Monkeys," Southeast Asian J. Trap. Med. Public Health, Sep. 2002, vol. 33, No. 3, pp. 589-599.
Zhang et al., "Passive Protection of Mice, Goats, and Monkeys Against Japanese Encephalitis With Monoclonal Antibodies," 1989, J. Med. Virol., vol. 29, pp. 133-138.
Mllar, L. et al., "Efficacy of a Tetravalent Dengue Vaccine in Children in Latin America," New England Journal of Medicine, Jan. 8, 2015, vol. 372, No. 2, pp. 113-123.
Aberle, J. et al., "A DNA Immunization Model Study with Constructs Expressing the Tick-Borne Encephalitis Virus Envelope Protein E in Different Physical Forms," Journal of Immunology, 1999, vol. 163, pp. 6756-6761.
Allison, S. et al., "Synthesis and Secretion of Recombinant Tick-Borne Encephalitis Virus Protein E in Soluble and Particulate Form," Journal of Virology, Sep. 1995, vol. 69, No. 9, pp. 5816-5820.
Alvarez, R. et al., "A Phase I Study of Recombinant Adenovirus Vector-Mediated Delivery of an Anti-erbB-2 Single-Chain (sFv) Antibody Gene for Previously Treated Ovarian and Extraovarian Cancer Patients," Mary Ann Liebert, Inc., Human Gene Therapy, Jan. 20, 1997, vol. 8, pp. 229-242.
Anderson, J. et al., "Isolation of West Nile Virus from Mosquitoes, Crows, and a Cooper's Hawk in Connecticut", Ovid: Anderson: Science, vol. Dec. 17, 1999, vol. 286(5448), pp. 2331-2333.
Arroyo, J. et al., Molecular Basis for Attenuation of Neurovirulence of a Yellow Fever Virus/Japanese Encephalitis Virus Chimera Vaccine (ChimeriVax-JE), Journal of Virology, Jan. 2001, vol. 75, No. 2, pp. 934-942.
Asnis, D. et al., "The West Nile Virus Outbreak of 1999 in New York: The Flushing Hospital Experience," Clinical Infectious Diseases, 2000, vol. 30, pp. 413-418.
Azevedo, V. et al., "Main features of DNA-based immunization vectors," Brazilian Journal of Medical and Biological Research 1999, vol. 32, No. 2, pp. 147-153.
Bhamarapravati, N. et al., "Immunization with a live attenuated dengue-2-virus candidate vaccine (?16681-PDK 53 : clinical, immunological and biological responses in adult volunteers," Bulletin of the World Health Organization, 1987, vol. 65, No. 2, pp. 189-195.
Bhamarapravati, N. et al., "Live attenuated tetravalent dengue vaccine," Cab International, Wallingford, OX, UK, 1997, Dengue and Dengue Hamorrhagic Fever, D.J. Gubler and G. Kuno (ed), Chapter 17, pp. 367-377.
Bhamarapravati, N. et al., "Live attenuated tetravalent dengue vaccine," Vaccine, 2000, vol. 18, pp. 44-47.
Bhatt, T. et al., "Growth characteristics of the chimeric Japanese encephalitis virus vaccine candidate, chimeriVax-je (YF/JE SA14-14-2), in culex tritaeniorhynchus, aedes albopictus, and aedes aegypti mosquitoes," Am. J. Trop. Med. Hyg., 2000, vol. 62, No. 4, pp. 480-484.
Blok, J. et al., "Comparison of a Dengue-2 Virus and Its Candidate Vaccine Derivative: Sequence Relationships with the Flaviviruses and Other Viruses," Virology, 1992, vol. 187, pp. 573-590.
Bray, M. et al., "Construction of intertypic chimeric dengue viruses by substitution of structural protein genes," Proc. Nat. Acad. Sci. USA, Medical Sciences, Nov. 1991, vol. 88, pp. 10342-10346.
Bray, M. et al., "Mice Immunized with Recombinant Vaccinia Virus Expressing Dengue 4 Virus Structural Proteins with or without Nonstructural Protein NS1 are Protected against Fatal Dengue Virus Encephalitis," Journal of Virology, Jun. 1989, vol. 63, No. 6, pp. 2853-2856.
Bray, M. et al., "Monkeys Immunized with Intertypic Chimeric Dengue Viruses Are Protected against Wild-Type Virus Challenge," Journal of Virology, Jun. 1996, vol. 70, No. 6, pp. 4162-4166.

(56) References Cited

OTHER PUBLICATIONS

Butrapet, S. et al., "Attenuation markers of a candidate dengue type 2 vaccine virus, strain 16681 (PDK-53), are defined by mutations in the 5' noncoding region and nonstructural proteins 1 and 3," J. Virol., Apr. 2000, vol. 74, No. 7, pp. 3111-3119.
Vidor, E., "The Nature and Consequences of Intra- and Inter-Vaccine Interference", J. Comp. Path. 2007, vol. 137, S62-S66.
Silva, Juliana Romualdo Nascimento et al., "Mutual interference on the immune response to yellow fever vaccine and combined vaccine against measles, mumps and rubella", Vaccine 29 (2011) 6327-6334.
ClinicalTrials.gov archive, History of Changes for Study: NCT01436396 "Study of Yellow Fever Vaccine Administrated With Tetravalent Dengue Vaccine in Healthy Toddlers" Apr. 9, 2020.
ClinicalTrials.gov archive, History of Changes for Study: NCT01488890 "Immune Response to Different Schedules of a Tetravalent Dengue Vaccine Given With or Without Yellow Fever Vaccine" Apr. 9, 2020.
EU Clinical Trials Register, Clinical trial results: "Immunogenicity and Safety of Yellow Fever Vaccine (Stamaril®) Administered Concomitantly with Tetravalent Dengue Vaccine in Healthy Toddlers at 12-13 Months of Age in Colombia and Peru" Clinical trial results 2014-001714-26 version 1, EU CTR publication date: Feb. 8, 2016.
Kirstein, et al. "Immunogenicity of the CYD tetravalent dengue vaccine using an accelerated schedule: randomised phase II study in US adults" BMC Infectious Diseases (2018) 18:475.
Lang, Jean et al, "Q&A Session Oct. 6, 2011—I International Symposium on Dengue, FMUSP, Sao Paulo" Rev. Inst. Med. Trop. Sao Paulo 54(Suppl. 18):S28-S30, Oct. 2012.
SAGE Working Group on Yellow Fever Vaccine: Interference between YF vaccine and other vaccines, Jan. 11, 2012; BNSDOCID: XP_55222731A_I_.
MMWR Morbidity and Mortality Weekly Report "Yellow Fever Vaccine Recommendations of the Advisory Committee on Immunization Practices (ACIP)" Jul. 30, 2010 / vol. 59 / No. RR-7.
Nasveld, Peter E., et al, "Concomitant or sequential administration of live attenuated Japanese encephalitis chimeric virus vaccine and yellow fever 17D vaccine" Human Vaccines 6:11, 906-914; Nov. 2010; © 2010 Landes Bioscience.
Fujita, Nobuya et al, "Research on Dengue in Tissue Culture" Kobe J. Med. Sci. 15, 163-180, Dec. 1969.
Guy, Bruno et al, "Preclinical and clinical development of YFV 17D-based chimeric vaccines against dengue, West Nile and Japanese encephalitis viruses" Vaccine 28 (2010) 632-649.
Anderson, Kathryn B. et al, "Interference and Facilitation between Dengue Serotypes in a Tetravalent Live Dengue Virus Vaccine Candidate" JID 2011:204 (Aug. 1) 442-450.
Clinical Study Report; Title of study: "Immunogenicity and Safety of Yellow Fever Vaccine (Stamaril®) Administered Concomitantly with Tetravalent Dengue Vaccine in Healthy Toddlers at 12-13 Months of Age in Colombia and Peru" Sponsor: Sanofi Pasteur; According to template: QSD-001970 Version N° 7.0 (Nov. 26, 2019).
CYD51 results summary, Title of the study: "Evaluation of the Immune Response to Different Schedules of a Tetravalent Dengue Vaccine Administered With or Without Yellow Fever Vaccine in US Adults", Sponsor: Sanofi Pasteur, Jul. 22, 2020.
US office action issued Sep. 7, 2023 for U.S. Appl. No. 17/229,109.
US office action issued Sep. 13, 2023 for U.S. Appl. No. 17/478,537.
Jianrong Tang, "Current status of research and development of new dengue vaccines", Foreign Medical Sciences (Section of Biological Products for Prophylaxis, Diagnosis and Therapy), vol. 04, pp. 145-147.
Pengfei Li et al., "Advances in Research of Dengue Virus Vaccines", Progress in Microbiology and Immunology, vol. 06; Dec. 2012, vol. 40, No. 6., pp. 46-53.
CN Office Action + English translation for CN application 2023072602931350 dated Jul. 26, 2023.

Sato, Y. et al., "Immunostimulatory DNA Sequences Necessary for Effective Intradermal Gene Immunization," Science, Jul. 19, 1996, vol. 273, No. 5273, pp. 352-354.
Seeger, C. et al., "The cloned genome of ground squirrel hepatitis virus is infectious in the animal," Proc. Nat. Acad. Sci. USA, Medical Sciences, Sep. 1984, vol. 81, pp. 5849-5852.
Smithburn, K. et al., "A Neurotropic Virus Isolated From the Blood of a Native of Uganda," Am. J. Trop. Med. Hyg., 1940, vol. 20, pp. 471-492.
Sumiyoshi, H. et al., "Complete Nucleotide Sequence of Japanese Encephalitis Virus Genome RNA," Virology, 1987, vol. 161, pp. 497-510.
Takeda Vaccines, Anonymous, "Immunogenicity and Safety of Tetravalent Dengue Vaccine (TDV) Co-administered With an Hepatitis A Virus Vaccine", May 15, 2018, pp. 1-12.
Tardei, G et al., "Evaluation of Immunoglobulin M (IgM) and IgG Enzyme Immunoassays in Serologic Diagnosis of West Nile Virus Infection," J. Clin. Microbiol. Jun. 2000, vol. 38, No. 6, pp. 2232-2239.
Troyer, J. et al., "A Live Attenuated Recombinant Dengue-4 Virus Vaccine Candidate With Restricted Capacity for Dissemination in Mosquitoes and Lack of Transmission From Vaccinees to Mosquitoes," Am. J. Trop. Med. Hyg., 2001, vol. 65, No. 5, pp. 414-419.
Tsai, T. et al., "Japanese Encephalitis Vaccines," In Vaccines, (2nd edition), Plotkin and Mortimer (eds.), W.B. Saunders Co., Philadelphia, PA. Chapter 24, 1994, pp. 671-713.
Van Der Most, R. et al., "Chimeric yellow fever/dengue virus as a candidate dengue vaccine: quantification of the dengue virus-specific CD8 T-cell response," Journal of Virology, Sep. 1, 2000 2(Sep. 1, 2000), vol. 74. No. 17, pp. 8094-8101.
Vaughn, D. et al., "Testing of dengue 2 live-attenuated vaccine (strain 16681 PDK 53) in ten American volunteers," Vaccine 1996, vol. 14 No. 4, pp. 329-336.
Venugopal, K. et al., "Immunity to St. Louis encephalitis virus by sequential immunization with recombinant vaccinia and baculovirus derived PrM/E proteins," Vaccine, 1995, vol. 13, No. 11, pp. 1000-1005.
Wallace, D. et al., Presentation: "Takeda's dengue vaccine candidate in children: one or two doses?", Abstract 5th Pan American Dengue Research Network Meeting, age Apr. 20-23, 2016, DEN-204, p. 86.
Wallace, D., Presentation: "Persistence of neutralizing antibodies one year after two doses of a candidate recombinant tetra-valent dengue vaccine in subjects aged from 1.5 to 45 years," ASTMH 64th Annual Meeting, Oct. 27, 2015, DEN-203, 2 pages.
Wolff, J. et al., "Long-term persistence of plasmid DNA and foreign gene expression in mouse muscle," Hum. Mol. Genet., 1992, vol. 1, No. 6, pp. 363-369.
Xie, X. et al., "Membrane Topology and Function of Dengue Virus NS2A Protein," Journal of Virology, Apr. 2013, vol. 87, No. 8, pp. 4609-4622.
Yamshchikov, V. et al., "Processing of the Intracellular Form of the West Nile Virus Capsid Protein by the Viral NS2B-NS3 Protease: an In Vitro Study," Journal of Virology, LNKDPUBMED:8057458, Sep. 1994, vol. 68, No. 9, pp. 5765-5771.
Yang, X. et al., "A p300/CBP-associated factor that competes with the adenoviral oncoprotein E1A," Nature, Jul. 25, 1996, vol. 382.
Yoksan, S. et al., "Dengue Virus Vaccine Development: Study on Biological Markers of Uncloned Dengue 1-4 Viruses Serially Passaged in Primary Kidney Cells," Arbovirus Research in Australia—Proceedings 4th Symposium, T. D. St. George, B.H. Kay, and J. Blok (eds.), CSIRO/QIMR, Brisbane 1986, pp. 35-38.
Zhang, Y. et al., "Immunization of Mice with Dengue Structural Proteins and Nonstructural Protein NS1 Expressed by Baculovirus Recombinant Induces Resistance to Dengue Virus Encephalitis," J. Viro., Aug. 1988, vol. 62, No. 8, pp. 3027-3031.
Zhao, B. et al., "Cloning Full-Length Dengue Type 4 Viral DNA Sequences: Analysis of Genes Coding for Structural Proteins," Virology, 1986, vol. 155, pp. 77-88.
Zhao, B. et al., "Expression of Dengue Virus Structural Proteins and Nonstructural Protein NS1 by a Recombinant Vaccinia Virus," Journal of Virology, Dec. 1987, vol. 61, No. 12, pp. 4019-4022.

(56) References Cited

OTHER PUBLICATIONS

Brito, Luis A., et al., " Vaccine adjuvant formulations: A pharmaceutical perspective," Seminars in Immunology, vol. 25, No. 2, pp. 130-145, Jan. 2, 2013.
Ginley, D.M., "The development of a performance test procedure and measurement technique in a batch system NBS IR 85-3030." National Institute of Standards and Technology (NIST), Jul. 1985, pp. 1-152, retrieved from the Internet Dec. 31, 1985.
*AK Steel Corporation v. Sollac and Ugine*; United States Court of Appeals for the Federal Circuit; http://laws.lp.findlaw.com/fed/031074.html (24.09.2003), 8 pages.
Anonymous, "Guidelines for plaque reduction neutralization testing of human antibodies to dengue viruses," Sep. 21, 2007 (Sep. 21, 2007), p. 1-36,; Retrieved from the Internet:; URL:http://apps.who.int/iris/bitstream/handle/10665/69687/who_ivb_07.07_eng.pdf;jsessionid=E54172674C933124415AFC5BB972E6B9?sequence=1; XP055519586.
Arnon Ruth "Synthetic Vaccines vol. I" CRC Press, Inc. Boca Raton, Florida pp. 83-92.
Beatty et al., "Dengue virus NS1 triggers endothelial permeability and vascular leak that is prevented by NS1 vaccination," Sci. Transl. Med. Sep. 9, 2015, vol. 7, No. 304, pp. 1-13.
Benjamin, Sarah, "Optimization and analysis of live attenuated denvax-4 constructs," Masters Thesis: Colorado State University, Summer 2013, 97 pages.
Bhatt et al., "The global distribution and burden of dengue," Nature, Apr. 25, 2013, vol. 496 (7446), pp. 504-507.
Biswal et al., "Efficacy of a Tetravalent Dengue Vaccine in Healthy Children Aged 4-16 years: a randomised, placebo-controlled, phase 3 trial," Lancet, Mar. 17, 2020, vol. 395, pp. 1423-1433.
Biswal et al., "Efficacy of a Tetravalent Dengue Vaccine in Healthy Children and Adolescents," New England Journal of Medicine, Nov. 21, 2019, vol. 381, No. 21, pp. 2009-2019.
Biswal Presentation "Takeda Tetravalent Dengue Vaccine (TDV) Candidate: An Update (DEN-204)," Asia Dengue Summit, Jan. 13, 2016, 17 pages.
Brewoo et al., "Immunogenicity and efficacy of chimeric dengue vaccine (DENVax) formulations in interferon- deficient AG129 mice," Vaccine, Feb. 1, 2012, vol. 30, No. 8, pp. 1513-1520.
Capeding et al., "Clinical efficacy and safety of a novel tetravalent dengue vaccine in healthy children in Asia: a phase 3, randomised, observer-masked, placebo-controlled trial," Lancet, 2014, vol. 384, pp. 1358-1365.
Chu et al., "CD8+ T-cell Responses in Flavivirus-Naïve Individuals Following Immunization with a Live-Attenuated Tetrava-lent Dengue Vaccine Candidate" Major Article, JID, Nov. 15, 2015, vol. 212, pp. 1618-1628.
Crevat et al., "First Experience of Concomitant Vaccination Against Dengue and MMR in Toddlers," Pediatric Infectious Disease Journal, Aug. 1, 2015, vol. 34, No. 8, pp. 884-892.
Database UniProt Accession No. D2KQW7 Database UniProt SubName: Full=Polyprotein (ECO:0000313 EMBL: ADA00411.1); XP002731516, retrieved from EBI accession No. UNIPROT:D2KQW7, http://ibis/exam/dbfetch.jsp?id=UNIPROT:D2KQW7 Feb. 9, 2010, 2 pages.
Database UniProt Accession No. P29991 "RecName: Full=Genome polyprotein; Contains: RecName: Full=Capsid protein C; AltName: Full=Core protein; Contains: RecName: Full=prM; Contains," XP002731514, retrieved from EBI accession No. Uniprot: P29991; Apr. 1, 1993 http://ibis/exam/dbfetch.jsp?id=UNIPROT%3AP29991 .6 pages.
Database UniProt Accession No. Q9WLZ7, XP-002731515, http://ibis/exam/dbfetch.jsp?id=UNIPROT%3AQ9WLZ7, 2 pages.
DeLaBarrera et al., "Comparative Evaluation of Three Assays for Measurement of Dengue Virus Neutralizing Antibodies," Dengue Virus NS1 Disrupts the Endothelial Glycocalyx, Leading to Hyperpermeability, Jul. 1, 2008, vol. 79, No. 1, pp. 115-122.
Dubey et al., "Immunogenicity and safety of a tetravalent dengue vaccine in healthy adults in India: A randomized, observer-blind, placebo-controlled phase II trial," Human Vaccines and Immunotherapeutics, Aug. 20, 2015, vol. 12, No. 2, pp. 512-518.
Endy, "Dengue Human Infection Model Performance Parameters," Journal Infectious Diseases, 2014, vol. 209 (Suppl. 2), pages S56-S60.
European Search Report dated Feb. 12, 2019 for corresponding EP application 18192701.3, 22 pages.
European Search Report dated May 3, 2019 for corresponding EP application 19161184.7, 16 pages.
European Search Report dated Nov. 13, 2018 for corresponding EP application 18192701.3, 20 pages.
European Search Report dated Nov. 13, 2018 for corresponding EP application 18192711.2, 16 pages.
European Search Report dated Nov. 13, 2018 for corresponding EP application 18192717.9, 16 pages.
European Search Report dated Nov. 13, 2018 for corresponding EP application 18192787.2, 18 pages.
European Search Report dated Nov. 13, 2018 for corresponding EP application 18192793.0, 16 pages.
European Search Report dated Nov. 13, 2018 for corresponding EP application 18192800.3, 18 pages.
European Search Report dated Nov. 13, 2018 for corresponding EP application 18192814.4, 16 pages.
European Search Report dated Nov. 29, 2018 for corresponding EP application 18192776.5, 17 pages.
Gentry et al., "Identification of distinct antigenic determinants on dengue-2 virus using monoclonal antibodies," May 1982, Am. J. Trop. Med. Hyg., vol. 31, No. 3, Pt. 1, pp. 548-555.
Glasner et al., "Dengue virus NS1 cytokine-independent vascular leak is dependent on endothelial glycocalyx components," PloS Pathog., Nov. 9, 2017, vol. 13, No. 11, pp. 1-22.
Hadinegoro et al., "Efficacy and Long-Term Safety of a Dengue Vaccine in Regions of Endemic Disease," New England Journal of Medicine, Sep. 24, 2015, vol. 373, No. 13, p. 1195-1206.
Henchal et al., "Epitopic Analysis of Antigenic Determinants on the Surface of Dengue-2 Virions Using Monoclonal Antibod-ies," Am. J. Trop. Med. Hyg., 1985, vol. 34, No. 1, pp. 162-169.
Jackson et al., "A phase 1 study of safety and immunogenicity following intradermal administration of a tetravalent dengue vaccine candidate," Vaccine, May 19, 2018, vol. 36, pp. 3976-3983.
King et al., "Simultaneous administration of childhood vaccines: An important public health policy that is safe and effica-cious," Pediatric Infectious Disease Jour, Lippincott Williams & Wilkins, US, Jan. 1, 1994, vol. 13, No. 5, pp. 394-407.
Lanciotti R. et al., "Origin of the West Nile Virus Responsible for an Outbreak of Encephalitis in the Northeastern United States," Science, Dec. 17, 1999, vol. 286, pp. 2333-2337.
Lorenzato Presentation "Update of Takeda's dengue candidate vaccine development programme (DEN-204)," Brazilian Tropical Medicine Congress (Medtrop) Sep. 5, 2018, 29 pages.
López et al., "Immunogenicity and Safety of Yellow Fever Vaccine (Stamaril) When Administered Concomitantly With a Tet-ravalent Dengue Vaccine Candidate in Healthy Toddlers at 12-13 Months of Age in Colombia and Peru : A Randomized Trial," Pediatric Infectious Disease Journal, Oct. 1, 2016, vol. 35, No. 10, pp. 1140-1147.
López-Medina et al., "'Effcacy of a Dengue Vaccine Candidate (TAK-003) in Healthy Children and Adolescents 2 Years after Vaccination,'" The Journal of Infectious Diseases, 2021, pp. 1-12.
McInotsh Presentation "Takeda vacuna contra el dengue," ALAPE Sep. 5-8, 2018, Luque Asunción, Paraguay, 27 pages.
Melo et al., "Immunogenicity and Safety of a Booster Injection of DTap-IPV//Hib (Pentaxim) Administered Concomitantly With Tetravalent Dengue Vaccine in Healthy Toddlers 15-18 Months of Age in Mexico : A Randomized Trial," Pediatric Infec-tious Disease Journal, Jun. 1, 2017, vol. 36, No. 6, pp. 602-608.
Mullard, "Sanofi's dengue vaccine rounds final corner," Nature Reviews Drug Discovery, Nov. 2014, vol. 13, pp. 801-802.
NCT02425098 "Safety and Immunogenicity With Two Different Serotype 2 Potencies of Takeda's Tetravalent Dengue Vac-cine Candidate (TDV) in Adults in Singapore," Clinical Trials.gov, Jul. 16, 2019—DEN 205, Retrieved from internet Jul. 4, 2019, 12 pages.

(56) References Cited

OTHER PUBLICATIONS

Novello et al., "Update: West Nile Virus Activity—Northeastern United States, 2000," http://www.cdc.gov/mmwr/preview/mmwrhtml/mm4936a4.htm MMWR Weekly Sep. 15, 2000 / vol. 49, No. 36, pp. 820-822.
Osatomi et al., "Nucleotide Sequence of Dengue Type 3 Virus Genomic RNA Encoding Viral Structural Proteins," Virus Genes, Oct. 1988, vol. 2, No. 1, pp. 99-108. Abstract Only.
Osorio et al., "A recombinant, chimeric tetravalent dengue vaccine candidate based on a dengue virus serotype 2 back-bone," Expert Review of Vaccines, Apr. 2, 2016, vol. 15, No. 4, pp. 497-508.
Osorio et al., "Safety and immunogenicity of a recombinant live attenuated tetravalent dengue vaccine (DENVax) in fla-vivirus-naive healthy adults in Colombia: a randomised, placebo-controlled, phase 1 study," Lancet Infectious Diseases, Sep. 1, 2014, vol. 14, No. 9, pp. 830-838.
Pinheiro-Michelsen et al., "Anti-dengue Vaccines: From Development to Clinical Trials," Frontiers in Immunology, Jun. 18, 2020, vol. 11, Art. 1252, pp. 1-18.
Press Release: "Potential Impact of Takeda's Dengue Vaccine Candidate Reinforced by Long-Term Safety and Efficacy Results," May 22, 2021, 5 pages.
Press Release: "Takeda Begins Regulatory Submissions for Dengue Vaccine Candidate in EU and Dengue-Endemic Countries," Mar. 25, 2021, 4 pages.

Figure 1

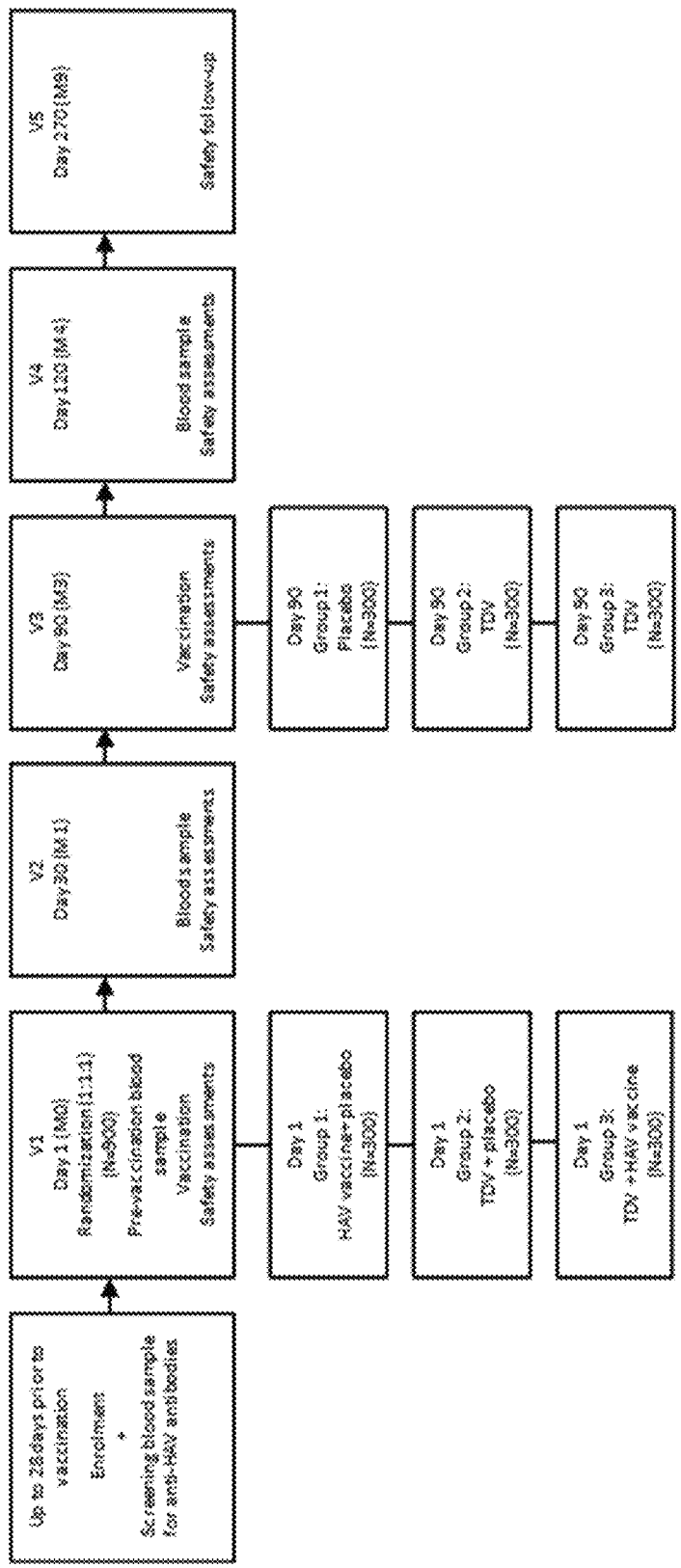

SEQUENCE LISTING

```
Sequence total quantity: 16
SEQ ID NO: 1         moltype = DNA   length = 10723
FEATURE              Location/Qualifiers
source               1..10723
                     mol_type = other DNA
                     note = chimeric dengue seroytpe 2/1 (MVS)
``` organism = synthetic construct
SEQUENCE: 1

```
agttgttagt ctacgtggac cgacaaagac agattctttg agggagctaa gctcaatgta   60
gttctaacag tttttaatt agagagcaga tctctgatga ataaccaacg gaaaaaggcg   120
aaaaacacgc cttcaatat gctgaaacgc gagagaaacg gcgtgtcgac tgtgcaacag   180
ctgacaaaga gattctcact tggaatgctg cagggacgag gaccattaaa actgttcatg   240
gccctggtgg cgttccttcg tttcctaaca atcccaccaa cagcagggat attgaagaga   300
tggggaacaa ttaaaaaatc aaaagctatt aatgttttga gagggttcag gaaagagatt   360
ggaaggatgc tgaacatctt gaataggaga cgcagatctg caggcatgat cattatgctg   420
attccaacag tgatggcgtt ccatttaacc acgcgtgggg gagagccgca tatgatagtt   480
agcaagcagg aaagaggaaa gtcacttttg ttcaagacct ctgcaggtgt caacatgtgc   540
accctcattg cgatggattt gggagagttg tgtgaggaca cgatgaccta caaatgcccc   600
cggatcactg aggcggaacc agatgacgtt gactgttggt gcaatgccac ggacacatgg   660
gtgaccatg gaacgtgctc tcaaactggc gaacaccgac gagacaaacg ttccgtcgaa   720
ttggccccac acgtggggct tggcctagaa acaagagccg aaacgtggat gtcctctgaa   780
ggtgcttgga acagataca aaagtagag acttgggctc tgagacatcc aggattcacg   840
gtgatagccc tttttctagc acatgccata ggaacatcca tcacccagaa agggatcatt   900
ttcatttgc tgatgctggt aacaccatct atggccatgc gatgcgtggg aataggcaac   960
agagacttcg tggaaggact gtcaggagca acatgggtgg atgtggtact ggagcatgga  1020
agttgcgtca ccaccatggc aaaaaacaaa ccaaactgg acattgaact cttgaagacg  1080
gaggtcacaa accctgcagt tctgcgtaaa ttgtgcattg aagctaaaat atcaaacacc  1140
accaccgatt cgagatgtcc aacacaagga gaagccacac tggttgaaga acaagacgg  1200
aactttgtgt gccgacgaac gttcgtggac agaggctggg gcaatggctg tgggctattc  1260
ggaaaaggta gtcaataac gtgtgccaag tttaagtgtg tgacaaaact agaaggaaag  1320
atagttcaat atgaaaacct aaaatattca gtgatagtca ccgtccacac tggagatcag  1380
caccaggtgg gaaatgagac tacagaacat ggaaccacca acctcaagct  1440
cctacgtcgg aaatacagct gaccgactac ggaacccta cattagattg ttcacctagg  1500
acagggctag attttaacga gatggtgttg ctgacaatga agaaagatc atggcttgtc  1560
cacaaacaat ggttcctaga cttaccactg ccttggacct ctggggcttc aacatcccaa  1620
gagacttgga acagacaaga tttactggtc acatttaaga cagctcatgc aaagaagcag  1680
gaagtagtcg tactaggatc acaagaagga gcaatgcaca ctgcgctgac tggagcgaca  1740
gaaatccaaa cgtcaggaac gacaacaatt ttcgcaggac acctaaatg cagactaaaa  1800
atggacaaac taactttaaa agggatgtca tatgtgatgt gcacaggctc attcaagtta  1860
gagaagaag tggctgagac ccagcatgga actgttctgg tgcaggttaa atatgaagga  1920
acagcgcac catgcaagat tccctttcg acccaagtg agaaggagc aacccagaat  1980
gggagattaa taacagccaa ccccatagtc actgacaaag aaaaaccagt caatattgag  2040
gcagaaccac cctttggtga gagctacatc gtggtaggag caggtgaaaa agcttttaaa  2100
ctaagctggt tcaagaaagg aagcagcata gggaaaatgt ttgaagcaac tgcccgagga  2160
gcacgaagga tggccattct gggagacacc gcatggagact tcggttctat aggaggagtg  2220
ttcacgtcta tgggaaaact ggtacaccag gttttggaa ctgcatatgg agttttgtt  2280
agcggagttt cttggaccat gaaaatagga atagggattc tgctgacatg gctaggatta  2340
aattcaagga acacgtccct ttcgatgatg tgcatcgcag ccggcattgt gacactgtat  2400
ttgggagtca tggtgcaggc cgatagtggt tgcgttgtga gctgaaaaa caaagaactg  2460
aaatgtggca gtgggatttt catcacagac aacgtgcaca catggacaga acaatacaag  2520
ttccaaccag aatccccttc aaaactagct tcagctatcc agaaagccca tgaagaggac  2580
atttgtgaa tccgctcagt aacaagactg agaatctga tgtggaaaca aataaccacca  2640
gaattgaatc acattctatc atgaaaatgag gtgaagttaa ctattatgac aggagacatc  2700
aaaggaatca tgcaggcagg aaaacgatct ctgcggcctc agcccactga gctgaagtat  2760
tcatggaaaa catggggcaa agcaaaaatg ctctctacag agtctcataa ccagaccttt  2820
ctcattgatg ccccgaaac agcagaatgc cccaacacaa atagagcttg gaattcgttg  2880
gaagttgaag actatggctt tggagtattc accaccaata tatggctaaa attgaaagaa  2940
aaacaggatg tattctgcga ctcaaaactc atgtcagcgg ccataaaaga caacagagcc  3000
gtccatgccg atatgggtta ttggataga agtgcactca atgacacatg gaagatagag  3060
aaagcctctt tcattgaagt taaaaactgc cactggccaa aatcacacac cctctggagc  3120
aatggagtgc tagaaagtga gatgataatt ccaaagagtc tcgctggaca gtgtctcaa  3180
cacaactata gaccaggcta ccatacacaa ataacaggac catggcatct aggtaagctt  3240
gagatggact ttgatttctg tgatggaaca acagtggtag tgactgagga ctgcggaaat  3300
agaggaccct ctttgagaac aaccactgcc tctggaaaac tcataacaga atggtgctgc  3360
cgatcttgca cattaccacc gctaagatac agaggtgagg atggtgctg gtacgggatg  3420
gaaatcagac cattgaagga gaaagaagag aatttggtca actccttggt cacagcgtgg  3480
catgggcagg tcgacaactt ttcactagga gtcttgggca tggcattgtt cctgaggaa  3540
atgcttagga cccgagtagg aacgaaacat gcaatactac tagttgcagt tctttttgtg  3600
acattgatca cagggaacat gtcctttaga gacctggaa gagtgatggt tatggtaggc  3660
gccactatga cggatgacat aggtatgggc gtgactttc ttgccctact agcagccttc  3720
aaagtcagac caactttttgc agctggacta ctcttgagaa agctgaccctc caaggaattg  3780
atgatgacta ctataggaat tgtactcctc tcccagagca cctaccagga gccattctt  3840
gagttgactg atgcgttagc cttaggcatg atggtcctca aatggtgag aaatatgaa  3900
aagtatcaat tggcagtgac tatcatggct atcttgtgcg tcccaaacgc agtgatatta  3960
caaaacgcat ggaaagtgag ttgcacaata ttggcagtgg tgtccgtttc cccactgttc  4020
ttaacatcct cacagcaaaa aacagattgg ataccattag cattgacgat caaaggtctc  4080
aatccaacag ctatttttct aaccaccctc tcaagaacca gcaagaaaag gagctggcca  4140
ttaaatgagg ctatcatggc agtcgggatg gtgagcattt tagccagttc tctcctaaaa  4200
aatgatattc ccatgacagg accattagtg gctgagggc cctcactgt gtgctacgtg  4260
ctcactggac gatcggccga tttgaactg gagagagcag ccgatgtcaa atggaagac  4320
caggcagaga tatcaggaag cagtccaatc ctgtcaataa caatatcaga agatggtagc  4380
atgtcgataa aaaatgaaga ggaagatcaa acactgacca tactcattag aacaggattg  4440
ctggtgatct caggacttttt tcctgtatca ataccaatca cggcagcagc atggtacctg  4500
tgggaagtga agaaacaacg ggccggagta ttgtgggatg ttccttcacc cccacccatg  4560
ggaaaggctg aactggaaga tggagcctat agaattaagc aaaaagggat tcttggatat  4620
```

```
tcccagatcg gagccggagt tacaaagaa ggaacattcc atacaatgtg gcatgtcaca    4680
cgtggcgctg ttctaatgca taaaggaaag aggattgaac catcatgggc ggacgtcaag    4740
aaaagaccta tatcatatgg aggaggctgg aagttagaag gagaatgaa ggaaggagaa    4800
gaagtccagg tattggcact ggagcctgga aaaaatccaa gagccgtcca aacgaaacct    4860
ggtcttttca aaaccaacgc cggaacaata ggtgctgtat ctctggactt ttctcctgga    4920
acgtcaggat ctccaattat cgacaaaaaa ggaaaagttg tgggtcttta tggtaatggt    4980
gttgttacaa ggagtggagc atatgtgagt gctatagccc agactgaaaa aagcattgaa    5040
gacaacccag atcgaagaa tgacattttc gaaagagaa gactgaccat catggacctc    5100
cacccaggag cgggaaagac gaagagatac cttccggcca tagtcagaga agctataaaa    5160
cggggtttga gaacattaat cttgccccc actagagttg tggcagctga aatggaggaa    5220
gcccttagag gacttccaat aagataccag accccagcca tcagagctgt gcacaccggg    5280
cgggagattg tggacctaat gtgtcatgcc acatttacca tgaggctgct atcaccagtt    5340
agagtgccaa actacaacct gattatcatg gacgaagcc atttcacaga cccacaagt    5400
atagcagcta gaggatacat ctcaactcga gtgggagatg gtgaggcagc tgggattttt    5460
atgacagcca ctccccgggg aagcagagac ccatttcctc agagcaatgc accaatcata    5520
gatgaagaaa gagaaatccc tgaacgctcg tggaattccg gacatgaatg ggtcacggat    5580
tttaaaggga agactgtttg gttcgttcca agtataaaag caggaaatga tatagcagct    5640
tgcctgagga aaaatggaaa gaaagtgata caactcagta ggaagaccct tgattctgag    5700
tatgtcaaga ctagaaccaa tgattgggac ttcgtggtta caactgacat ttcagaaatg    5760
ggtgccaatt tcaaggctga gagggttata gaccccagac gctgcatgaa accagtcata    5820
ctaacagatg gtgaagagcg ggtgattctg gcaggcctta tgccagtgac ccactctagt    5880
gcagcacaaa gaagagggag aataggaaga aatccaaaaa atgagatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaggtgg atgccattga tggcgaatac cgcttgagag gagaagcaag gaaaaccttt    6120
gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga aatctggaca aagaaggg aaaggaagaa attgaaccc    6300
agatggttgg atgctaggat ctattctgac ccactggcgc taaaagaatt taaggaattt    6360
gcagccggaa gaaagtctct gaccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
ctttactga cacttctggc tacagtcacg ggagggatct ttttattctt gatgagcgca    6600
aggggcatag ggaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaa cagagaacac cccaagacaa ccaactgacc    6780
tacgttgtca tagccatcct cacagtggtg gccgcaacca tggcaaacga tgggtttc    6840
ctagaaaaaa cgaagaaaga tctcggattg ggaagcattg caacccagca acccgagagc    6900
aacatcctgg acatagatct acgtcctgca tcagcatgga cgctgtatgc cgtgccaaca    6960
acatttgtta caccaatgtt gagacatagc attgaaaatt cctcagtgaa tgtgtcccta    7020
acagctatag ccaaccaagc cacagtgtta atgggtctcg ggaaaggatg gccattgtca    7080
aagatggaca tcgagttcc ccttctcgcc attggatgct actcacaagt caaccccata    7140
actctcacag cagctcttt cttattggta gcacattatg ccatcatagg gccaggactc    7200
caagcaaaag caaccagaga agctcagaaa agagcagcgg cgggcatcat gaaaaaccca    7260
actgtcgatg gaataacagt gattgaccta gatccaatac cttatgatcc gaagtttgaa    7320
aagcagttgg gacaagtaat gctcctagtc tctctgcgtga ctcaagtatt gatgatgagg    7380
actacatggg ctctctgtga ggctttaacc ttagctaccg ggcccatctc cacattgtgt    7440
gaaggaaatc cagggagtt ttggaacact accattgcgg tgtcaatggc taacattttt    7500
agagggagtt acttggccgg agctggactt ctcttttcta ttatgaagaa cacaaccaac    7560
acaagaaggg gaactggcaa cataggagag acgcttggag agaaatgaa aagccgattg    7620
aacgcattgg gaaaaagtga attccagatc tacaagaaaa gtggaatcca ggaagtgat    7680
agaaccttag caaagaagg cattaaaaga ggagaaacgg accatcacgc tgtgtcgcga    7740
ggctcagcaa aactgagatg gttcgttgag agaacatgg tcacaccaga agggaaagta    7800
gtggacctcg gttgtggcag aggaggctgg tcatactatt gtgaggact aaagaatgta    7860
agagaagtca aaggcctaac aaaaggagga ccaggacacg aagaaccat cccatgtca    7920
acatatgggt ggaatctagt gcgtcttcaa agtggagttg acgttttctt catcccgcca    7980
gaaaagtgtg acacattatt gtgtgacata ggggagtcat caccaaatcc cacagtggaa    8040
gcaggacgaa cactcagagt ccttaactta gtagaaaatt ggttgaacaa caacactcaa    8100
ttttgcataa aggttctcaa cccatatatg cctcagtca tagaaaaaat ggaagcacta    8160
caaaggaaat atggaggagc cttagtgagg aatccactct cacgaaactc cacacatgag    8220
atgtactggg tatccaatgc ttccgggaac atagtgtcat cagtgaacat gatttcaagg    8280
atgttgatca acagatttac aatgagatac aagaaagcca cttacgagcc ggatgttgac    8340
ctcggaagcg gaacccgtaa catcgggatt gaaagtgaga taccaaacct agatataatt    8400
gggaaaagaa tagaaaaat aaagcaagag catgaaactc tgccaagac caccatatca    8460
cacccataca aaaacgtggc ataccatggt agctatgaaa caaaacagac tggatcagca    8520
tcatccatgg tcaacggagt ggtcaggctg ctgacaaaac cttgggacgt cgtccccatg    8580
gtgacacaga tggcaatgac agacacgact ccatttggac aacagcgcgt ttttaaagag    8640
aaagtggaca cgagaaccca agaaccgaaa gaaggcacga gaaaactaat gaaaataca    8700
gcagagtggg tttggaaaga attagggaag aaaaagacac ccaggatgtg caccagagaa    8760
gaattcacaa gaaaggtgag aagcaatgca gccttggggg ccatattcac tgatgagaac    8820
aagtggaagt cggcacgtga ggctgttgaa gatagtaggt ttgggagct ggttgacaag    8880
gaaaggaatc tccatcttga aggaaagtgt gaaacatgtg tgtacaacat gatgggaaaa    8940
agagagaaga agctagggga attcggcaag gcaaaggca gcagagccat atggtacatg    9000
tggcttggag cacgcttctt agagtttgaa gccctaggat tcttaaatga agatcactgg    9060
ttctccagag agaactccct gagtggagtg gaaggagaag gctgcacaa gctaggttac    9120
attctaagag acgtgagcaa gaaagaggga ggagcaatgt atgccgatga caccgcagga    9180
tgggatacaa gaatcacact agaagaccta aaaaatgaag aaatggtaac aaaccacatg    9240
gaaggagaac acaagaaact agccgaggcc attttcaaac taacgtacca aaacaaggtg    9300
gtgcgtgtgc aaagaccaac accaagaggc acagtaatgg acatcatatc gagaagagac    9360
```

```
caaagaggta gtggacaagt tggcacctat ggactcaata ctttcaccaa tatggaagcc  9420
caactaatca gacagatgga gggagaagga gtctttaaaa gcattcagca cctaacaatc  9480
acagaagaaa tcgctgtgca aaactggtta gcaagagtgg ggcgcgaaag gttatcaaga  9540
atggccatca gtggagatga ttgtgttgtg aaaccttttag atgacaggtt cgcaagcgct  9600
ttaacagctc taaatgacat gggaaagatt aggaaagaca tacaacaatg ggaaccttca  9660
agaggatgaa atgattggac acaagtgccc ttctgttcac accatttcca tgagttaatc  9720
atgaaagacg tcgcgtact cgttgttcca tgtagaaacc aagatgaact gattggcaga  9780
gcccgaatct cccaaggagc agggtggtct ttgcgggaga cggcctgttt ggggaagtct  9840
tacgccccaaa tgtggagctt gatgtacttc cacacgacgcg acctcaggct ggcggcaaat  9900
gctatttgct cggcagtacc atcacattgg gttccaacaa gtcgaacaac ctggtccata  9960
catgctaaac atgaatggat gacaacgaaa gacatgctga cagtctggaa cagggtgtgg 10020
attcaagaaa acccatggat ggaagacaaa actccagtgg aatcatggga ggaaatccca 10080
tacttgggga aagagaaga ccaatggtgc ggctcattga ttgggttaac aagcagggcc 10140
acctgggcaa agaacatcca agcagcaata atcaagtta gatcccttat aggcaatgaa 10200
gaatacacag attacatgcc atccatgaaa agattcagaa gagaagagga agaagcagga 10260
gttctgtggt agaaagcaaa actaacatga aacaaggcta gaagtcaggt cggattaagc 10320
catagtacgg aaaaaactat gctacctgtg agccccgtcc aaggacgtta aagaagtca 10380
ggccatcata cttgataaa ctatgcgaacc tgtagctcca cctgagaagg 10440
tgtaaaaaat ccggaggcc acaaaccatg gaagctgtac gcatggcgta gtggactagc 10500
ggttagagga gacccctccc ttacaaatcg cagcaacaat gggggcccaa ggcgagatga 10560
agctgtagtc tcgctggaag gactagaggt tagaggagac cccccgaaa caaaaaacag 10620
catattgacg ctgggaaaga ccagagatcc tgctgtctcc tcagcatcat tccaggcaca 10680
gaacgccaga aaatggaatg tgctgttga atcaacaggt tct               10723

SEQ ID NO: 2                moltype = AA  length = 3391
FEATURE                     Location/Qualifiers
source                      1..3391
                            mol_type = protein
                            note = chimeric dengue serotype 2/1 (MVS)
                            organism = synthetic construct
SEQUENCE: 2
MNNQRKKAKN TPFNMLKRER NRVSTVQQLT KRFSLGMLQG RGPLKLFMAL VAFLRFLTIP    60
PTAGILKRWG TIKKSKAINV LRGFRKEIGR MLNILNRRRR SAGMIIMLIP TVMAFHLTTR   120
GGEPHMIVSK QERGKSLLFK TSAGVNMCTL IAMDLGELCE DTMTYKCPRI TEAEPDDVDC   180
WCNATDTWVT YGTCSQTGEH RRDKRSVALA PHVGLGLETR AETWMSSEGA WKQIQKVETW   240
ALRHPGFTVI ALFLAHAIGT SITQKGIIFI LLMLVTPSMA MRCVGIGNRD FVEGLSGATW   300
VDVVLEHGSC VTTMAKNKPT LDIELLKTEV TNPAVLRKLC IEAKISNTTT DSRCPTQGEA   360
TLVEEQDANF VCRRTFVDRG WGNGCGLFGK GSLITCAKFK CVTKLEGKIV QYENLKYSVI   420
VTVHTGDQHQ VGNETTEHGT TATITPQAPT SEIQLTDYGT LTLDCSPRTG LDFNEMVLLT   480
MKERSWLVHK QWFLDLPLPW TSGASTSQET WNRQDLLVTF KTAHAKKQEV VVLGSQEGAM   540
HTALTGATEI QTSGTTTIFA GHLKCRLKMD KLTLKGMSYV MCTGSFKLEK EVAETQHGTV   600
LVQVKYEGTD APCKIPFSTQ DEKGATQNGR LITANPIVTD KEKPVNIEAE PPFGESYIVV   660
GAGEKALKLS WFKKGSSIGK MFEATARGAR RMAILGDTAW DFGSIGGVFT SMGKLVHQVF   720
GTAYGVLFSG VSWTMKIGIG ILLTWLGLNS RNTSLSMMCI AAGIVTLYLG VMVQADSGCV   780
VSWKNKELKC GSGIFITDNV HTWTEQYKFQ PESPSKLASA IQKAHEEDIC GIRSVTRLEN   840
LMWKQITPEL NHILSENEVK LTIMTGDIKG IMQAGKRSLR PQPTELKYSW KTWGKAKMLS   900
TESHNQTFLI DGPETAECPN TNRAWNSLEV EDYGFGVFTT NIWLKLKEKQ DVFCDSKLMS   960
AAIKDNRAVH ADMGYWIESA LNDTWKIEKA SFIEVKNCHW PKSHTLWSNG VLESEMIIPK  1020
NLAGPVSQHN YRPGYHTQIT GPWHLGKLEM DFDFCDGTTV VVTEDCGNRG PSLRTTTASG  1080
KLITEWCCRS CTLPPLRYRG EDGCWYGMEI RPLKEKEENL VNSLVTAGHG QVDNFSLGVL  1140
GMALFLEEML RTRVGTKHAI LLVAVSFVTL ITGNMSFRDL GRVMVMVGAT MTDDIGMGVT  1200
YLALLAAFKV RPTFAAGLLL RKLTSKELMM TTIGIVLLSQ STLPETILEL TDALALGMMV  1260
LKMVRNMEKY QLAVTIMAIL CVPNAVILQN AWKVSCTILA VVSVSPLFLT SSQQKTDWIP  1320
LALTIKGLNP TAIFLTTLSR TSKKRSWPLN EAIMAVGMVS ILASSLLKND IPMTGPLVAG  1380
GLLTVCYVLT GRSADLELER AADVKWEDQA EISGSSPILS ITISEDGSMS IKNEEEDGTL  1440
TILIRTGLLV ISGLFPVSIP ITAAAWYLWE VKKQRAGVLW DVPSPPPMGK AELEDGAYRI  1500
KQKGILGYSQ IGAGVYKEGT FHTMWHVTRG AVLMHKGKRI EPSWADVKKD LISYGGGWKL  1560
EGEWKEGEEV QVLALEPGKN PRAVQTKPGL FKTNAGTIGA VSLDFSPGTS GSPIIDKKGK  1620
VVGLYGNGVV TRSGAYVSAI AQTEKSIEDN PEIEDDIFRK RRLTIMDLHP GAGKTKRYLP  1680
AIVREAIKRG LRTLILAPTR VVAAEMEEAL RGLPIRYQTP AIRAVHTGRE IVDLMCHATF  1740
TMRLLSPVRV PNYNLIIMDE AHFTDPASIA ARGYISTRVE MGEAAGIFMT ATPPGSRDPF  1800
PQSNAPIIDE EREIPERSWN SGHEWVTDFK GKTVWFVPSI KAGNDIAACL RKNGKKVIQL  1860
SRKTFDSEYV KTRTNDWDFV VTTDISEMGA NFKAERVIDP RRCMKPVILT DGEERVILAG  1920
PMPVTHSSAA QRRGRIGRNP KNENDQYIYM GEPLENDEDC AHWKEAKMLL DNINTPEGII  1980
PSMFEPEREK VDAIDGEYRL RGEARKTFVD LMRRGDLPVW LAYRVAAEGI NYADRRWCFD  2040
GVKNNQILEE NVEVEIWTKE GERKKLKPRW LDARIYSDPL ALKEFKEFAA GRKSLTLNLI  2100
TEMGRLPTFM TQKARDALDN LAVLHTAEAG GRAYNHALSE LPETLETLLL LTLLATVTGG  2160
IPLFLMSARG IGKMTLGMCC IITASILLWY AQIQPHWIAS SIILEFFLIV LLIPEPEKQR  2220
TPQDNQLTYV VIAILTVVAA TMANEMGFLE KTKKDLGLGS IATQQPESNI LDIDLRPASA  2280
WTLYAVATTF VTPMLRHSIE NSSVNVSLTA IANQATVLMG LGKGWPLSKM DIGVPLLAIG  2340
CYSQVNPITL TAALFLLVAH YAIIGPGLQA KATREAQKRA AAGIMKNPTV DGITVIDLDP  2400
IPYDPKFEKQ LGQVMLLVLC VTQVLMMRTT WALCEALTLA TGPISTLWEG NPGRFWNTTI  2460
AVSMANIFRG SYLAGAGLLF SIMKNTTNTR RGTGNIGETL GEKWKSRLNA LGKSEFQIYK  2520
KSGIQEVDRT LAKEGIKRGE TDHHAVSRGS AKLRWFVERN MVTPEGKVVD LGCGRGGWSY  2580
YCGGLKNVRE VKGLTKGGPG HEEPIPMSTY GWNLVRLQSG VDVFFIPPEK CDTLLCDIGE  2640
SSPNPTVEAG RTLRVLNLVE NWLNNNTQFC IKVLNPYMPS VIEKMEALQR KYGGALVRNP  2700
LSRNSTHEMY WVSNASGNIV SSVNMISRML INRFTMRYKK ATYEPDVDLG SGTRNIGIES  2760
EIPNLDIIGK RIEKIKQEHE TSWHYDQDHP YKTWAYHGSY ETKQTGSASS MVNGVVRLLT  2820
KPWDVVPMVT QMAMTDTTPF GQQRVFKEKV DTRTQEPKEG TKKLMKITAE WLWKELGKKK  2880
```

```
TPRMCTREEF TRKVRSNAAL GAIFTDENKW KSAREAVEDS RFWELVDKER NLHLEGKCET  2940
CVYNMMGKRE KKLGEFGKAK GSRAIWYMWL GARFLEFEAL GFLNEDHWFS RENSLSGVEG  3000
EGLHKLGYIL RDVSKKEGGA MYADDTAGWD TRITLEDLKN EEMVTNHMEG EHKKLAEAIF  3060
KLTYQNKVVR VQRPTPRGTV MDIISRRDQR GSGQVGTYGL NTFTNMEAQL IRQMEGEGVF  3120
KSIQHLTITE EIAVQNWLAR VGRERLSRMA ISGDDCVVKP LDDRFASALT ALNDMGKIRK  3180
DIQQWEPSRG WNDWTQVPFC SHHFHELIMK DGRVLVVPCR NQDELIGRAR ISQGAGWSLR  3240
ETACLGKSYA QMWSLMYFHR RDLRLAANAI CSAVPSHWVP TSRTTWSIHA KHEWMTTEDM  3300
LTVWNRVWIQ ENPWMEDKTP VESWEEIPYL GKREDQWCGS LIGLTSRATW AKNIQAAINQ  3360
VRSLIGNEEY TDYMPSMKRF RREEEEAGVL W                                3391

SEQ ID NO: 3             moltype = DNA   length = 10723
FEATURE                  Location/Qualifiers
source                   1..10723
                         mol_type = other DNA
                         note = dengue serotype 2 (MVS)
                         organism = synthetic construct
SEQUENCE: 3
agttgttagt ctacgtggac cgacaaagac agattctttg agggagctaa gctcaatgta   60
gttctaacag tttttttaatt agagagcaga tctctgatga ataaccaacg gaaaaaggcg  120
aaaaacacgc cttccaatat gctgaaacgc gagagaaacc gcgtgtcgac tgtgcaacag  180
ctgacaaaga gattctcact tggaatgctg cagggacgag gaccattaaa actgttcatg  240
gccctggtgg cgttccttcg tttcctaaca atcccaccaa cagcagggat attgaagaga  300
tggggaacaa ttaaaaaatc aaaagctatt aatgtttttga gagggttcag gaaagagatt  360
ggaaggatgc tgaacatctt gaataggaga cgcagatctg caggcatgat cattatgctg  420
attccaacag tgatggcgtt ccatttaacc acacgtaacg gagaaccaca catgatcgtc  480
agcagacaag agaaagggaa aagtcttctg tttaaaacag aggttggcgt gaacatgtgt  540
accctcatgg ccatggacct tggtgaattg tgtgaagaca caatcacgta cgagtgtccc  600
cttctcaggc agaatgagcc agaagacata gactgttggt gcaactctac gtccacgtgg  660
gtaacttatg ggacgtgtac caccatggga gaacatagaa gagaaaaag atcagtggca  720
ctcgttccac atgtgggaat gggactggag acacgaactg aaacatggat gtcatcagaa  780
ggggcctgga acatgtcca gagaattgaa acttggatct tgagacatcc aggcttcacc  840
atgatggcag caatcctggc atacaccata ggaacgacac atttccaaag agccctgatc  900
ttcatcttac tgcagctgt cactccttca atgacaatgc gttgcatagg aatgtcaaat  960
agagactttg tgaaggggt tcaggaggaa gctgggtttg acatagtctt agaacatgga 1020
agctgtgta cgacgatggc aaaaaacaaa ccaacattgg attttgaact gataaaaaca 1080
gaagccaaac agcctgccac cctaaggaag tactgtatag aggcaaagct aaccaacaca 1140
acaacagaat ctcgctgccc aacacaaggg gaacccagcc taaatgaaga gcaggacaaa 1200
aggttcgtct gcaaacactc catggtagac agaggatggg gaaatggatg tggactattt 1260
ggaaaggag gcattgtgac ctgtgctatg ttcagatgca aaaagaacat ggaaggaaaa 1320
gttgtgcaac cagaaaactt ggaatacacc attgtgataa cacctcactc aggggaagag 1380
catgcagtcg gaaatgacac aggaaaacat ggcaaggaaa tcaaaataac accacagagt 1440
tccatcacag aagcagaatt gacaggttat ggcactgtca atgagtg ctctccaaga 1500
acgggcctcg acttcaatga gatggtgttg ctgcagatgg aaaataaagc ttggctggtg 1560
cacaggcaat ggttcctaga cctgccgtta ccatggttgc ccggagcgga cacacaaggg 1620
tcaaattgga tacagaaaga gacattggtc actttcaaaa atcccatgc gaagaaacag 1680
gatgttgttg tttttaggatc caagaaggg gccatgcaca cagcacttac aggggccaca 1740
gaaatccaaa tgtcatcagg aaacttactc ttcacaggac atctcaagtg caggctgaga 1800
atggacaagc tacagctcaa aggaatgtca tactctatgt gcacaggaaa gtttaaagtt 1860
gtgaaggaaa tagcagaaac acaacatgga acaatagtta tcagagtgca atatgaaggg 1920
gacggctctc catgcaagat cccttttgag ataatggatt tggaaaaaag acatgtctta 1980
ggtcgcctga ttacagtcaa cccaattgtg acagaaaaag atgcccagt caacataga 2040
gcagaacctc catttggaga cagctacatc atcataggag tagagccggg acaactgaag 2100
ctcaactggt ttaagaaagg aagttctatc ggccaaatgt ttgagacaac aatgaggggg 2160
gcgaagagaa tggccatttt aggtgacaca gcctgggatt ttggatcctt ggggagagtg 2220
tttacatcta taggaaaggc tctccaccaa gtctttggaa caatctatgg agctgcctc 2280
agtgggggttt catggactat gaaaatcctc ataggagtca ttatcacatg gataggaatg 2340
aattcacgca gcacctcact gtctgtgaca ctagtattgg tgggaattgt gacactgtat 2400
ttgggagtca tggtgcaggc cgatagtggt tgcgttgtga ctggaaaaaa caagaactg 2460
aaatgtggca gtgggatttt catcacagac aacgtgcaca catggacaga acaatacaag 2520
ttccaaccag aatcccttc aaaactagct tcagctatcc agaaagccca tgaaggagac 2580
atttgtggaa tccgctcagt aacaagactg gagaatctga tgtggaaaca aataaccaca 2640
gaattgaatc acattctatc agaaaatgag gtgaagttaa ctattatgac aggagacatc 2700
aaaggaatca tgcaggcagg aaaacgatct ctgcggcctc agcccactga gctgaagtat 2760
tcatggaaaa catgggggcaa agcaaaaatg ctctctaagg agtctcataa ccagacctct 2820
ctcattgatg gccccgaaac agcagaatgc cccaacacaa atagagcttg gaattcgttg 2880
gaagttgaag actatggctt tggagtattc accaccaata tatggctaaa attgaaagaa 2940
aaacaggatg tattctgcga ctcaaaactc atgtcagcgg ccataaaaga caacagagcc 3000
gtccatgccg atatgggtta ttggatagaa agtgcactca atgacacatg gaagatagag 3060
aaagcctctt tcattgaagt taaaaactgc cactggccaa aatcacacac cctctgagc 3120
aatgagtgc tagaaagtga gatgataatt ccaagaatc tcgctggacc agtgtctcaa 3180
cacaactata gaccaggcta ccatacacaa ataacaggac catggcatct aggtaagctt 3240
gagatggact ttgatttctg tgatggaaca acagtgtag tgactgagga ctgcggaaat 3300
agaggaccct ctttgagaac aaccactgcc tctggaaaaa tcataacaga atggtgctgc 3360
cgatcttgca cattaccacc gctaagatac agggtgatg gtggtgctca tgcggggatg 3420
gaaatcagac cattgaagga aaagaagag aatttggtca actccttggt cacagctgga 3480
catgggcagg tcgacaactt ttcactagga gtcttgggaa tggcattgtt cctgaggaa 3540
atgcttagga cccgagtagg aacgaaacat gcaatactac tagttgcagt tctttttgtg 3600
acattgatca caggaacat gtcctttaga gacctgggaa gagtgatggt tatggtaggc 3660
gccactatga cggatgacat aggtatgggc gtgacttatc ttgcccctact agcagccttc 3720
```

```
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctattttcct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctgagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccgagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtgcgctgt ttcaatgca taaaggaaag aggattgaac catcatgggc ggacgtcaag   4740
aaagacctaa tatcatatgg aggaggctgg aagttagaag ggaatggga ggaaggagaa   4800
gaagtccagg tattggcact ggagcctgga aaaaatccaa gagccgtcca acgaaaccct   4860
ggtcttttca aaaccaacgc cggaacaata ggtgctgtat ctctggactt ttctcctgga   4920
acgtcaggat ctccaattat cgacaaaaaa ggaaagttg tgggtctta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catgaacctc   5100
cacccaggag cggaaagac gaagagatac cttccggcca tagtcagaga agctataaaa   5160
cggggtttga aacattaat cttggccccc actagagttg tggcagctga aatggaggaa   5220
gcccttagag gacttccaat aagataccag accccaggca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta aggatacat ctcaactcga gtggagatgg tgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa aagaagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aagtggtgt tttgatgag tcaagaacaa ccaaatccta   6240
gaaaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct ttttattctt gatgagcgca   6600
aggggcatag gaagatgac cctgggaatg tgctgcataa tcacggctag catcctccta   6660
tggtacgcac aaatacagcc acactggata gcagcttcaa taatactgga gttttttctc   6720
atagttttgc ttattccaga acctgaaaaa cagaacaa cccaagacaa ccaactgacg   6780
tacgttgtca tagccatcct cacagtggtg gccgcaacca tggcaaacga gatgggtttc   6840
ctagaaaaaa cgaagaaaga tctcggattg ggaagcattg caaccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caacccata   7140
actctcacag cagctcttt cttattggta gcacattatg ccatcatagg gccaggactc   7200
caagcaaaag caaccagaga agctcagaaa agagcagcg cgggcatcat gaaaaaccca   7260
actgtcgatg gaataacagt gattgaccta gatccaatac cttatgatcc aaagtttgaa   7320
aagcagttgg gacaagtaat gctcctagtc tctgcgtga ctcaagtatt gatgatgagg   7380
actacatggg ctctgtgtga ggctttaacc ttagctaccg gcccatctc cacattgtgg   7440
gaaggaaatc caggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag aaaatggaa aagccgattg   7620
aacgcattgg gaaaagtga attccagatc tacaagaaaa gtgaatcca ggaagtggat   7680
agaaccttag caaagaagg cattaaaaga ggagaaacgg accatcacgc tgtgtcgcga   7740
ggctcagcaa aactgagatg gttcgttgag agaaacatgg tcacaccaga agggaagta   7800
gtggacctcg gttgtggcag aggagctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg cctcagtca ggaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
```

-continued

```
cacccataca aaacgtgggc ataccatggt agctatgaaa caaaacagac tggatcagca 8520
tcatccatgg tcaacggagt ggtcaggctg ctgacaaaac cttgggacgt cgtccccatg 8580
gtgacacaga tggcaatgac agacacgact ccatttggac aacagcgcgt ttttaaagag 8640
aaagtggaca cgagaaccca agaaccgaaa gaaggcacga agaaactaat gaaaataaca 8700
gcagagtggc tttggaaaga attagggaag aaaaagacac ccaggatgtg caccagagaa 8760
gaattcacaa gaaaggtgag aagcaatgca gccttggggg ccgtattcac tgatgagaac 8820
aagtggaagt cggcacgtga ggctgttgaa gatagtaggt tttgggagct ggttgacaag 8880
gaaaggaatc tccatcttga aggaaagtgt gaaacatgtg tgtacaacat gatgggaaaa 8940
agagagaaga agctagggga attcggcaag gcaaaaggca gcagagccat atggtacatg 9000
tggcttggag cacgcttctt agagtttgaa gccctaggat tcttaaatga agatcactgg 9060
ttctccagag agaactccct gagtggagtg gaaggagaag ggctgcacaa gctaggttac 9120
attctaagag acgtgagcaa gaaagaggga ggagcaatgt atgccgatga caccgcagga 9180
tgggatacaa gaatcacact agaagaccta aaaaatgaag aaatggtaac aaaccacatg 9240
gaaggagaac acaagaaact agccgaggcc attttcaaac taacgtacca aaacaaggtg 9300
gtgcgtgtgc aaagaccaac accaagaggc acagtaatgg acatcatatc gagaagagac 9360
caaagaggta gtggacaagt tggcacctat ggactcaata ctttcaccaa tatggaagcc 9420
caactaatca gacagatgga gggagaagga gtctttaaaa gcattcagca cctaacaatc 9480
acagaagaaa tcgctgtgca aaactggtta gcaagagtgg ggcgcgaaag gttatcaaga 9540
atggccatca gtggagatga ttgtgttgtg aaacctttag atgacaggtt cgcaagcgct 9600
ttaacagctc taaatgacat gggaaagatt aggaaagaca tacaacaatg ggaaccttca 9660
agaggatgga atgattggac acaagtgccc ttctgttcac accatttcca tgagttaatc 9720
atgaaagacg gtcgcgtact cgttgttcca tgtagaaacc aagatgaact gattggcaga 9780
gcccgaatct cccaaggagc agggtggtct ttgcgggaga cggcctgttt ggggaagtct 9840
tacgcccaaa tgtggagctt gatgtacttc cacagacgcg acctcaggct ggcggcaaat 9900
gctatttgct cggcagtacc atcacattgg gttccaacaa gtcgaacaac ctggtccata 9960
catgctaaac atgaatggat gacaacggaa gacatgctga cagtctggaa cagggtgtgg 10020
attcaagaaa acccatggat ggaagacaaa actccagtgg aatcatggga ggaaatccca 10080
tacttgggga aaagagaaga ccaatggtgc ggctcattga ttgggttaac aagcagggcc 10140
acctgggcaa agaacatcca agcagcaata aatcaagtta gatcccttat aggcaatgaa 10200
gaatacacag attacatgcc atccatgaaa agattcagaa gagaagagga agaagcagga 10260
gttctgtggt agaaagcaaa actaacatga aacaaggcta gaagtcaggt cggattaagc 10320
catagtacgg aaaaaactat gctacctgtg agccccgtcc aaggacgtta aaagaagtca 10380
ggccatcata aatgccatag cttgagtaaa ctatgcagcc tgtagctcca cctgagaagg 10440
tgtaaaaaat ccgggaggcc acaaaccatg gaagctgtac gcatggcgta gtggactagc 10500
ggttagagga gacccctccc ttacaaatcg cagcaacaat gggggcccaa ggcgagatga 10560
agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct 10723

SEQ ID NO: 4 moltype = AA length = 3391
FEATURE Location/Qualifiers
source 1..3391
mol_type = protein
note = dengue seroytpe 2 (MVS)
organism = synthetic construct
SEQUENCE: 4
MNNQRKKAKN TPFNMLKRER NRVSTVQQLT KRFSLGMLQG RGPLKLFMAL VAFLRFLTIP 60
PTAGILKRWG TIKKSKAINV LRGFRKEIGR MLNILNRRRR SAGMIIMLIP TVMAFHLTTR 120
NGEPHMIVSR QEKGKSLLFK TEVGVNMCTL MAMDLGELCE DTITYECPLL RQNEPEDIDC 180
WCNSTSTWVT YGTCTTMGEH RREKRSVALV PHVGMGLETR TETWMSSEGA WKHVQRIETW 240
ILRHPGFTMM AAILAYTIGT THFQRALIFI LLTAVTPSMT MRCIGMSNRD FVEGVSGGSW 300
VDIVLEHGSC VTTMAKNKPT LDFELIKTEA KQPATLRKYC IEAKLTNTTT ESRCPTQGEP 360
SLNEEQDKRF VCKHSMVDRG WGNGCGLFGK GGIVTCAMFR CKKNMEGKVV QPENLEYTIV 420
ITPHSGEEHA VGNDTGKHGK EIKITPQSSI TEAELTGYGT VTMECSPRTG LDFNEMVLLQ 480
MENKAWLVHR QWFLDLPLPW LPGADTQGSN WIQKETLVTF KNPHAKKQDV VVLGSQEGAM 540
HTALTGATEI QMSSGNLLFT GHLKCRLRMD KLQLKGMSYS MCTGKFKVVK EIAETQHGTI 600
VIRVQYEGDG SPCKIPFEIM DLEKRHVLGR LITVNPIVTE KDSPVNIEAE PPFGDSYIII 660
GVEPGQLKLN WFKKGSSIGQ MFETTMRGAK RMAILGDTAW DFGSLGGVFT SIGKALHQVF 720
GAIYGAAFSG VSWTMKILIG VIITWIGMNS RSTSLSVTLV LVGIVTLYLG VMVQADSGCV 780
VSWKNKELKC GSGIFITDNV HTWTEQYKFQ PESPSKLASA IQKAHEEDIC GIRSVTRLEN 840
LMWKQITPEL NHILSENEVK LTIMTGDIKG IMQAGKRSLR PQPTELKYSW KTWGKAKMLS 900
TESHNQTFLI DGPETAECPN TNRAWNSLEV EDYGFGVFTT NIWLKLKEKQ DVFCDSKLMS 960
AAIKDNRAVH ADMGYWIESA LNDTWKIEKA SFIEVKNCHW PKSHTLWSNG VLESEMIIPK 1020
NLAGPVSQHN YRPGYHTQIT GPWHLGKLEM DFDFCDGTTV VVTEDCGNRG PSLRTTTASG 1080
KLITEWCCRS CTLPPLRYRG EDGCWYGMEI RPLKEKEENL VNSLVTAGHG QVDNFSLGVL 1140
GMALFLEEML RTRVGTKHAI LLVAVSFVTL ITGNMSFRDL GRVMVMVGAT MTDDIGMGVT 1200
YLALLAAFKV RPTFAAGLLL RKLTSKELMM TTIGIVLLSQ STIPETILEL TDALALGMMV 1260
LKMVRNMEKY QLAVTIMAIL CVPNAVILQN AWKVSCTILA VVSVSPLFLT SSQQKTDWIP 1320
LALTIKGLNP TAIFLTTLSR TSKKRSWPLN EAIMAVGMVS ILASSLLKND IPMTGPLVAG 1380
GLLTVCYVLT GRSADLELER AADVKWEDQA EISGSSPILS ITISEDGSMS IKNEEEEQTL 1440
TILIRTGLLV ISGLFPVSIP ITAAAWYLWE VKKQRAGVLW DVPSPPPMGK AELEDGAYRI 1500
KQKGILGYSQ IGAGVYKEGT FHTMWHVTRG AVLMHKGKRI EPSWADVKKD LISYGGGWKL 1560
EGEWKEGEEV QVLALEPGKN PRAVQTKPGL FKTNAGTIGA VSLDFSPGTS GSPIIDKKGK 1620
VVGLYGNGVV TRSGAYVSAI AQTEKSIEDN PEIEDDIFRK RRLTIMDLHP GAGKTKRYLP 1680
AIVREAIKRG LRTLILAPTR VVAAEMEEAL RGLPIRYQTP AIRAVHTGRE IVDLMCHATF 1740
TMRLLSPVRV PNYNLIIMDE AHFTDPASIA ARGYISTRVE MGEAAGIFMT ATPPGSRDPF 1800
PQSNAPIIDE EREIPERSWN SGHEWVTDFK GKTVWFVPSI KAGNDIACL RKNGKKVIQL 1860
SRKTFDSEYV KTRTNDWDFV VTTDISEMGA NFKAERVIDP RRCMKPVILT DGEERVILAG 1920
PMPVTHSSAA QRRGRIGRNP KNENDQYIYM GEPLENDEDC AHWKEAKMLL DNINTPEGII 1980

```
PSMFEPEREK VDAIDGEYRL RGEARKTFVD LMRRGDLPVW LAYRVAAEGI NYADRRWCFD   2040
GVKNNQILEE NVEVEIWTKE GERKKLKPRW LDARIYSDPL ALKEFKEFAA GRKSLTLNLI   2100
TEMGRLPTFM TQKARDALDN LAVLHTAEAG GRAYNHALSE LPETLETLLL LTLLATVTGG   2160
IFLFLMSARG IGKMTLGMCC IITASILLWY AQIQPHWIAA SIILEFFLIV LLIPEPEKQR   2220
TPQDNQLTYV VIAILTVVAA TMANEMGFLE KTKKDLGLGS IATQQPESNI LDIDLRPASA   2280
WTLYAVATTF VTPMLRHSIE NSSVNVSLTA IANQATVLMG LGKGWPLSKM DIGVPLLAIG   2340
CYSQVNPITL TAALFLLVAH YAIIGPGLQA KATREAQKRA AAGIMKNPTV DGITVIDLDP   2400
IPYDPKFEKQ LGQVMLLVLC VTQVLMMRTT WALCEALTLA TGPISTLWEG NPGRFWNTTI   2460
AVSMANIFRG SYLAGAGLLF SIMKNTTNTR RGTGNIGETL GEKWKSRLNA LGKSEFQIYK   2520
KSGIQEVDRT LAKEGIKRGE TDHHAVSRGS AKLRWFVERN MVTPEGKVVD LGCGRGGWSY   2580
YCGGLKNVRE VKGLTKGGPG HEEPIPMSTY GWNLVRLQSG VDVFFIPPEK CDTLLCDIGE   2640
SSPNPTVEAG RTLRVLNLVE NWLNNNTQFC IKVLNPYMPS VIEKMEALQR KYGGALVRNP   2700
LSRNSTHEMY WVSNASGNIV SSVNMISRML INRFTMRYKK ATYEPDVDLG SGTRNIGIES   2760
EIPNLDIIGK RIEKIKQEHE TSWHYDQDHP YKTWAYHGSY ETKQTGSASS MVNGVVRLLT   2820
KPWDVVPMVT QMAMTDTTPF GQQRVFKEKV DTRTQEPKEG TKKLMKITAE WLWKELGKKK   2880
TPRMCTREEF TRKVRSNAAL GAVFTDENKW KSAREAVEDS RFWELVDKER NLHLEGKCET   2940
CVYNMMGKRE KKLGEFGKAK GSRAIWYMWL GARFLEFEAL GFLNEDHWFS RENSLSGVEG   3000
EGLHKLGYIL RDVSKKEGGA MYADDTAGWD TRITLEDLKN EEMVTNHMEG EHKKLAEAIF   3060
KLTYQNKVVR VQRPTPRGTV MDIISRRDQR GSGQVGTYGL NTFTNMEAQL IRQMEGEGVF   3120
KSIQHLTITE EIAVQNWLAR VGRERLSRMA ISGDDCVVKP LDDRFASALT ALNDMGKIRK   3180
DIQQWEPSRG WNDWTQVPFC SHHFHELIMK DGRVLVVPCR NQDELIGRAR ISQGAGWSLR   3240
ETACLGKSYA QMWSLMYFHR RDLRLAANAI CSAVPSHWVP TSRTTWSIHA KHEWMTTEDM   3300
LTVWNRVWIQ ENPWMEDKTP VESWEEIPYL GKREDQWCGS LIGLTSRATW AKNIQAAINQ   3360
VRSLIGNEEY TDYMPSMKRF RREEEEAGVL W                                 3391

SEQ ID NO: 5           moltype = DNA   length = 10717
FEATURE                Location/Qualifiers
source                 1..10717
                       mol_type = other DNA
                       note = chimeric dengue serotype 2/3 (MVS)
                       organism = synthetic construct
SEQUENCE: 5
agttgttagt ctacgtggac cgacaaagac agattctttg agggagctaa gctcaatgta     60
gttctaacag ttttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tgggaacaa ttaaaaaatc aaaagctatt aatgttttga gagggttcag gaaagagatt    360
ggaaggatgc tgaacatctt gaataggaga cgcagatctg caggcatgat cattatgctg    420
attccaacag tgatgcgttc catttaacc acgcgtgatg gagagccgcg catgattgtg    480
gggaagaatg aaagaggaaa atccctactt ttcaagacag cctctggaat caacatgtgc    540
acactcatag ctatggatct gggagagatg tgtgatgaca cggtcactta caatgcccc    600
cacattaccg aagtggagcc tgaagacatt gactgctgt gcaaccttac atcgacatgg    660
gtgacttatg aacatgcaa tcaagctgga gagcatagac gcgataagag atcagtggcc    720
ttagctcccc atgttggcat gggactggac acacgcactc aaacctggat gtcggctgaa    780
ggagcttgga gacaagtcga gaaggtagag acatgggccc ttaggcaccc agggtttacc    840
atactagccc tattcttgc ccattacata ggcacttcct tgacccagaa agtggttatt    900
tttatactat taatgctggt tacccccatcc atgacaatga gatgtgtagg agtaggaaac    960
agagattttg tggaaggcct atcgggagct acgtgggttg acgtggtgct cgagcacggt   1020
gggtgtgtga ctaccatggc taagaacaag cccacgctgg acatagagct tcagaagacc   1080
gaggccaccc aactggcgac cctaaggaag ctatgcattg agggaaaaat taccaacata   1140
acaaccgact caagatgtcc cacccaaggg gaagcgattt tacctgagga gcaggaccag   1200
aactacgtgt gtaagcatac atacgtggac agaggctggg gaaacggttg ggtttgtttt   1260
ggcaagggaa gcttggtgac atgcgcgaaa tttcaatgtt tagaatcaat agagggaaaa   1320
gtggtgcaac atgagaacct caaatacacc gtcatcatca gtgtgcacac aggagaccaa   1380
caccaggtgg gaaatgaaac gcagggagtc acggctgaga taacacccca ggcatcaacc   1440
gctgaagcca ttttacctga atatggaacc ctcgggctag aatgctcacc acggacaggt   1500
ttggatttca tgaaatgat ctcattgaca atgaagaaca agcatggat ggtacataga   1560
caatggttct ttgacttacc cctaccatgg acatcaggag cttcagcaga aaccaccact   1620
tggaacagga aagagcttct tgtgacattt aaaaatgcac atgcaaaaga gcaagagta   1680
gttgttcttg gatcacaaga gggagcaatg cacacagcac tgacaggagc tacagagatc   1740
caaacctcag gaggcacaag tatctttgcg ggcacttaa atgtagact caagatggac   1800
aaaattggaac tcaaggggat gagctatgca atgtgcttga gtagctttgt gttgaagaaa   1860
gaagtctccg aaacgcagca tgggacaata tcattaagg ttagtacaa aggggaagat   1920
gcaccctgca agattcctttt ctccacggag gatggacaag gaaagctct caatggcaga   1980
ctgatcacag ccaatccagt ggtgaccaag aaggaggagc tgtcaacat gaggctgaa   2040
cctccttttg gagaaagtaa catagtaatt ggaattggag acaaagccct gaaaatcaac   2100
tggtacaaga agggaagctc gattgggaag atgttcgagg ccactgccag aggtgcaagg   2160
cgcatggcca tcttgggaga cacagcctgg gactttggat cagtgggtg tgttttgaat   2220
tcattaggga aaatggtcca ccaaatattt gggagtgctt acacagccct atttggtgga   2280
gtctcctgga tgatgaaaat tggaataggt gtcctcttaa cctggatagg gttgaactca   2340
aaaaatactt ctatgtcatt ttcatgcatc gcggccggca ttgtgacact gtatttggga   2400
gtcatggtgc aggccgatag tggttgcgtt gtgagctgga aaaacaaaga actgaaatgt   2460
ggcagtggca ttttcatcac agacaacgtg cacacatgga cagacaata caagttccaa   2520
ccagaatccc cttcaaaact agcttcagct atccagaaag cccatgaaga ggacatttgt   2580
ggaatccgct cagtaacaag actggagaat ctgatgtgga acaaataac accagaattg   2640
aatcacatt atcagaaaa tgaggtaag ttaactatta tgacaggaga catcaaagga   2700
atcatgcagg caggaaaacg atctctgcgc cctcagccca ctgagctgaa gtattcatgg   2760
aaaacatggg gcaaagcaaa aatgctctct acagagtctc ataaccagac cttctctcatt   2820
```

```
gatggccccg aaacagcaga atgcccaac  acaaatagag cttgaattc  gttggaagtt  2880
gaagactatg gctttggagt attcaccacc aatatatggc taaaattgaa agaaaaacag  2940
gatgtattct gcgactcaaa actcatgtca gcggccataa aagacaacag agccgtccat  3000
gccgatatgg gttattggat agaaagtgca ctcaatgaca catggaagat agagaaagcc  3060
tctttcattg aagttaaaaa ctgccactgg ccaaaatcac acaccctctg gagcaatgga  3120
gtgctagaaa gtgagatgat aattccaaag aatctcgctg gaccagtgtc tcaacacaac  3180
tatagaccag gctaccatac acaaataaca ggaccatggc atctaggtaa gcttgagatg  3240
gactttgatt tctgtgatgg aacaacagtg gtagtgactg aggactgcgg aaatagagga  3300
ccctctttga gaacaaccac tgcctctgga aaactcataa cagaatggtg ctgccgatct  3360
tgcacattac caccgctaag atacagaggt gaggatgggt gctggtacgg gatggaaatc  3420
agaccattga aggagaaaga agagaatttg gtcaactcct tggtcacagc tggacatggg  3480
caggtcgaca acttttcact aggagtcttg ggaatgcat  tgttcctgga ggaaatgctt  3540
aggacccgag taggaacgaa acatgcaata ctactagttg cagtttcttt tgtgacattg  3600
atcacaggga acatgtcctt tagagacctg ggaagagtga tggttatggt aggcgccact  3660
atgacggatg acataggtat gggcgtgact tatcttgccc tactagcagc cttcaaagtc  3720
agaccaactt tgcagctgg  actactcttg agaaagctga cctccaagga attgatgatg  3780
actactatag gaattgtact cctctcccag agcaccatac cagagaccat tcttgagttg  3840
actgatgcgt tagccttagg catgatggtc ctcaaaatgg tgagaaatat ggaaaagtat  3900
caattggcag tgactatcat ggctatcttg tgcgtcccaa acgcagtgat attacaaaac  3960
gcatggaaag tgagttgcac aatattggca gtggtgtccg tttccccact gttcttaaca  4020
tcctcacagc aaaaaacaga ttggatacca ttagcattga cgatcaaagg tctcaatcca  4080
acagctattt ttcaacaac  cctctcaaga accagcaaga aaggagctg  gccattaaat  4140
gaggctatca tggcagtcgg gatggtgagc attttagcca gttctctcct aaaaaatgat  4200
attcccatga caggaccatt agtggctgga gggctcctca ctgtgtgcta cgtgctcact  4260
ggacgatcgc ccgatttgga actggagaga gcagccgatg tcaaatggga agaccaggca  4320
gagatatcag gaagcagtcc aatcctgtca ataacaatat cagaagatgg tagcatgtcg  4380
ataaaaaatg aagaggaaga acaaacactg accatactca ttagaacagg attgctggtg  4440
atctcaggac ttttttcctgt atcaatacca atcacggcag cagcatggta cctgtgggaa  4500
gtgaagaaac aacgggccgg agtattgtgg gatgttcctt cacccccacc catgggaaag  4560
gctgaactgg aagatggagc ctatagaatt aagcaaaaag ggattcttgg atattcccag  4620
atcggagccg gagtttacaa agaaggaaca ttccatacaa tgtggcatgt cacacgtggc  4680
gctgttctaa tgcataaagg aaagaggatt gaaccatcat gggcggacgt caagaaagac  4740
ctaatatcat atggaggagg ctggaagtta gaaggagaat ggaaggaagg agaagaagtc  4800
caggtattgg cactggagcc tggaaaaaat ccaagaccg  tccaaacgaa acctggtctt  4860
ttcaaaacca acgccggaac aataggtgct gtatctctgg acttttctcc tggaacgtca  4920
ggatctccaa ttatcgacaa aaaaggaaaa gttgtgggtc tttatggtaa tggtgttgtt  4980
acaaggagtg gagcatatgt gagtgctata gcccagactg aaaaaagcat tgaagacaac  5040
ccagagatcg aagatgacat tttccgaaag agaagactga ccatcatgga cctccaccca  5100
ggagcgggaa agacgaagag ataccttccg gccatagtca gagaagctat aaaacgggct  5160
ttgagaacat taatcttggc ccccactcga gttgtggcag ctgaaatgga ggaagccctt  5220
agaggacttc caataagata ccagacccca gccatcagag ctgtgcacac cggcgggag  5280
attgtggacc taatgtgtca tgccacattt accatgagcc tgctatcacc agttagagtg  5340
ccaaactaca acctgattat catggacgaa gcccatttca cagacccagc aagtatagca  5400
gctagaggat acatctcaac tcgagtggag atgggtgagg cagctggat  ttttatgaca  5460
gccactcccc cgggaagcag agacccattt cctcagagca atgcaccaat catagatgaa  5520
gaaagagaaa tccctgaacg ctcgtggaat tccgacatg  aatgggtcac ggatttttaaa  5580
ggaagactg  tttggttcgt tccaagtata aaagcaggaa atgatatagc agcttgcctg  5640
aggaaaaatg gaaagaaagt gatacaactc agtaggaaga cctttgattc tgagtatgtc  5700
aagactagaa ccaatgattg ggacttcgtg gttacaactg acatttcaga aatgggtgcc  5760
aatttcaagg ctgagagggt tatagacccc agacgctgca tgaaaccagt catactaaca  5820
gatggtgaag agcgggtgat tctggcagga cctatgccag tgacccactc tagtgcagca  5880
caaagaagag ggagaatagg aagaaatcca aaaaatgaga atgaccagta catatacatg  5940
ggggaacctc tggaaaatga tgaagactgt gcacactgga aagaagctaa atgctcta   6000
gataacatca cacgccaga  aggaatcatt cctagcatgt tcgaaccaga gcgtgaaaag  6060
gtggatgcca ttgatggcga ataccgcttg agaggagaag caaggaaaac ctttgtagac  6120
ttaatgagaa gaggagacct accagtctgg ttggcctaca gagtggcagc tgaaggcatc  6180
aactacgcag acagaaggtg gtgtttgat  ggagtcaaga caaccaaat  cctagaagaa  6240
aacgtggaag ttgaaatctg gacaaaagaa ggggaaagga gaaattgaa  acccagatgg  6300
ttggatgcta ggatctattc tgacccactg gcgctaaaag aatttaagga atttgcagcg  6360
ggaagaaagt ctctgacccct gaacctaatc acagaaatgg gtaggctccc aaccttcatg  6420
actcagaagg caagagacgc actggacaac ttagcagtgc tgcacacggc tgaggcaggt  6480
ggaagggcgt acaaccatgc ctcagtgaa  ctgccggaga ccctggagac attgcttta   6540
ctgacacttc tggctacagt cacggagggg atctttttat tcttgatgag cgcaaggggc  6600
ataggaaga tgaccctggg aatgtgctgc ataatcacgg ctagcatcct ccatggtac   6660
gcacaaatac agccacactg gatagcagct tcaataatac tggagttttt tctcatagtt  6720
ttgcttattc cagaacctga aaacagaga  acacccaag  acaaccaact gacctacgtt  6780
gtcatagcca tcctcacagt ggtggccgca accatgcaa  acgagatggg tttcctgaaa  6840
aaaacgaaga aagatctcgg attgggaagc attgcaactc agcaacccga gagcaatctc  6900
ctggacatag atctacgtcc tgcatcagca tggacgctgt atgccgtgcc cacaacattt  6960
gttacaccaa tgttgagaca tagcattgaa aattcctcag tgaatgtgtc cctaacagct  7020
atagccaacc aagccacagt gttaatgggt ctcgggaaag gatgccatt  gtcaaagatg  7080
gacatcggag ttccccttct cgccattgga tgctactcac aagtcaaccc cataactctc  7140
acagcagctc tttttcttatt ggtagcacat tatgccatca tagggccagg actccaagca  7200
aaagcaacca gagaagctca gaaaagagca gcggcgggca tcatgaaaaa cccaactgtc  7260
gatgaataa  cagtgattga cctagatcca atacctatg  atccaaagtt gaaaagcag   7320
ttgggacaag taatgctcct agtcctctgc gtgactcaag tattgatgat gaggactaca  7380
tgggctctgt gtgaggcttt aaccttagct accgggccca tctccacatt gtgggaagga  7440
aatccaggga ggttttggaa cactaccatt gcggtgtcaa tggctaacat ttttagaggg  7500
agttacttgg ccggagctgg acttctcttt tctattatga agaacacaac caacacaaga  7560
```

```
aggggaactg gcaacatagg agagacgctt ggagagaaat ggaaaagccg attgaacgcg  7620
ttgggaaaaa gtgaattcca gatctacaag aaaagtggaa tccaggaagt ggatagaacc  7680
ttagcaaaag aaggcattaa aagaggagaa acggaccatc acgctgtgtc gcgaggctca  7740
gcaaaactga gatggttcgt tgagagaaac atggtcacac cagaagggaa agtagtggac  7800
ctcggttgtg gcagaggagg ctggtcatac tattgtgagg gactaaagaa tgtaagagaa  7860
gtcaaaggcc taacaaaagg aggaccagga cacgaagaac ccatccccat gtcaacatat  7920
gggtggaatc tagtgcgtct tcaaagtgga gttgacgttt tcttcatccc gccagaaaag  7980
tgtgacacat tattgtgtga catgggggag tcatcaccaa atcccacagt ggaagcagga  8040
cgaacactca gagtccttaa cttagtagaa aattggttga acaacaacac tcaattttgc  8100
ataaaggttc tcaacccata tatgccctca gtcatagaaa aaatggaagc actacaaagg  8160
aaatatggag gagccttagt gaggaatcca ctctcacgaa actccacaca tgagatgtac  8220
tgggtatcca atgcttccgg gaacatagtg tcatcagtga acatgatttc aaggatgttg  8280
atcaacagat ttacaatgag atacaagaaa gccacttacg agccggatgt tgacctcgga  8340
agcggaaccc gtaacatcgg gattgaaagt gagataccaa actagatat aattgggaaa  8400
agaatagaaa aaataaagca agagcatgaa acatcatggc actatgacca agaccaccca  8460
tacaaaacgt gggcatacca tggtagctat gaaacaaaac agactggatc agcatcatcc  8520
atggtcaacg gagtggtcag gctgctgaca aaaccttggg acgtcgtccc catggtgaca  8580
cagatggcaa tgacagacac gactccattt ggacaacagc gcgttttaa agagaaagtg  8640
gacacgagaa cccaagaacc gaagaaggcc acgaagaaac taatgaaaat aacagcagag  8700
tggctttgga aagaattagg gaagaaaaag acacccagga tgtgcaccag agaagaattc  8760
acaagaaagg tgagaagcaa tgcagccttg ggggccatat tcactgatga aacaagtgg   8820
aagtcggcac gtgaggctgt tgaagatagt aggttttggg agctggttga caaggaaagg  8880
aatctccatc ttgaaggaaa gtgtgaaaca tgtgtgtaca acatgatggg aaaaagagag  8940
aagaagctag ggaattcgg caaggcaaaa ggcagcagag ccatatggta catgtggctt  9000
ggagcacgct tcttagagtt tgaagcccta ggattcttaa atgaagatca ctggttctcc  9060
agagagaact ccctgagtgg agtgaaggaa gaaggctgc acaagctagg ttacattcta  9120
agagacgtga gcaagaaaga gggaggagca atgtatgccg atgacaccgc aggatgggat  9180
acaagaatca cactagaaga cctaaaaaat gaagaaatgg taacaaacca catggaagga  9240
gaacacaaga aactagccga ggccattttc aaactaacgt accaaacaa ggtggtgcgt  9300
gtgcaaagac caaccaag aggcacagta atggcagtca tatcgagaag agaccaaaga  9360
ggtagtggac aagttggcac ctatggactc aatacttca ccaatatgga agcccaacta  9420
atcagacaga tggaggggaga aggagtcttt aaaagcattc agcacctaac aatcacagaa  9480
gaaatcgctg tgcaaaactg gttagcaaga gtggggcgcg aaaggttatc aagaatggcc  9540
atcagtggag atgattgtgt tgtgaaacct ttagtagaca ggttcgcaac cgcttttaaca  9600
gctctaaatg acatgggaaa gattaggaaa gacatacaac aatgggaacc ttcaagagga  9660
tggaatgatt ggacacaagt gcccttctgt tcacaccatt tccatgagtt aatcatgaaa  9720
gacggtcgcg tactcgttgt tccatgtaga accaagatg aactgattgg cagagcccga  9780
atctcccaag gagcagggtg gtctttgcgg gagacggcct gtttggggaa gtcttacgcc  9840
caaatgtgga gcttgatgta cttccacaga cgcgacctca ggctggcggc aaatgctatt  9900
tgctcggcag taccatcaca ttgggttcca acaagtcgaa caacctgtc catacatgct  9960
aaacatgaat ggatgacaac ggaagacatg ctgacagtct ggaacagggt gtggattcaa  10020
gaaaacccat ggatggaaga caaaactcca gtggaatcat gggaggaaat cccatacttg  10080
gggaaaagag aagaccaatg gtgcggctca ttgattggt taacaagcag gccacctgg  10140
gcaaagaaca tccaagcagc aataaatcaa gttagatccc ttataggcaa tgaagaatac  10200
acagattaca tgccatccat gaaaagattc agaagaag aggaagaagc aggagttctg  10260
tggtagaaag caaaactaac atgaaacaag gctagaagtc aggtcggatt aagccatagt  10320
acggaaaaaa ctatgctacc tgtgagcccc gtccaaggac gttaaaagaa gtcaggccat  10380
cataaatgcc atagcttgag taaactatgc agcctgtagc tccacctgag aaggtgtaaa  10440
aaatccggga ggccacaaac catggaagct gtacgcatgg cgtagtggac tagcggttag  10500
aggagacccc tcccttacaa atcgcagcaa caatgggggc ccaaggcgag atgaagctgt  10560
agtctcgctg gaaggactag aggttagagg agaccccccc gaaacaaaaa acagcatatt  10620
gacgctggga aagaccagag atcctgctgt ctcctcagca tcattccagg cacagaacgc  10680
cagaaaatgg aatggtgctg ttgaatcaac aggttcct                         10717
```

```
SEQ ID NO: 6              moltype = AA   length = 3389
FEATURE                   Location/Qualifiers
source                    1..3389
                          mol_type = protein
                          note = chimeric dengue serotype 2/3 (MVS)
                          organism = synthetic construct
SEQUENCE: 6
MNNQRKKAKN TPFNMLKRER NRVSTVQQLT KRFSLGMLQG RGPLKLFMAL VAFLRFLTIP   60
PTAGILKRWG TIKKSKAINV LRGFRKEIGR MLNILNRRRR SAGMIIMLIP TVMAFHLTTR  120
DGEPRMIVGK NERGKSLLFK TASGINMCTL IAMDLGEMCD DTVTYKCPHI TEVEPEDIDC  180
WCNLTSTWVT YGTCNQAGEH RRDKRSVALA PHVGMGLDTR TQTWMSAEGA WRQVEKVETW  240
ALRHPGFTIL ALFLAHYIGT SLTQKVVIFI LLMLVTPSMT MRCVGVGNRD FVEGLSGATW  300
VDVVLEHGGC VTTMAKNKPT LDIELQKTEA TQLATLRKLC IEGKITNITT DSRCPTQGEA  360
ILPEEQDQNY VCKHTYVDRG WGNGCGLFGK GSLVTCAKFQ CLESIEGKVV QHENLKYTVI  420
ITVHTGDQHQ VGNETQGVTA EITPQASTAE AILPEYGTLG LECSPRTGLD FNEMISLTMK  480
NKAWMVHRQW FFDLPLPWTS GASAETPTWN RKELLVTFKN AHAKKQEVVV LGSQEGAMHT  540
ALTGATEIQT SGGTSIFAGH LKCRLKMDKL ELKGMSYAMC LSSFVLKKEV SETQHGTILI  600
KVEYKGEDAP CKIPFSTEDG QGKALNGRLI TANPVVTKKE EPVNIEAEPP FGESNIVIGI  660
GDKALKINWY KKGSSIGKMF EATARGARRM AILGDTAWDF GSVGGVLNSL GKMVHQIFGS  720
AYTALFGGVS WMMKIGIGVL LTWIGLNSKN TSMSFSCIAA GIVTLYLGVM VQADSGCVVS  780
WKNKELKCGS GIFITDNVHT WTEQYKFQPE SPSKLASAIQ KAHEEDICGI RSVTRLENLM  840
WKQITPELNH ILSENEVKLT IMTGDIKGIM QAGKRSLRPQ PTELKYSWKT WGKAMLSTE   900
SHNQTFLIDG PETAECPNTN RAWNSLEVED YGFGVFTTNI WLKLKEKQDV FCDSKLMSAA  960
IKDNRAVHAD MGYWIESALN DTWKIEKASF IEVKNCHWPK SHTLWSNGVL ESEMIIPKNL 1020
AGPVSQHNYR PGYHTQITGP WHLGKLEMDF DFCDGTTVVV TEDCGNRGPS LRTTTASGKL 1080
```

```
ITEWCCRSCT LPPLRYRGED GCWYGMEIRP LKEKEENLVN SLVTAGHGQV DNFSLGVLGM 1140
ALFLEEMLRT RVGTKHAILL VAVSFVTLIT GNMSFRDLGR VMVMVGATMT DDIGMGVTYL 1200
ALLAAFKVRP TFAAGLLLRK LTSKELMMTT IGIVLLSQST IPETILELTD ALALGMMVLK 1260
MVRNMEKYQL AVTIMAILCV PNAVILQNAW KVSCTILAVV SVSPLFLTSS QQKTDWIPLA 1320
LTIKGLNPTA IFLTTLSRTS KKRSWPLNEA IMAVGMVSIL ASSLLKNDIP MTGPLVAGGL 1380
LTVCYVLTGR SADLELERAA DVKWEDQAEI SGSSPILSIT ISEDGSMSIK NEEEEQTLTI 1440
LIRTGLLVIS GLFPVSIPIT AAAWYLWEVK KQRAGVLWDV PSPPPMGKAE LEDGAYRIKQ 1500
KGILGYSQIG AGVYKEGTFH TMWHVTRGAV LMHKGKRIEP SWADVKKDLI SYGGGWKLEG 1560
EWKEGEEVQV LALEPGKNPR AVQTKPGLFK TNAGTIGAVS LDFSPGTSGS PIIDKKGKVV 1620
GLYGNGVVTR SGAYVSAIAQ TEKSIEDNPE IEDDIFRKRR LTIMDLHPGA GKTKRYLPAI 1680
VREAIKRGLR TLILAPTRVV AAEMEEALRG LPIRYQTPAI RAVHTGREIV DLMCHATFTM 1740
RLLSPVRVPN YNLIIMDEAH FTDPASIAAR GYISTRVEMG EAAGIFMTAT PPGSRDPFPQ 1800
SNAPIIDEER EIPERSWNSG HEWVTDFKGK TVWFVPSIKA GNDIAACLRK NGKKVIQLSR 1860
KTFDSEYVKT RTNDWDFVVT TDISEMGANF KAERVIDPRR CMKPVILTDG EERVILAGPM 1920
PVTHSSAAQR RGRIGRNPKN ENDQYIYMGE PLENDEDCAH WKEAKMLLDN INTPEGIIPS 1980
MFEPEREKVD AIDGEYRLRG EARKTFVDLM RRGDLPVWLA YRVAAEGINY ADRRWCFDGV 2040
KNNQILEENV EVEIWTKEGE RKKLKPRWLD ARIYSDPLAL KEFKEFAAGR KSLTLNLITE 2100
MGRLPTFMTQ KARDALDNLA VLHTAEAGGR AYNHALSELP ETLETLLLLT LLATVTGGIF 2160
LFLMSARGIG KMTLGMCCII TASILLWYAQ IQPHWIAASI ILEFFLIVLL IPEPEKQRTP 2220
QDNQLTYVVI AILTVVAATM ANEMGFLEKT KKDLGLGSIA TQQPESNILD IDLRPASAWT 2280
LYAVATTFVT PMLRHSIENS SVNVSLTAIA NQATVLMGLG KGWPLSKMDI GVPLLAIGCY 2340
SQVNPITLTA ALFLLVAHYA IIGPGLQAKA TREAQKRAAA GIMKNPTVDG ITVIDLDPIP 2400
YDPKFEKQLG QVMLLVLCVT QVLMRRTTWA LCEALTLATG PISTLWEGNP GRFWNTTIAV 2460
SMANIFRGSY LAGAGLLFSI MKNTTNTRRG TGNIGETLGE KWKSRLNALG KSEFQIYKKS 2520
GIQEVDRTLA KEGIKRGETD HHAVSRGSAK LRWFVERNMV TPEGKVVDLG CGRGGWSYYC 2580
GGLKNVREVK GLTKGGPGHE EPIPMSTYGW NLVRLQSGVD VFFIPPEKCD TLLCDIGESS 2640
PNPTVEAGRT LRVLNLVENW LNNNTQFCIK VLNPYMPSVI EKMEALQRKY GGALVRNPLS 2700
RNSTHEMYWV SNASGNIVSS VNMISRMLIN RFTMRYKKAT YEPDVDLGSG TRNIGIESEI 2760
PNLDIIGKRI EKIKQEHETS WHYDQDHPYK TWAYHGSYET KQTGSASSMV NGVVRLLTKP 2820
WDVVPMVTQM AMTDTTPFGQ QRVFKEKVDT RTQEPKEGTK KLMKITAEWL WKELGKKKTP 2880
RMCTREEFTR KVRSNAALGA IFTDENKWKS AREAVEDSRF WELVDKERNL HLEGKCETCV 2940
YNMMGKREKK LGEFGKAKGS RAIWYMWLGA RFLEFEALGF LNEDHWFSRE NSLSGVEGEG 3000
LHKLGYILRD VSKKEGGAMY ADDTAGWDTR ITLEDLKNEE MVTNHMEGEH KKLAEAIFKL 3060
TYQNKVVRVQ RPTPRGTVMD IISRRDQRGS GQVGTYGLNT FTNMEAQLIR QMEGEGVFKS 3120
IQHLTITEEI AVQNWLARVG RERLSRMAIS GDDCVVKPLD DRFASALTAL NDMGKIRKDI 3180
QQWEPSRGWN DWTQVPFCSH HFHELIMKDG RVLVVPCRNQ DELIGRARIS QGAGWSLRET 3240
ACLGKSYAQM WSLMYFHRRD LRLAANAICS AVPSHWVPTS RTTWSIHAKH EWMTTEDMLT 3300
VWNRVWIQEN PWMEDKTPVE SWEEIPYLGK REDQWCGSLI GLTSRATWAK NIQAAINQVR 3360
SLIGNEEYTD YMPSMKRFRR EEEEAGVLW                                  3389

SEQ ID NO: 7           moltype = DNA   length = 10723
FEATURE                Location/Qualifiers
source                 1..10723
                       mol_type = other DNA
                       note = chimeric dengue seroytpe 2/4 (MVS)
                       organism = synthetic construct
SEQUENCE: 7
agttgttagt ctacgtggac cgacaaagac agattctttg agggagctaa gctcaatgta   60
gttctaacag ttttttaatt agagagcaga tctctgatga ataaccaacg gaaaaaggcg  120
aaaaacacgc ctttcaatat gctgaaacgc gagagaaacc gcgtgtcgac tgtgcaacag  180
ctgacaaaga gattctcact tggaatgctg cagggacgag gaccttttaa actgttcatg  240
gccctggtgg cgttccttcg tttcctaaca atcccaccaa cagcaggat  attgaagaga  300
tggggaacaa ttaaaaaatc aaaagctatt aatgttttga gagggttcag gaaagagatt  360
ggaaggatgc tgaacatctt gaataggaga cgcagctctg caggcatgat cattatgctg  420
attccaacag tgatggcgtt ccatttaacc acgcgtgatg gcgaacccct catgatagtg  480
gcaaaacatg aaaggggggag acctctcttg tttaagacaa cagagggat caacaaatgc  540
actctcattg ccatggactt gggtgaaatg tgtgaggaca ctgtcacgta taatgcccc  600
ttactggtca ataccgaacc tgaagacatt gattgctggt gcaatctcac gtctacctgg  660
gtcatgtatg gacatgcac ccagagcgga gaacgggagc gagagaaagcg ctcagtagct  720
ttaacaccac attcaggaat gggattggaa acaagactg agacatggat gtcatcggaa  780
ggggcttgga agcatgctca gagagtagag agctggatac tcagaaaccc aggattcgcg  840
ctcttgcag gatttatggc ttatatgatt gggcaaacag gaatccagcg aactgtcttc  900
tttgtcctaa tgatgctggt cgcccccatcc tacgaatgc gatgcgtagg agtaggaaac  960
agagactttg tggaaggagt ctcaggtgga gcatggtgta atctggtgct agaacatgga 1020
ggatgcgtca caaccatggc ccagggaaaa ccaaccttgg attttgaact gactaagaca 1080
acagccaagg aagtggctct gttaagaacc tattgcattg aagcctcaat atcaaacata 1140
accacggcaa caagatgtcc aacgcaagga gagccttatc taaaagagga acaagaccaa 1200
cagtcacattt gccggagaga tgtggtagac agagggtggg gcaatggctg tggcttgttt 1260
ggaaaaggag gagttgtgac atgtgcgaag ttttcatgtc cgggggaagat aacaggcaat 1320
ttggtccaaa ttgagaacct tgaatacaca gtggttgtaa cagtccacaa tggagacacc 1380
catgcagtag gaaatgacac gtccaatcat ggagttacag ccacgataac tcccaggtca 1440
ccatcggtgg aagtcaaatt gccggactat ggagaactaa cactcgattg tgaacccagg 1500
tctggaattg acttaatga tgatgatttctg atgaaatga aaagaaaac atggcttgtg 1560
cataagcaat ggttttttgga tctacctcta ccatgacag cggagcaga cacatcagag 1620
gttcactgga attacaaaga gagaatggtg acatttaagg ttcctcatgc caagagacag 1680
gatgtgcacg tgctgggatc tcaggaagga gccatgcatt ctgccctcgc tggagccaca 1740
gaagtggact ccgtgatgg aaatcacatg tttgcaggac atctcaagtg caaagtccgt 1800
atggagaaat tgagaatcaa gggaatgtca tacacgatgt gttcaggaaa gttctcaatt 1860
gacaaagaga tggcagaaac acagcatggg acaacagtgg tgaaagtcaa gtatgaaggt 1920
```

```
gctggagctc cgtgtaaagt ccccatagag ataagagatg tgaacaagga aaaagtggtt   1980
gggcgtatca tctcatccac cccttttggct gagaatacca acagtgtaac caacatagag   2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtgaaaca gcttgggatt ttggttccgt tggtggactg   2220
ttcacatcat tgggaaaggc tgtgcaccag gttttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatcccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcgcgccc agcccactga gctgaagtat   2760
tcatggaaaa catggggcaa agcaaaaatg ctctctacag agtctcataa ccagacccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaaagcctctt tcattgaagt taaaaactgc cactggccaa aatcacacac cctctggagc   3120
aatgagtgc tagaaagtga gatgataatt ccaagaatc tcgctggacc agtgtctcaa   3180
cacaactata gaccaggcta ccatacacaa ataacaggac atgcatct aggtaagctt   3240
gagatggact ttgattttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga gcggtgacat aggtatgggc gtgacttatc ttgccctact agcagccttc   3720
aaagtcagac caacttttgc agctggacta ctcttgagaa agctgaccte carggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaacccte tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggaggc tcctcactgt gtgctacgtg   4260
ctcactggac gatcggccga tttgaactg gagagagcag ccgatgtcaa atggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatggg ggacgtcaag   4740
aaagacctaa tatcatatgg aggaggctgg aagttagaag gagaatgaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatgat   4980
gttgttacaa ggagtggagc atatgtgagt gctatagccc agactgaaaa aagcattgaa   5040
gacaacccag agatcgaaga tgacattttc cgaaagagaa gactgaccat catggaccte   5100
cacccaggag cggaaagac gaagagatac cttccggcca tagtcagaga agctataaaa   5160
cggggtttga gaacattaat cttggcccc actagagttg tggcagctga aatggaggaa   5220
gcccttagag gacttccaat aagataccag acccccagcca tcagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga tccagcaagt   5400
atagcagcta gaggatacat ctcaactcga gtggagatgg gtgaggcagc tgggattttt   5460
atgacagcca ctccccgggg aagcagagac ccatttcctc agagcaatgc accaatcata   5520
gatgaagaaa gagaaatccc tgaacgctcg tggaattccg acatgaatg ggtcacggat   5580
tttaagggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtgttga caactgacat ttcagaaatg   5760
ggtgccaatt tcaaggctga gagggttata gaccccagac gctgcatgaa accagtcata   5820
ctaacagatg gtgaagagcg ggtgattctg cgaggaccta gccagtgac ccactctagt   5880
gcagcacaaa aagagggag aataggaaga aatccaaaaa atgagaatga ccagtacata   5940
tacatggggg aacctctgga aaatgatgaa gactgtgcac actggaagga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga atctggaca aagaagggg aaaggaagaa attgaaaccc   6300
agatggttga atctaggat ctattctgac caactgccaa tcagaaatt taaggaatt   6360
gcagccggaa gaaagtctct gaccctgaac ctaatcacag aaatgggtag ctcccaacc   6420
ttcatgactc agaaggtaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatc ttttattctt gatgagcgca   6600
aggggcatag ggaagatgac cctgggaatg tgctgcataa tcacgcgctag catcctccta   6660
```

```
tggtacgcac aaatacagcc acactggata gcagcttcaa taatactgga gttttttctc  6720
atagttttgc ttattccaga acctgaaaaa cagagaacac cccaagacaa ccaactgacc  6780
tacgttgtca tagccatcct cacagtggtg gccgcaacca tggcaaacga gatgggtttc  6840
ctagaaaaaa cgaagaaaga tctcggattg gaagcattg caacccagca acccgagagc  6900
aacatcctgg acatagatct acgtcctgca tcagcatgga cgctgtatgc cgtggccaca  6960
acatttgtta caccaatgtt gagacatagc attgaaaatt cctcagtgaa tgtgtcccta  7020
acagccatag ccaaccaagc cacagtgtta atgggtctcg ggaaaggatg gccattgtca  7080
aagatggaca tcggagttcc ccttctcgcc attggatgct actcacaagt caaccccata  7140
actctcacag cagctctttt cttattggta gcacattatg ccatcatagg gccaggactc  7200
caagcaaaag caaccagaga agctcagaaa agagcagcga cgggcatcat gaaaaaccca  7260
actgtcgatg gaataacagt gattgaccta gatccaatac cttatgatcc aaagtttgaa  7320
aagcagttgg gacaagtaat gctcctagtc tctgcgtga ctcaagtatt gatgatgagg  7380
actacatggg ctctgtgtga ggctttaacc ttagctaccg ggcccatctc cacattgtgg  7440
gaaggaaatc cagggaggtt ttggaacact accattgcgg tgtcaatggc taacatttttt  7500
agagggagtt acttgccgg agctggactt ctctttttcta ttatgaagaa cacaaccaac  7560
acaagaaggg gaactggcaa cataggagag acgcttggag agaaatggaa aagccgattg  7620
aacgcattgg gaaaagtga attccagatc tacaagaaaa gtggaatcca ggaagtggat  7680
agaaccttag caaaagaagg cattaaaaga ggagaaacgg accatcacgc tgtgtcgcga  7740
ggctcagcaa aactgagatg gttcgttgag agaaacatgg tcacaccaga agggaaagta  7800
gtggacctcg gttgtggcag aggaggctgg tcatactatt gtggaggact aaagaatgta  7860
agagaagtca aaggcctaac aaaaggagga ccaggacacg aagaacccat ccccatgtca  7920
acatatgggt ggaatctagt gcgtcttcaa agtggagttg acgttttctt catcccgcca  7980
gaaaagtgtg acacattatt gtgtgacata ggggagtcat caccaaatcc cacagtggaa  8040
gcaggacgaa cactcagagt ccttaactta gtagaaaatt ggttgaacaa caacactcaa  8100
ttttgcataa aggttctcaa cccatatatg ccctcagtca tagaaaaaat ggaagcacta  8160
caaagaaat atggaggagc cttagtgagg aatccactct cacacatggg  8220
atgtactggg tatccaatgc ttccgggaac atagtgtcat cagtgaacat gatttcaagg  8280
atgttgatca acagatttac aatgagatac aagaaagcca cttacgagcc ggatgttgac  8340
ctcggaagcg gaacccgtaa catcgggatt gaaagtgaga taccaaacct agatataatt  8400
gggaaaagaa tagaaaaaat aaagcaagga catgaaacat catggcacta tgaccaagac  8460
caccatacgg aaacgtgggc ataccatggt agctatgaaa caaaacagac tggatcagca  8520
tcatccatgg tcaacggagt ggtcaggctg ctgacaaaac cttgggacgt cgtcccatg  8580
gtgacacaga tggcaatgac agacacgact ccatttggac aacagcgcgt ttttaaagag  8640
aaagtggaca cgagaaccca agaaccgaaa gaaggcacga agaaactaat gaaaataaca  8700
gcagagtggc tttggaaaga attagggaag aaaaagcacc cggatgtg caccagagaa  8760
gaattcacaa gaaaggtgag aagcaatgca gccttggggg ccatattcac tgatgagaac  8820
aagtggaagt cggcacgtga ggctgttgaa gatagtaggt ttgggagct ggttgacaag  8880
gaaaggaatc tccatcttga aggaaagtgt gaaacatgtg tgtacaacat gatgggaaaa  8940
agagagagaa agctagggga attcggcaag gcaaaagcc gcagagccat atggtacatg  9000
tggcttggag cacgcttctt agagtttgaa gccctaggat tcttaaatga agatcactgg  9060
ttctccagag agaactccct gagtggagtg gaaggagaag gctgcacaa gctaggttac  9120
attctaagag acgtgagcaa gaaagaggga ggagcaatgt atgccgatga caccgcagga  9180
tgggatacaa gaatcacact aatgaagacct aaaaatggtaac aaaccacatg  9240
gaaggagaac acaagaaact agccgaggcc attttcaaac taacgtacca aaacaaggtg  9300
gtgcgtgtgc aaagaccaac accaagaggc acagtaatgg acatcatatc gagaagagac  9360
caaagaggta gtggacaagt tggcacctat ggactcaata ctttccacca tatggaagcc  9420
caactaatca gacagatgga gggagaagga gtctttaaaa gcattcagca cctaaccaatc  9480
acagaagaaa tcgctgtgca aaaactggta gcaagagtgg ggcgcgaaag gttatcaaga  9540
atggccatca gtgagatgaaa ttgtgttgtg aaacctttag atgacaggtt cgcaagcgct  9600
ttaacagctc taaatgacat gggaaagatt aggaaagaca taacaatg gaaccttca  9660
agaggatgga atgattggac acaagtgccc ttctgttcac accattcca tgagttaatc  9720
atgaaagacg gtcgcgtact cgttgttccc tgtagaaacc aagatgaact gattggcaga  9780
gcccgaatct cccaaggagc agggtggtc ttgcgggaga cggcctgttt gggggaagtct  9840
tacgcccaaa tgtggagctt gatgtacttc cacagacgcg acctcaggct ggcggcaaat  9900
gctatttgct cggcagtacc atcacattgg gttccaacaa gtcgaacgac ctggtccata  9960
catgctaaac atgaatggat gacaacggaa gacatgctga cagtctggaa cagggtgtgg 10020
attcaagaaa acccatggat ggaagacaaa actccagtgg aatcatggga ggaaatccca 10080
tacttgggga aagagaaga ccaatggtgc ggctcattga ttgggttaac aagcagggcc 10140
acctgggcaa agaacatcca agcagcaata aatcaagtta gatcccttat aggcaatgaa 10200
gaatacacag attacatgcc atccatgaaa agattcagaa gagaagagga agaagcagga 10260
gttctgtggt agaaagcaaa actaacatga aacaaggcta gaagtcaggt cggattaagc 10320
catagtacga aaaaactat gctacctgtg agccccgtcc aaggacgtta aaagaagtca 10380
ggccatcata aatgccatag cttgagtaaa ctatgcagcc tgtagctcca cctgagaagg 10440
tgtaaaaaat ccgggaggcc acaaaccatg gaagctgtac gcatggcgta gtggactagc 10500
ggttagagga gaccccctccc ttacaaatcg cagcaacaat ggggccaa ggcgagatga 10560
agctgtagtc tcgctggaag gactagaggt tagaggagac cccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct             10723

SEQ ID NO: 8        moltype = AA  length = 3391
FEATURE             Location/Qualifiers
VARIANT             1226
                    note = X = R or K
source              1..3391
                    mol_type = protein
                    note = chimeric dengue serotype 2/4 (MVS)
                    organism = synthetic construct
SEQUENCE: 8
MNNQRKKAKN TPFNMLKRER NRVSTVQQLT KRFSLGMLQG RGPLKLFMAL VAFLRFLTIP  60
```

```
PTAGILKRWG TIKKSKAINV LRGFRKEIGR MLNILNRRRS SAGMIIMLIP TVMAFHLTTR  120
DGEPLMIVAK HERGRPLLFK TTEGINKCTL IAMDLGEMCE DTVTYKCPLL VNTEPEDIDC  180
WCNLTSTWVM YGTCTQSGER RREKRSVALT PHSGMGLETR AETWMSSEGA WKHAQRVESW  240
ILRNPGFALL AGFMAYMIGQ TGIQRTVFFV LMMLVAPSYG MRCVGVGNRD FVEGVSGGAW  300
VDLVLEHGGC VTTMAQGKPT LDFELTKTTA KEVALLRTYG IEASISNITT ATRCPTQGEP  360
YLKEEQDQQY ICRRDVVDRG WGNGCGLFGK GGVVTCAKFS CSGKITGNLV QIENLEYTVV  420
VTVHNGDTHA VGNDTSNHGV TATITPRSPS VEVKLPDYGE LTLDCEPRSG IDFNEMILMK  480
MKKKTWLVHK QWFLDLPLPW TAGADTSEVH WNYKERMVTF KVPHAKRQDV TVLGSQEGAM  540
HSALAGATEV DSGDGNHMFA GHLKCKVRME KLRIKGMSYT MCSGKFSIDK EMAETQHGTT  600
VVKVKYEGAG APCKVPIEIR DVNKEKVVGR IISSTPLAEN TNSVTNIELE PPFGDSYIVI  660
GVGNSALTLH WFRKGSSIGK MFESTYRGAK RMAILGETAW DFGSVGGLFT SLGKAVHQVF  720
GSVYTTLFGG VSWMIRILIG FLVLWIGTNS RNTSMAMTCI AAGIVTLYLG VMVQADSGCV  780
VSWKNKELKC GSGIFITDNV HTWTEQYKFQ PESPSKLASA IQKAHEEDIC GIRSVTRLEN  840
LMWKQITPEL NHILSENEVK LTIMTGDIKG IMQAGKRSLR PQPTELKYSW KTWGKAKMLS  900
TESHNQTFLI DGPETAECPN TNRAWNSLEV EDYGFGVFTT NIWLKLKEKQ DVFCDSKLMS  960
AAIKDNRAVH ADMGYWIESA LNDTWKIEKA SFIEVKNCHW PKSHTLWSNG VLESEMIIPK  1020
NLAGPVSQHN YRPGYHTQIT GPWHLGKLEM DFDFCDGTTV VVTEDCGNRG PSLRTTTASG  1080
KLITEWCCRS CTLPPLRYRG EDGCWYGMEI RPLKEKEENL VNSLVTAGHG QVDNFSLGVL  1140
GMALFLEEML RTRVGTKHAI LLVVAVSFVTL ITGNMSFRDL GRVMVMVGAT MTGDIGMGVT  1200
YLALLAAFKV RPTFAAGLLL RKLTSXELMM TTIGIVLLSQ STIPETILEL TDALALGMMV  1260
LKMVRNMEKY QLAVTIMAIL CVPNAVILQN AWKVSCTILA VVSVSPLFLT SSQQKTDWIP  1320
LALTIKGLNP TAIFLTTLSR TSKKRSWPLN EAIMAVGMVS ILASSLLKND IPMTGPLVAG  1380
GLLTVCYVLT GRSADLELER AADVKWEDQA EISGSSPILS ITISEDGSMS IKNEEEEQTL  1440
TILIRTGLLV ISGLFPVSIP ITAAAWYLWE VKKQRAGVLW DVPSPPPMGK AELEDGAYRI  1500
KQKGILGYSQ IGAGVYKEGT FHTMWHVTRG AVLMHKGKRI EPSWADVKKD LISYGGGWKL  1560
EGEWKEGEEV QVLALEPGKN PRAVQTKPGL FKTNAGTIGA VSLDFSPGTS GSPIIDKKGK  1620
VVGLYGNGVV TRSGAYVSAI AQTEKSIEDN PEIEDDIFRK RRLTIMDLHP GAGKTKRYLP  1680
AIVREAIKRG LRTLILAPTR VVAAEMEEAL RGLPIRYQTP AIRAVHTGRE IVDLMCHATF  1740
TMRLLSPVRV PNYNLIIMDE AHFTDPASIA ARGYISTRVE MGEAAGIFMT ATPPGSRDPF  1800
PQSNAPIIDE EREIPERSWN SGHEWVTDFK GKTVWFVPSI KAGNDIAACL RKNGKKVIQL  1860
SRKTFDSEYV KTRTNDWDFV VTTDISEMGA NFKAERVIDP RRCMKPVILT DGEERVILAG  1920
PMPVTHSSAA QRRGRIGRNP KNENDQYIYM GEPLENDEDC AHWKEAKMLL DNINTPEGII  1980
PSMFEPEREK VDAIDGEYRL RGEARKTFVD LMRRGDLPVW LAYRVAAEGI NYADRRWCFD  2040
GVKNNQILEE NVEVEIWTKE GERKKLKPRW LDARIYSDPL ALKEFKEFAA GRKSLTLNLI  2100
TEMGRLPTFM TQKVRDALDN LAVLHTAEAG GRAYNHALSE LPETLETLLL LTLLATVTGG  2160
IFLFLMSARG IGKMTLGMCC IITASILLWY AQIQPHWIAA SIILEFFLIV LLIPEPEKQR  2220
TPQDNQLTYV VIAILTVVAA TMANEMGFLE KTKKDLGLGS IATQQPESNI LDIDLRPASA  2280
WTLYAVATTF VTPMLRHSIE NSSVNVSLTA IANQQATVLMG LGKGWPLSKM DIGVPLLAIG  2340
CYSQVNPITL TAALFLLVAH YAIIGPGLQA KATREAQKRA AAGIMKNPTV DGITVIDLDP  2400
IPYDPKFEKQ LGQVMLLVLC VTQVLMMRTT WALCEALTLA TGPISTLWEG NPGRFWNTTI  2460
AVSMANIFRG SYLAGAGLLF SIMKNTTNTR RGTGNIGETL GEKWKSRLNA LGKSEFQIYK  2520
KSGIQEVDRT LAKEGIKRGE TDHHAVSRGS AKLRWFVERN MVTPEGKVVD LGCGRGGWSY  2580
YCGGLKNVFR VKGLTKGGPG HEEPIPMSTY GWNLVRLQSG VDVFFIPPEK CDTLLCDIGE  2640
SSPNPTVEAG RTLRVLNLVE NWLNNNTQFC IKVLNPYMPS VIEKMEALQR KYGGALVRNP  2700
LSRNSTHEMY WVSNASGNIV SSVNMISRML INRFTMRYKK ATYEPDVDLG SGTRNIGIES  2760
EIPNLDIIGK RIEKIKQEHE TSWHYDQDHP YKTWAYHGSY ETKQTGSASS MVNGVVRLLT  2820
KPWDVVPMVT QMAMTDTTPF GQQRVFKEKV DTRTQEPKEG TKKLMKITAE WLWKELGKKK  2880
TPRMCTREEF TRKVRSNAAL GAIFTDENKW KSAREAVEDS RFWELVDKER NLHLEGKCET  2940
CVYNMMGKRE KKLGEFGKAK GSRAIWYMWL GARFLEFEAL GFLNEDHWFS RENSLSGVEG  3000
EGLHKLGYIL RDVSKKEGGA MYADDTAGWD TRITLEDLKN EEMVTNHMEG EHKKLAEAIF  3060
KLTYQNKVVR VQRPTPRGTV MDIISRRDQR GSGQVGTVGL NTFTNMEAQL IRQMEGEGVF  3120
KSIQHLTITE EIAVQNWLAR VGRERLSRMA ISGDDCVVKP LDDRFASALT ALNDMGKIRK  3180
DIQQWEPSRG WNDWTQVPFC SHHFHELIMK DGRVLVVPCR NQDELIGRAR ISQGAGWSLR  3240
ETACLGKSYA QMWSLMYFHR RDLRLAANAI CSAVPSHWVP TSRTTWSIHA KHEWMTTEDM  3300
LTVWNRVWIQ ENPWMEDKTP VESWEEIPYL GKREDQWCGS LIGLTSRATW AKNIQAAINQ  3360
VRSLIGNEEY TDYMPSMKRF RREEEEAGVL W                                3391

SEQ ID NO: 9          moltype = DNA    length = 10735
FEATURE               Location/Qualifiers
source                1..10735
                      mol_type = other DNA
                      note = dengue virus
                      organism = synthetic construct
SEQUENCE: 9
agttgttagt ctacgtggac cgacaagaac agtttcgaat cggaagcttg cttaacgtag   60
ttctaacagt tttttattag agagcagatc tctgatgatc aaccaacgaa aaaagacggg  120
tcgaccgtct tcaatatgc tgaaacgcgc gagaaaccgc gtgtcaactg tttcacagtt  180
ggcgaagaga ttctcaaaag gattgctctc aggccaagga cccatgaaat tggtgatggc  240
tttcatagca ttccttaagat ttctagccat accccccaaca gcaggaattt tggctagtag  300
gggctcattc aagaagaatg gagcgattaa agtgttacgg ggtttcaaga gagaaatctc  360
aaacatgcta acataatga acaggaggaa agatccgtg accatgctcc ttatgctgct  420
gcccacagcc ctggcgttcc atctgacgac acgaggggga gagccgcata tgatagttag  480
caagcaggaa agaggaaagt cacttttgtt caagacctct gcaggtgtca acatgtgcac  540
cctcattgcg atgatttgg gagagttgtg taggacctca atgacccccg  600
gatcactgag gcggaaccag atgacgttga ctgttggtgc aatgccacgg acacatgggt  660
gacctatgga acgtgctctc aaactggcga caccgacgaa gacaaacgtt ccgtcgcatt  720
ggccccacac gtgggcttg cctagaaac aagagccgaa acgtggatgt cctctgaagg  780
tgcttggaaa cagatacaaa aagtagagac ttgggctctg agacatccag gattcacggt  840
gatagcccct tttctagcac atgccatagg aacatccatc acccagaaag ggatcatttt  900
```

```
cattttgctg atgctggtaa caccatctat ggccatgcga tgcgtgggaa taggcaacag    960
agacttcgtg gaaggactgt caggagcaac atgggtggat gtggtactgg agcatggaag   1020
ttgcgtcacc accatggcaa aaaacaaacc aacactggac attgaactct tgaagacgga   1080
ggtcacaaac cctgcagttc tgcgtaaatt gtgcattgaa gctaaaatat caaacaccac   1140
caccgattcg agatgtccaa cacaaggaga agccacactg gtggaagaac aagacgcgaa   1200
ctttgtgtgc cgacgaacgt tcgtggacag aggctgggc  aatggctgtg ggctattcgg   1260
aaaaggtagt ctaataacgt gtgccaagtt taagtgtgtg acaaaactag aaggaaagat   1320
agttcaatat gaaaacctaa aatattcagt gatagtcacc gtccacactg gagatcagca   1380
ccaggtggga aatgagacta cagaacatgg aacaactgca accataacac ctcaagctcc   1440
tacgtcggaa atacagctga ccgactacgg aacccttaca ttagattgtt cacctaggac   1500
agggctagat tttaacgaga tggtgttgct gacaatgaaa gaaagatcat ggcttgtcca   1560
caaacaatgg tttctagact taccactgcc ttggacctct ggggcttcaa catcccaaga   1620
gacttggaac agacaagatt tactggtcac atttaagaca gctcatgcaa agaagcagga   1680
agtagtcgta ctaggatcac aagaaggagc aatgcacact gcgctgactg gagcgacaga   1740
aatccaaacg tcaggaacga caacaatttt cgcaggacac ctaaaatgca gactaaaaat   1800
ggacaaacta actttaaaag ggatgtcata tgtgatgtgc acaggctcat tcaagttaga   1860
gaaagaagtg gctgagaccc agcatggaac tgttctggtg caggttaaat atgaaggaac   1920
agacgcacca tgcaagattc ccttttcgac ccaagatgga aaaggagcaa cccgaagtga   1980
gagattaata acagccaacc ccatagtcac tgacaaagaa aaaccagtca atattgaggc   2040
agaaccaccc tttggtgaga gctacatcgt ggtaggagca ggtgaaaaag ctttgaaact   2100
aagctggttc aagaaaggaa gcagcatagg gaaaatgttt gaagcaactg cccgaggagc   2160
acgaaggatg gccattctgg gagacaccgc atgggacttc ggttctatag gaggagtgtt   2220
cacgtctatg ggaaaactgg tacaccaggt ttttggaact gcatatgag  ttttgtttag   2280
cggagtttct tggaccatga aaataggaat agggattctg ctgacatggc taggattaaa   2340
ttcaaggaac acgtcccttt cgatgatgtg catcgcagtt ggcatggtca cactgtacct   2400
aggagtcatg gttcaggcag attcgggatg tgtaatcaac tggaaaggca gagaacttaa   2460
atgtggaagc ggcattttg  tcactaatga agttcacact tggacagagc aatacaaatt   2520
ccaggctgac tcccccaaga gactatcagc agccattggg aaggcatggg aggagggtgt   2580
gtgtggaatc cgatcagcca ctcgtctcga aacatcatg  tggaaacaaa tatcaaatga   2640
attgaaccac atcctacttg aaaatgacat gaaatttcac gtggtcgtgg gagatgttag   2700
tggaatcttg gcccaaggga aaaaaatgat taggccacac cccatggaac acaaatactc   2760
gtggaaaagc tggggaaaag ccaaaatcat aggagcggat gtacagaaca ccaccttcat   2820
catcgacggc ccaaacaccc cagaatgccc tgacaatcaa agagcatgga atatttggga   2880
agtagaggac tatggatttg ggatttttac gacaaacata tggttgaaac tgcgtgactc   2940
ctacacccaa gtatgtgacc accgctgat  gtcagctgcc attaaggaca gcaaggcagt   3000
ccatgctgac atgggtact  ggatagaaag tgaaagaac  gagacatgga agttggcgag   3060
agcctccttt atagaagtta agacatgcat ctggccaaaa tcccacactc tatgagcaa   3120
tggagttctg gaaagtgaaa tgataattcc aaagatatat ggaggaccaa tatctcagca   3180
caactacaga ccaggatatt tcacacaaac agcagggccg tggcacctag gcaagttgga   3240
actagatttc gattttgtg  aaggtaccac agttgttgtg gatgaacatt gtggaaatcg   3300
aggaccatct ctcagaacca caacagtcac aggaaagata atccatgaat ggtgctgcag   3360
atcttgtacg ctaccccccc tacgtttcaa aggggaagac gggtgttggt acggcatgga   3420
aatcagacca gtgaaggaca aggaagagaa cctggtcaag tcaatggtct gtcagggtt   3480
aggagaagtg gacagctttt cactaggact gctatgcata tcaataatga ttgaagaagt   3540
gatgagatcc agatggagca aaaaaatgct gatgactgga acactggctg tgttcctcct   3600
tcttataatg ggacaattga catggagtga tctgatcagg ttatgtatta tggttggagc   3660
caacgcttca gacaagatgg ggatgggaac aacgtaccta gctttaatgg ccactttcaa   3720
aatgagacca atgttcgccg tcgggctatt atttcgcaga ctaacatcta gagaagttct   3780
tcttcttaca attggcttga gcctggtggc atccgtggag ctaccaagtt ccctagagga   3840
gctggggat  ggacttgcaa taggcatcat gatgttgaaa ttattgactg attttcagtc   3900
acaccagcta tgggctactc tgctatcctt gacatttatt aaaacaactt tttcattgca   3960
ctatgcatgg aagacaatgg ctatggtact gtcaattgta tctctcttcc ctttatgcct   4020
gtccacgacc tctcaaaaaa caacatggct tccggtgctg ttgggatctc ttggatgcaa   4080
accactaccc atgtttctta acagaaaaa  caaaatctgg ggaaggaaga gttggcccct   4140
caatgaagga attatggctg ttggaatagt tagtattcta ctaagttcac ttttaaaaaa   4200
tgatgtgccg ctagccggcc cattaatagc tggaggcatg ctaatagcat gttatgtcat   4260
atccggaagc tcagctgatt tatcactgga gaaagcggct gaggtctcct gggaggaaga   4320
agcagaacac tcaggcgcct cacacaacat actagtagag gttcaagatg atggaaccat   4380
gaagataaaa gatgaagaga gagatgacac gctcaccatt ctccttaaag caactctgct   4440
ggcagtctca ggggtgtacc caatgtcaat accagcgacc cttttgtgt  ggtatttttg   4500
gcagaaaaag aaacagagat caggagtgct atgggacaca cccagccccc cagaagtgga   4560
aagagcagtt cttgatgatg gcatctatag aattttgcaa agaggactgt gggcaggtc    4620
ccaagtagga gtaggagttt tccaagaagg cgtgttccac acaatgtggc acgtcactag   4680
gggagctgtc ctcatgtatc aaggaaaaag gctggaacca agctgggcca gtgtcaaaaa   4740
agacttgatc tcatatggag gaggttgag  gtttcaagga tcctggaaca cgggagaaga   4800
agtacaggtg attgctgttg aaccgggaaa aaacccaaaa aatgtacaaa caacgccggg   4860
taccttcaag acccctgaag cgaagttgg  agccatagcc ttagacttta aacctggcac   4920
atctggatct cccatcgtaa acagagaggg aaaaatagta ggtctttatg gaaatggagt   4980
ggtgacaaca agcggaactt acgttagtgc catagctcaa gctaaggcat cacagaaagg   5040
gcctctacca gagattgagg acgaggtgtt taggaaaaga aacttaacaa taatggacct   5100
acatccagga tcgggaaaaa caagaagata ccttccagcc atagtccgtg aggcataaa    5160
aaggaagctg cgcacgctaa tcctagctcc cacaagagtt gtcgcttctg aaatggcaga   5220
ggcactcaag ggagtgccaa taggtatca  gacaacagca gtgaagagtg aacacacagg   5280
aaaggagata gttgacctta tgtgccacgc cactttcacc atgcgcctcc tgtctccgt    5340
gagagttccc aattataaca tgattatcat ggatgaagca cacttcaccg atccagccag   5400
catagcagcc agagggtaca tctcaacccg agtgggtatg ggtgaagcag ctgcgatctt   5460
tatgacagcc actcccccag gatcggtgga ggcctttcca cagagcaatg caattatcca   5520
agatgaggaa agagacattc ctgagagatc atggaactca ggctatgact ggatcactga   5580
ttttccaggt aaaacagtct ggtttgttcc aagcatcaaa tcaggaaatg acattgccaa   5640
```

```
ctgtttaaga aaaaacggga aacgggtgat ccaattgagc agaaaaacct ttgacactga   5700
gtaccagaaa acaaaaaaca acgactggga ctatgtcgtc acaacagaca tttccgaaat   5760
gggagcaaat ttccgggccg acagggtaat agacccaagg cggtgtctga aaccggtaat   5820
actaaaagat ggtccagagc gcgtcattct agccggaccg atgccagtga ctgtggccag   5880
tgccgcccag aggagaggaa gaattggaag gaaccaaaac aaggaaggtg atcagtatat   5940
ttacatggga cagcctttaa acaatgatga ggaccacgct cattggacag aagcaaagat   6000
gctccttgac aatataaaca caccagaagg gattatccca gccctctatg agccggagag   6060
agaaaagagt gcagctatag acggggaata cagactgcgg ggtgaagcaa ggaaaacgtt   6120
cgtgggagctc atgagaagag gggatctacc agtctggcta tcctacaaag ttgcctcaga   6180
aggcttccag tactccgaca gaaggtggtg cttcgatggg gaaaggaaca accaggtgtt   6240
ggaggagaac atggacgtgg agatctggac aaaagaagga gaaagaaaga aactacgacc   6300
tcgctggttg gacgccagaa catactctga cccactggct ctgcgcgagt ttaaagagtt   6360
tgcagcagga agaagaagcg tctcaggtga cctaatatta gaaataggga aacttccaca   6420
acatttgacg caaagggccc agaatgcttt ggacaacttg gtcatgttgc acaattccga   6480
acaaggagga aaagcctata gacatgctat ggaagaactg ccagacacaa tagaaacgtt   6540
gatgctccta gccttgatag ctgtgttgac tggtggagtg acgctgttct tcctatcagg   6600
aagaggtcta ggaaaaacat ctatcggctt actctgcgtg atggcctcaa gcgcactgtt   6660
atggatggcc agtgtggagc cccattggat agcggcctcc atcatactgg agttcttttct   6720
gatggtactg cttattccag agccagacag acagcgcact ccacaggaca accagctagc   6780
atatgtggta ataggtctgt tattcatgat attgacagtg gcagccaatg agatgggatt   6840
attggaaacc acaagaaag acctgggat tggccatgta gctgctgaaa accaccacca   6900
tgctacaatg ctggacgtga acctacatcc agcttcagtc tggaccctct atgcagtggc   6960
cacaacaatc atcactccta tgatgagaca cacaattgaa aacacaacgg caaatatttc   7020
cctgacagcc atcgcaaacc aagcagctat attgatggga cttgacaagg atgccaat    7080
atcgaagatg gacataggag ttccacttct cgccttgggg tgctattccc aagtgaatcc   7140
gctgacactg atagccggca gtattgatgc agtagctcat acgccataa ttggacctgg    7200
actgcaagca aaagctacta gagaagctca aaaaagaaca gcggctggaa taatgaaaaa   7260
tccaactgtc gacgggattg ttgcaataga cttagatccc gtggtttacg atgcaaaatt   7320
tgaaaaacaa ctaggccaaa taatgttgtt gatactttgc acatcacaga ttctttttgat  7380
gcggactaca tgggccttgt gtgaatccat cacattggctt actggacctc tgaccactct   7440
ttgggaggga tctccaggaa aattctggaa caccacaata gcggtatcca tggcaaacat   7500
tttcaggggg agttatctag caggagcagg tctggcctcc tcattaatga aatctctagg   7560
aggaggtagg agaggcacgg gagccccaag ggaaacactg ggagaaaaat ggaaaagaca   7620
actaaaccaa ctgagcaagt cagaattcaa tacttacaag aggagtggga ttatggaggt   7680
ggatagatcc gaagccaaag agggactgaa aagaggagaa acaaccaaac acgcagtatc   7740
gagaggaacg gccaaactga ggtggttcgt ggagaggaac cttgtgaaac cagaagggaa   7800
agtcatagac ctccggttgtg gaagaggtgg ctggtcatat tattgcgctg ggctgaagaa   7860
agtcacagaa gtgaaaggat acacaaaagg aggacctgga catgaggaac caatcccaat   7920
ggcgacctat ggatggaacc tagtaaagct gcactccgga aaagatgtat tttttatacc   7980
acctgacgaa tgtgacaccc ttttgtgtga tattggtgag tcctctccga acccaactat   8040
agaggaagga gaacgttac gtgttctgaa aatggtggaa ccatggctca gaggaaacca   8100
attttgcata aaaattctaa atccctatat gccgagcgtg gtagaaactc tggaacaaat   8160
gcaaagaaaa catggaggaa tgctagtgcg aaacccactc tcaagaaatt ccacccatga   8220
aatgtactgg gtttcatgtg gaacaggaaa cattgtgtca gcagtaaaca tgacatctag   8280
aatgttgcta aatcggttca atggctcaag gaagcca acatatgaaaa gagacgtgga    8340
cttaggcgct ggaacaagac atgtggcagt agaaccagag gtagccaacc tagatatcat   8400
tggccagagg atagagaata taaaaaatga acataagtca acattg atgatgagga      8460
caatccatac aaaacatggg cctatcatga atcatatgag gttaagccat caggatcggc   8520
ctcatccatg gtcaatggcg tggtgagatt gctcaccaaa ccatgggatg ttatccccat   8580
ggtcacacaa atagccatga ctgataccac acccttgga caacgagggg tgtttaaaga   8640
gaaagttgac acgcgcacac caaagcaaa acgtggcaca gacaaatta tggaagtgac    8700
agccaggtgg ttatgggtt tccttttctag aaacaaaaaa cccagaattt gcacaagaga   8760
ggagtttaca agaaagtta ggtcaaacgc agctattgga gcagtgttcg ttgatgaaaa    8820
tcaatgggaac tcggcaaaag aagcagtgga agacgaacgg ttctgggaac ttgtccacag   8880
agagagggaa cttcataaac aggggaaatg tgccacgtgt gtctacaata tgatggggaa   8940
gagagagaaa aaattaggag agttcggag ggcaaaagga agtcgtgcaa tatggtacat   9000
gtggttggga gcacgcttcc tagagtttga agccttggt ttcatgaatg aagatcactg   9060
gttcagtaga gagaattcac tcagtggagt ggaaggagaa ggactccaca acttggata    9120
catactcaga gacatatcaa ggattccagg ggaacatg tatgcagatg acacagccgg    9180
atgggacaca agaataacag aggatgatct ccagaatgga gctaaaatca ctgacatcat   9240
ggagcccgaa catgccctgc tggctacgtc aatctttaag ctgacctacc aaaataaggt   9300
ggtaagggtg cagagaccag caaaaaatgg aaccgtgatg gatgttatat ccagacgtga   9360
ccagagaggc agtggacagg ttggaactta tggcttaaac actttcacca acatggaggc   9420
ccaactgata agacaaatgg agtccgaggg aatcttttta cccagcgaat tggaaacccc   9480
aaatctagcc ggaagagttc tcgactggtt ggaaaatat ggtgtcgaaa ggctgaaaag   9540
aatggcaatc agcggagatg actgtgtggt gaaaccaatt gatgacaggt tcgcaacagc   9600
cttaacagct ttgaatgaca tgggaaagt aagaaaagac ataccacaat gggaaccttc   9660
aaaaggatgg aatgattggc aacaagtgcc ttttgtttca caccacttcc accagctaat   9720
tatgaaggat gggagggaga tagtggtgcc atgccgcaac caagatgaac ttgtggggag   9780
ggccagagta tcacaaggcg ccggatggag cctgagagaa accgcatgcc taggcaagtc   9840
atatgcacaa atgtggcagc tgatgtattt ccacaggaga gacctgagac tggcggctaa   9900
cgctatttgt tcagccgttc cagttgattg gtcccaacc agccgcacca cctggtcgat   9960
ccatgcccat caccaatgga tgacaacaga agacatgtta tcagtatgga ataggtctg  10020
gatagaggaa aacccatgga tggaggataa gactcatgtg tccagttggg aagaagttcc  10080
ataccttgga aagaggggaag atcagtggtg tggatccctg ataggcttaa cagcaagggc  10140
cacctgggcc actaatatac aagtggccat aaaccaagtg agaaggctca ttgggaatga  10200
gaattatcta gattacatga catcaatgaa gagattcaag aatgagagtg atcccgaagg  10260
ggcactctgg taagtcaaca cattcacaaa ataaggaaa ataaaaaatc aaatgaggca  10320
agaagtcagg ccagattaag ccatagtacg gtaagagcta tgctgcctgt gagccccgtc  10380
```

```
caaggacgta aaatgaagtc aggccgaaag ccacggtttg agcaagccgt gctgcctgtg   10440
gctccatcgt ggggatgtaa aaacccggga ggctgcaacc catggaagct gtacgcatgg   10500
ggtagcagac tagtggttag aggagacccc tcccaagaca caacgcagca gcggggccca   10560
acaccagggg aagctgtacc ctggtggtaa ggactagagg ttagaggaga ccccccgcgt   10620
aacaataaac agcatattga cgctgggaga gaccagagat cctgctgtct ctacagcatc   10680
attccaggca cagaacgcca gaaaatggaa tggtgctgtt gaatcaacag gttct         10735
```

```
SEQ ID NO: 10           moltype = AA   length = 3392
FEATURE                 Location/Qualifiers
source                  1..3392
                        mol_type = protein
                        organism = dengue virus
SEQUENCE: 10
MINQRKKTGR PSFNMLKRAR NRVSTVSQLA KRFSKGLLSG QGPMKLVMAF IAFLRFLAIP     60
PTAGILARWG SFKKNGAIKV LRGFKREISN MLNIMNRRKR SVTMLLMLLP TALAFHLTTR    120
GGEPHMIVSK QERGKSLLFK TSAGVNMCTL IAMDLGELCE DTMTYKCPRI TEAEPDDVDC    180
WCNATDTWVT YGTCSQTGEH RRDKRSVALA PHVGLGLETR AETWMSSEGA WKQIQKVETW    240
ALRHPGFTVI ALFLAHAIGT SITQKGIIFI LLMLVTPSMA MRCVGIGNRD FVEGLSGATW    300
VDVVLEHGSC VTTMAKNKPT LDIELLKTEV TNPAVLRKLC IEAKISNTTT DSRCPTQGEA    360
TLVEEQDANF VCRRTFVDRG WGNGCGLFGK GSLITCAKFK CVTKLEGKIV QYENLKYSVI    420
VTVHTGDQHQ VGNETTEHGT TATITPQAPT SEIQLTDYGT LTLDCSPRTG LDFNEMVLLT    480
MKERSWLVHK QWFLDLPLPW TSGASTSQET WNRQDLLVTF KTAHAKKQEV VVLGSQEGAM    540
HTALTGATEI QTSGTTTIFA GHLKCRLKMD KLTLKGMSYV MCTGSFKLEK EVAETQHGTV    600
LVQVKYEGTD APCKIPFSTQ DEKGATQNGR LITANPIVTD KEKPVNIEAE PPFGESYIVV    660
GAGEKALKLS WFKKGSSIGK MFEATARGAR RMAILGDTAW DFGSIGGVFT SMGKLVHQVF    720
GTAYGVLFSG VSWTMKIGIG ILLTWLGLNS RNTSLSMMCI AVGMVTLYLG VMVQADSGCV    780
INWKGRELKC GSGIFVTNEV HTWTEQYKFQ ADSPKRLSAA IGKAWEEGVC GIRSATRLEN    840
IMWKQISNEL NHILLENDMK FTVVVGDVSG ILAQGKKMIR PQPMEHKYSW KSWGKAKIIG    900
ADVQNTTFII DGPNTPECPD NQRAWNIWEV EDYGFGIFTT NIWLKLRDSY TQVCDHRLMS    960
AAIKDSKAVH ADMGYWIESE KNETWKLARA SFIEVKTCIW PKSHTLWSNG VLESEMIIPK   1020
IYGGPISQHN YRPGYFTQTA GPWHLGKLEL DFDFCEGTTV VVDEHCGNRG PSLRTTTVTG   1080
KIIHEWCCRS CTLPPLRFKG EDGCWYGMEI RPVKDKEENL VKSMVSAGSG EVDSFSLGLL   1140
CISIMIEEVM RSRWSKKMLM TGTLAVFLLL IMGQLTWSDL IRLCIMVGAN ASDKMGMGTT   1200
YLALMATFKM RPMFAVGLLF RRLTSREVLL LTIGLSLVAN VELPSSLEEL GDGLAIGIMM   1260
LKLLTDFQSH QLWATLLSLT FIKTTFSLHY AWKTMAMVLS IVSLFPLCLS TTSQKTTWLP   1320
VLLGSLGCKP LPMFLITENK IWGRKSWPLN EGIMAVGIVS ILLSSLLKND VPLAGPLIAG   1380
GMLIACYVIS GSSADLSLEK AAEVSWEEEA EHSGASHNIL VEVQDDGTMK IKDEERDDTL   1440
TILLKATLLA VSGVYPMSIP ATLFVWYFWQ KKKQRSGVLW DTPSPPEVER AVLDDGIYRI   1500
LQRGLLGRSQ VGVGVFQEGV FHTMWHVTRG AVLMYQGKRL EPSWASVKKD LISYGGGWRF   1560
QGSWNTGEEV QVIAVEPGKN PKNVQTTPGT FKTPEGEVGA IALDFKPGTS GSPIVNREGK   1620
IVGLYGNGVV TTSGTYVSAI AQAKASQEGP LPEIEDEVFR KRNLTIMDLH PGSGKTRRYL   1680
PAIVREAIKR KLRTLILAPT RVVASEMAEA LKGVPIRYQT TAVKSEHTGK EIVDLMCHAT   1740
FTMRLLSPVR VPNYNMIIMD EAHFTDPASI AARGYISTRV GMGEAAAIFM TATPPGSVEA   1800
FPQSNAIIQD EERDIPERSW NSGYDWITDF PGKTVWFVPS IKSGNDIANC LRKNGKRVIQ   1860
LSRKTFDTEY QKTKNNDWDY VVTTDISEMG ANFRADRVID PRRCLKPVIL KDGPERVILA   1920
GPMPVTVASA AQRRGRIGRN QNKEGDQYIY MGQPLNNDED HAHWTEAKML LDNINTPEGI   1980
IPALYEPERE KSAAIDGEYR LRGEARKTFV ELMRRGDLPV WLSYKVASEG FQYSDRRWCF   2040
DGERNNQVLE ENMDVEIWTK EGERKKLRPR WLDARTYSDP LALREFKEFA AGRRSVSGDL   2100
ILEIGKLPQH LTQRAQNALD NLVMLHNSEQ GGKAYRHAME ELPDTIETLM LLALIAVLTG   2160
GVTLFFLSGR GLGKTSIGLL CVMASSALLW MASVEPHWIA ASIILEFFLM VLLIPEPDRQ   2220
RTPQDNQLAY VVIGLLFMIL TVAANEMGLL ETTKKDLGIG HVAAENHHHA TMLDVDLHPA   2280
SAWTLYAVAT TIITPMMRHT IENTTANISL TAIANQAAIL MGLDKGWPIS KMDIGVPLLA   2340
LGCYSQVNPL TLIAAVLMLV AHYAIIGPGL QAKATREAQK RTAAGIMKNP TVDGIVAIDL   2400
DPVVYDAKFE KQLGQIMLLI LCTSQILLMR TTWALCESIT LATGPLTTLW EGSPGKFWNT   2460
TIAVSMANIF RGSYLAGAGL AFSLMKSLGG GRRGTGAQGE TLGEKWKRQL NQLSKSEFNT   2520
YKRSGIMEVD RSEAKEGLKR GETTKHAVSR GTAKLRWFVE RNLVKPEGKV IDLGCGRGGW   2580
SYYCAGLKKV TEVKGYTKGG PGHEEPIPMA TYGWNLVKLH SGKDVFFIPP EKCDTLLCDI   2640
GESSPNPTIE EGRTLRVLKM VEPWLRGNQF CIKILNPYMP SVVETLEQMQ RKHGGMLVRN   2700
PLSRNSTHEM YWVSCGTGNI VSAVNMTSRM LLNRFTMAHR KPTYERDVDL GAGTRHVAVE   2760
PEVANLDIIG QRIENIKNEH KSTWHYDEDN PYKTWAYHGS YEVKPSGSAS SMVNGVVRLL   2820
TKPWDVIPMV TQIAMTDTTP FGQQRVFKEK VDTRTPKAKR GTAQIMEVTA RWLWGFLSRN   2880
KKPRICTREE FTRKVRSNAA IGAVFVDENQ WNSAKEAVED ERFWELVHRE RELHKQGKCA   2940
TCVYNMMGKR EKKLGEFGKA KGSRAIWYMW LGARFLEFEA LGFMNEDHWF SRENSLSGVE   3000
GEGLHKLGYI LRDISRIPGG NMYADDTAGW DTRITEDDLQ NEAKITDIME PEHALLATSI   3060
FKLTYQNKVV RVQRPAKNGT VMDVISRRDQ RGSGQVGTYG LNTFTNMEAQ LIRQMESEGI   3120
FLPSELETPN LAGRVLDWLE KYGVERLKRM AISGDDCVVK PIDDRFATAL TALNDMGKVR   3180
KDIPQWEPSK GWNDWQQVPF CSHHFHQLIM KDGREIVVPC RNQDELVGRA RVSQGAGWSL   3240
RETACLGKSY AQMWQLMYFH RRDLRLAANA ICSAVPVDWV PTSRTTWSIH AHHQWMTTED   3300
MLSVWNRVWI EENPWMEDKT HVSSWEEVPY LGKREDQWCG SLIGLTARAT WATNIQVAIN   3360
QVRRLIGNEN YLDYMTSMKR FKNESDPEGA LW                                 3392
```

```
SEQ ID NO: 11           moltype = DNA   length = 10723
FEATURE                 Location/Qualifiers
source                  1..10723
                        mol_type = other DNA
                        note = dengue virus
                        organism = synthetic construct
SEQUENCE: 11
agttgttagt ctacgtggac cgacaaagac agatt

```
gttctaacag ttttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tgggaacaa ttaaaaaatc aaaagctatt aatgttttga gagggttcag gaaagagatt    360
ggaaggatgc tgaacatctt gaataggaga cgcagatctg caggcatgat cattatgctg    420
attccaacag tgatggcgtt ccatttaacc acacgtaacg gagaaccaca catgatcgtc    480
agcagacaag agaaagggaa aagtcttctg tttaaaacag aggatggcgt gaacatgtgt    540
accctcatgg ccatggacct tggtgaattg tgtgaagaca caatcacgta caagtgtccc    600
cttctcaggc agaatgagcc agaagacata gactgttggt gcaactctac gtccacgtgg    660
gtaacttatg ggacgtgtac caccatggga gaacatagaa gagaaaaaag atcagtggca    720
ctcgttccac atgtgggaat gggactggag acacgaactg aaacatggat gtcatcagaa    780
ggggcctgga aacatgtcca gagaattgaa acttggatct tgagacatcc aggcttcacc    840
atgatggcag caatcctggc ataccatata ggaacgacac atttccaaag agcccctgatt    900
ttcatcttac tgacagctgt cactccttca atgacaatgc gttgcatagg aatgtccaaat    960
agagactttg tggaaggggt ttcaggagga agctggttg acatagtctt agaacatgga   1020
agctgtgtga cgacgatggc aaaaaacaaa ccaacattgg attttgaact gataaaaaca   1080
gaagccaaac agcctgccac cctaaggaag tactgtatag aggcaaagct aaccaacaca   1140
acaacagaat ctcgctgccc aacacaaggg gaacccagcc taatgaaga gcaggacaaa   1200
aggttcgtct gcaaacactc catggtagac agaggatggg gaaatggatg tggactattt   1260
ggaaagggag gcattgtgac ctgtgctatg ttcagatgca aaaagaacat ggaaggaaaa   1320
gttgtgcaac cagaaaactt ggaatacacc aatttgtaaa cacctcactc aggggaagag   1380
catgcagtcg gaaatgacac aggaaaacat ggcaaggaaa tcaaaataac accacagagt   1440
tccatcacag aagcagaatt gacaggttat ggcactgtca caatgagtgc ctctccaaga   1500
acgggcctcg acttcaatga gatggtgttg ctgcagatgg aaaataaagc ttggctggtg   1560
cacaggcaat ggttcctaga cctgccgtta ccatggttgc ccggagcgga cacacagggg   1620
tcaaattgga tacagaaaga gacattggtc actttcaaaa atccccatgc gaagaaacag   1680
gatgttgttg ttttaggatc ccaagaaggg gccatgcaca cagcacttac aggggccaca   1740
gaaatccaaa tgtcatcagg aaacttactc ttcacaggac atctcaagtg caggctgaga   1800
atggacaagc tacagctcaa aggaatgtca tactctatgt gcacaggaaa gtttaaagtt   1860
gtgaaggaaa tagcagaaac acaacatgga acaatagtta tcagagtgca atatgaaggg   1920
gacggctctc catgcaagat cccttttgag ataatggatt tggaaaaaag acatgtctta   1980
ggtcgcctga ttacagtcaa cccaattgtg acagaaaaag atagcccagt caacatagaa   2040
gcagaacctc cattcggaga cagctacatc atcatagagg cgggg acaactgaag   2100
ctcaactggt ttaagaaagg aagttctatc ggccaaatgt ttgagacaac aatgaggggg   2160
gcgaagagaa tggccatttt aggtgacaca gcctgggatt ttggatcctt gggaggagtg   2220
tttacatcta taggaaaggc tctccaccaa gtctttggag caatctatgg agctgccttc   2280
agtggggttt catggactat gaaaatcctc ataggagtca ttatcacatg gataggaatg   2340
aattcacgca gcacctcact gtctgtgaca ctagtattgg tgggaattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatcccctc aaaactagct tcagctatcc agaaagccca tgaagagggc   2580
atttgtggaa tccgctcagt aacaagactg gagaatctgg tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catgggcaa agcaaaaatg ctctctacag agtctcataa ccagacccttt   2820
ctcattgatg gccccgaaac atgcagaatgc cccaacacaa atagacttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaca tcataacaga atggtgctgc   3360
cgatcttgca cattaccacc gctaagatac agaggtgagg atgggtgctg gtacgggatg   3420
gaaatcagac cattcaagga aaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatgat tatggtaggc   3660
gccactatga cggatgacat aggtatgggc gtgacttatc ttgccctact agcagccttc   3720
aaagtcagac caactttgc agctggacta ctcttgagaa gctgacctc caaggaattg   3780
atgatgacta ctataggaat tgtactcctc tcccagcaa ccataccaga gaccattctt   3840
gagttgactg atgcgttagc cttaggcatg atggtcctca aatggtggaa aatatgaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgctc   4020
ttaacatcct cacagcaaaa aacagattgg ataccattag cattgacgat caaaggtctc   4080
aatccaacag ctattttct aaacacacctc tcaagaacga gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttgaactg gagagagcag ccgatgtcaa atgggaagac   4320
caggcagaga tatcaggaag cagtccaatc ctgtcaataa caatatcaga agatggtagc   4380
atgtcgataa aaatgaaga ggaagaacaa acactgacca tactcattag aacaggattg   4440
ctggtgatca cagctttttc tctgtatca ataccaatcg cagccagc atgtacctg   4500
tgggaagtga agaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtgcgctg ttcaatgca taaggaaag aggattgaac catcatggc ggacgtcaag   4740
aaagacctaa tatcatatgg aggaggctgg aagttagaag gagaatggaa ggaaggagaa   4800
```

```
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacCATttttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctga gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgcacagcc aCTCCCCCgGG aagcagagac ccatttcctc agagcaatgc accaatcata   5520
gatgaagaaa gagaaatccc tgaacgttcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggccc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctgcc tacagtcacg ggagggatct ttttattctt gatgagcgga   6600
aggggcatag gaagatgacc cctgggaatg tgctgcataa tcacggctag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggttc    6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaccaagc cacagtgtta atgggtctcg ggaaaggatg gccattgtca   7080
aagatggaca tcggagttcc cctttctcgc cattggatgct actcacaagt caacccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc tctgcgttga ctcaagtatt gatgatgagg   7380
actacatggg ctctgtgtga ggctttaacc ttagctaccg gccccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagagggg gaactggcaa cataggagag acgcttggag agaaatggaa aagccgattg   7620
aacgcattgg gaaaagtga attccagatc tacaagaaaa gtggaatcca ggaagtggat   7680
agaaccttag caaagaagg cattaaaaga ggagaaacgg accatcacgc tgtgtcgcga   7740
ggctcagcaa aactgagatg gttcgttgag agaaacatgt tcacaccaga agggaaagta   7800
gtgaaccteg gttgtgcag aggaggctgg tcatactatt gtggaaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caactgtcaa   8100
ttttgcataa aggttctcaa cccatatatg ccctcagtca tagaaaaaat ggaagcacta   8160
caaaggaaat atgagggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtcccatg    8580
gtgacacaga tggcaatgac agacacgact ccatttggac aacagcgcgt tttaaagag    8640
aaagtggaca cgagaaccca agaaccgaaa gaaggcacga agaaactaat gaaaataaca   8700
gcagagtggc tttggaaaga attagggaag aaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tgggagct ggttgacaag    8880
gaaaggaatc tccatcttga aggaaagtgt gtaacaatgat gtgggaaaa                8940
agagagaaga agctagggga attcggcaag gcaaaaggca gcagccat atggtacatg    9000
tggcttggag cacgcttctt agagtttgaa gccctaggtt tcttaaatga agatcactgg   9060
ttctccagag agaactccct gagtggagtg gaggagaag ggctgcacaa gctaggttac    9120
attctaagag acgtgagcaa gaaagaggga ggagcaatgt atgccgatga caccgcagga   9180
tggacaacaa gaatcacact aaaaatgcta aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtgacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
```

```
atggccatca gtggagatga ttgtgttgtg aaacctttag atgacaggtt cgcaagcgct    9600
ttaacagctc taaatgacat gggaaagatt aggaaagaca tacaacaatg ggaaccttca    9660
agaggatgga atgattggac acaagtgccc ttctgttcac accatttcca tgagttaatc    9720
atgaaagacg tcgcgtact cgttgttcca tgtagaaacc aagatgaact gattggcaga    9780
gcccgaatct cccaaggagc agggtggtct ttgcggagaa cggcctgttt ggggaagtct    9840
tacgcccaaa tgtggagctt gatgtacttc cacagacgcg acctcaggct ggcggcaaat    9900
gctatttgct cggcagtacc atcacattgg gttccaacaa gtcgaacaac ctggtccata    9960
catgctaaac atgaatggat gacaacgaaa gacatgctga cagtctgaa cagggtgtgg   10020
attcaagaaa acccatggat ggaagacaaa actccagtgg aatcatggga ggaaatcctt   10080
tacttgggga aaagaagaa ccaatggtgc ggctcattga ttggggttaac aagcagggcc   10140
acctgggcaa agaacatcca agcagcaata aatcaagtta gatcccttat aggcaatgaa   10200
gaatacacag attacatgcc atccatgaaa agattcagaa gagaagagga agaagcagga   10260
gttctgtggt agaaagcaaa actaacatga aacaaggcta gaagtcaggt cggattaagc   10320
catagtacgg aaaaaactat gctacctgtg agccccgtcc aaggacgtta aaagaagtca   10380
ggccatcata aatgccatag ctggagtaaa ctatgcagcc tgtagctcca cctgagaagg   10440
tgtaaaaaaat ccggggaggcc acaaaccatg gaagctgtac gcatggcgta gtggactagc   10500
ggttagagga gaccccctccc ttacaaatcg cagcaacaat gggggcccaa ggcgagatga   10560
agctgtagtc tcgctggaag gactagaggt tagaggagac cccccgaaa caaaaaaacag   10620
catattgacg ctgggaaaga ccagagatcc tgctgtctcc tcagcatcat tccaggcaca   10680
gaacgccaga aaatggaatg gtgctgttga atcaacaggt tct                      10723
```

```
SEQ ID NO: 12          moltype = AA   length = 3391
FEATURE                Location/Qualifiers
source                 1..3391
                       mol_type = protein
                       organism = dengue virus
SEQUENCE: 12
MNNQRKKAKN TPFNMLKRER NRVSTVQQLT KRFSLGMLQG RGPLKLFMAL VAFLRFLTIP     60
PTAGILKRWG TIKKSKAINV LRGFRKEIGR MLNILNRRRR SAGMIIMLIP TVMAFHLTTR    120
NGEPHMIVSR QEKGKSLLFK TEDGVNMCTL MAMDLGELCE DTITYKCPLL RQNEPEDIDC    180
WCNSTSTWVT YGTCTTMGEH RREKRSVALV PHVGMGLETR TETWMSSEGA WKHVQRIETW    240
ILRHPGFTMM AAILAYTIGT THFQRALIFI LLTAVTPSMT MRCIGMSNRD FVEGVSGGSW    300
VDIVLEHGSC VTTMAKNKPT LDFELIKTEA KQPATLRKYC IEAKLTNTTT ESRCPTQGEP    360
SLNEEQDKRF VCKHSMVDRG WGNGCGLFGK GGIVTCAMFR CKKNMEGKVV QPENLEYTIV    420
ITPHSGEEHA VGNDTGKHGK EIKITPQSSI TEAELTGYGT VTMECSPRTG LDFNEMVLLQ    480
MENKAWLVHR QWFLDLPLPW LPGADTQGSN WIQKETLVTF KNPHAKKQDV VVLGSQEGAM    540
HTALTGATEI QMSSGNLLFT GHLKCRLRMD KLQLKGMSYS MCTGKFKVVK EIAETQHGTI    600
VIRVQYEGDG SPCKIPFEIM DLEKRHVLGR LITVNPIVTE KDSPVNIEAE PPFGDSYIII    660
GVEPGQLKLN WFKKGSSIGQ MFETTMRGAK RMAILGDTAW DFGSLGGVFT SIGKALHQVF    720
GAIYGAAFSG VSWTMKILIG VIITWIGMNS RSTSLSVTLV LVGIVTLYLG VMVQADSGCV    780
VSWKNKELKC GSGIFITDNV HTWTEQYKFQ PESPSKLASA IQKAHEEGIC GIRSVTRLEN    840
LMWKQITPEL NHILSENEVK LTIMTGDIKG IMQAGKRSLR PQPTELKYSW KTWGKAKMLS    900
TESHNQTFLI DGPETAECPN TNRAWNSLEV EDYGFGVFTT NIWLKLKEKQ DVFCDSKLMS    960
AAIKDNRAVH ADMGYWIESA LNDTWKIEKA SFIEVKNCHW PKSHTLWSNG VLESEMIIPK   1020
NLAGPVSQHN YRPGYHTQIT GPWHLGKLEM DFDFCDGTTV VVTEDCGNRG PSLRTTTASG   1080
KLITEWCCRS CTLPPLRYRG EDGCWYGMEI RPLKEKEENL VNSLVTAGHG QVDNFSLGVL   1140
GMALFLEEML RTRVGTKHAI LLVAVSFVTL ITGNMSFRDL GRVMVMVGAT MTDDIGMGVT   1200
YLALLAAFKV RPTFAAGLLL RKLTSKELMM TTIGIVLLSQ STIPETILEL TDALALGMMV   1260
LKMVRNMEKY QLAVTIMAIL CVPNAVILQN AWKVSCTILA VVSVSPLLLT SSQQKTDWIP   1320
LALTIKGLNP TAIFLTTLSR TSKKRSWPLN EAIMAVGMVS ILASSLLKND IPMTGPLVAG   1380
GLLTVCYVLT GRSADLELER AADVKWEDQA EISGSSPILS ITISEDGSMS IKNEEEEQTL   1440
TILIRTGLLV ISGLFPVSIP ITAAAWYLWE VKKQRAGVLW DVPSPPPMGK AELEDGAYRI   1500
KQKGILGYSQ IGAGVYKEGT FHTMWHVTRG AVLMHKGKRI EPSWADVKKD LISYGGGWKL   1560
EGEWKEGEEV QVLALEPGKN PRAVQTKPGL FKTNAGTIGA VSLDFSPGTS GSPIIDKKGK   1620
VVGLYGNGVV TRSGAYVSAI AQTEKSIEDN PEIEDDIFRK RRLTIMDLHP GAGKTKRYLP   1680
AIVREAIKRG LRTLILAPTR VVAAEMEEAL RGLPIRYQTP AIRAEHTGRE IVDLMCHATF   1740
TMRLLSPVRV PNYNLIIMDE AHFTDPASIA ARGYISTRVE MGEAAGIFMT ATPPGSRDPF   1800
PQSNAPIIDE EREIPERSWN SGHEWVTDFK GKTVWFVPSI KAGNDIAACL RKNGKKVIQL   1860
SRKTFDSEYV KTRTNDWDFV VTTDISEMGA NFKAERVIDP RRCMKPVILT DGEERVILAG   1920
PMPVTHSSAA QRRGRIGRNP KNENDQYIYM GEPLENDEDC AHWKEAKMLL DNINTPEGII   1980
PSMFEPEREK VDAIDGEYRL RGEARKTFVD LMRRGDLPVW LAYRVAAEGI NYADRRWCFD   2040
GVKNNQILEE NVEVEIWTKE GERKKLKPRW LDARIYSDPL ALKEFKEFAA GRKSLTLNLI   2100
TEMGRLPTFM TQKARDALDN LAVLHTAEAG GRAYNHALSE LPETLETLLL LTLLATVTGG   2160
IFLFLMSGRG IGKMTLGMCC IITASILLWY AQIQPHWIAA SIILEFFLIV LLIPEPEKQR   2220
TPQDNQLTYV VIAILTVVAA TMANEMGFLE KTKKDLGLGS IATQQPESNI LDIDLRPASA   2280
WTLYAVATTF VTPMLRHSIE NSSVNVSLTA IANQATVLMG LGKGWPLSKM DIGVPLLAIG   2340
CYSQVNPITL TAALFLLVAH YAIIGPGLQA KATREAQKRA AAGIMKNPTV DGITVIDLDP   2400
IPYDPKFEKQ LGQVMLLVLC VTQVLMMRTT WALCEALTLA TGPISTLWEG NPGRFWNTTI   2460
AVSMANIFRG SYLAGAGLLF SIMKNTTNTR RGTGNIGETL GEKWKSRLNA LGKSEFQIYK   2520
KSGIQEVDRT LAKEGIKRGE TDHHAVSRGS AKLRWFVERN MVTPEGKVVD LGCGRGGWSY   2580
YCGGLKNVRE VKGLTKGGPG HEEPIPMSTY GWNLVRLQSG VDVFFIPPEK CDTLLCDIGE   2640
SSPNPTVEAG RTLRVLNLVE NWLNNNTQFC IKVLNPYMPS VIEKMEALQR KYGGALVRNP   2700
LSRNSTHEMY WVSNASGNIV SSVNMISRML INRFTMRYKK ATYEPDVDLG SGTRNIGIES   2760
EIPNLDIIGK RIEKIKQEHE TSWHYDQDHP YKTWAYHGSY ETKQTGSASS MVNGVVRLLT   2820
KPWDVVPMVT QMAMTDTTPF GQQRVFKEKV DTRTQEPKEG TKKLMKITAE WLWKELGKKK   2880
TPRMCTREEF TRKVRSNAAL GAIFTDENKW KSAREAVEDS RFWELVDKER NLHLEGKCET   2940
CVYNMMGKRE KKLGEFGKAK GSRAIWYMWL GARFLEFEAL GFLNEDHWFS RENSLSGVEG   3000
EGLHKLGYIL RDVSKKEGGA MYADDTAGWD TRITLEDLKN EEMVTNHMEG EHKKLAEAIF   3060
KLTYQNKVVR VQRPTPRGTV MDIISRRDQR GSGQVGTYGL NTFTNMEAQL IRQMEGEGVF   3120
```

```
KSIQHLTITE EIAVQNWLAR VGRERLSRMA ISGDDCVVKP LDDRFASALT ALNDMGKIRK    3180
DIQQWEPSRG WNDWTQVPFC SHHFHELIMK DGRVLVVPCR NQDELIGRAR ISQGAGWSLR    3240
ETACLGKSYA QMWSLMYFHR RDLRLAANAI CSAVPSHWVP TSRTTWSIHA KHEWMTTEDM    3300
LTVWNRVWIQ ENPWMEDKTP VESWEEIPYL GKREDQWCGS LIGLTSRATW AKNIQAAINQ    3360
VRSLIGNEEY TDYMPSMKRF RREEEEAGVL W                                  3391

SEQ ID NO: 13           moltype = DNA   length = 10696
FEATURE                 Location/Qualifiers
source                  1..10696
                        mol_type = other DNA
                        note = dengue virus
                        organism = synthetic construct
SEQUENCE: 13
agttgttagt ctacgtggac cgacaagaac agtttcgact cggaagcttg cttaacgtag      60
tgctgacagt tttttattag agagcagatc tctgatgaac aaccaacgga aaaagacggg     120
aaaaccgtct atcaatatgc tgaaacgcgt gagaaaccgt gtgtcaactg gatcacagtt     180
ggcgaagaga ttctcaagag gattgctgaa cggccaagga ccaatgaaat tggttatggc     240
atttatagct ttcctcagat ttctagccat tccaccgaca gcaggagtcc tggctagatg     300
gggtacctttt aagaagtcgg gggctattaa ggtcttaaaa ggcttcaaga aggagatctc     360
aaacatgctg agcattatca acaaacggaa aaagacatcg ctctgtctca tgatgatgtt     420
accagcaaca cttgctttcc acttaacttc acgagatgga gagccgcgca tgattgtggg     480
gaagaatgaa agaggaaaat ccctactttt caagacaagc tctggaatca acatgtgcac     540
actcatagcc atggatctgg agagatgtg tgatgacacg gtcacttaca aatgcccca     600
cattaccgaa gtggagcctg aagacattga ctgctggtgc aaccttacat cgacatgggt     660
gacttatgga acatgcaatc aagctggaga gcatagacgc gataagagat cagtggcgtt     720
agctccccat gttggcatgg gactggacac acgcactcaa acctggatgt cggctgaagg     780
agcttggaga caagtcgaga aggtagagac atgggccctt aggcacccag ggttaccat     840
actagcccta tttcttgccc attacataggg cacttccttg acccagaaag tggttatttt     900
tatactatta atgctggtta ccccatccat gacaatgaga tgtgtaggag taggaaacag     960
agatttttgtg gaaggcctat cgggagctac gtgggttgac gtgggtgctcg agcacggtgg    1020
gtgtgtgact accatggcta agaacaagcc cacgctggac atagagcttc agaagaccga    1080
ggccacccaa ctggcgaccc taaggaagct atgcattgag ggaaaaatta ccaacataac    1140
aaccgactca agatgtccca cccaagggga agcgatttta cctgaggagc aggaccagaa    1200
ctacgtgtgt aagcatacat acgtggacag aggctgggga aacggttgtg gtttgtttg    1260
caagggaagc ttggtgacat gcgcgaaatt tcaatgttta gaatcaatag agggaaaagt    1320
ggtgcaacat gagaacctca aataccgt catcatcaca gtgcacacag gagaccaaca    1380
ccaggtggga aatgaaacgc agggagtcac ggctgagata cacccccagg catcaaccgc    1440
tgaagtcatt ttacctgaat atggaaccct cgggctagaa tgctcaccac ggacaggttt    1500
ggatttcaat gaaatgatct cattgacaat gaagaacaaa gcatggatgg tacatagaca    1560
atggttcttt gacttacccc taccatggac atcaggagct acagcagaaa caccaacttg    1620
gaacaggaaa gagcttcttg tgacatttaa aaatgcacat gcaaaaaagc aagaagtagt    1680
tgttcttgga tcaagagg gagcaatgca tacagcactg acaggagcta cagagatcca    1740
aacctcagga ggcacaagta tctttgcggg gcacttaaca tgtagactca agatggacaa    1800
attggaactc aaggggatga gctatgcaat gtgcttgagt agctttgtgt gaagaaaga    1860
agtctccgaa acgcagcatg ggacaatact cattaaggtt gagtacaaag ggaagatgc    1920
accctgcaag attcctttct ccacggagga tggacaagga aaagctcaca atggcagact    1980
gatcacagca aatccagtgg tgaccaagaa ggaggagcct gtcaacattg aggctgaacc    2040
tccttttgga gaaagtaaca tagtaattgg aattggagac aaagccctga aaatcaactg    2100
gtacaagaag ggaagctcga ttgggaagat gttcgaggcc actgccagag tgcaaggcg    2160
catggccatc ttgggagaca cagcctggga ctttggatca gtgggtggtg ttttgaattc    2220
attagggaaa atggtccacc aaatattgg gagtgcttac acagccctat ttggtgtgat    2280
ctcctggatg atgaaaattg gaataggtgt cctcttaacc tggatagggt gaactcaaa    2340
aaatacttct atgtcatttt catgcatcgc gataggaatc attacactct atctgggagc    2400
cgtggtgcaa gctgacatgg ggtgtgtcat aaactggaaa ggcaagaac tcaaatgtgg    2460
aagtggaatt ttcgtcacta atgaggtcca cacctgacta gagcaataca aatttcaagc    2520
agactccccc aagagactgg caacagccat tgcaggcgct tgggaaaatg gagtgtgcgg    2580
aattaggtca caaccagaa tggagaacct cttgtggaag caaatagcca tgaactgaa    2640
ttacatatta tggaaaaaca acattaaatt aacggtagtt gtaggcgaca taactggggt    2700
cttagagcaa gggaaaagaa cactaacacc acaacccatg gagctaaaat tcttggaa    2760
aacatgggga aaggcaaaaa tagtgacagc tgaaacacaa aattcctctt tcataatga    2820
tgggccaagc acaccggagt gtccaagtgc ctcaagagca tggaatgtgt ggaaggtgg    2880
ggattacggg ttcggagttt tcacaaccaa catatggctg aaactccgag aggtgtacac    2940
ccaactatgt gaccatagg taatgtcggc agccgtcaag gatgagaggg ctgtacatgc    3000
cgacatggcg tattggatag aagccaaaa gaatgggat tggaagctag aaaaagcatc    3060
cttcatagag gtgaaaacct gcacatggcc aaaatcacac actctctgga gcaatggtgt    3120
gctagagagt gacatgatta tcccaaagag tctagctggt cccatttcgc aacacaacca    3180
caggcccgga taccacaccc aaacggcagg acctgcac ttaggaaaat ggagctgga    3240
cttcaactat tgtgaaggaa caacagttgt catctcagaa aactgtggga caagaggccc    3300
atcattgaga acaacacgg tgtcaggaaa gttgatacac gaatggtgtc gccgctgtg    3360
cacacttcct cccctacgat acatgggaga gacggctgcc tggtatgca tggaaatcag    3420
acccattaat gagaaagaag agaatatggt aaagtctcta gcctcagcag ggagtggaaa    3480
ggtggacaac ttcacaatgg gtgtcttgtg tttggcaatc ctctttgaag aggtgatgag    3540
aggaaaattt gggaaaaac acatgattgc aggggtctc ttcacgtttg tgctcctcct    3600
ctcaggaaca ataacatgga gagacatggc gcacacttta ataatgattg gtccaacgc    3660
ctctgacaga atggggatgg gcgtcactta cctagctcta attgcaacat ttaaaattca    3720
gccattcctg gctttgggat tcttcctgag gaaactgaca tctagagaaa atttattgct    3780
gggagttggg ttgccatgg cagcaacgtt acgactgcca gaggacattg aacagatggc    3840
gaatggaatt gctttgggc tcatggctct taaactgata acacaatttg aaacatacca    3900
actatggacg gcattagttt ccctaacgtg ttcaaataca attttcacgt tgactgttgc    3960
```

```
ctggagaaca gccactctga tttagccgg aatttcgctt ttgccagtgt gccagtcttc   4020
gagcatgagg aaaacagatt ggctcccaat gactgtggca gctatgggag ctcaaccct    4080
accactttt  attttcagtc tgaaagatac actcaaaagg agaagctggc cactgaatga   4140
gggggtgatg gcagttggac ttgtgagcat tctagctagt tctctcctta ggaatgatgt   4200
gcctatggct ggaccattag tggctggggg cttgctgata gcgtgctacg tcataactgg   4260
cacgtcagca gacctcactg tagaaaaagc agcagatgta acatgggagg aagaggccga   4320
gcaaacagga gtgtcccaca atttaatggt cacagttgat gatgatgaa  caatgagaat   4380
aaaagatgac gagactgaga acatcttaac agtgctttta aaaacagcac tactaatagt   4440
atcaggcatc tttccatact ccatacccgc aacactgttg gtctggcata cttggcaaaa   4500
gcaaacccaa agatccggcg tcctatggga cgtacccagc ccccagaga  cacagaaagc   4560
ggaactggaa aagggggtct ataggatcaa acagcaagga attttggga  aaacccaagt   4620
gggggttgga gtacagaaag aaggagtttt ccacaccatg tggcatgtca caagagggc   4680
agtgttgaca cacaatggga aaagactgga accaaactgg gctagcgtga aaaaagatct   4740
gatttcatac ggaggaggat ggagattgag tgcaatgg   caaaagggggg aggaggtgca   4800
ggttattgcc gtagagcctg ggaagaaccc aaagaacttt caaaccatgc caggcatttt   4860
tcagacaaca acaggggaaa taggagcaat tgcactggat tcaagcctg  gaacttcagg   4920
atctcccatc ataaacagag agggaaggt  agtgggactg tatggcaatg gagtggttac   4980
aaagaatgga ggctatgtca gtggaatagc gcaaacaaat gcagaaccag atggaccgac   5040
accagagttg gaagaagaga tgttcaaaaa gcgaaatcta accataatgg atctccatcc   5100
tgggtcagga aagacgcgga aatatcttcc agctattgtt agagaggcaa tcaagagacg   5160
cttaaggact ctaattttgg caccaacaag ggtagttgca gctgagatgg aagaagcatt   5220
gaaagggctc ccaataaggt atcaaacaac tgcaacaaa  tctgaacaca caggaagaga   5280
gattgttgat ctaatgtgtc acgcaacgtt cacaatgcgc ttgctgtcac cagtcagggt   5340
tccaaactac aacttgataa taatggatga ggcccatttc acagacccag ccagtatagc   5400
ggctagaggg tacatatcaa ctcgtgtagg aatgggagag gcagccgcaa ttttcatgac   5460
agcaaccccc ctggaacagc tgatgcctt  tcctcagagc aacgctccaa ttcaagatga   5520
agagagagc  ataccggaac gctcatgaa  ttcaggcaat gaatggatta ctgactttgt   5580
tgggaagaca gtgtggtttg tccctagcat caaagccgga aatgacatag caaactgctt   5640
gcggaaaaat ggaaaaaagg ttattcaact cagcaggaag acctttgaca cagaatatca   5700
aaagaccaaa ctgaatgatt gggactttgt ggtgacaaca gacatttcga aatgggagc   5760
caatttcaaa gcagatagag tgatcgaccc aagaagatgt ctcaagccgg tgattttgac   5820
agatggaccc gagcgggtga tcctggctgg accaatgcca gtcaccgtag cgagcgctgc   5880
gcaaggagga gggagagttg gcaggaaccc acaaaaagaa aatgaccagt acatattcat   5940
gggccagcct ctcaacaatg atgaagacca tgctcactgg acagaagcaa aatgctgct    6000
ggacaacatc aacacaccag aagggattat accagctctc tttgaaccag aaagggagaa   6060
gtcagccgcc atagacggcg aataccgcct gaagggtgag tccaggaaga ctttcgtgga   6120
actcatgagg aggggtgacc tcccagtttg gctagcccat aaagtagcat cagaagggat   6180
caaatataca gatagaaat  ggtgctttga tggagaacgt aataatcaaa ttttagagga   6240
gaatatggat gtggaaatct ggacaaagga aggagaaaa  aaaaactga gcctaggtg    6300
gcttgatgcc cgcacttatt cagatcctt  agcactcaaa gaattcaagg attttgcagc   6360
tggcagaaag tcaatcgccc ttgatcttgt gacagaaata ggaagagtgc cttcacactt   6420
agcccacaga acgagaaacg ccctggataa tttggtgatg ctgcacacgt cagaacatgg   6480
cggtaggcc  tacaggcatg cagtggaaga actaccagaa acgatggaa  cactcttact   6540
cctgggactg atgatcttgt taacaggtgg agcaatgctc ttcttgatat caggtaaagg   6600
gattggaaag acttcaatag gactcatttg tgtaattgct tccagcggca tgttatggat   6660
ggctgatgtc ccactccaat ggatcgcatc ggctatagtc ctggagtttt ttatgatggt   6720
gttgctcata ccagaaccag aaaagcagag aactccccaa gacaaccaac tcgcatatgt   6780
cgtgataggc atacttacat tggctgcaat agtagcggcc aatgaaatgg gactgttgga   6840
aactacaaaa agagatttag gaatgtctaa agaaccaggt gttgtttctc aaccagctta   6900
tttgatgtg  gacttgcacc cagcatcagc ctggacattg tacgccgtgg ccacaacagt   6960
aataacacca atgttgagac acaccataga gaattccaca gcaaatgtgt ctctggcagt   7020
catagctaac caggcagtgg tcctgatggg tttagacaaa ggatggccga tatcgaaat    7080
ggacttgggc gtaccactat ggcactgggt tgctattca  caagtgaacc cactaactct   7140
tgcagcggca gtacttttgc tagtcacaca ttatgcaatt ataggtccag gattgcaggc   7200
aaaagccacc cgtgaagctc agaaaaggac agctgctgga ataatgaaga atccaacggt   7260
ggatgaata  atgacaatag acctagatcc tgtaatatat gattcaaaat ttgaaaagca   7320
actaggacag gtcatgctcc tggttctgtg tgcagtccaa ctttattga  tgagaacatc   7380
atgggccttg tgtgaagttc taaccctagc cacaggacca ataacaacac tctgggaagg   7440
atcctgggg  aagttctgga acaccacgat agctgtttcc atggccgaaca tctttagagg   7500
gagctattta gcaggagctg ggcttgcttt ttctatcatg aaatcagttg gaacaggaag   7560
gagaggaaca gggtcacaag gtgaaacctt aggagaaag  tggaaaaga  aattaaatca   7620
gttatcccgg aaaagagttg accttacaa  gaaatccgga atcaccgaag tggatagaac   7680
agaagccaaa gaagggttaa aaagaggaga ataacacac  catgccgtgt ccagaggcag   7740
cgcaaaactt caatggttcg tggagaaaac catggtcatt cctgaaggaa ggtcataga   7800
cctaggctgt ggaagaggag gctggtcata ttactgtgca ggactgaaaa aagttacaga   7860
agtgcgagga tacacaaaag gcggcccagg acacgaagaa ccagtaccta tgtctacata   7920
cggatgaac  atagtcaagt taatgagtgg aaaggatgtt ttttatctgc cacctgaaaa   7980
gtgtgatacc ctattgtgtg acattggaga atcttcacca agccaacag  tggaagaaag   8040
cagaaccata agagttttga gatggttga  accatgcta  aagaacaacc agttttgcat   8100
taaagtattg aacccataca tgccaactgt gattgagcac ttagaaagac tacaaaggaa   8160
acatggagga atgcttgtga aaatccact  ctcacgaaac tccacgcacg aaatgtattg   8220
gatatccaat ggtacaggca atatcgtctc ttcagtcaac atggtatcca gattgctact   8280
gaacagattc acaatgacac acaggagacc caccatagag aaagatgtgg atctaggagc   8340
aggaacccga agtgtcaatg cggaaccaga aacccaac  atgatgtca ttggggaaag   8400
aataaaaagg atcaaagagg agcatagttc aactggcac  tatgatgatg aaaatcctta   8460
caaacgtgg  gcttaccatg gatccctatg agtaaaagcc acaggctcag cctcctccat   8520
gataaatgga gtcgtgaaac tcctcacaaa accatggat  tggtgccca tggtgacaca   8580
gatggcaatg acagatacaa ctccattcgg ccagcaaaga gttttaaag  agaaagtgga   8640
caccaggaca cctaggccca tgccaggaac aagaaaggtt atggagatca cagcggagtg   8700
```

```
gctttggagg acccctgggaa ggaacaaaag acccagatta tgcacaaggg aggaattcac   8760
aaagaaggtc agaaccaacg cagctatggg cgctgtcttc acagaagaga accaatggga   8820
cagtgcgaga gctgctgttg aggacgaaga attttggaaa cttgtggaca gagaacgtga   8880
actccacaaa ctgggcaagt gtggaagctg cgtttacaac atgatgggca agagagagaa   8940
aaaacttgga gagtttggta aagcaaaagg cagtagggcg atatggtaca tgtggttggg   9000
agccaggtac cttgagttcg aggcgctcgg attcctcaat gaagaccact ggttctcgcg   9060
tgaaaactct tacagtggag tagaaggaga aggactgcac aagctgggat acatcttgag   9120
agatatttcc aagatacccg gaggagccat gtatgctgat gacacagccg gttgggacac   9180
aagaataaca gaagatgacc tgcacaatga ggaaaaaatc acacagcaga tggacccctga   9240
acacaggcag ctagcgaacg ctatattcaa gctcacatac caaaacaaag tggtcaaagt   9300
ccaacgacca actccaaagg gcacggtaat ggacatcata tctaggaaag accaaagagg   9360
cagtggacag gtgggaactt atggtctgaa cacattcacc aacatggaag cccagctaat   9420
cagacaaatg gaaggagaag cgtgttgtc aaaggcagac ctcgagaacc cccatccgct   9480
agagaagaaa attacacaat ggttggaaac taaaggagtg gaaaggttaa aaagaatggc   9540
catcagcggg gatgattgcg ttgtgaaacc aatcgacgac agattcgcca tgcccctgct   9600
tgccctgaac gatatgggaa aggttagaaa ggacatacct caatggcagc catcaaaggg   9660
atggcatgat tggcaacagg tcccccttctg ctccccaccac tttcatgaat tgatcatgaa   9720
agatggaaga aagttggtag ttcccctgcag accccaggac gaactaatag gaagagcgag   9780
aatctcccaa ggagcaggat ggagcctag agaaactgca tgtctaggga aagcctacgc   9840
tcaaatgtgg gctctcatgt attttcacag aagagatctt agactagcat ccaacgccat   9900
atgttcagca gtaccagtcc actgggtccc cacgagcaga acgacatggt ctattcatgc   9960
tcaccatcag tggatgacta cagaagacat gcttactgtc tggaacaggg tgtggataga  10020
ggacaatcca tggatggaag acaaaactcc agtcacaacg tgggaagatg ttccatatct  10080
agggaagaga gaagaccaat ggtgcgatc actcataggt ctcacttcca gagcaacctg  10140
ggcccagaac atactcacag caatccaaca ggtgagaagc ctcataggca atgaagagtt  10200
tctggactac atgccttcga tgaagagatt caggaaggag gaggagtcag agggagccat  10260
ttggtaaaag caggaggtaa actgtcaggc cacattaagc cacagtacgg aagaagctgt  10320
gcagcctgtg agccccgtcc aaggacgtta aagaagaag tcaggcccaa aagccacggt  10380
ttgagcaaac cgtgctgcct gtagctccgt cgtggggacg taaagcctgg gaggctgcaa  10440
accgtggaag ctgtacgcac ggtgtagcag actagtggtt agaggagacc cctcccatga  10500
cacaacgcag cagcggggcc cgagcactga gggaagctgt acctccttgc aaaggactag  10560
aggttagagg agaccccccg caaacaaaaa cagcatattg acgctgggag agaccagaga  10620
tcctgctgtc tcctcagcat cattccaggc acagaacgcc agaaaatgga atggtgctgt  10680
tgaatcaaca ggttct                                                   10696
```

```
SEQ ID NO: 14           moltype = AA   length = 3390
FEATURE                 Location/Qualifiers
source                  1..3390
                        mol_type = protein
                        organism = dengue virus SEQUENCE: 14
MNNQRKKTGK PSINMLKRVR NRVSTGSQLA KRFSRGLLNG QGPMKLVMAF IAFLRFLAIP    60
PTAGVLARWG TFKKSGAIKV LKGFKKEISN MLSIINKRKK TSLCLMMMLP ATLAFHLTSR   120
DGEPRMIVGK NERGKSLLFK TASGINMCTL IAMDLGEMCD DTVTYKCPHI TEVEPEDIDC   180
WCNLTSTWVT YGTCNQAGEH RRDKRSVALA PHVGMGLDTR TQTWMSAEGA WRQVEKVETW   240
ALRHPGFTIL ALFLAHYIGT SLTQKVVIFI LLMLVTPSMT MRCVGVGNRD FVEGLSGATW   300
VDVVLEHGGC VTTMAKNKPT LDIELQKTEA TQLATLRKLC IEGKITNITT DSRCPTQGEA   360
ILPEEQDQNY VCKHTYVDRG WGNGCGLFGK GSLVTCAKFQ CLESIEGKVV QHENLKYTVI   420
ITVHTGDQHQ VGNETQGVTA EITPQASTAE VILPEYGTLG LECSPRTGLD FNEMISLTMK   480
NKAWMVHRQW FFDLPLPWTS GATAETPTWN RKELLVTFKN AHAKKQEVVV LGSQEGAMHT   540
ALTGATEIQT SGGTSIFAGH LKCRLKMDKL ELKGMSYAMC LSSFVLKKEV SETQHGTILI   600
KVEYKGEDAP CKIPFSTEDG QGKAHNGRLI TANPVVTKKE EPVNIEAEPP FGESNIVIGI   660
GDKALKINWY KKGSSIGKMF EATARGARRM AILGDTAWDF GSVGGVLNSL GKMVHQIFGS   720
AYTALFGGVS WMMKIGIGVL LTWIGLNSKN TSMSFSCIAI GIITLYLGAV VQADMGCVIN   780
WKGKELKCGS GIFVTNEVHT WTEQYKFQAD SPKRLATAIA GAWENGVCGI RSTTRMENLL   840
WKQIANELNY ILWENNIKLT VVVGDITGVL EQGKRTLTPQ PMELKYSWKT WGKAKIVTAE   900
TQNSSFIIDG PSTPECPSAS RAWNVWEVED YGFGVFTTNI WLKLREVYTQ LCDHRLMSAA   960
VKDERAVHAD MGYWIESQKN GSWKLEKASF IEVKTCTWPK SHTLWSNGVL ESDMIIPKSL  1020
AGPISQHNHR PGYHTQTAGP WHLGKLELDF NYCEGTTVVI SENCGTRGPS LRTTTVSGKL  1080
IHEWCCRSCT LPPLRYMGED GCWYGMEIRP INEKEENMVK SLASAGSGKV DNFTMGVLCL  1140
AILFEEVMRG KFGKKHMIAG VLFTFVLLLS GQITWRDMAH TLIMIGSNAS DRMGMGVTYL  1200
ALIATFKIQP FLALGFFLRK LTSRENLLLG VGLAMAATLR LPEDIEQMAN GIALGLMALK  1260
LITQFETYQL WTALVSLTCS NTIFTLTVAW RTATLILAGI SLLPVCQSSS MRKTDWLPMA  1320
VAAMGAQPLP LFIFSLKDTL KRRSWPLNEG VMAVGLVSIL ASSLLRNDVP MAGPLVAGGL  1380
LIACYVITGT SADLTVEKAA DVTWEEEAEQ TGVSHNLMVT VDDDGTMRIK DDETENILTV  1440
LLKTALLIVS GIFPYSIPAT LLVWHTWQKQ TQRSGVLWDV PSPPETQKAE LEEGVYRIKQ  1500
QGIFGKTQVG VGVQKEGVFH TMWHVTRGAV LTHNGKRLEP NWASVKKDLI SYGGGWRLSA  1560
QWQKGEEVQV IAVEPGKNPK NFQTMPGIFQ TTTGEIGAIA LDFKPGTSGS PIINREGKVV  1620
GLYGNGVVTK NGGYVSGIAQ TNAEPDGPTP ELEEEMFKKR NLTIMDLHPG SGKTRKYLPA  1680
IVREAIKRRL RTLILAPTRV VAAEMEEALK GLPIRYQTTA TKSEHTGREI VDLMCHATFT  1740
MRLLSPVRVP NYNLIIMDEA HFTDPASIAA RGYISTRVGM GEAAAIFMTA TPPGTADAFP  1800
QSNAPIQDEE RDIPERSWNS GNEWITDFVG KTVWFVPSIK AGNDIANCLR KNGKKVIQLS  1860
RKTFDTEYQK TKLNDWDFVV TTDISEMGAN FKADRVIDPR RCLKPVILTD GPERVILAGP  1920
MPVTVASAAQ RRGRVGRNPQ KENDQYIFMG QPLNNDEDHA HWTEAKMLLD NINTPEGIIP  1980
ALFEPEREKS AAIDGEYRLK GESRKTFVEL MRRGDLPVWL AHKVASEGIK YTDRKWCFDG  2040
ERNNQILEEN MDVEIWTKEG EKKKLRPRWL DARTYSDPLA LKEFKDFAAG RKSIALDLVT  2100
EIGRVPSHLA HRTRNALDNL VMLHTSEHGG RAYRHAVEEL PETMETLLLL GMILLTGGA  2160
MLFLISGKGI GKTSIGLICV IASSGMLWMA DVPLQWIASA IVLEFFMMVL LIPEPEKQRT  2220
PQDNQLAYVV IGILTLAAIV AANEMGLLET TKRDLGMSKE PGVVSPTSYL DVDLHPASAW  2280
```

```
TLYAVATTVI TPMLRHTIEN STANVSLAAI ANQAVVLMGL DKGWPISKMD LGVPLLALGC    2340
YSQVNPLTLA AAVLLLVTHY AIIGPGLQAK ATREAQKRTA AGIMKNPTVD GIMTIDLDPV    2400
IYDSKFEKQL GQVMLLVLCA VQLLLMRTSW ALCEVLTLAT GPITTLWEGS PGKFWNTTIA    2460
VSMANIFRGS YLAGAGLAFS IMKSVGTGKR GTGSQGETLG EKWKKKLNQL SRKEFDLYKK    2520
SGITEVDRTE AKEGLKRGEI THHAVSRGSA KLQWFVERNM VIPEGRVIDL GCGRGGWSYY    2580
CAGLKKVTEV RGYTKGGPGH EEPVPMSTYG WNIVKLMSGK DVFYLPPEKC DTLLCDIGES    2640
SPSPTVEESR TIRVLKMVEP WLKNNQFCIK VLNPYMPTVI EHLERLQRKH GGMLVRNPLS    2700
RNSTHEMYWI SNGTGNIVSS VNMVSRLLLN RFTMTHRRPT IEKDVDLGAG TRHVNAEPET    2760
PNMDVIGERI KRIKEEHSST WHYDDENPYK TWAYHGSYEV KATGSASSMI NGVVKLLTKP    2820
WDVVPMVTQM AMTDTTPFGQ QRVFKEKVDT RTPRPMPGTR KVMEITAEWL WRTLGRNKRP    2880
RLCTREEFTK KVRTNAAMGA VFTEENQWDS ARAAVEDEEF WKLVDRERFL HKLGKCGSCV    2940
YNMMGKREKK LGEFGKAKGS RAIWYMWLGA RYLEFEALGF LNEDHWFSRE NSYSGVEGEG    3000
LHKLGYILRD ISKIPGGAMY ADDTAGWDTR ITEDDLHNEE KITQQMDPEH RQLANAIFKL    3060
TYQNKVVKVQ RPTPKGTVMD IISRKDQRGS GQVGTYGLNT FTNMEAQLIR QMEGEGVLSK    3120
ADLENPHPLE KKITQWLETK GVERLKRMAI SGDDCVVKPI DDRFANALLA LNDMGKVRKD    3180
IPQWQPSKGW HDWQQVPFCS HHFHELIMKD GRKLVVPCRP QDELIGRARI SQGAGWSLRE    3240
TACLGKAYAQ MWALMYFHRR DLRLASNAIC SAVPVHWVPT SRTTWSIHAH HQWMTTEDML    3300
TVWNRVWIED NPWMEDKTPV TTWEDVPYLG KREDQWCGSL IGLTSRATWA QNILTAIQQV    3360
RSLIGNEEFL DYMPSMKRFR KEEESEGAIW                                     3390

SEQ ID NO: 15          moltype = DNA  length = 10648
FEATURE                Location/Qualifiers
source                 1..10648
                       mol_type = other DNA
                       note = dengue virus
                       organism = synthetic construct
SEQUENCE: 15
agttgttagt ctgtgtggac cgacaaggac agttccaaat cggaagcttg cttaacacag     60
ttctaacagt ttgtttgaat agagagcaga tctctggaaa aatgaaccaa cgaaaaaagg    120
tggttagacc acctttcaat atgctgaaac gcgagagaaa ccgcgtatca accccctcaag    180
ggttggtgaa gagattctca accggacttt tttctgggaa aggaccctta cggatggtgc    240
tagcattcat cacgtttttg cgagtccttt ccatcccacc aacagcaggg attctgaaaa    300
gatgggggaca gttgaagaaa ataaggcca tcaggatact gattggattc aggaaggaga    360
taggccgcat gctgaacatc ttgaacggga gaaaaaggtc aacgataaca ttgctgtgct    420
tgattcccac cgtaatggcg tttcacttgt caacaagaga tggcgaaccc ctcatcatgag    480
tggcaaaaca tgaaaggggg agaccctctc tgtttaagac aacagagggg atcaacaaat    540
gcactctcat tgccatggac ttgggtgaaa tgtgtgagga cactgtcacg tataaatgcc    600
ccttactggt caataccgaa cctgaagaca ttgattgctg gtgcaatctc acgtctacct    660
gggtcatgta tgggacatgc acccagagcg gagaacggag acgagagaag cgctcagtag    720
ctttaacacc acattcagga atgggattgg aaacaagagc tgagacatgg atgtcatcgg    780
aaggggcttg gaagcatgct cagagagtag agagctggat actcagaaac ccaggattcg    840
cgctcttggc aggatttatg gcttatatga ttgggcaaac aggaatccag cgaactgtct    900
tctttgtcct aatgatgctg gtcgcccat cctacgaaca gcgatgcgta ggagtaggaa    960
acagagactt tgtggaagga gtctcaggtg gagcatgggg cgatctggtg ctagaacatg    1020
gaggatgcgt cacaaccatg gcccaggaa accaaccett ggattttgaa ctgactaaga    1080
caacagccca ggaagtggct ctgttaagaa cctattgcat tgaagcctca atatcaaaca    1140
taacaacggc aacaagatgt ccaacgcaag gagagcctta tctaaaagag gaacaagcac    1200
aacagtacat ttgccggaga gatgtggtag acagagggtg gggcaatggc tgtggcttgt    1260
ttggaaaagg aggagttgtg acatgtgcga gttttcatg ttcggggaag ataacaggca    1320
atttggtcca aattgagaac cttgaataca cagtggttgt aacagtccac aatggagaca    1380
cccatgcagt aggaaatgac acatccaatc atggttac agccacgata actcccaggt    1440
caccatcggt ggaagtcaaa ttgccggact atggagaact aacactcgat tgtgaaccca    1500
ggtctggaat tgactttaat gagatgattc tgatgaaaat gaaaagaaa acatggcttg    1560
tgcataagca atggttttg gatctaccte taccatggac agcaggagca gacacatcag    1620
aggttcactg gaattacaaa gagagaatgg tgacattaa ggttcctcat gccaagagac    1680
aggatgtgac agtgctggga tctcaggaag gagccatgca ttctgccctc gctgagcca    1740
cagaagtgga ctccggtgat ggaaatcaca gtgtttcagg acatctcaag tgcaaagtcc    1800
gtatggaaga attgagaatc aagggaatgt catacacgat gtgttcagga aagttctcaa    1860
ttgacaaaga gatggcagaa acacacatg ggacaacagt ggtgaaagtc aagtatgaag    1920
gtgctggagc tccgtgtaaa gtccccatag agataagagt gtgaacaag gaaaaagtg    1980
ttgggcgtat catctcatcc accccttgg ctgagaatac caacagtgca accaacatgg    2040
agttagaacc cccctttggg gacagctaca tagtgatagg tgttgaaaac agtgcattaa    2100
cactccattg gttcaggaaa gggagttcca ttggcaagat gtttgagtcc acatacagag    2160
gtgcaaaacg aatggcatt ctaggtgaaa cagcttggta tttttggttcc gttggtgac    2220
tgttcacatc attgggaaag ctgtgcacc aggttttgg aagtgtgtat acaaccatgt    2280
ttggaggagt ctcatggatg attagaatcc taattgggtt cctagtcttg tggatggca    2340
cgaactcaag gaacacttca atggctatga cgtgcatagc tgttgaggga atcactctgt    2400
ttctgggctt cacagttcaa gcagacatgg ttgtgtggt gtcatggagt gggaaagaat    2460
tgaagtgtgg aaagcggaatt tttgtggttg acaacgtgca cattggaca gaacagtaca    2520
aatttcaacc ggagtcccca gcgagactag cgtctgcaat attgaatgcc cacaaagatg    2580
gggtctgtgg aattagatca accacgaggc tggaaatgt catgtggaag caaataacca    2640
acgagctaaa ttatgttctc tgggaaggag acatgacct cactgtagtg ctggggatg    2700
tgaaggggt gttgaccgaa ggcaagagag cactcacacc cccagtgaat gatctgaaat    2760
attgaaggga aaagcaaaaa tcttcactgg aaagcaaga aatgacat    2820
tttaatgaa cggaccagac acctccgaat gccccaatga acgaagagca tggaactttc    2880
ttgaggtgga agactatgga tttgcatgt tcacgaccaa catatggatg aaattccgag    2940
aaggaagttc agagtgtgt gaccacaggt taatgtcagc ggcaattaa gatcagaaag    3000
ctgtgcatgc tgacatgggt tattggatag agagctcaaa aaaccagacc tggcagatag    3060
agaaagcatc tcttattgaa gtgaaaacat gtctgtggcc caagacccac acattgtgga    3120
```

```
gcaatggagt gctggaaagc cagatgctca ttccaaaatc atatgcgggc ccttttttcac   3180
agcacaatta ccgccagggc tatgccacgc aaaccgtggg cccatggcac ttaggcaaat   3240
tagagataga ctttggagaa tgccccggaa caacagtcgc aattcaggag gattgtgacc   3300
atagaggccc atctttgagg accaccactg catctggaaa actagtcacg caatggtgct   3360
gccgctcctg cacgatgcct cccttaaggt tcttggagaa agatggttgc tggtatggga   3420
tggagattag gcccttgagt gaaaaagaag agaacatggt caaatcacag gtaacggccg   3480
gacagggcac atcagaaact ttttctatgg gtctgttgtg cctgaccttg tttgtggaag   3540
aatgcttgag gagaagagtc actaggaaac acatgatatt ggttgtggtg atcactcttt   3600
gtgccatcat cctaggaggc ctcacatgga tggacttact acgagccctc atcatgttgg   3660
gggacactat gtctggtaga ataggaggac agatccacct agccatcatg gcagtgttca   3720
agatgtcacc aggatacgtg ctgggtgtgt ttttaaggaa actcacttca agagagacag   3780
cactaatggt aataggaatg gccatgacaa cggtgctttc aattccacat gaccttatgg   3840
aactcattga tggaatatca ctgggctaa ttttgctaaa aatagtgaca cattttgaca   3900
acacccaagt gggaaccta gcccttttcct tgaccttcat aagatcaaca atgccattgg   3960
tcatggcttg gaggaccatt atggctgtgt tgtttgtggt cacactcatt cctttgtgca   4020
ggacaagctg tcttcaaaaa cagtctcatt gggtagaaat aacagcactc atcctaggag   4080
cccaagctct gccagtgtac ctaatgactc ttatgaaagg agcctcaaga agatcttggc   4140
ctcttaacga gggcataatg gctgtgtgtt tggttagtct cttaggaagc gctctttaa   4200
agaatgatgt ccctttagct ggcccaatgg tggcaggagg cttacttctg gcggcttacg   4260
tgatgagtgg tagctcagca gatctgtcac tagagaaggc cgccaatgtg cagtgggatg   4320
aaaatggcaga cataacaggc tcaagcccaa tcatagaagt gaagcaggat gaagatggct   4380
ctttctccat acgggacgtc gaggaaacca atatgataac ccttttggtg aaactggcac   4440
tgataacagt gtcaggtctc tacccccttgg caattccagt cacaatgacc ttatggtaca   4500
tgtggcaagt gaaaacacaa agatcaggag ccctgtggga cgtcccctca cccgctgcca   4560
ctcaaaaagc cgcactgtct gaaggagtgt acaggatcat gcaagagggg ttatttggga   4620
aaactcaggt tggagtaggg atacacatgg aagtgtatt tcacacaatg tggcatgtaa   4680
caagaggatc agtgatctgc catgagactg ggagattgga gccatcttgg gctgacgtca   4740
ggaatgacat gatatcatac ggtggggat ggagacttgg agacaaatgg gacaaagaag   4800
aagatgttca ggtcctcgcc atagaaccag gaaaaaatcc taaacatgtc caaacgaaac   4860
ccggcctttt caagaccta actggagaaa ttggagcagt aacattagat ttcaaacccg   4920
gaacgtctgg ttctcccatc atcaacagga aggaaaagt catcggactc tatggaaatg   4980
gagtagttac caaatcaggt gattacgtca gtgccataac gcaagccgaa agaattggag   5040
agccagatta tgaagtggat gaggactttt ttcgaaagaa aagattaact ataatggact   5100
tacaccccgg agctggaaag acaaaaagaa ttcttccatc aatagtgaga gaagccttaa   5160
aaaggaggcc gcgaaccttg attttggctc ccacgagagt ggtggcggcc gagatggaag   5220
aggccctacg tggactgcca atccgttatc agacccagcg tgtgaaatca gaacacacag   5280
gaagagagat tgtagacctc atgtgtcatg caaccttcac aacaagactt ttgtcatcaa   5340
ccagagttcc aaattacaac ctcatagtga tggatgaagc acatttcacc gatcctccta   5400
gtgtcgcggc tagaggatac atctcgacca gggtggaaaa gggagaggca gcagccatct   5460
tcatgaccgc aaccccctccc ggagcgacag atcccttttcc ccagagcaac agcccaatag   5520
aagacatcga gagggaaatt ccggaaaggt catggaacac agggtcgac tggataacag   5580
actaccaagg gaaaactgtg tggttttgttc ccagcataaa agctggaaat gacattgcaa   5640
attgtttgag aaagtcggga aagaaagtta tccagttgag taggaaaacc tttgatacag   5700
agtatccaaa aacgaaactc acggactggg attttgtggt cactacagac atatctgaaa   5760
tgggggccaa ttttagagct gggagagtga tagaccctag gagatgcctc aagccagtta   5820
tcctaacaga tgggccagag agagtcattt tagcaggtcc tattccagtg actccagcaa   5880
gcgctgctca gagaagaggg cgaataggaa ggaacccagc acaagaagac gaccaatacg   5940
tttttctccgg agaccactaa aaaatgatg aagatcatgc ccactggaca gaagcaaaga   6000
tgctgcttga caatatctac accccagaag ggatcattcc aacattgttt ggtccggaaa   6060
gggaaaaaac ccaagccatt gatggagagt ttcgcctcag aggggaacaa aggaagactt   6120
ttgtgaatt aatgaggaga ggagaccttc cggtgtgtct gagctataag gtagcttctg   6180
ctggcatttc ttacaaagat cgggaatggt gcttcacagg ggaaaggaat aaccaaattt   6240
tagaagaaaa catggaggtt gaaatttgga ctagagaggg agaaaagaaa aagctaaggc   6300
caagatggtt agatgcacgt gtatacgctg accccatggc tttgaaggat tttaaggagt   6360
ttgctagtgg aaggaagagc ataactctcg acatcctaac agagattgcc agtttgccaa   6420
cttacctttc ctctagggcc aagctcgcc ttgataacat agtcatgctc cacacaacag   6480
aaagaggagg gagggcctac caacacgccc tgaacgaact cccggagtca ctggaaacac   6540
ttatgcttgt agctttacta ggtgctatga cagcaggtat cttcctgttt ttcatgcaag   6600
ggaaggaat aggggaattg tcaatgggtt tgataaccat tgcggtggct agtgcttgc   6660
tctgggtagc agaaattcaa ccccagtgga tagcggcctc aatcatacta gagttttttc   6720
tcatggtact gttgataccg gaaccagaaa acaaaggac cccacaagac aatcaattga   6780
tctacgtcat attgaccatt ctcaccatta ttggtctcat agcagccaac gagatggggc   6840
tgattgaaaa aacaaaaacg gattttgggt tttaccaggt aaaaacagaa accaccatcc   6900
tcgatgtgga cttgagacca gcttcagcat ggacgcttca tgcagtagcc accacaattc   6960
tgactcccat gctgagacac accatagaaa acacgtcggc caacctatct ctagcagcca   7020
ttgccaacca ggcggccgtc ctaatgggc ttggaaaagg atggccgctc cacagaatgg   7080
acctcggtgt gccgctgtta gcaatgggat gctattctca agtgaaccca acaactttga   7140
cagcatcctt agtcatgctt ttagtccatt atgcaataat aggtccagga ttgcaggcaa   7200
aagccacaag agaggccag aaaaggacag ctgctgggat catgaaaaac ccacggtga   7260
acggataac agtaatagat ctagaaccaa tatcctatga cccaaaattt gaaaagcaat   7320
tagggcaggt catgctactc gtcttgtgtg ctggacaact actcttgatg agaacaacat   7380
gggcttttct tgaagtcttg actttggcca caggaccaat cttgaccttg tgggagggca   7440
acccgggaag gttttggaac acgaccatag ccgtatccac cgccaacatt tcagggaa   7500
gttacctggc agagtggtga tggcttttt cactcataaa gaatgtacaa accctagga   7560
ggggaactgg gaccacagga gagacactgg agagaagtg gaagagacag ctaaactcat   7620
tagacagaaa agagtttgaa gagtataaaa gaagtggaat actagaagtg gacaggactg   7680
aagccaagtc tgccctgaaa gatggggtcta aaatcaagca tgcagtatct agagggtcca   7740
gtaagattag atggattgtt gagagaggga tggtaaagcc aaaagggaaa gttgtagatc   7800
ttggctgtgg gagaggagga tggtcttatt acatggcgac gctcaagaac gtgactgaag   7860
```

```
tgaaagggta tacaaaagga ggtccaggac atgaagaacc gattcccatg gctacttatg  7920
gctggaattt ggtcaaactc cattcagggg ttgacgtgtt ctacaaaccc acagagcaag  7980
tggacaccct gctctgtgat attggggagt catcttctaa tccaacaata gaggaaggaa  8040
gaacattaag agttttgaag atggtggagc catggctctc ttcaaaacct gaattctgca  8100
tcaaagtcct taacccctac atgccaacag tcatagaagg agctggagaa ctgcagagaa  8160
aacatggtgg gaaccttgtc agatgcccgc tgtccaggaa ctccaccccat gagatgtatt  8220
gggtgtcagg agcgtcggga acattgtga gctctgtgaa cacaaacatca aagatgttgt  8280
tgaacaggtt cacaacaagg catagggaac ccacttatga gaaggacgta gatcttgggg  8340
caggaacgag aagtgtctcc actgaaacag aaaaaccaga catgacaatt attgggagaa  8400
ggcttcagcg attgcaagag gagcacaaag aaacctgca ttatgatcag gaaaacccat  8460
acagaacctg ggcgtatcat ggaagctatg aagctcctc gacaggctct gcatcctcca  8520
tggtgaacgg ggtagtaaaa ctgctaacaa aaccttggga tgtggttcca atggtgaccc  8580
agttagccac gacagacaca accccttttg ggcaacaaag agtgttcaaa gagaaggtgg  8640
ataccagaac accacaacca aaacccggta cacgaccatt tatgaccacg acagccaatt  8700
ggctgtgggc cctccttggg aagaagaaaa atcccagact gtgcacaagg gaagagttca  8760
tctcaaaagt tagatcaaac gcagccatag gcgcagtctt tcaggaagaa cagggatgga  8820
catcagccag tgaagctgtg aatgacagcc ggttttggga actggttgac aaagaaaggg  8880
ccctacacca ggaagggaaa tgtgaatcgt gtgtctacaa catgatggga aaacgtgaga  8940
aaaagttagg agagtttggc agagccaagg gaagccgagc aatctggtac atgtggctgg  9000
gagcgcggtt tctggaattt gaagcccctgg gttttttgaa tgaagatcac tggtttggca  9060
gagaaaattc atggagtgga gtggaagggg aaggtctgca cagattggga tatatcctgg  9120
aggagataga caaggaaggat ggagacctaa tgtatgctga tgacacagca ggctgggaca  9180
caagaatcac tgaggatgac cttcaaaatg aagaactgat cacggaacag atggcccccc  9240
accacaagat cctagccaaa gccattttca aactaaccta tcaaaacaaa gtggtgaaag  9300
tcctcagacc cacaccgaga ggagcggtga tggatatcat atccaggaaa gaccaaagag  9360
gtagtggaca agttgaaca tatggtttga acacattcac caacatggaa gttcaactca  9420
tccgccaaat ggaagctgaa ggagtcatca cacaagatga catgcagaac ccaaaagggt  9480
tgaaagaaag agttgagaaa tggctgaaag agtgtggtgt cgacaggtta aagaggatgg  9540
caatcagtgg agacgattgc gtggtgaagc cctggtgatga gaggtttggc acttccctcc  9600
tcttcttgaa cgacatggga aaggtagga aagacattcc gcagtgggca ccatctaagg  9660
gatgaaaaaa ctggcaagag gttccttttt gctcccacca ctttcacaag atcttcatga  9720
aggatggccg ctcactagtt gttccatgta gaaaccagga tgaactgata gggagagcca  9780
gaatctcgca gggggctgga tggagcttaa gagaaacagc ctgcctgggc aaagcttacg  9840
cccagatgtg gtcgctcatg tacttccaca aaagggatct gcgtttagcc tccatggccg  9900
tatgctcagc agttccaacg gaatggtttc caacaagcag aacaacatgg tcaatccacg  9960
ctcatcatca gtggatgacc actgaagata tgctcaaagt gtgaacaga gtgtggatag 10020
aagcaaccc taatatgact gacaagactc cagtccattc gtgggaagat ataccttacc 10080
tagggaaaag agaggatttg tggtgtggat ccctgattgg actttcttcc agagccacct 10140
gggcgaagaa cattcacacg gccataaccc aggtcagaaa cctgatcgga aagaggaat 10200
acgtggatta catgccagta atgaaagat acacgcgctcc ttcagagagt gaaggagttc 10260
tgtaattacc aacaacaaac accaaggct attgaagtca ggccacttgt gccacggctt 10320
gagcaaaccg tgctgcctgt agctccgcca ataatgggag gcgtgaaatc cctagggagg 10380
ccatgcgcca cggaagctgt acgcgtggca tattggacta gggttaggag agaccccctc 10440
ccatcactga caaaacgcag caaaagggggg cccgaagcca ggaggaagct gtactcctgg 10500
tggaaggact agaggttaga ggagacccccc ccaacacaaa aacagcatat tgacgctggg 10560
aaagaccaga gatcctgctg tctctgcaac atcaatccag gcacagagcg ccgcaagatg 10620
gattggtgtt gttgatccaa caggttct                                    10648

SEQ ID NO: 16          moltype = AA  length = 3387
FEATURE                Location/Qualifiers
source                 1..3387
                       mol_type = protein
                       organism = dengue virus
SEQUENCE: 16
MNQRKKVVRP PFNMLKRERN RVSTPQGLVK RFSTGLFSGK GPLRMVLAFI TFLRVLSIPP   60
TAGILKRWGQ LKKNKAIRIL IGFRKEIGRM LNILNGRKRS TITLLCLIPT VMAFHLSTRD  120
GEPLMIVAKH ERGRPLLFKT TEGINKCTLI AMDLGEMCED TVTYKCPLLV NTEPEDIDCW  180
CNLTSTWVMY GTCTQSGERR REKRSVALTP HSGMGLETRA ETWMSSEGAW KHAQRVESWI  240
LRNPGFALLA GFMAYMIGQT GIQRTVFFVL MMLVAPSYGM RCVGVGNRDF VEGVSGGAWV  300
DLVLEHGGCV TTMAQGKPTL DFELTKTTAK EVALLRTYCI EASISNITTA TRCPTQGEPY  360
LKEEQDQQYI CRRDVVDRGW GNGCGLFGKG GVVTCAKFSC SGKITGNLVQ IENLEYTVVV  420
TVHNGDTHAV GNDTSNHGVT ATITPRSPSV EVKLPDYGEL TLDCEPRSGI DFNEMILMKM  480
KKKTWLVHKQ WFLDLPLPWT AGADTSEVHW NYKERMVTFK VPHAKRQDVT VLGSQEGAMH  540
SALAGATEVD SGDGNHMFAG HLKCKVRMEK LRIKGMSYTM CSGKFSIDKE MAETQHGTTV  600
VKVKYEGAGA PCKVPIEIRD VNKEKVVGRI ISSTPLAENT NSATNIELEP PFGDSYIVIG  660
VGNSALTLHW FRKGSSIGKM FESTYRGAKR MAILGETAWD FGSVGGLFTS LGKAVHQVFG  720
SVYTTMFGGV SWMIRILIGF LVLWIGTNSR NTSMAMTCIA VGGITLFLGF TVQADMGCVV  780
SWSGKELKCG SGIFVVDNVH TWTEQYKFQP ESPARLASAI LNAHKDGVCG IRSTTRLENV  840
MWKQITNELN YVLWEGGHDL TVVAGDVKGV LTKGKRALTP PVNDLKYSWK TWGKAKIFTP  900
EARNSTFLID GPDTSECPNE RRAWNFLEVE DYGFGMFTTN IWMKFREGSS EVCDHRLMSA  960
AIKDQKAVHA DMGYWIESSK NQTWQIEKAS LIEVKTCLWP KTHTLWSNGV LESQMLIPKS 1020
YAGPFSQHNY RQGYATQTVG PWHLGKLEID FGECPGTTVA IQEDCDHRGP SLRTTTASGK 1080
LVTQWCCRSC TMPPLRFLGE DGCWYGMEIR PLSEKEENMV KSQVTAGQGT SETFSMGLLC 1140
LTLFVEECLR RRVTRKHMIL VVVITLCAII LGGLTWMDLL RALIMLGDTM SGRIGGQIHL 1200
AIMAVFKMSP GYVLGVFLRK LTSRETALMV IGMAMTTVLS IPHDLMELID GISLGLILLK 1260
IVTHFDNTQV GTLALSLTFI RSTMPLVMAW RTIMAVLFVV TLIPLCRTSC LQKQSHWVEI 1320
TALILGAQAL PVYLMTLMKG ASRRSWPLNE GIMAVGLVSL LGSALLKNDV PLAGPMVAGG 1380
LLLAAYVMSG SSADLSLEKA ANVQWDEMAD ITGSSPIIEV KQDEDGSFSI RDVEETNMIT 1440
LLVKLALITV SGLYPLAIPV TMTLWYMWQV KTQRSGALWD VPSPAATQKA ALSEGVYRIM 1500
```

-continued

```
QRGLFGKTQV GVGIHMEGVF HTMWHVTRGS VICHETGRLE PSWADVRNDM ISYGGGWRLG  1560
DKWDKEEDVQ VLAIEPGKNP KHVQTKPGLF KTLTGEIGAV TLDFKPGTSG SPIINRKGKV  1620
IGLYGNGVVT KSGDYVSAIT QAERIGEPDY EVDEDIFRKK RLTIMDLHPG AGKTKRILPS  1680
IVREALKRRL RTLILAPTRV VAAEMEEALR GLPIRYQTPA VKSEHTGREI VDLMCHATFT  1740
TRLLSSTRVP NYNLIVMDEA HFTDPSSVAA RGYISTRVEM GEAAAIFMTA TPPGATDPFP  1800
QSNSPIEDIE REIPERSWNT GFDWITDYQG KTVWFVPSIK AGNDIANCLR KSGKKVIQLS  1860
RKTFDTEYPK TKLTDWDFVV TTDISEMGAN FRAGRVIDPR RCLKPVILTD GPERVILAGP  1920
IPVTPASAAQ RRGRIGRNPA QEDDQYVFSG DPLKNDEDHA HWTEAKMLLD NIYTPEGIIP  1980
TLFGPEREKT QAIDGEFRLR GEQRKTFVEL MRRGDLPVWL SYKVASAGIS YKDREWCFTG  2040
ERNNQILEEN MEVEIWTREG EKKKLRPRWL DARVYADPMA LKDFKEFASG RKSITLDILT  2100
EIASLPTYLS SRAKLALDNI VMLHTTERGG RAYQHALNEL PESLETLMLV ALLGAMTAGI  2160
FLFFMQGKGI GKLSMGLITI AVASGLLWVA EIQPQWIAAS IILEFFLMVL LIPEPEKQRT  2220
PQDNQLIYVI LTILTIIGLI AANEMGLIEK TKTDFGFYQV KTETTILDVD LRPASAWTLY  2280
AVATTILTPM LRHTIENTSA NLSLAAIANQ AAVLMGLGKG WPLHRMDLGV PLLAMGCYSQ  2340
VNPTTLTASL VMLLVHYAII GPGLQAKATR EAQKRTAAGI MKNPTVDGIT VIDLEPISYD  2400
PKFEKQLGQV MLLVLCAGQL LLMRTTWAFC EVLTLATGPI LTLWEGNPGR FWNTTIAVST  2460
ANIFRGSYLA GAGLAFSLIK NVQTPRRGTG TTGETLGEKW KRQLNSLDRK EFEEYKRSGI  2520
LEVDRTEAKS ALKDGSKIKH AVSRGSSKIR WIVERGMVKP KGKVVDLGCG RGGWSYYMAT  2580
LKNVTEVKGY TKGGPGHEEP IPMATYGWNL VKLHSGVDVF YKPTEQVDTL LCDIGESSSN  2640
PTIEEGRTLR VLKMVEPWLS SKPEFCIKVL NPYMPTVIEE LEKLQRKHGG NLVRCPLSRN  2700
STHEMYWVSG ASGNIVSSVN TTSKMLLNRF TTRHRKPTYE KDVDLGAGTR SVSTETEKPD  2760
MTIIGRRLQR LQEEHKETWH YDQENPYRTW AYHGSYEAPS TGSASSMVNG VVKLLTKPWD  2820
VVPMVTQLAM TDTTPFGQQR VFKEKVDTRT PQPKPGTRMV MTTTANWLWA LLGKKKNPRL  2880
CTREEFISKV RSNAAIGAVF QEEQGWTSAS EAVNDSRFWE LVDKERALHQ EGKCESCVYN  2940
MMGKREKKLG EFGRAKGSRA IWYMWLGARF LEFEALGFLN EDHWFGRENS WSGVEGEGLH  3000
RLGYILEEID KKDGDLMYAD DTAGWDTRIT EDDLQNEELI TEQMAPHHKI LAKAIFKLTY  3060
QNKVVKVLRP TPRGAVMDII SRKDQRGSGQ VGTYGLNTFT NMEVQLIRQM EAEGVITQDD  3120
MQNPKGLKER VEKWLKECGV DRLKRMAISG DDCVVKPLDE RFGTSLLFLN DMGKVRKDIP  3180
QWEPSKGWKN WQEVPFCSHH FHKIFMKDGR SLVVPCRNQD ELIGRARISQ GAGWSLRETA  3240
CLGKAYAQMW SLMYFHRRDL RLASMAICSA VPTEWFPTSR TTWSIHAHHQ WMTTEDMLKV  3300
WNRVWIEDNP NMTDKTPVHS WEDIPYLGKR EDLWCGSLIG LSSRATWAKN IHTAITQVRN  3360
LIGKEEYVDY MPVMKRYSAP SESEGVL                                    3387
```

METHODS FOR PREVENTING DENGUE AND HEPATITIS A

CROSS REFERENCE TO RELATED APPLICATIONS

This application is a Continuation of U.S. application Ser. No. 16/809,268 filed on Mar. 4, 2020, which is a Continuation-in-part of U.S. application Ser. No. 16/561,953 filed on Sep. 5, 2019, which claims the benefit of priority from European Application 19161184.7 filed on Mar. 7, 2019, European Application 19154334.7 filed on Jan. 29, 2019, European Application 18192701.3 filed on Sep. 5, 2018, European Application 18192776.5 filed on Sep. 5, 2018, European Application 18192787.2 filed on Sep. 5, 2018, European Application 18192793.0 filed on Sep. 5, 2018, European Application 18192800.3 filed on Sep. 5, 2018, European 18192711.2 filed on Sep. 5, 2018, European Application 18192717.9 filed on Sep. 5, 2018, and European Application 18192814.4 filed on Sep. 5, 2018. The entire contents of these applications are incorporated herein by reference in their entirety.

SEQUENCE LISTING

The instant application contains an amended Sequence Listing which is submitted in electronically readable XML ST.26 format via Patent Center on Aug. 20, 2024, and is hereby incorporated by reference in its entirety. The amended electronic Sequence Listing file was created on Jul. 12, 2024, is named "T08269US3C1 Amended.xml" and is 127 KB in size.

FIELD OF THE INVENTION

The present invention relates to a method for administering a unit dose of a dengue vaccine composition to a subject or a subject population simultaneously on the same day with a hepatitis A vaccine. The unit dose according to this invention provides immune responses against all serotypes of dengue virus, i.e. DENV-1, DENV-2, DENV-3 and DENV-4 and against hepatitis A virus.

BACKGROUND OF THE INVENTION

Vaccines for protection against viral infections have been effectively used to reduce the incidence of human disease. One of the most successful technologies for viral vaccines is to immunize animals or humans with a weakened or attenuated virus strain (a "live attenuated virus"). Due to limited replication after immunization, the attenuated virus strain does not cause disease. However, the limited viral replication is sufficient to express the full repertoire of viral antigens and can generate potent and long-lasting immune responses to the virus. Thus, upon subsequent exposure to a pathogenic virus strain, the immunized individual is protected from the disease. These live attenuated viral vaccines are among the most successful vaccines used in public health.

Dengue disease is a mosquito-borne disease caused by infection with a dengue virus. Dengue virus infections can lead to debilitating and painful symptoms, including a sudden high fever, headaches, joint and muscle pain, nausea, vomiting and skin rashes. To date, four serotypes of dengue virus have been identified: dengue-1 (DENV-1), dengue-2 (DENV-2), dengue-3 (DENV-3) and dengue-4 (DENV-4). Dengue virus serotypes 1-4 can also cause dengue hemorrhagic fever (DHF) and dengue shock syndrome (DSS). In the most severe cases, DHF and DSS can be life threatening. Dengue viruses cause 50-100 million cases of debilitating dengue fever, 500,000 cases of DHF/DSS, and more than 20,000 deaths each year, a large portion of which are children. All four dengue virus serotypes are endemic throughout the tropical regions of the world and constitute the most significant mosquito-borne viral threat to humans there. Dengue viruses are transmitted to humans primarily by *Aedes aegypti* mosquitoes, but also by *Aedes albopictus* mosquitoes. Infection with one dengue virus serotype results in life-long protection from re-infection by that serotype, but does not prevent secondary infection by one of the other three dengue virus serotypes. In fact, previous infection with one dengue virus serotype may lead to an increased risk of severe disease (DHF/DSS) upon secondary infection with a different serotype.

To date, only one vaccine, a tetravalent dengue vaccine based on a yellow fever backbone, CYD-TDV (Dengvaxia®, Sanofi Pasteur, Lyon, France), has been licensed in several countries based on the clinical demonstration of an overall vaccine efficacy (VE) against virologically-confirmed dengue (VCD) of 56-61% in children in Asia and Latin America (Capeding M R et al. Clinical efficacy and safety of a novel tetravalent dengue vaccine in healthy children in Asia: a phase 3, randomised, observer-masked, placebo-controlled trial. Lancet 2014, 384:1358-65; Villar L A et al. Safety and immunogenicity of a recombinant tetravalent dengue vaccine in 9-16 year olds: a randomized, controlled, phase II trial in Latin America. Pediatr Infect Dis J 2013, 32:1102-9). However, clinical trials have shown that Dengvaxia® can enhance, rather than reduce, the risk of severe disease due to dengue infection in individuals who had not been previously infected by a dengue virus (seronegative populations). Therefore, Dengvaxia® is only recommended for use in individuals who had been previously infected with at least one dengue virus serotype (seropositive populations). More specifically, according to the European Medicine Agencys European Public Assessment report (EPAR) for the product, Dengvaxia® is only for use in people from 9 to 45 years of age who have been infected with dengue virus before and who live in areas where this infection is endemic. Endemic areas are areas where the disease occurs regularly throughout the year. See also Sridhar S et al. Effect of Dengue Serostatus on Dengue Vaccine Safety and Efficacy. N Engl J Med 2018, 379:327-40; and World Health Organization. Dengue vaccine: WHO position paper—September 2018. Wkly. Epidemiol. Rec. 2018, 93:457-476. S. R. Hadinegoro et al. report in the New England Journal of Medicine, Vol. 373, page 1195, in "Efficacy and Long-Term Safety of a Dengue Vaccine in Regions of Endemic Disease" a pooled risk of hospitalization for virologically-confirmed dengue disease among those under the age of 9 years of 1.58 indicating an increased risk for the vaccinated group with respect to severe dengue. This leaves a substantial unmet need for an effective vaccine with a good safety profile in both dengue-naïve and seropositive individuals, including those dengue-naïve populations living in endemic areas, younger individuals who may not have developed any seropositive response to dengue or been exposed to dengue, and travelers and individuals from non-endemic regions. There is also a need for outbreak control or travel vaccination, offering a reduction in the risk of dengue after only one dose.

One further disadvantage of the only currently approved dengue vaccine, Dengvaxia®, is that it must only be given to people who have had a positive test result showing a previous infection with dengue virus (EPAR), i.e. individuals with known serostatus for dengue. Thus, individuals with unknown serostatus for dengue cannot be vaccinated with Dengvaxia®.

There is hence a need for a dengue vaccine and corresponding method of inoculation that stimulates an immune response to all dengue serotypes, preferably a balanced immune response to all serotypes, and protects against dengue disease of any severity (including DSS, DHF), both in seronegative and seropositive populations, which is safe for a larger group of ages, in particular also for subjects of 9 years and younger. The development of a safe and effective vaccine capable of protecting all populations, including both seronegative and seropositive populations, and in particular children and young adults and elderly subjects in endemic settings and for the purpose of traveling, represents an important approach to the prevention and control of this global disease.

There is thus a medical need for a dengue vaccine and corresponding method of inoculation which, as well as being safe and efficacious irrespective of serostatus and in a broad age group. There is a need for a dengue vaccine and corresponding method of inoculation that avoids costly and time consuming serostatus tests or seroprevalence considerations. There is a need for a dengue vaccine and corresponding method of inoculation that can be used in an outbreak situation. Furthermore there is a medical need for a dengue vaccine which as well as being safe and effective can also be administered to individuals with unknown dengue serostatus, children under 9 years and seronegative individuals.

There is also a need for a vaccine that is administered in fewer doses than the current Dengvaxia® dosing schedule of 3 doses, 6 months apart, such as a vaccine that can be administered in only two doses or one dose to be efficacious.

The above objects are commensurate with the research priorities provided by the WHO in the Dengue Vaccine: WHO position paper—September 2018 (Wkly. Epidemiol. Rec. 2018, 93:457-476).

Hepatitis A is a liver disease caused by the hepatitis A virus (HAV). The virus is primarily spread when an uninfected (and unvaccinated) person ingests food or water that is contaminated with the feces of an infected person. The disease is closely associated with unsafe water or food, inadequate sanitation and poor personal hygiene. The virus can also be transmitted through close physical contact with an infectious person. Unlike hepatitis B and C, hepatitis A infection does not cause chronic liver disease and is rarely fatal, but it can cause debilitating symptoms and fulminant hepatitis (acute liver failure), which is often fatal. Hepatitis A occurs sporadically and in epidemics worldwide, with a tendency for cyclic recurrences.

The hepatitis A virus is one of the most frequent causes of foodborne infection. Epidemics related to contaminated food or water can erupt explosively, such as the epidemic in Shanghai in 1988 that affected about 300,000 people. Hepatitis A viruses persist in the environment and can withstand food-production processes routinely used to inactivate and/ or control bacterial pathogens. The disease can lead to significant economic and social consequences in communities. It can take weeks or months for people recovering from the illness to return to work, school, or daily life. The impact on food establishments identified with the virus, and local productivity in general, can be substantial. In developing countries with poor sanitary conditions and hygienic practices, most children (90%) have been infected with the hepatitis A virus before the age of 10 years.

The number of people traveling internationally has grown substantially in recent decades. According to the United Nations World Tourism Organization (UNWTO), over 1.1 billion tourists travelled abroad in 2014. The risk of becoming ill during international travel depends on many factors, such as the region of the world visited, the length of the trip, and the diversity of planned activities. Vaccine recommendations are a prominent part of health preparations before international travel. Vaccination against hepatitis A virus is commonly recommended for travelers to at-risk areas around the world including Asia, Africa, and Latin America.

For routine hepatitis A vaccination, a two-dose schedule is recommended, particularly in travelers at substantial risk of contracting hepatitis A and in immunocompromised individuals. However, in healthy individuals, comparable effectiveness has been achieved with a single dose. The vaccination schedule for children/adolescents (12 months through 18 years of age) as well as for adults ($\geq$19 years of age) consists of a primary dose administered intramuscularly, and a further booster dose administered intramuscularly 6 to 18 months later.

Available hepatitis A vaccines include HAVRIX® and VAQTA®.

Hence, there is a need for a safe and effective method of simultaneously preventing dengue disease and hepatitis A. In particular, there is a need for hepatitis A and dengue vaccines which provide non-inferiority when administered simultaneously to a subject or subject population and a suitable administration schedule for achieving synergy.

Furthermore, there is a need of effectively and safely preventing dengue disease and hepatitis A in subjects being unaware of their hepatitis A and/or dengue serostatus, in particular in subjects from non-endemic countries which travel into dengue and hepatitis A endemic countries.

OBJECTS AND SUMMARY

It is an object of the present invention to provide a safe and effective protection against dengue disease and hepatitis A.

It is an object of the present invention to provide a method of administration for preventing hepatitis A and dengue disease which is useful in typical vaccination settings wherein the subjects are unaware of their serostatus for dengue and/or hepatitis A and a corresponding serotest is unavailable, unpractical or unreliable.

It is an object of the present invention to provide a safe and effective protection against dengue disease and hepatitis A for travelers from hepatitis A and dengue non-endemic countries, in particular for travelers being vaccinated in travel clinics. In this context it is beneficial if multiple during the same medical appointments are avoided and vaccination can be conducted simultaneously for more than one disease.

It is an object of the present invention to provide a safe and effective vaccine for preventing hepatitis A and dengue disease in a subject or subject population and a corresponding method of preventing hepatitis A and dengue disease in a subject or a subject population from a dengue-endemic and dengue non-endemic region and for a broad range of ages, in particular for subjects between 2 to 60 years of age, preferably for subjects between 18 and 60 years of age, and independent of previous exposure to any dengue virus serotype and/or to hepatitis A virus and independent of corresponding seropositivity or seronegativity with respect to dengue and/or hepatitis A before vaccination.

It is an object of the invention to provide vaccines and a corresponding method of preventing hepatitis A and dengue disease which avoids testing for individual dengue and/or hepatitis A serostatus before individual administration of a hepatitis A and a dengue vaccine to a subject or subject population, or analysis of seroprevalence rates of dengue and/or hepatitis A in subjects or subject populations to be vaccinated.

It is an object of the present invention to provide a dengue vaccine and a hepatitis A vaccine which can be safely co-administered with TDV as travel vaccines before an international travel of a subject to HAV and dengue endemic countries and a method of safely administering these vaccines.

Therefore, the present invention is directed to a method of preventing dengue disease as well as hepatitis A.

The present invention is further directed to a method of preventing hepatitis A and dengue disease in a subject or subject population, the method comprising simultaneously on the same day administering a hepatitis A vaccine and a unit dose of a dengue vaccine composition, wherein said unit dose comprises a tetravalent dengue virus composition including four live, attenuated dengue virus strains.

Definitions

In describing the present invention, the following terms are to be used as indicated below. As used herein, the singular forms "a," "an," and "the" include plural references unless the context clearly indicates otherwise.

As used herein, the terms "unit dose of a dengue vaccine composition", "unit dose" and "unit dose of the invention as described herein" refer to the amount of a dengue vaccine which is administered to a subject in a single dose. In one embodiment, one unit dose is present in a vial and this unit dose is administered to a subject, e.g. optionally after reconstitution. In one embodiment, more than one unit dose of the dengue vaccine composition may be present in a vial so that with the content of one vial more than one subject can be vaccinated.

A "lyophilized unit dose" or "unit dose in lyophilized form" refers to the unit dose that is obtained by subjecting a given volume of the liquid dengue vaccine composition, such as 0.5 mL, to lyophilization. Thus, the aqueous formulations of the dengue vaccine composition being produced by combining the pharmaceutically acceptable excipients and the dengue virus composition comprising the four dengue virus strains, preferably TDV-1 to TDV-4, is subjected to lyophilization to obtain the lyophilized unit dose.

A "reconstituted unit dose" or "unit dose in reconstituted form" is obtained from the lyophilized dose by reconstitution with a pharmaceutically acceptable diluent. The diluent does not contain dengue virus. The reconstituted unit dose is a liquid which can be administered to a subject, for example by injection, such as subcutaneous injection.

As used herein, the term "upon reconstitution with 0.5 mL" is not limiting the reconstitution to be performed using 0.5 mL of the diluent, but refers to the concentration of the dengue viruses that will be present in the reconstituted unit dose when 0.5 mL diluent are used for reconstitution. While using a different volume for reconstitution (e.g. 0.8 mL) will result in a different concentration of dengue viruses in the reconstituted unit dose, the administration of the total volume of the unit dose (e.g. 0.8 mL) will result in the same total amount of dengue virus being administered.

As used herein, a "concentration of at least X log 10 pfu/0.5 mL" refers to the concentration of a dengue serotype in 0.5 mL, but is not limiting the unit dose to be 0.5 mL. If the unit dose has a volume different than 0.5 mL, or is lyophilized from a volume different than 0.5 mL, or is reconstituted with a volume different than 0.5 mL, said concentration will differ from the "concentration of at least X log 10 pfu/0.5 mL". However, if the unit dose has a volume of 0.5 mL, or is lyophilized from a volume of 0.5 mL, or is reconstituted with a volume of 0.5 mL, said concentration will be the "concentration of at least X log 10 pfu/0.5 mL". Thus, while the concentration may differ, the total amount of virus in the unit dose remains the same.

As used herein, the term "dengue serotype" refers to a species of dengue virus which is defined by its cell surface antigens and therefore can be distinguished by serological methods known in the art. At present, four serotypes of dengue virus are known, i.e. dengue serotype 1 (DENV-1), dengue serotype 2 (DENV-2), dengue serotype 3 (DENV-3) and dengue serotype 4 (DENV-4).

As used herein, the term "tetravalent dengue virus composition" refers to a dengue virus composition comprising four different immunogenic components from the four different dengue serotypes DENV-1, DENV-2, DENV-3 and DENV-4, preferably comprising four different live, attenuated dengue viruses, each representing one dengue serotype, and which aims to stimulate immune responses to all four dengue serotypes.

As used herein, the term "live attenuated dengue virus" refers to a viable dengue virus which is mutated to provide reduced virulence. The live attenuated dengue virus can be a dengue virus in which all components are derived from the same dengue serotype or it can be a chimeric dengue virus having parts from two or more dengue serotypes or a mixed chimeric dengue virus having parts from other flaviviruses.

A "virus strain" and in particular a "dengue virus strain" is a genetic subtype of a virus, in particular of a dengue virus, which is characterized by a specific nucleic acid sequence. A dengue serotype may comprise different strains with different nucleic acid sequences which have the same cell surface antigens. A dengue virus strain can be a dengue virus in which all components are derived from the same dengue serotype or it can be a chimeric dengue virus having parts from two or more dengue serotypes.

As used herein, "TDV-2" refers to a molecularly characterized and cloned dengue serotype 2 strain derived from the live attenuated DEN-2 PDK-53 virus strain. The PDK-53 strain is described for example in Bhamarapravati et al. (1987) Bulletin of the World Health Organization 65(2): 189-195. In one embodiment, the TDV-2 strain served as a backbone for the chimeric TDV-1, TDV-3 and TDV-4 strains into which parts from the TDV-1, TDV-3 and TDV-4 strains were introduced.

A "non-chimeric dengue virus" or "non-chimeric dengue serotype strain" or "non-chimeric dengue strain" comprises only parts from one dengue serotype. In particular, a non-chimeric dengue virus does not include parts from a different flavivirus such as yellow fever virus, Zika virus, West Nile virus, Japanese encephalitis virus, St. Louis encephalitis virus, tick-borne encephalitis virus. TDV-2 is an example of a non-chimeric dengue virus.

A "chimeric dengue virus" or "chimeric dengue serotype strain" or "chimeric dengue strain" comprises parts from at least two different dengue serotypes. As used herein, the chimeric dengue virus does not include parts from a different flavivirus such as yellow fever virus, Zika virus, West Nile virus, Japanese encephalitis virus, St. Louis encephalitis virus, tick-borne encephalitis virus. In particular, the chimeric dengue virus described herein does not include parts from the yellow fever virus. As used herein, a "chimeric dengue serotype 2/1 strain" or "DENV-2/1 chimera" or "TDV-1" refers to a dengue virus chimeric construct which comprises parts from both DENV-2 and DENV-1. In particular, in the chimeric dengue serotype 2/1 strain the prM and E proteins from DENV-1 replace the prM and E proteins from DENV-2 as detailed below. As used herein, a "chimeric dengue serotype 2/3 strain" or "DENV-2/3 chimera" or "TDV-3" refers to a dengue virus chimeric construct which comprises parts from both DENV-2 and DENV-3. In particular, in the chimeric dengue serotype 2/3 strain the prM and E proteins from DENV-3 replace the prM and E proteins from DENV-2 as detailed below. As used herein, a "chimeric dengue serotype 2/4 strain" or "DENV-2/4 chimera" or "TDV-4" refers to a dengue virus chimeric construct which comprises parts from both DENV-2 and DENV-4. In particular, in the chimeric dengue serotype 2/4 strain the prM and E proteins from DENV-4 replace the prM and E proteins from DENV-2 as detailed below. A mixed chimeric dengue virus has parts from other flaviviruses.

As used herein, "TDV" refers to a tetravalent live attenuated dengue vaccine that comprises a mixture of the four live attenuated dengue virus strains TDV-1, TDV-2, TDV-3 and TDV-4 expressing surface antigens from the four dengue serotypes DENV-1, DENV-2, DENV-3 and DENV-4, respectively. In one embodiment (e.g. also in the examples), TDV-1 has the nucleotide sequence according to SEQ ID No. 1 and/or the amino acid sequence according to SEQ ID No. 2. In one embodiment, TDV-2 has the nucleotide sequence according to SEQ ID No. 3 and/or the amino acid sequence according to SEQ ID No. 4. In one embodiment, TDV-3 has the nucleotide sequence according to SEQ ID No. 5 and/or the amino acid sequence according to SEQ ID No. 6. In one embodiment, TDV-4 has the nucleotide sequence according to SEQ ID No. 7 and/or the amino acid sequence according to SEQ ID No. 8.

As used herein, the term "dengue disease" refers to the disease which is caused by infection with dengue virus. Symptoms of dengue disease include sudden high fever, headaches, joint and muscle pain, nausea, vomiting and skin rashes. The term dengue disease also includes the more severe forms of dengue hemorrhagic fever (DHF) and dengue shock syndrome (DSS). Symptoms of DHF include increased vascular permeability, hypovolemia and abnormal blood clotting mechanisms. Subjects with DHF may present with severe manifestations of plasma leakage and hemorrhage. When a subject with DHF experiences shock he or she will be categorized as having DSS. Symptoms of DSS include bleeding that may appear as tiny spots of blood on the skin and larger patches of blood under the skin. Prolonged shock is the main factor associated with complications including massive gastrointestinal hemorrhage that can lead to death. As used herein, DHF cases are defined as VCD cases meeting WHO 1997 DHF criteria. In the context of preventing dengue disease in elderly subjects, the term "preventing dengue disease" preferably includes preventing DHF and/or DSS. In the context of preventing dengue disease in elderly subjects, the term "preventing dengue disease" preferably includes preventing severe end-organ manifestations of dengue such as hepatomegaly and acute renal failure.

As used herein, "preventing dengue disease" refers to preventing a subject from developing one or more symptoms of dengue disease because of an infection with a dengue virus. In particular, preventing dengue disease is achieved by vaccinating or inoculating a subject with a dengue vaccine composition, such as the reconstituted unit dose described herein. As used herein, the term "prophylactically treating dengue disease" is equivalent to "preventing dengue disease". In a particular embodiment, preventing dengue disease includes preventing DHS and/or DSS.

As used herein, the terms "virologically-confirmed dengue disease", "VCD case", or "VCD fever" refer to febrile illness or illness clinically suspected to be dengue disease with a positive serotype-specific reverse transcriptase polymerase chain reaction (RT-PCR). The term "virologically confirmable dengue" disease refers to a subject having febrile illness or illness clinically suspected to be dengue disease, wherein testing the subject, e.g. using RT-PCR, would confirm the presence of at least one dengue serotype. Severe forms of VCD fever will be identified as follows: Dengue Hemorrhagic Fever (DHF) was defined according to the WHO 1997 criteria. Severe dengue was defined through an assessment of an independent Dengue Case Adjudication Committee which will assess all hospitalized VCD cases (severe/non-severe) based on criteria redefined in a charter. All non-hospitalized cases are considered non-severe.

As used herein, the term "febrile illness" is defined as temperature ≥38° C. on any 2 of 3 consecutive days.

As used herein, the terms "virologically-confirmed dengue disease with hospitalization", is considered to be a surrogate for severe dengue and the "incidence of virologically-confirmed dengue disease with hospitalization" is used as a safety parameter. As used herein, the "relative risk with respect to virologically-confirmed dengue disease with hospitalization" means the number of events of virologically confirmed dengue disease with hospitalization divided by the number of subjects treated with the unit dose as disclosed herein over the number of events of virologically confirmed dengue disease with hospitalization divided by the number of subjects treated with placebo. If the "relative risk with respect to virologically-confirmed dengue disease with hospitalization" is 1 or lower the vaccine provides for the same or less risk for virologically-confirmed dengue disease with hospitalization as placebo and is considered "safe". In this context the risk of virologically-confirmed dengue disease with hospitalization may be also 0.9 or less, 0.8 or less, 0.7 or less, 0.6 or less, 0.5 or less, 0.4 or less, 0.3 or less, 0.2 or less, or 0.1 or less, in particular when determined from 30 days after a second administration until 12 months after a second administration, in particular when determined in age groups selected from the age group of 4 to 16 year old subjects, the age group of 4 to under 9 year old subjects, the age group of 2 to under 9 year old subjects, the age group of 4 to 5 year old subjects, the age group of 6 to 11 year old subjects, and the age group of 12 to 16 year old subjects.

As used herein, alternatively a vaccine is considered "safe" when the vaccine efficacy (VE) with respect to virologically-confirmed dengue disease with hospitalization is 0% or higher. This means that the vaccine provides for the same likelihood or less for virologically-confirmed dengue disease with hospitalization as placebo. In particular considered "safe" is the combined vaccine efficacy against virologically-confirmed dengue with hospitalization against all four serotypes with a 2-sided 95% confidence interval, wherein the lower bound is more than 25%, in particular when measured against placebo in a subject population of at least 1,500 or at least 2,000 healthy subjects (in particular when measured in age groups selected in particular from the age group of 4 to 16 year old subjects, the age group of 4 to under 9 year old subjects, the age group of 2 to under 9 year old subjects, the age group of 4 to 5 year old subjects, the age group of 6 to 11 year old subjects, and the age group of 12 to 16 year old subjects) being seronegative against all serotypes at baseline or being seropositive against at least one serotype at baseline, in particular when said unit dose or said placebo is administered at least twice within less than 6 months, such as within 3 months, about from first administration or from 30 days after the second or last administration of the administration schedule until at least 12 months, until 12 to 18 months, until 12 months, or until 18 months after the second or last administration of the administration schedule. In particular, the lower bound may be more than 30%, more than 40%, more than 50%, more than 60%, more than 65%, more than 66%, more than 67%, more than 68% more than 70%, or more than 75%. In particular, the 2-sided 95% confidence interval of the combined vaccine efficacy against virologically-confirmed dengue with hospitalization against all four serotypes when comparing seropositive and seronegative subjects provides for lower bounds of the 2-sided confidence interval which are within 10% points or within 15% points or within 20% points. In a particular embodiment "safe" means providing a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline from first administration of the administration schedule until 12 to 18 months after the last administration of the administration schedule.

If one of the criteria as defined above for the term "safe" is fulfilled, the vaccine is considered safe within the meaning of this invention. In this context, safe in particular refers to a vaccine that is safe for all subjects irrespective of their serostatus at baseline. This means that the vaccine can be administered without the need to determine the occurrence of a previous dengue infection in the subject before administration. Preferably, the vaccine is safe as defined above with respect to all age groups starting from 4 years of age and preferably irrespective of the serostatus, in particular from 4 years of age to 60 years of age, or 4 years of age to 16 years of age. Relevant subgroups in this context are under 9 years of age, from 2 years of age to under 9 years of age, from 4 years of age to under 9 years of age, 4 to 5 years of age, 6 to 11 years of age and 12 to 16 years of age or any age group within 4 to 16 years of age. For further definitions of VE against virologically-confirmed dengue disease with hospitalization reference is made to the disclosure below with respect to certain methods of treatment.

As used herein, "vaccine efficacy" or "VE" measure the proportionate reduction in cases among vaccinated persons. Vaccine efficacy (VE) is measured by calculating the risk of disease among vaccinated and unvaccinated persons and determining the percentage reduction in risk of disease among vaccinated persons relative to unvaccinated persons. The greater the percentage reduction of illness in the vaccinated group, the greater the vaccine efficacy. For example, a VE of 90% indicates a 90% reduction in disease occurrence among the vaccinated group, or a 90% reduction from the number of cases you would expect if they have not been vaccinated. The vaccine efficiency is calculated by the formula: $100*(1-HR)$, wherein HR is the Hazard Ratio which is defined as the Hazard rate of vaccine ($\lambda v$) divided by the Hazard rate of placebo ($\lambda c$), i.e. $HR=\lambda v/\lambda c$. $\lambda v$ denote the hazard rate for the subjects vaccinated with a tetravalent dengue vaccine composition as disclosed herein and $\lambda c$ denote the hazard rate for unvaccinated subjects, i.e. subjects receiving placebo. The hazard rate ratio HR is estimated from a Cox proportional hazard model with study vaccine as a factor, adjusted for age, and stratified by region. As used herein the term "combined vaccine efficacy against all four serotypes" is defined as the vaccine efficacy in relation to the risk of dengue disease irrespective of the serotype being responsible for the virologically-confirmed dengue disease and the subject baseline serostatus. A vaccine is considered "effective" in case the combined vaccine efficacy is above 30%. In this context the combined vaccine efficacy may be also 40% or more, 50% or more, 60% or more, 70% or more, 72% or more, or 80% or more, in particular when determined from 30 days after a second administration until 12 months after a second administration or 18 months after a second vaccination, in particular when determined in age groups selected from the age group of 4 to 16 year old subjects, the age group of 4 to under 9 year old subjects, the age group of 2 to under 9 year old subjects, the age group of 4 to 5 year old subjects, the age group of 6 to 11 year old subjects, and the age group of 12 to 16 year old subjects. In this context, effective in particular refers to a vaccine that is effective for all subjects irrespective of their serostatus at baseline. Preferably, the vaccine is effective with respect to all age groups starting from 4 years of age and preferably irrespective of the serostatus, in particular from 4 years of age to 60 years of age or from 4 years of age to 16 years of age and irrespective of the serostatus. Relevant subgroups in this context are under 9 years of age, from 2 years of age to under 9 years of age, from 4 years of age to under 9 years of age, 4 to 5 years of age, 6 to 11 years of age and 12 to 16 years of age or any age group within 4 to 16 years of age. In certain embodiments "effective" means providing a combined vaccine efficacy against all four serotypes, in preventing virologically confirmable dengue disease with a 2-sided 95% confidence interval, wherein the lower bound is more than 60%, when measured against placebo in a subject population of at least 5,000 healthy subjects irrespective of serostatus at baseline and 4 to 16 years of age, from the first administration of the administration schedule until 18 months after the last administration of the administration schedule. Further specific efficacies can be defined. As used herein, "combined vaccine efficacy against all four serotypes in seronegative subjects" refers to the efficacy measured in subjects which are seronegative at baseline. As used herein, "vaccine efficacy against a specific serotype, e.g. serotype 1" refers to the efficacy in relation to a specific serotype being responsible for the virologically-confirmed dengue disease. As used herein, "combined vaccine efficacy against all four serotypes against virologically-confirmed dengue with hospitalization" refers to the efficacy wherein only virologically-confirmed dengue cases with hospitalization are considered. Such vaccine efficacies can be determined with respect to subjects being seronegative or seropositive at baseline and for different age groups.

As used herein, the "relative risk" means the number of events of virologically confirmed dengue disease divided by the number of subjects treated with the unit dose as disclosed herein over the number of events of virologically confirmed dengue disease divided by the number of subjects treated with placebo. As used herein the term "combined relative risk against all four serotypes" is defined as the relative risk in relation to the risk of dengue disease irrespective of the serotype being responsible for the virologically-confirmed dengue disease and the subject baseline serostatus.

As used herein, "vaccinating" or "inoculating" refers to the administration of a vaccine to a subject, with the aim to prevent the subject, from developing one or more symptoms of a disease. As used herein, "vaccinating against dengue disease" or "inoculating against dengue disease" refers to the administration of a dengue vaccine composition to a subject, with the aim to prevent the subject, from developing one or more symptoms of dengue disease. In principle the method comprises a primary vaccination and optionally one or more booster vaccinations. The primary vaccination is defined as the primary administration schedule for administering the composition or unit dose as disclosed herein to establish a protective immune response and e.g. consists of two administrations e.g. within three months. Whenever an administration is mentioned within this disclosure such administration refers to the primary vaccination unless it is specified as booster vaccination. The booster vaccination refers to an administration or administration schedule which takes place after the primary vaccination e.g. at least 1 year, or 4 to 4.5 years, or even 5 or 10 years after the last administration, e.g. the second administration, of the primary vaccination schedule. The booster administration attempts at enhancing or reestablishing the immune response of the primary vaccination.

As used herein, the terms "subject" or "subjects" are limited to human subjects (e.g. infants, children or adults). The terms "elderly subject" or "elderly subjects" refer to subjects with an age of more than 60 years, such as 61 years to 100 years, 61 years to 90 years, 61 years to 80 years, 61 years to 75 years, or 61 years to 70 years.

As used herein, "subject population" refers to a group of subjects. The subject population may refer to least 40 subjects, at least 50 subjects, at least 60 subjects, at least 100 subjects or at least 1000 subjects and is defined by certain parameters. The parameters that may be used to define a subject population include, but are not limited to, the age of the subjects, whether the subjects are from a dengue endemic region or from a dengue non-endemic region and the serostatus of the subjects.

As used herein, "endemic region" refers to a region where a disease or infectious agent is constantly present and/or usually prevalent in a population within this region. As used herein, "non-endemic region" refers to a region from which the disease is absent or in which it is usually not prevalent. Accordingly, a "dengue endemic region" refers to geographic areas in which an infection with dengue virus is constantly maintained at a baseline level. A "dengue non-endemic region" is a geographic area in which an infection with dengue virus is not constantly maintained at a baseline level. Accordingly, subject populations or subjects "from a dengue endemic region" or "from a dengue non-endemic region" refer to subject populations or subjects living in geographic areas as defined above. Whether a geographic area or a subject population is dengue-endemic or not can be determined by different calculatory methods such as the ones described in Bhatt et al. (2013) Nature 496 (7446): 504-507 and supplementary material and in Stanaway et al. (2016) Lancet Infect Dis. 16(6): 712-723 and supplementary material. Overviews of dengue endemic regions and dengue epidemiology are regularly published, for example, by the WHO or CDC. Typical dengue-endemic regions are in Latin America, Southeast Asia and the Pacific islands and dengue endemic countries include, but are not limited to, Australia, Brazil, Bangladesh, Colombia, China, Dominican Republic, Indonesia, India, Mexico, Malaysia, Nicaragua, Nigeria, Pakistan, Panama, Philippines, Puerto Rico, Singapore, Sri Lanka, Thailand and Vietnam. The area's force of infection is measured by seroprevalence surveys provided as seroprevalence rate. Areas with very high force of infection are considered to have a seroprevalence rate of more than 80%. As used herein the term "region" when it concerns seroprevalence rates refers to a geographic area where the seroprevalence rate could be determined or is known, e.g. a village, a town, a city, a region, a county, a state, a province or parts of the foregoing or a whole country.

As used herein, "serostatus" refers to the amount of antibodies a subject has with respect to a certain infectious agent, in particular dengue virus. As used herein, "seronegative" or "seronaïve" means that the subject does not have neutralizing antibodies against any one of dengue serotypes DENV-1, DENV-2, DENV-3 and DENV-4 in the serum. A seronegative or seronaïve subject or subject population is defined by a neutralizing antibody titer of less than 10 for each one of the four dengue serotypes. A subject or subject population having a neutralizing antibody titer of equal to or more than 10 for at least one dengue serotype is defined as being "seropositive" with respect to said dengue serotype. Serostatus at baseline refers to the serostatus before the administration of a dengue vaccine composition as described herein.

As used herein, a "neutralizing antibody titer" refers to the amount of antibodies in the serum of a subject that neutralize the respective dengue serotype. The neutralizing antibody titer against DENV-1, DENV-2, DENV-3 and DENV-4 is determined in a serum sample of the subject using known methods such as the plaque reduction neutralization test (PRNT) as described in the WHO Guidelines (World Health Organization Department of Immunization Vaccines Biologicals (2007) Guidelines for plaque reduction neutralization testing of human antibodies to dengue viruses, WHO/IVB/07.07) or a microneutralization (MNT50) assay as described herein. As used herein, the "ratio of not more than 20 for the neutralizing antibody titer of dengue serotype 2 to the neutralizing antibody titer of dengue serotype 4" means that the neutralizing antibody titer of dengue serotype 2 is divided by the neutralizing antibody titer of dengue serotype 4 and that the ratio obtained hereby is no more than 20. In other words, the neutralizing antibody titer of dengue serotype 2 is not more than 20-times higher than the neutralizing antibody titer of dengue serotype 4 in the subject.

As used herein, the terms "geometric mean neutralizing antibody titer" and "GMT" refer to the geometric mean value of the titer of neutralizing antibodies against the corresponding dengue serotype in the serum of subjects in a subject population. The geometric mean value is calculated by a well-known formula. As used herein, the "ratio of not more than 20 for the GMT of dengue serotype 2 to the GMT of dengue serotype 4" means that the geometric mean neutralizing antibody titer of dengue serotype 2 (GMT DENV-2) is divided by the geometric mean neutralizing antibody titer of dengue serotype 4 (GMT DENV-4) and that the ratio obtained hereby is no more than 20. In other words, the geometric mean neutralizing antibody titer of dengue serotype 2 is not more than 20-times higher than the geometric mean neutralizing antibody titer of dengue serotype 4 in the subject population.

As used herein, an "immune response" refers to a subject's response to the administration of the dengue vaccine. In particular, the immune response includes the formation of neutralizing antibodies to one or more dengue serotypes. It may also include the stimulation of a cell-mediated response or the formation of antibodies to non-structural proteins such as NS1. An immune response is stimulated by the administration of a unit dose of the invention as described herein, if the titer of neutralizing antibodies against at least one dengue virus serotype and preferably against all four dengue virus serotypes is increased after said administration of said unit dose. An immune response is stimulated by the administration of a unit dose of the invention as described herein, if the secretion of interferon gamma by peripheral blood mononuclear cells stimulated with peptides from dengue virus proteins is increased after said administration of said unit dose. An immune response is stimulated by the administration of a unit dose of the invention as described herein, if the titer of antibodies to non-structural proteins such as NS1 is increased after said administration of said unit dose. In a particular embodiment, the administration of a reconstituted unit dose of the present invention as described herein stimulates the formation of neutralizing antibodies to one or more dengue serotypes, a cell-mediated response and the formation of antibodies to non-structural proteins such as NS1.

As used herein, a "balanced immune response" means that the immune response to the four dengue serotypes is sufficient to provide protection against infection by all four dengue serotypes and preferably the immune response to the four dengue serotypes has a similar strength. In particular, the neutralizing antibody titer against the four dengue serotypes at day 180 or day 365 after administration of a first reconstituted unit dose of the invention as described herein is similar, i.e. it differs by less than factor 30, by less than factor 25 or by less than factor 20.

The "total concentration in pfu/0.5 ml" which serves as a base value for the calculation of the percentage concentration for each individual component of a tetravalent dengue vaccine is shown for one exemplary tetravalent vaccine composition comprising dengue serotype 1 in a concentration of 3.60 log 10 pfu/0.5 ml, a dengue serotype 2 concentration of 4.00 log 10 pfu/0.5 ml, a dengue serotype 3 concentration of 4.60 log 10 pfu/0.5 ml and a dengue serotype 4 concentration of 5.11 log 10 pfu/0.5 ml. Primarily, the logarithmic values of the concentrations are converted into numerical values. The results of this conversion are $4 \times 10^3$ pfu/0.5 ml for serotype 1, $1 \times 10^4$ pfu/0.5 ml for serotype 2, $4 \times 10^4$ pfu/0.5 ml for serotype 3 and $1.3 \times 10^5$ pfu/0.5 ml for serotype 4. The total concentration in pfu/0.5 ml is the sum of the preceding numerical values resulting in $1.84 \times 10^5$ pfu/0.5 ml.

The "percentage concentration" for each of the serotypes 1, 2, 3 and 4 is obtained by dividing the numerical concentration value (expressed as pfu/0.5 ml) of an individual serotype by the total concentration (expressed in pfu/0.5 ml) and multiplying the result by 100 i.e.:

Percentage concentration of serotype 1=($4 \times 10^3$ pfu/0.5 ml÷$1.84 \times 10^5$ pfu/0.5 ml)×100=2%

Percentage concentration of serotype 2=($1 \times 10^4$ pfu/0.5 ml÷$1.84 \times 10^5$ pfu/0.5 ml)×100=5%

Percentage concentration of serotype 3=($4 \times 10^4$ pfu/0.5 ml÷$1.84 \times 10^5$ pfu/0.5 ml)×100=22%

Percentage concentration of serotype 4=($1.3 \times 10^5$ pfu/0.5 ml÷$1.84 \times 10^5$ pfu/0.5 ml)×100=71%.

The percentage concentrations are rounded to whole numbers.

As used herein "simultaneous" administration means an administration of at least two different vaccines such as a dengue vaccine and a hepatitis A vaccine on the same day. "On the same day" has the ordinary meaning of within 24 hours, such as e.g. within one calendar day. The simultaneous administration may be administered by the same medical practitioner, such as during the same medical appointment.

As used herein "sequential" administration means an administration of at least two different vaccines, such as a dengue vaccine and a yellow fever vaccine, or a dengue vaccine and a hepatitis A vaccine on different or subsequent days, such as within 90 days, but in a combined administration schedule.

As used herein, the term "chronic disease or condition" includes those diseases and conditions which persist in an elderly subject for three months or more. In particular, it includes diabetes, hypertension, allergies, previous strokes, ischemic heart disease, chronic renal impairment and chronic obstructive pulmonary disease.

As used herein, the term "impaired immune system" means that at least one function of at least one component of the immune system is weaker than in younger subjects, i.e. in subjects with an age of less than 60 years. These functions include a lower antioxidant response of monocytes against oxidative stress induced by dengue virus and lower T cell responses and cytokine production in response to dengue virus infection.

As used herein, "solicited systemic adverse events" in children under 6 years are defined as fever, irritability/fussiness, drowsiness and loss of appetite that occurred within 14 days after each vaccination, and in children of 6 years or more are defined as fever, headache, asthenia, malaise and myalgia that occurred within 14 days after each vaccination.

As used herein, "solicited local adverse events" are injection site pain, injection site erythema and injection site swelling that occurred within 7 days after each vaccination.

As used herein, "unsolicited adverse events" are any adverse events (AEs) that are not solicited local or systemic AEs, as defined above.

As used herein, a "serious adverse event" or "SAE" is any untoward medical occurrence or effect that at any dose results in death, is life-threatening, requires inpatient hospitalization or prolongation of existing hospitalization, results in persistent or significant disability/incapacity, is a congenital anomaly/birth defect or is medically important due to other reasons than the above mentioned criteria.

The relationship of each AE, including solicited systemic AEs (solicited local AEs are considered as related) to trial vaccine(s) will be assessed using the following categories: As used herein, "IP-Related AE" or "vaccine related AE" means that there is suspicion that there is a relationship between the vaccine and the AE (without determining the extent of probability); there is a reasonable possibility that the vaccine contributed to the AE. As used herein, "Non-IP Related" or "non-vaccine related" means that there is no suspicion that there is a relationship between the vaccine and the AE; there are other more likely causes and administration of the vaccine is not suspected to have contributed to the AE.

As used herein, a subject or subject population being "2 to 60 years of age" "or 18 to 60 years of age" refers to a subject or subject population being 2 to 60 years of age or 18 to 60 years of age on the first day of the administration of the dengue vaccine composition as described herein.

As used herein "%-points" refers to the difference of two %-values in a %-value. For example two values in % which are within 5%-points refers to e.g. one value at 1% and a second value at 6%.

As used herein, the term "determination of the previous dengue infection in the subject before administration" means that a previous dengue infection has to be assessed before vaccination in that there is a laboratory confirmed history of dengue or through an appropriately validated serological test e.g. by the method as disclosed herein such as the MNT50 test described in Example 2 or any serotesting with adequate performance in terms of specificity and cross reactivity based on the locale disease epidemiology.

As used herein % w/v refers to % mg/ml wherein e.g. 150 mg/ml are 15% w/v.

As used herein, the term "hepatitis A virus" may be abbreviated as "HAV".

As used herein, the term "placebo" may be abbreviated as "Pbo".

As used herein, "hepatitis A seronegative at baseline" or "hepatitis A naïve (at baseline)" each mean that a subject does not have a predefined amount of anti-hepatitis A antibodies in the serum. Quantitatively, the hepatitis A seronegativity of a subject is defined as an anti-hepatitis A antibody level of <10 mIU/ml. When anti-hepatitis A antibody levels are determined by ELISA, the lower level of quantification is 12.5 mIU/ml which is effectively the lower anti-HAV antibody level for determining seronegativity. Subjects having anti-hepatitis A antibody levels of ≥12.5 mIU/ml are defined as hepatitis A seropositive. An ELISA for determining the anti-hepatitis A antibodies is for example disclosed in Beck et al. J Travel Med 2004; 11:201-207.

As used herein, "at baseline" refers to the time point of the last measurement of a subject's serostatus prior to the first vaccination.

As used herein, the unit "mIU/ml" refers to milli-international unit per milliliter. This concentration unit refers to a quantity of anti-hepatitis A antibodies in a subject's serum (e.g. when measured prior or after vaccination). As used herein, the "viral antigen activity of hepatitis A vaccines" of the present invention is expressed in terms of a standard recommendation of the WHO using an enzyme-linked immunosorbent assay (ELISA). According to this recommendation of the WHO (see WHO Information Sheet "Observed Rate of Vaccine Reactions—Hepatitis A Vaccine", published June 2012), the viral antigen activity of a hepatitis A vaccine is expressed in terms of ELISA Units (EL.U.). The viral antigen activity of a hepatitis A vaccine can for example be determined by an ELISA according to Andre F E., Hepburn A. D'Hondt E., "Inactivated candidate vaccines for hepatitis", A. Prog Med Virol 1990; 37:72-95.

As used herein, the term "CCID" refers to the quantity of virus (e.g. vaccinal virus) infecting 50% of the cell culture. The CCID50 assay is a limit dilution assay with statistical titer calculation (Morrison D et al, J Infect Dis. 2010; 201(3):370-7)).

"Non-inferiority", as used herein, with respect to a simultaneous on the same day administration of a hepatitis A vaccine and a tetravalent dengue vaccine is in particular concluded, if the seroprotection rate (SPR) difference between the SPR of a subject group receiving HAV and placebo (simultaneously on the same day, i.e. control subject population) and the SPR of a subject group receiving HAV and TDV (simultaneously on the same day) has an upper bound of a two-sided 95% confidence interval which is lower than the non-inferiority margin set at 10%, wherein seroprotection rates are based on measurements on day 30 after the simultaneous administration on day 1, calculated using the Newcombe score method. A non-inferiority clinical study is a study designed to provide a comparison between at least two methods of treatments, in the present case between a simultaneous administration of a dengue vaccine and a hepatitis A vaccine and a mono-administration of either a dengue vaccine or a hepatitis A vaccine.

As used herein, the term "seroprotection rate", abbreviated "SPR", is defined by the proportion/percentage of HAV or DEN-naïve subjects at baseline who are seroprotected against HAV or DENV, respectively, at day 30 (month 1) after the first vaccination.

As used herein, the term "control subject population" refers to a group of subjects which does not receive a simultaneous administration of a hepatitis A vaccine and a unit dose of a dengue vaccine composition, but a single verum (such as a hepatitis A vaccine or a unit dose of a dengue vaccine composition) and a placebo on the same day in a clinical study setting as e.g. in a non-inferiority clinical study.

As used herein, the term "synergism" or "synergy" is defined as an effect of simultaneously on the same day administering the hepatitis A vaccine and the unit dose of the dengue vaccine composition to a subject or subject population, wherein said administering provides a higher anti-hepatitis A antibody concentration and/or a higher mean titer of neutralizing antibodies against each of the dengue virus serotypes than the corresponding simultaneous administration of a hepatitis A vaccine and a placebo on the same day and/or the simultaneous administration of a unit dose of the dengue vaccine composition and a placebo on the same day (mono-administrations). Such higher antibody concentrations after simultaneous administration in comparison to the mono-administrations are signs in favor of the simultaneous administration.

BRIEF DESCRIPTION OF THE DRAWINGS

FIG. 1: Genetic structure of the four dengue strains contained in TDV. The solid red triangles indicate the three attenuating mutations present in the 5'NCR, NS1 and NS3 proteins. The TDV-1, TDV-3 and TDV-4 strains are chimeric viruses where the prM and E genes from dengue serotype 1, 3 and 4, respectively, are inserted into the TDV-2 backbone.

FIG. 6: Scheme of the trial design of the simultaneous HAV and TDV administration study described in Example 4.

DETAILED DESCRIPTION

Denaue Virus Strains

Figure 2:
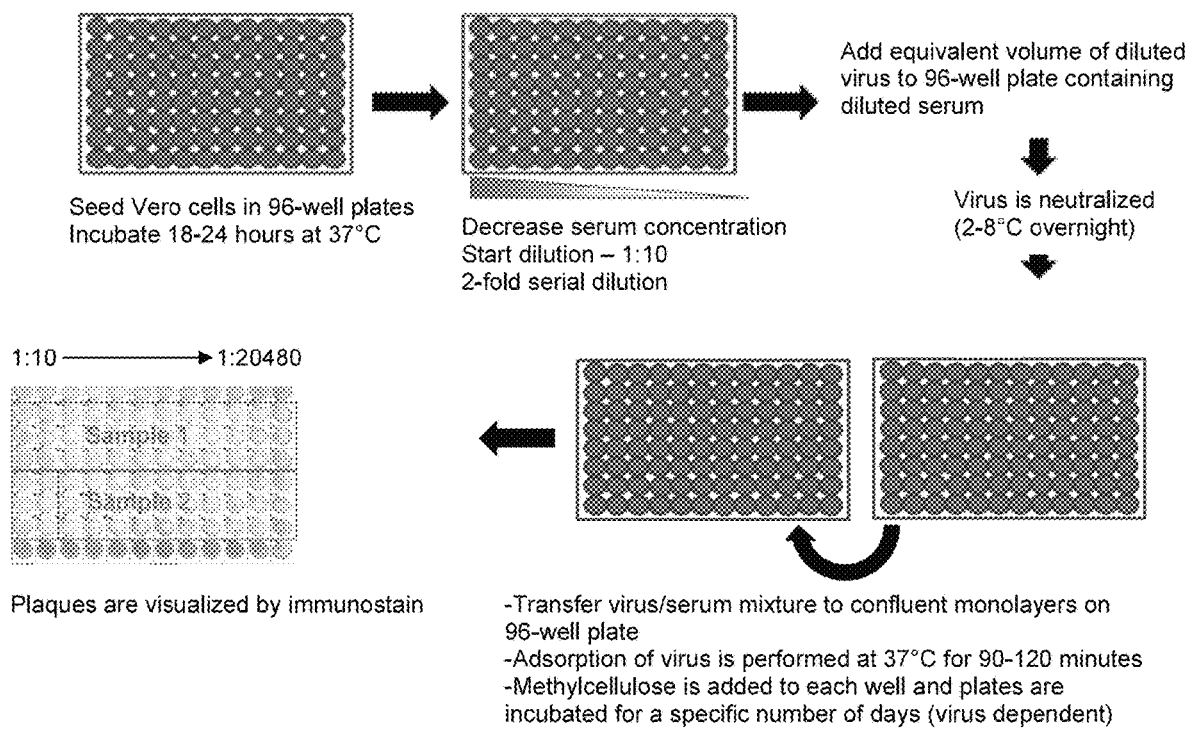
FIG. 2: Schematic drawing illustrating the microneutralization test (MNT) used to determine the titer of neutralizing antibodies.

The dengue virus is a single stranded, positive sense RNA virus of the family flaviviridae. The taxonomy is outlined in Table 1. The family flaviviridae includes three genera, flavivirus, hepacivirus and pestivirus. The genus flavivirus contains highly pathogenic and potentially hemorrhagic fever viruses, such as yellow fever virus and dengue virus, encephalitic viruses, such as Japanese encephalitis virus, Murray Valley encephalitis virus and West Nile virus, and a number of less pathogenic viruses.

TABLE 1

Dengue Virus Taxonomy of the GMO Parental Strain

| | |
|---|---|
| Family | Flaviviridae |
| Genus | Flavivirus |
| Species | Dengue virus |
| Strains | Dengue Serotype 2 (Strain 16681), Strain DEN-2 PDK-53 |
| GMO parent | TDV-2 |

Figure 1:
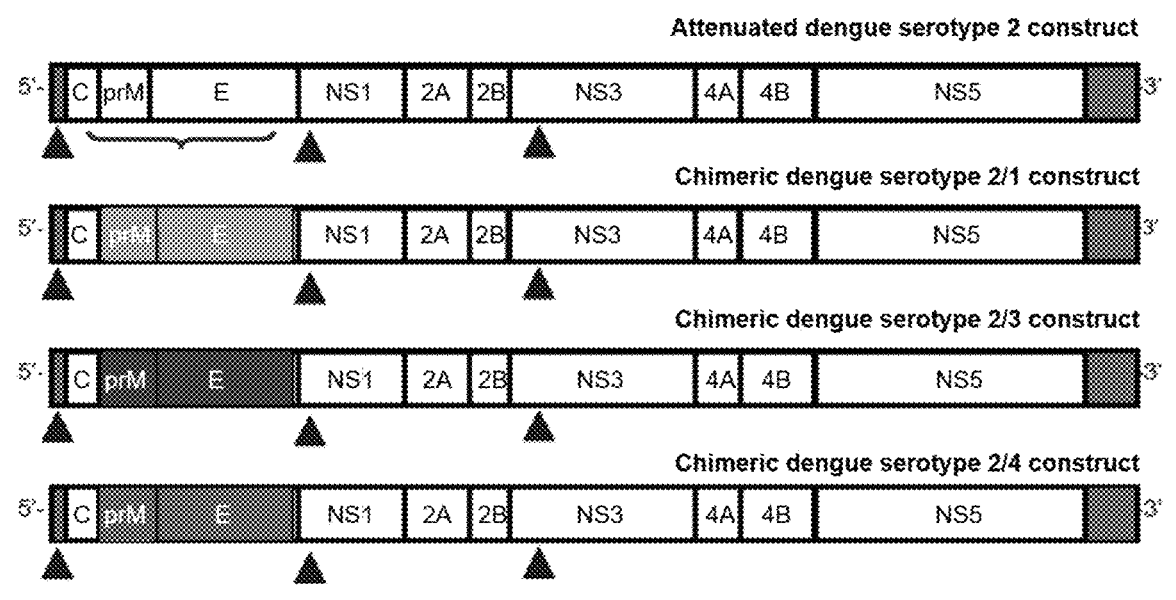

The flavivirus genome comprises in 5' to 3' direction (see FIG. 1):
- a 5-noncoding region (5'-NCR),
- a capsid protein (C) encoding region,
- a pre-membrane protein (prM) encoding region,
- an envelope protein (E) encoding region,
- a region encoding nonstructural proteins (NS1, NS2A, NS2B, NS3, NS4A, NS4B, NS5) and
- a 3' noncoding region (3-NCR).

The viral structural proteins are C, prM and E, and the nonstructural proteins are NS1 to NS5. The structural and nonstructural proteins are translated as a single polyprotein and processed by cellular and viral proteases.

The unit dose of the invention as described herein comprises a dengue virus composition that comprises four live attenuated dengue virus strains (tetravalent dengue virus composition) representing dengue serotype 1, dengue serotype 2, dengue serotype 3 and dengue serotype 4. Preferably the composition comprises chimeric dengue viruses and optionally at least one non-chimeric dengue virus, in particular a molecularly characterized and cloned dengue serotype 2 strain derived from the live attenuated DEN-2 PDK-53 virus strain (TDV-2), and three chimeric dengue strains derived from the TDV-2 strain by replacing the structural proteins prM and E from TDV-2 with the corresponding structural proteins from the other dengue serotypes, resulting in the following chimeric dengue strains:
- a DENV-2/1 chimera (TDV-1),
- a DENV-2/3 chimera (TDV-3) and
- a DENV-2/4 chimera (TDV-4).

The genetically modified tetravalent dengue vaccine TDV is based on a molecularly characterized and cloned dengue-2 virus strain (TDV-2). This attenuated TDV-2 strain was generated by cDNA cloning of the attenuated laboratory-derived DEN-2 PDK-53 virus strain that was originally isolated at Mahidol University, Bangkok, Thailand (Kinney et al. (1997) Virology 230(2): 300-308). DEN-2 PDK-53 was generated by 53 serial passages in primary dog kidney (PDK) cells at 32° C. (Bhamarapravati et al. (1987) Bull. World Health Organ. 65(2): 189-195).

The attenuated DEN-2 PDK-53 strain (the precursor of TDV-2) was derived from the wild type virus strain DEN-2 16681 (SEQ ID NO 11) and differs in nine nucleotides from the wild type as follows (Kinney et al. (1997) Virology 230(2): 300-308):
- (i) 5-noncoding region (NCR)-57 (nt-57 C-to-T): major attenuation locus
- (ii) prM-29 Asp-to-Val (nt-524 A-to-T)
- (iii) nt-2055 C-to-T (E gene) silent mutation
- (iv) NS1-53 Gly-to-Asp (nt-2579 G-to-A): major attenuation locus
- (v) NS2A-181 Leu-to-Phe (nt-4018 C-to-T)
- (vi) NS3-250 Glu-to-Val (nt-5270 A-to-T): major attenuation locus
- (vii) nt-5547 (NS3 gene) T-to-C silent mutation
- (viii) NS4A-75 Gly-to-Ala (nt-6599 G-to-C)
- *nt-8571 C-to-T (NS5 gene) silent mutation The three nucleotide changes located in the 5' noncoding region (NCR) (nucleotide 57) (mutation (i)), the NS-1 (amino acid 828 of SEQ ID NO. 4) (mutation (iv)) and NS-3 genes (amino acid 1725 of SEQ ID NO. 4) (mutation (vi)) form the basis for the attenuation phenotype of the DEN-2 PDK-53 strain (Butrapet et al. (2000) J. Virol. 74(7): 3111-3119) (Table 2). These three mutations are referred to herein as the "attenuating mutations" and are comprised in TDV-1, TDV-2, TDV-3 and TDV-4.

TABLE 2

Attenuating mutations in the common genetic backbone of all TDV strains

| Location of Mutation | Nucleotide Change in TDV-2 | Amino Acid Change in TDV-2 |
|---|---|---|
| 5' Noncoding Region (5'NCR) | 57 C to T | Not applicable (silent) |
| Nonstructural Protein 1 (NS1) | 2579 G to A | 828 Gly to Asp |
| Nonstructural Protein 3 (NS3) | 5270 A to T | 1725 Glu to Val |

In one embodiment, TDV-2 comprises in addition to the three attenuating mutations one or more mutations selected from:
- a) a mutation in the prM gene at nucleotide 524 from adenine to thymine resulting in an amino acid change at position 143 from aspartic acid to valine, and/or
- b) a silent mutation in the E gene at nucleotide 2055 from cytosine to thymine, and/or
- c) a mutation in the NS2A gene at nucleotide 4018 from cytosine to thymine resulting in an amino acid change at position 1308 from leucine to phenylalanine, and/or
- d) a silent mutation in the NS3 gene at nucleotide 5547 from thymine to cytosine, and/or
- e) a mutation in the NS4A gene at nucleotide 6599 from guanine to cytosine resulting in an amino acid change at position 2168 from glycine to alanine, and/or
- f) a silent mutation in the prM gene at nucleotide 900 from thymine to cytosine.

The silent mutation in the NS5 gene at nucleotide 8571 from cytosine to thymine of DEN-2 PDK-53 is not present in the TDV-2 strain.

In another embodiment, TDV-2 comprises in addition to the three attenuating mutations one or more mutations selected from:
- g) a mutation in the prM gene at nucleotide 592 from adenine to guanine resulting in an amino acid change at position 166 from lysine to glutamic acid, and/or
- h) a mutation in the NS5 gene at nucleotide 8803 from adenine to guanine resulting in an amino acid change at position 2903 from isoleucine to valine.

In another embodiment, TDV-2 comprises in addition to the three attenuating mutations the mutations a) and g), preferably the mutations a), g), c), e) and h), more preferably the mutations a), g), c), e), h) and b), even more preferably the mutations a), g), c), e), h), b) and d), and most preferably the mutations a) to h). The nucleotide positions and amino acids positions of TDV-2 refer to the nucleotide sequence as shown in SEQ ID NO. 3 and amino acid sequence as shown in SEQ ID NO. 4.

The dengue virus structural envelope (E) protein and pre-membrane (prM) protein have been identified as the primary antigens that elicit a neutralizing protective antibody response (Plotkin 2001). For creation of the tetravalent dengue vaccine (TDV), TDV-2 was modified by replacing the nucleic acid sequence encoding the DENV-2 prM and E glycoproteins with the nucleic acid sequence encoding the corresponding wild type prM and E glycoproteins from the DENV-1, DENV-3, and DENV-4 wild type strains DENV-1 16007, DENV-3 16562 or DENV-4 1036 virus, respectively, (see Table 3) using standard molecular genetic engineering methods (Huang et al. (2003) J. Virol. 77 (21): 11436-11447).

TABLE 3

Viral origin of prM/E gene regions of the TDV virus strains

| Virus | Strain | Origin | Source | Reference | Nucleotide sequence | Amino acid sequence |
|---|---|---|---|---|---|---|
| DENV-1 | 16007 | Thailand, 1964 | DHF/DSS patient | Halstead and Simasthien, 1970 | SEQ ID NO. 9 | SEQ ID NO. 10 |
| DENV-2 | 16681 | Thailand, 1964 | DHF/DSS patient | Halstead and Simasthien, 1970 | SEQ ID NO. 11 | SEQ ID NO. 12 |
| DENV-3 | 16562 | Philippines, 1964 | DHF patient | Halstead and Simasthien, 1970 | SEQ ID NO. 13 | SEQ ID NO. 14 |
| DENV-4 | 1036 | Indonesia, 1976 | DF patient | Gubler et al., 1979 | SEQ ID NO. 15 | SEQ ID NO. 16 |

A diagram of the four TDV strains comprised in the dengue vaccine composition is shown in FIG. 1.

The chimeric dengue strains TDV-1, TDV-3 and TDV-4 express the surface antigens prM and E of the DENV-1, DENV-3 or DENV-4 viruses, as depicted in Table 3 respectively, and retain the genetic alterations responsible for the attenuation of TDV-2. Thus, each of the TDV-1, TDV-3 and TDV-4 strains comprises the attenuating mutations described in Table 2.

In one embodiment, TDV-1 comprises in addition to the three attenuating mutations one or more mutations selected from:
c) a mutation in the NS2A gene at nucleotide 4018 from cytosine to thymine resulting in an amino acid change at position 1308 from leucine to phenylalanine, and/or
d) a silent mutation in the NS3 gene at nucleotide 5547 from thymine to cytosine, and/or
e) a mutation in the NS4A gene at nucleotide 6599 from guanine to cytosine resulting in an amino acid change at position 2168 from glycine to alanine, and/or
i) a silent mutation in the E gene at nucleotide 1575 from thymine to cytosine, and/or
j) a silent mutation in the junction site between the prM-E gene and the DEN-2 PDK-53 backbone at nucleotide 453 from adenine to guanine, and/or
k) a mutation in the junction site between the prM-E gene and the DEN-2 PDK-53 backbone at nucleotides 2381/2382 from thymine-guanine to cytosine-cytosine resulting in an amino acid change at position 762 from valine to alanine.

In another embodiment, TDV-1 comprises in addition to the three attenuating mutations one or more mutations selected from:
l) a mutation in the NS2A gene at nucleotide 3823 from adenine to cytosine resulting in an amino acid change at position 1243 from isoleucine to leucine, and/or
m) a mutation in the NS2B gene at nucleotide 4407 from adenine to thymine resulting in an amino acid change at position 1437 from glutamic acid to aspartic acid, and/or
n) a silent mutation in the NS4B gene at nucleotide 7311 from adenine to guanine.

In another embodiment, the TDV-1 strain comprises in addition to the three attenuating mutations the mutations l) and m), preferably the mutations l), m), c) and e), even more preferably the mutations l), m), c), e), d) and n), and most preferably the mutations l), m), c), e), d), n), i), j) and k). The nucleotide positions and amino acids positions of TDV-1 refer to the nucleotide sequence as shown in SEQ ID NO. 1 and amino acid sequence as shown in SEQ ID NO. 2.

In one embodiment, TDV-3 comprises in addition to the three attenuating mutations one or more mutations selected from:
c) a mutation in the NS2A gene at nucleotide 4012 from cytosine to thymine resulting in an amino acid change at position 1306 from leucine to phenylalanine, and/or
d) a silent mutation in the NS3 gene at nucleotide 5541 from thymine to cytosine, and/or
e) a mutation in the NS4A gene at nucleotide 6593 from guanine to cytosine resulting in an amino acid change at position 2166 from glycine to alanine, and/or
j) a silent mutation in the junction site between the prM-E gene and the DEN-2 PDK-53 backbone at nucleotide 453 from adenine to guanine, and/or
k) a mutation in the junction site between the prM-E gene and the DEN-2 PDK-53 backbone at nucleotides 2375/2376 from thymine-guanine to cytosine-cytosine resulting in an amino acid change at position 760 from valine to alanine, and/or
o) a silent mutation in the prM gene at nucleotide 552 from cytosine to thymine, and/or
p) a mutation in the E gene at nucleotide 1970 from adenine to thymine resulting in an amino acid change at position 625 from histidine to leucine.

In another embodiment, TDV-3 comprises in addition to the three attenuating mutations one or more mutations selected from:
q) a mutation in the E gene at nucleotide 1603 from adenine to thymine resulting in an amino acid change at position 503 from threonine to serine, and/or
r) a silent mutation in the NS5 gene at nucleotide 7620 from adenine to guanine.

In another embodiment, TDV-3 comprises in addition to the three attenuating mutations the mutations p) and q), preferably the mutations p), q), c) and e), even more preferably the mutations p), q), c), e), d) and r), and most preferably the mutations p), q), c), e), d), r), j), k) and o). The nucleotide positions and amino acids positions of TDV-3 refer to the nucleotide sequence as shown in SEQ ID NO. 5 and amino acid sequence as shown in SEQ ID NO. 6.

In one embodiment, TDV-4 comprises in addition to the three attenuating mutations one or more mutations selected from:
c) a mutation in the NS2A gene at nucleotide 4018 from cytosine to thymine resulting in an amino acid change at position 1308 from leucine to phenylalanine, and/or d) a silent mutation in the NS3 gene at nucleotide 5547 from thymine to cytosine, and/or
e) a mutation in the NS4A gene at nucleotide 6599 from guanine to cytosine resulting in an amino acid change at position 2168 from glycine to alanine, and/or
j) a silent mutation in the junction site between the prM-E gene and the DEN-2 PDK-53 backbone at nucleotide 453 from adenine to guanine, and/or
k) a mutation in the junction site between the prM-E gene and the DEN-2 PDK-53 backbone at nucleotides 2381/2382 from thymine-guanine to cytosine-cytosine resulting in an amino acid change at position 762 from valine to alanine, and/or
s) a mutation in the C gene at nucleotide 396 from adenine to cytosine resulting in an amino acid change at position 100 from arginine to serine, and/or
t) a silent mutation in the E gene at nucleotide 1401 from adenine to guanine, and/or
u) a mutation in the E gene at nucleotide 2027 from cytosine to thymine resulting in an amino acid change at position 644 from alanine to valine, and/or
v) a mutation in the E gene at nucleotide 2275 from adenine to cytosine resulting in an amino acid change at position 727 from methionine to leucine.

In another embodiment, TDV-4 comprises in addition to the three attenuating mutations one or more mutations selected from:
w) a silent mutation in the C gene at nucleotide 225 from adenine to thymine, and/or
x) a mutation in the NS2A gene at nucleotide 3674 from adenine to guanine resulting in an amino acid change at position 1193 from aspartic acid to glycine, and/or
y) a mutation in the NS2A gene at nucleotide 3773 from adenine to an adenine/guanine mix resulting in an amino acid change at position 1226 from lysine to a lysine/arginine_mix, and/or
z) a silent mutation in the NS3 gene at nucleotide 5391 from cytosine to thymine, and/or
aa) a mutation in the NS4A gene at nucleotide 6437 from cytosine to thymine resulting in an amino acid change at position 2114 from alanine to valine, and/or
bb) a silent mutation in the NS4B gene at nucleotide 7026 from thymine to a thymine/cytosine mix, and/or
cc) a silent mutation in the NS5 gene at nucleotide 9750 from adenine to cytosine.

In another embodiments, TDV-4 comprises in addition to the three attenuating mutations the mutation s), u) and v), preferably the mutations s), u), v), c), e), x), y) and aa), even more preferably the mutations s), u), v), c), e), x), y), aa) and w), even more preferably the mutations s), u), v), c), e), x), y), aa), w), d), z), bb) and cc), and most preferably the mutations s), u), v), c), e), x), y), aa), w), d), z), bb), cc), j), k) and t). The nucleotide positions and amino acids positions of TDV-4 refer to the nucleotide sequence as shown in SEQ ID NO. 7 and amino acid sequence as shown in SEQ ID NO. 8.

In a preferred embodiment, TDV-1 has the nucleotide sequence of SEQ ID NO. 1, TDV-2 has the nucleotide sequence of SEQ ID NO. 3, TDV-3 has the nucleotide sequence of SEQ ID NO. 5, and/or TDV-4 has the nucleotide sequence of SEQ ID NO. 7. In a further preferred embodiment, TDV-1 has the amino acid sequence of SEQ ID NO. 2, TDV-2 has the amino acid sequence of SEQ ID NO. 4, TDV-3 has the amino acid sequence of SEQ ID NO. 6, and TDV-4 has the amino acid sequence of SEQ ID NO. 8. In a further preferred embodiment, TDV-1 has a nucleotide sequence encoding the amino acid sequence of SEQ ID NO. 2, TDV-2 has a nucleotide sequence encoding the amino acid sequence of SEQ ID NO. 4, TDV-3 has a nucleotide sequence encoding the amino acid sequence of SEQ ID NO. 6, and TDV-4 has a nucleotide sequence encoding the amino acid sequence of SEQ ID NO. 8.

TABLE 4

Sequences of the TDV virus strains

| SEQ ID NO. | dengue virus strain | sequence type |
| --- | --- | --- |
| SEQ ID NO. 1 | TDV-1 | nucleotide sequence |
| SEQ ID NO. 2 | TDV-1 | amino acid sequence |
| SEQ ID NO. 3 | TDV-2 | nucleotide sequence |
| SEQ ID NO. 4 | TDV-2 | amino acid sequence |
| SEQ ID NO. 5 | TDV-3 | nucleotide sequence |
| SEQ ID NO. 6 | TDV-3 | amino acid sequence |
| SEQ ID NO. 7 | TDV-4 | nucleotide sequence |
| SEQ ID NO. 8 | TDV-4 | amino acid sequence |

Thus, in a particularly preferred embodiment, the unit dose of the invention as described herein comprises the live attenuated dengue virus strains TDV-1, TDV-2, TDV-3 and TDV-4, wherein TDV-1, TDV-3 and TDV-4 are based on TDV-2 and comprise the prM and E regions of DENV-1, -3 and -4, respectively. In another particularly preferred embodiment, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

The E protein of DENV-3 has two fewer amino acids than the E protein of DENV-2. Therefore, the nucleotides and encoded amino acid backbone of TDV-2 starting after the E region of DENV-3 at nucleotide 2374 of SEQ ID NO. 5 and amino acid 760 of SEQ ID NO. 6 are 6 nucleotides less and 2 amino acids less than the original TDV-2 nucleotide and amino acid positions, respectively.

Dengue Vaccine Composition

The present invention is in part directed to a unit dose of a dengue vaccine composition as described. The dengue vaccine composition comprises a tetravalent dengue virus composition, also referred to as dengue virus composition, and pharmaceutically acceptable excipients.

Dengue Virus Composition, Virus Concentrations and %-Concentrations

The present invention is in part directed to a unit dose of a dengue vaccine composition, wherein the dengue vaccine composition comprises a tetravalent dengue virus composition including four live attenuated dengue virus strains:
(i) a dengue serotype 1 preferably in a concentration of at least 3.3 log 10 pfu/0.5 mL,
(ii) a dengue serotype 2 preferably in a concentration of at least 2.7 log 10 pfu/0.5 mL,
(iii) a dengue serotype3 preferably in a concentration of at least 4.0 log 10 pfu/0.5 mL, and
(iv) a dengue serotype 4 preferably strain in a concentration of at least 4.5 log 10 pfu/0.5 mL.

In one embodiment, the dengue vaccine composition comprises a tetravalent dengue virus composition including four live attenuated dengue virus strains:
 (i) a dengue serotype 1 preferably in a concentration of at least 3.3 log 10 pfu/0.5 mL to 3.8 log 10 pfu/0.5 mL,
 (ii) a dengue serotype 2 preferably in a concentration of at least 2.7 log 10 pfu/0.5 mL,
 (iii) a dengue serotype 3 preferably in a concentration of at least 4.0 log 10 pfu/0.5 mL, and
 (iv) a dengue serotype 4 preferably strain in a concentration of at least 4.5 log 10 pfu/0.5 ml or 4.6 log 10 pfu/0.5 mL, optionally to 6.2 log 10 pfu/0.5 ml.

The present invention is further in part directed to a unit dose of a dengue vaccine composition, wherein the dengue vaccine composition comprises a tetravalent dengue virus composition including four live attenuated dengue virus strains:
 (i) a chimeric dengue serotype 2/1 strain in a concentration of at least 3.3 log 10 pfu/0.5 mL,
 (ii) a dengue serotype 2 strain in a concentration of at least 2.7 log 10 pfu/0.5 mL,
 (iii) a chimeric dengue serotype 2/3 strain in a concentration of at least 4.0 log 10 pfu/0.5 mL, and
 (iv) a chimeric dengue serotype 2/4 strain in a concentration of at least 4.5 log 10 pfu/0.5 mL.

In one embodiment, the dengue vaccine composition comprises a tetravalent dengue virus composition including four live attenuated dengue virus strains:
 (i) a chimeric dengue serotype 2/1 strain in a concentration of at least 3.3 log 10 pfu/0.5 mL to 3.8 log 10 pfu/0.5 ml,
 (ii) a dengue serotype 2 strain in a concentration of at least 2.7 log 10 pfu/0.5 mL,
 (iii) a chimeric dengue serotype 2/3 strain in a concentration of at least 4.0 log 10 pfu/0.5 mL, and
 (iv) a chimeric dengue serotype 2/4 strain in a concentration of at least 4.5 log 10 pfu/0.5 mL or at least 4.6 log 10 pfu/0.5 mL to optionally 6.2 log 10 pfu/0.5 ml.

Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4.

In one embodiment, the dengue vaccine composition comprises a tetravalent dengue virus composition including four live attenuated dengue virus strains wherein:
 (i) the dengue serotype 1 (e.g. chimeric dengue serotype 2/1 strain) has a concentration of 3.3 log 10 pfu/0.5 mL to 5.3 log 10 pfu/0.5 mL,
 (ii) the dengue serotype 2 (e.g. dengue serotype 2 strain) has a concentration of 2.7 log 10 pfu/0.5 mL to 5.0 log 10 pfu/0.5 mL,
 (iii) the dengue serotype 3 (e.g. chimeric dengue serotype 2/3 strain) has a concentration of 4.0 log 10 pfu/0.5 mL to 6.0 log 10 pfu/0.5 mL, and
 (iv) the dengue serotype 4 (e.g. chimeric dengue serotype 2/4 strain) has a concentration of 4.5 log 10 pfu/0.5 mL to 6.5 log 10 pfu/0.5 mL.

In one such embodiment, the dengue vaccine composition comprises a tetravalent dengue virus composition including four live attenuated dengue virus strains wherein:
 (i) the dengue serotype 1 (e.g. chimeric dengue serotype 2/1 strain) has a concentration of 3.3 log 10 pfu/0.5 mL to 5.0 log 10 pfu/0.5 mL,
 (ii) the dengue serotype 2 (e.g. dengue serotype 2 strain) has a concentration of 2.7 log 10 pfu/0.5 mL to 4.9 log 10 pfu/0.5 mL,
 (iii) the dengue serotype 3 (e.g. chimeric dengue serotype 2/3 strain) has a concentration of 4.0 log 10 pfu/0.5 mL to 5.7 log 10 pfu/0.5 mL, and
 (iv) the dengue serotype 4 (e.g. chimeric dengue serotype 2/4 strain) has a concentration of 4.5 log 10 pfu/0.5 mL to 6.2 log 10 pfu/0.5 mL.

In a further such embodiment, the dengue vaccine composition comprises a tetravalent dengue virus composition including four live attenuated dengue virus strains wherein:
 (i) a dengue serotype 1 (e.g. chimeric dengue serotype 2/1 strain) has a concentration of 3.3 log 10 pfu/dose to 5.0 log 10 pfu/dose,
 (ii) a dengue serotype 2 (e.g. dengue serotype 2 strain) has a concentration of 2.7 log 10 pfu/dose to 4.9 log 10 pfu/dose,
 (iii) a dengue serotype 3 (e.g. chimeric dengue serotype 2/3 strain) has a concentration of 4.0 log 10 pfu/dose to 5.7 log 10 pfu/dose, and
 (iv) a dengue serotype 4 (e.g. chimeric dengue serotype 2/4 strain) has a concentration of 4.5 log 10 pfu/dose to 5.5 log 10 pfu/dose.

In a further such embodiment, the dengue vaccine composition comprises a tetravalent dengue virus composition including four live attenuated dengue virus strains wherein:
 (i) a dengue serotype 1 (e.g. chimeric dengue serotype 2/1 strain) has a concentration of 3.3 log 10 pfu/dose to 4.1 log 10 pfu/dose,
 (ii) a dengue serotype 2 (e.g. dengue serotype 2 strain) has a concentration of 2.7 log 10 pfu/dose to 3.6 log 10 pfu/dose,
 (iii) a dengue serotype 3 (e.g. chimeric dengue serotype 2/3 strain) has a concentration of 4.0 log 10 pfu/dose to 4.7 log 10 pfu/dose, and
 (iv) a dengue serotype 4 (e.g. chimeric dengue serotype 2/4 strain) has a concentration of 4.5 log 10 pfu/dose to 5.3 log 10 pfu/dose.

In a further such embodiment, the dengue vaccine composition comprises a tetravalent dengue virus composition including four live attenuated dengue virus strains wherein:
 (i) a dengue serotype 1 (e.g. chimeric dengue serotype 2/1 strain) has a concentration of 3.3 log 10 pfu/0.5 mL to 3.6 log 10 pfu/0.5 mL,
 (ii) a dengue serotype 2 (e.g. dengue serotype 2 strain) has a concentration of 2.7 log 10 pfu/0.5 mL to 4.0 log 10 pfu/0.5 mL,
 (iii) a dengue serotype 3 (e.g. chimeric dengue serotype 2/3 strain) has a concentration of 4.0 log 10 pfu/0.5 mL to 4.6 log 10 pfu/0.5 mL, and
 (iv) a dengue serotype 4 (e.g. chimeric dengue serotype 2/4 strain) has a concentration of 4.5 log 10 pfu/0.5 ml or 4.6 log 10 pfu/0.5 mL to 5.1 log 10 pfu/0.5 mL.

In another embodiment, the dengue vaccine composition comprises a tetravalent dengue virus composition including four live attenuated dengue virus strains wherein:
 (i) the dengue serotype 1 (e.g. chimeric dengue serotype 2/1 strain) has a concentration of 4.3 log 10 pfu/0.5 mL to 4.4 log 10 pfu/0.5 mL,
 (ii) the dengue serotype 2 (e.g. dengue serotype 2 strain) has a concentration of 3.7 log 10 pfu/0.5 mL to 3.8 log 10 pfu/0.5 mL,
 (iii) the dengue serotype 3 (e.g. chimeric dengue serotype 2/3 strain) has a concentration of 4.5 log 10 pfu/0.5 mL to 5.0 log 10 pfu/0.5 mL, and
 (iv) the dengue serotype 4 (e.g. chimeric dengue serotype 2/4 strain) has a concentration of 5.5 log 10 pfu/0.5 mL to 5.6 log 10 pfu/0.5 mL.

In a particularly preferred embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 4.4 log 10 pfu/0.5 mL,
(ii) the dengue serotype 2 (e.g. dengue serotype 2 strain) has a concentration of 3.8 log 10 pfu/0.5 mL,
(iii) the dengue serotype 3 (e.g. chimeric dengue serotype 2/3 strain) has a concentration of 4.5 log 10 pfu/0.5 mL, and
(iv) the dengue serotype 4 (e.g. chimeric dengue serotype 2/4 strain) has a concentration of 5.6 log 10 pfu/0.5 mL.

In another particularly preferred embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 3.6 log 10 pfu/0.5 mL,
(ii) the dengue serotype 2 (e.g. dengue serotype 2 strain) has a concentration of 4.0 log 10 pfu/0.5 mL,
(iii) the dengue serotype 3 (e.g. chimeric dengue serotype 2/3 strain) has a concentration of 4.6 log 10 pfu/0.5 mL, and
(iv) the dengue serotype 4 (e.g. chimeric dengue serotype 2/4 strain) has a concentration of 5.1 log 10 pfu/0.5 mL.

In another preferred embodiment, the dengue vaccine composition comprises a tetravalent dengue virus composition including four live attenuated dengue virus strains wherein the arithmetic sum of all four serotypes is less than 6.7 log 10 pfu/0.5 mL, preferably less than 5.5 log 10 pfu/0.5 mL. In certain such embodiments, the arithmetic sum of all four serotypes is at least 4.6 log 10 pfu/0.5 mL. In a preferred embodiment, the dengue vaccine composition comprises a tetravalent dengue virus composition including four live attenuated dengue virus strains wherein the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL.

Preferably, in said embodiments the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

The present invention is in part directed to a unit dose of a dengue vaccine composition, wherein the dengue vaccine composition comprises a tetravalent dengue virus composition including four live attenuated dengue virus strains:
(i) a dengue serotype 1 (e.g. chimeric dengue serotype 2/1 strain) in a concentration of at least 3.3 log 10 pfu/dose,
(ii) a dengue serotype 2 (e.g. dengue serotype 2 strain) in a concentration of at least 2.7 log 10 pfu/dose,
(iii) a dengue serotype 3 (e.g. chimeric dengue serotype 2/3 strain) in a concentration of at least 4.0 log 10 pfu/dose, and
(iv) a dengue serotype 4 (e.g. chimeric dengue serotype 2/4 strain) in a concentration of at least 4.5 log 10 pfu/dose.

In one embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 3.3 log 10 pfu/dose to 5.3 log 10 pfu/dose,
(ii) the dengue serotype 2 (e.g. dengue serotype 2 strain) has a concentration of 2.7 log 10 pfu/dose to 5.0 log 10 pfu/dose,
(iii) the dengue serotype 3 (e.g. chimeric dengue serotype 2/3 strain) has a concentration of 4.0 log 10 pfu/dose to 6.0 log 10 pfu/dose, and
(iv) the dengue serotype 4 (e.g. chimeric dengue serotype 2/4 strain) has a concentration of 4.5 log 10 pfu/dose to 6.5 log 10 pfu/dose.

In one such embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 3.3 log 10 pfu/dose to 5.0 log 10 pfu/dose,
(ii) the dengue serotype 2 (e.g. dengue serotype 2 strain) has a concentration of 2.7 log 10 pfu/dose to 4.9 log 10 pfu/dose,
(iii) the dengue serotype 3 (e.g. chimeric dengue serotype 2/3 strain) has a concentration of 4.0 log 10 pfu/dose to 5.7 log 10 pfu/dose, and
(iv) the dengue serotype 4 (e.g. chimeric dengue serotype 2/4 strain) has a concentration of 4.5 log 10 pfu/dose to 6.2 log 10 pfu/dose.

In a further such embodiment, the dengue vaccine composition comprises a tetravalent dengue virus composition including four live attenuated dengue virus strains wherein:
(i) a dengue serotype 1 (e.g. chimeric dengue serotype 2/1 strain) has a concentration of 3.3 log 10 pfu/dose to 5.0 log 10 pfu/dose,
(ii) a dengue serotype 2 (e.g. dengue serotype 2 strain) has a concentration of 2.7 log 10 pfu/dose to 4.9 log 10 pfu/dose,
(iii) a dengue serotype 3 (e.g. chimeric dengue serotype 2/3 strain) has a concentration of 4.0 log 10 pfu/dose to 5.7 log 10 pfu/dose, and
(iv) a dengue serotype 4 (e.g. chimeric dengue serotype 2/4 strain) has a concentration of 4.5 log 10 pfu/dose to 5.5 log 10 pfu/dose.

In a further such embodiment, the dengue vaccine composition comprises a tetravalent dengue virus composition including four live attenuated dengue virus strains wherein:
(i) a dengue serotype 1 (e.g. chimeric dengue serotype 2/1 strain) has a concentration of 3.3 log 10 pfu/dose to 4.1 log 10 pfu/dose,
(ii) a dengue serotype 2 (e.g. dengue serotype 2 strain) has a concentration of 2.7 log 10 pfu/dose to 3.6 log 10 pfu/dose,
(iii) a dengue serotype 3 (e.g. chimeric dengue serotype 2/3 strain) has a concentration of 4.0 log 10 pfu/dose to 4.7 log 10 pfu/dose, and
(iv) a dengue serotype 4 (e.g. chimeric dengue serotype 2/4 strain) has a concentration of 4.5 log 10 pfu/dose to 5.3 log 10 pfu/dose.

In a further such embodiment, the dengue vaccine composition comprises a tetravalent dengue virus composition including four live attenuated dengue virus strains wherein:
(i) a dengue serotype 1 (e.g. chimeric dengue serotype 2/1 strain) has a concentration of 3.3 log 10 pfu/dose to 3.6 log 10 pfu/dose, (ii) a dengue serotype 2 (e.g. dengue serotype 2 strain) has a concentration of 2.7 log 10 pfu/dose to 4.0 log 10 pfu/dose,
(iii) a dengue serotype 3 (e.g. chimeric dengue serotype 2/3 strain) has a concentration of 4.0 log 10 pfu/dose to 4.6 log 10 pfu/dose, and
(iv) a dengue serotype 4 (e.g. chimeric dengue serotype 2/4 strain) has a concentration of 4.5 log 10 pfu/dose 4.6 log 10 pfu/dose to 5.1 log 10 pfu/dose.

In another embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 4.3 log 10 pfu/dose to 4.4 log 10 pfu/dose,
(ii) the dengue serotype 2 (e.g. dengue serotype 2 strain) has a concentration of 3.7 log 10 pfu/dose to 3.8 log 10 pfu/dose,
(iii) the dengue serotype 3 (e.g. chimeric dengue serotype 2/3 strain) has a concentration of 4.5 log 10 pfu/dose to 5.0 log 10 pfu/dose, and
(iv) the dengue serotype 4 (e.g. chimeric dengue serotype 2/4 strain) has a concentration of 5.5 log 10 pfu/dose to 5.6 log 10 pfu/dose.

In a particularly preferred embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 4.4 log 10 pfu/dose,
(ii) the dengue serotype 2 (e.g. dengue serotype 2 strain) has a concentration of 3.8 log 10 pfu/dose,
(iii) the dengue serotype 3 (e.g. chimeric dengue serotype 2/3 strain) has a concentration of 4.5 log 10 pfu/dose, and
(iv) the dengue serotype 4 (e.g. chimeric dengue serotype 2/4 strain) has a concentration of 5.6 log 10 pfu/dose.

In another particularly preferred embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 3.6 log 10 pfu/dose,
(ii) the dengue serotype 2 (e.g. dengue serotype 2 strain) has a concentration of 4.0 log 10 pfu/dose,
(iii) the dengue serotype 3 (e.g. chimeric dengue serotype 2/3 strain) has a concentration of 4.6 log 10 pfu/dose, and
(iv) the dengue serotype 4 (e.g. chimeric dengue serotype 2/4 strain) has a concentration of 5.1 log 10 pfu/dose.

In another preferred embodiment, the dengue vaccine composition comprises a tetravalent dengue virus composition including four live attenuated dengue virus strains wherein the arithmetic sum of all four serotypes is less than 6.7 log 10 pfu/dose, preferably less than 5.5 log 10 pfu/dose. In certain such embodiments, the arithmetic sum of all four serotypes is at least 4.6 log 10 pfu/dose. in a preferred embodiment, the dengue vaccine composition comprises a tetravalent dengue virus composition including four live attenuated dengue virus strains wherein the arithmetic sum of all four serotypes is in the range of 4.6 log 10 pfu/dose to 6.7 log 10 pfu/dose, preferably in the range of 4.6 log 10 pfu/dose to 5.5 log 10 pfu/dose.

In one embodiment in the composition (i), (ii), (iii), and (iv) provide a total concentration of pfu/0.5 mL and based on said concentration, the concentration of (iii) at least 10% of the total concentration in pfu/0.5 mL.

In one embodiment in the composition (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 6%, or at least 8%, or at least 10%, or at least 12%, or at least 14%, or at least 16%, or at least 18%.

It is preferred that the concentration in the reconstituted unit dose of (iii) in pfu/0.5 mL is at least 10%.

In one embodiment in the composition (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6%.

Preferably, in said embodiments the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

The concentration of the different dengue viruses is preferably determined by an immuno-focus assay known in the art. For example, the concentration may be determined by an immuno-focus assay wherein serial dilutions of dengue virus are applied to monolayers of adherent cells, such as Vero cells. After a period of time which allows infectious viruses to bind to the cells and to be taken up by the cells, an overlay containing thickening agents, such as agarose or carboxymethylcellulose, is added to prevent diffusion of viruses so that progeny viruses can only infect cells adjacent to the original infected cells. After a period of incubation to allow viral replication, cells are fixed and stained using serotype-specific anti-dengue monoclonal antibodies and a secondary antibody such as an antibody labeled with alkaline phosphatase. The foci are stained by adding a suitable substrate for the enzyme attached to the secondary antibody, such as 5-bromo-4-chloro-3-indolyl-phosphate/nitro blue tetrazolium phosphatase substrate. The number of plaques on the plate corresponds to the plaque forming units of the virus in the solutions applied to the cells. For example, a concentration of 1,000 pfu/μl indicates that 1 μl of the solution applied to the cells contains enough viruses to produce 1,000 plaques in a cell monolayer.

The dengue vaccine composition comprises a tetravalent dengue virus composition including four live attenuated dengue virus strains, wherein a chimeric dengue serotype 2/1 strain, a dengue serotype 2 strain, a chimeric dengue serotype 2/3 strain, and a chimeric dengue serotype 2/4 strain provide a total concentration in pfu/0.5 mL. The term "total concentration in pfu/0.5 mL" or "total concentration in pfu/dose" is the sum of the concentrations of the dengue serotype 1 (e.g. chimeric dengue serotype 2/1 strain), dengue serotype 2 (e.g. the dengue serotype 2 strain), the dengue serotype 3 (e.g. chimeric dengue serotype 2/3 strain) and the dengue serotype 4 (e.g. chimeric dengue serotype 2/4 strain), preferably the sum of the concentrations of TDV-1, TDV-2, TDV-3 and TDV-4, and is defined as 100% of the dengue virus concentration as determined by pfu (plaque forming units) in 0.5 mL or in a dose.

In one embodiment, the dengue vaccine composition comprises a tetravalent dengue virus composition including four live attenuated dengue virus strains, wherein a dengue serotype 1 (e.g. chimeric dengue serotype 2/1 strain), a dengue serotype 2 (e.g. dengue serotype 2 strain), a dengue serotype 3 (e.g. chimeric dengue serotype 2/3 strain), and a dengue serotype 4 (e.g. chimeric dengue serotype 2/4 strain) provide a total concentration in pfu/0.5 mL, wherein based on said total concentration the concentration of a dengue serotype 2 (e.g. dengue serotype 2 strain) measured in pfu/0.5 mL is less than 10% of the total concentration, or less than 8%, or less than 6% of the total concentration, and wherein the concentration of a dengue serotype 4 (e.g. chimeric dengue serotype 2/4 strain) measured in pfu/0.5 mL is at least 50% or at least 60% or at least 65% of the total concentration. In one embodiment, based on said total concentration the concentration of a dengue serotype 2 (e.g. dengue serotype 2 strain) measured in pfu/0.5 mL is 0.3 to 10% or 0.5 to 8% of the total concentration and the concentration of a dengue serotype 4 (e.g. chimeric dengue serotype 2/4 strain) measured in pfu/0.5 mL is 50% to 90% or 60% to 88% of the total concentration. This means that the concentration of the dengue serotype 2 (e.g. dengue serotype 2 strain) is lower than the concentration of the dengue serotype 4 (e.g. chimeric dengue serotype 2/4 strain).

In one such embodiment, the concentration of a dengue serotype 1 (e.g. chimeric dengue serotype 2/1 strain) measured in pfu/0.5 mL is at least 1% of the total concentration, and/or the concentration of a dengue serotype 3 (e.g. chimeric dengue serotype 2/3 strain) measured in pfu/0.5 mL is at least 6% of the total concentration, or at least 7% or 8%, 10%, 12%, 14%, 16% or 18% of the total concentration. In one such embodiment, the concentration of a dengue serotype 2 (e.g. chimeric dengue serotype 2/1 strain) measured in pfu/0.5 mL is 1% to 7% or 2% to 6% or 2.0% to 5.0% of the total concentration, and/or the concentration of a dengue serotype 3 (e.g. chimeric dengue serotype 2/3 strain) measured in pfu/0.5 mL is 6% to 25% or 7% to 25% or 10% to 25% or 18% to 25% of the total concentration. This means that the concentration of the dengue serotype 1 (e.g. chimeric dengue serotype 2/1 strain) is lower than the concentration of the dengue serotype 3 (e.g. chimeric dengue serotype 2/3 strain).

In a preferred embodiment, the concentration of a dengue serotype 2 strain, such as TDV-2, measured in pfu/0.5 mL is less than 10% of the total concentration, preferably less than 6% or less than 2%, the concentration of a dengue serotype 4 (e.g. chimeric dengue serotype 2/4 strain), such as TDV-4, measured in pfu/0.5 mL is at least 50% of the total concentration, preferably at least 65%, the concentration of a dengue serotype 1 (e.g. chimeric dengue serotype 2/1 strain), such as TDV-1, measured in pfu/0.5 mL is at least 1% of the total concentration, preferably between 1% and 7% or 2.0% to 5.0%, and the concentration of a dengue serotype 3 (e.g. chimeric dengue serotype 2/3 strain), such as TDV-3, measured in pfu/0.5 mL is at least 6% of the total concentration, preferably between 6% and 25% or 10% to 25% or 18% to 25%.

In a further preferred embodiment, a dengue virus composition comprising a dengue serotype 1 (e.g. chimeric dengue serotype 2/1 strain), a dengue serotype 2 (e.g. dengue serotype 2 strain), a dengue serotype 1 (e.g. chimeric dengue serotype 2/3 strain), and a dengue serotype 4 (e.g. chimeric dengue serotype 2/4 strain), such as TDV-1, TDV-2, TDV-3 and TDV-4, is provided, wherein the concentration of the dengue serotype 1 (e.g. chimeric dengue serotype 2/1 strain) measured in pfu/0.5 mL is at least 1% of the total concentration, preferably between 1% and 7% or 2.0% and 5.0%, the concentration of the dengue serotype 2 (e.g. dengue serotype 2 strain) measured in pfu/0.5 mL is less than 10% of the total concentration, preferably less than 6% or less than 2% and the concentration of the dengue serotype 3 (e.g. chimeric dengue serotype 2/3 strain) measured in pfu/0.5 mL is at least 6% of the total concentration, preferably between 6% and 25% or 10% to 25% or 18% to 25%. It is particularly preferred that the dengue serotype 4 (e.g. chimeric dengue serotype 2/4 strain) has the highest concentration of all four dengue serotypes.

In a further preferred embodiment, the dengue vaccine composition comprises a tetravalent dengue virus composition including four live attenuated dengue virus strains, wherein the concentration of the dengue serotype 1 (e.g. chimeric dengue serotype 2/1 strain) measured in pfu/0.5 mL is 1% to 7% of the total concentration, the concentration of the dengue serotype 2 (e.g. dengue serotype 2 strain) measured in pfu/0.5 mL is less than 8% of the total concentration, such as in the range of 1% to 8% of the total concentration, the concentration of the dengue serotype 3 (e.g. chimeric dengue serotype 2/3 strain) measured in pfu/0.5 mL is at least 10% of the total concentration, and the concentration of the dengue serotype 4 (e.g. chimeric dengue serotype 2/4 strain) measured in pfu/0.5 mL is at least 65% of the total concentration, such as in the range of 65% to 80%. In certain such embodiments, the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL.

In a further preferred embodiment the dengue serotype 1 (e.g. chimeric dengue serotype 2/1 strain) such as TDV-1 and the dengue serotype 2 (e.g. dengue serotype 2 strain) such as TDV-2 are present each in a concentration based on the total concentration in pfu/0.5 mL which is within 5%-points of each other and/or are together less than about 10% of the total concentration in pfu/0.5 mL. In certain such embodiments the dengue serotype 3 (e.g. chimeric dengue serotype 2/3 strain) such as TDV-3 is preferably at least about 10% of the total concentration in pfu/0.5 mL and more preferably the dengue serotype 4 (e.g. chimeric dengue serotype 2/4 strain) such as TDV-4 is at least about 70% of the total concentration in pfu/0.5 mL. In certain such embodiments the dengue serotype 4 (e.g. chimeric dengue serotype 2/4 strain) such as TDV-4 represents the highest concentration in the composition of all four serotypes, preferably with at least about 70% of the total concentration in pfu/0.5 mL, dengue serotype 3 (e.g. chimeric dengue serotype 2/3 strain) such as TDV-3 represents the second highest concentration in the composition of all four serotypes, preferably with at least about 10% of the total concentration in pfu/0.5 mL, and dengue serotype 1 (e.g. chimeric dengue serotype 2/1 strain) such as TDV-1 and dengue serotype 2 (e.g. dengue serotype 2 strain) such as TDV-2 each represent lower concentrations than the concentration of serotype 3 (e.g. chimeric dengue serotype 2/3 strain) such as TDV-3, and optionally together represent less than about 10% of the total concentration in pfu/0.5 mL.

Preferably, in said embodiments the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

According to a further embodiment, the chimeric dengue serotype 2/4 strain, preferably TDV-4, has the highest concentration in the dengue vaccine composition, followed by the chimeric dengue serotype 2/3 strain, preferably TDV-3, followed by the chimeric dengue serotype 2/1 strain, preferably TDV-1, followed by the dengue serotype 2 strain, preferably TDV-2. It is particularly preferred that the dengue serotype 2 strain has the lowest concentration of the four strains present in the dengue vaccine composition.

Whenever reference is made to a concentration/0.5 ml, this does not limit the volume of the unit dose described herein to 0.5 ml. 0.5 ml is the reference volume for the determination of the concentrations of the virus strains in the composition in pfu/ml. The volume and/or amount per unit dose is described in the respective chapter.

Pharmaceutically Acceptable Excipients

The present invention is in part directed to a unit dose of a dengue vaccine composition, wherein the dengue vaccine composition comprises one or more pharmaceutically acceptable excipients. In one embodiment, the dengue vaccine composition comprises a non-reducing sugar, a surfactant, a protein and an inorganic salt. Preferably, the non-reducing sugar is trehalose, the surfactant is poloxamer 407, the protein is human serum albumin and the inorganic salt is sodium chloride.

In one embodiment, the unit dose of a dengue vaccine composition comprises the following pharmaceutically acceptable excipients:
from about 10% w/v to about 20% w/v $\alpha,\alpha$-trehalose dihydrate or an equimolar amount of other forms of $\alpha,\alpha$-trehalose,
from about 0.5% w/v to about 1.5% w/v poloxamer 407,
from about 0.05% w/v to about 2% w/v human serum albumin, and
from about 70 mM to 140 mM sodium chloride.

In one embodiment, the unit dose of a dengue vaccine composition comprises the following pharmaceutically acceptable excipients when measured in 0.5 ml:
from about 10% w/v to about 20% w/v $\alpha,\alpha$-trehalose or an equimolar amount of other forms of $\alpha,\alpha$-trehalose,
from about 0.5% w/v to about 1.5% w/v poloxamer 407,
from about 0.05% w/v to about 2% w/v human serum albumin, and
from about 70 mM to 140 mM sodium chloride, and preferably
has a pH of 7 to 8.5.

In one embodiment, the unit dose of a dengue vaccine composition comprises the following pharmaceutically acceptable excipients when measured in 0.5 ml:
from about 143 mg/ml to about 185 mg/ml $\alpha,\alpha$-trehalose dihydrate or an equimolar amount of other forms of $\alpha,\alpha$-trehalose,
from about 9.1 mg/ml to about 12.4 mg/ml poloxamer 407,
from about 0.88% mg/ml to about 1.32 mg/ml human serum albumin, and
from about 70 mM to 140 mM sodium chloride, and preferably
has a pH of 7 to 8.5.

In a preferred embodiment, the lyophilized unit dose of the invention as described herein comprises the following pharmaceutically acceptable excipients:
about 15% w/v $\alpha,\alpha$-trehalose dihydrate,
about 1% w/v poloxamer 407,
about 0.1% w/v human serum albumin, and
about 100 mM sodium chloride.

In a preferred embodiment, the lyophilized unit dose of the invention as described herein comprises the following pharmaceutically acceptable excipients when measured in 0.5 ml:
about 15% w/v $\alpha,\alpha$-trehalose,
about 1% w/v poloxamer 407,
about 0.1% w/v human serum albumin, and
about 100 mM sodium chloride.

In a preferred embodiment, the lyophilized unit dose of the invention as described herein comprises the following pharmaceutically acceptable excipients:
about 82.9 mg $\alpha,\alpha$-trehalose dihydrate,
about 5 mg poloxamer 407,
about 0.5 mg human serum albumin, and
about 50 µmoles sodium chloride.

In a preferred embodiment, the reconstituted unit dose of the invention as described herein comprises the following pharmaceutically acceptable excipients:
about 15% w/v $\alpha,\alpha$-trehalose dihydrate,
about 1% w/v poloxamer 407,
about 0.1% w/v human serum albumin, and
about 137 mM sodium chloride, and preferably
has a pH of 7 to 8.5

In a preferred embodiment, the reconstituted unit dose of the invention as described herein comprises the following pharmaceutically acceptable excipients when measured in 0.5 ml:
about 15% w/v $\alpha,\alpha$-trehalose,
about 1% w/v poloxamer 407,
about 0.1% w/v human serum albumin, and preferably
about 137 mM sodium chloride and preferably
has a pH of 7 to 8.5.

In a preferred embodiment, the reconstituted unit dose of the invention as described herein comprises the following pharmaceutically acceptable excipients:
about 82.9 mg $\alpha,\alpha$-trehalose dihydrate,
about 5 mg poloxamer 407,
about 0.5 mg human serum albumin, and preferably
about 68.5 µmoles sodium chloride, and preferably
has a pH of 7 to 8.5.

The human serum albumin may be a native or recombinant human serum albumin (rHSA). The poloxamer 407 may be e.g. Pluronic F127.

In one embodiment, the unit dose further comprises a buffer. The buffer may be phosphate buffered saline (PBS). The buffer may include at least one of sodium chloride (NaCl), monosodium dihydrogen phosphate ($NaH_2PO_4$), disodium hydrogen phosphate ($Na_2HPO_4$), potassium chloride (KCl), and potassium dihydrogen phosphate ($KH_2PO_4$). In a preferred embodiment, the buffer may include disodium hydrogen phosphate ($Na_2HPO_4$), potassium chloride (KCl), and potassium dihydrogen phosphate ($KH_2PO_4$). The buffer may have a pH in the range of 7.0 to 8.5 at 25° C.

Unit Dose

The present invention is directed in part to a unit dose of a dengue vaccine composition comprising a tetravalent dengue virus composition as described herein and pharmaceutically acceptable excipients as described herein.

The present invention is directed in part to a unit dose of a dengue vaccine composition as described above e.g. of
(i) a dengue serotype 1 (e.g. chimeric dengue serotype 2/1 strain) with a concentration of at least 3.3 log 10 pfu/0.5 mL,
(ii) a dengue serotype 2 (e.g. dengue serotype 2 strain) with a concentration of at least 2.7 log 10 pfu/0.5 mL,
(iii) a dengue serotype 3 (e.g. chimeric dengue serotype 2/3 strain) with a concentration of at least 4.0 log 10 pfu/0.5 mL, and
(iv) a dengue serotype 4 (e.g. chimeric dengue serotype 2/4 strain) with a concentration of at least 4.5 log 10 pfu/0.5 mL.

Preferably, the chimeric dengue serotype 2/1 strain is TDV-1, the dengue serotype 2 strain is TDV-2, the chimeric dengue serotype 2/3 strain is TDV-3, and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

In one embodiment, the unit dose is lyophilized. In one such embodiment, the lyophilized unit dose is obtained by subjecting a volume of 0.5 mL of the aqueous dengue vaccine composition produced by combining pharmaceutically acceptable excipients as described herein and the dengue vaccine composition as described herein comprising the four dengue virus strains, in particular TDV-1 to TDV-4, to lyophilization. In a preferred embodiment the residual moisture content as determined by Karl Fischer Determination is equal to or less than 5.0%, preferably equal to or less than 3%.

In another embodiment, the unit dose is reconstituted. The reconstituted unit dose is obtained by subjecting the lyophilized unit dose to reconstitution with a pharmaceutically acceptable diluent, preferably before administration of the dengue vaccine. In one such embodiment, reconstitution will be accomplished by adding a pharmaceutically acceptable diluent, such as water for injection, phosphate buffered saline or an aqueous sodium chloride solution, to the lyophilized unit dose. In one embodiment, an aqueous sodium chloride solution, such as a 37 mM aqueous sodium chloride solution, is added to the lyophilized unit dose for reconstitution. In one such embodiment, the lyophilized unit dose will be reconstituted with 0.3 to 0.8 mL, or 0.4 to 0.7 mL, or 0.5 mL of diluent. In a preferred embodiment, the lyophilized unit dose is reconstituted with 0.3 to 0.8 mL, 0.4 to 0.7 mL or 0.5 mL of 37 mM aqueous sodium chloride solution. In a more preferred embodiment, the lyophilized unit dose is reconstituted with 0.5 mL of 37 mM aqueous sodium chloride solution. The reconstituted unit dose can subsequently be administered subcutaneously.

It is preferred that the unit dose in lyophilized form is the final product after manufacture of the unit dose and the storage form of the unit dose, wherein the unit dose in reconstituted form is prepared before administration of the unit dose to a subject.

The present invention is, moreover, directed in part to a unit dose of a dengue vaccine composition comprising:
a tetravalent virus composition including four live attenuated dengue virus strains, wherein the unit dose is lyophilized and upon reconstitution with 0.5 mL of a pharmaceutically acceptable diluent comprises:
(i) a dengue serotype 1, such as a chimeric dengue serotype 2/1 strain, in a concentration of at least 3.3 log 10 pfu/0.5 ml,
(ii) a dengue serotype 2, such as a dengue serotype 2 strain, in a concentration of at least 2.7 log 10 pfu/0.5 ml,
(iii) a dengue serotype 3, such as a chimeric dengue serotype 2/3 strain, in a concentration of at least 4.0 log 10 pfu/0.5 ml, and
(iv) a dengue serotype 4, such as a chimeric dengue serotype 2/4 strain, in a concentration of at least 4.5 log 10 pfu/0.5 ml.

In one embodiment, the reconstituted unit dose has a volume of e.g. 0.5 mL, wherein upon reconstitution with a pharmaceutically acceptable diluent (i), (ii), (iii), and (iv) provide a total concentration of pfu/0.5 mL and based on said concentration, the concentration of (iii) at least 10% of the total concentration in pfu/0.5 mL.

In another embodiment the reconstituted unit dose has a volume of e.g. 0.5 mL, wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 6%, or at least 8%, or at least 10%, or at least 12%, or at least 14%, or at least 16%, or at least 18%.

It is preferred that the concentration in the reconstituted unit dose of (iii) in pfu/0.5 mL is at least 10%.

In one embodiment the reconstituted unit dose has a volume of e.g. 0.5 mL, wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6%.

In one embodiment, the present invention is directed to a lyophilized unit dose of a dengue vaccine composition comprising upon reconstitution with 0.5 mL of a pharmaceutically acceptable diluent a dengue serotype 1 (e.g. chimeric dengue serotype 2/1 strain) with a concentration of at least 3.3 log 10 pfu/0.5 mL, a dengue serotype 2 (e.g. dengue serotype 2 strain) with a concentration of at least 2.7 log 10 pfu/0.5 mL, a dengue serotype 3 (e.g. chimeric dengue serotype 2/3 strain) with a concentration of at least 4.0 log 10 pfu/0.5 mL, and a dengue serotype 4 (e.g. chimeric dengue serotype 2/4 strain) with a concentration of at least 4.5 log 10 pfu/0.5 mL and pharmaceutically acceptable excipients as described herein, wherein the unit dose is preferably formulated in 0.5 mL before lyophilization. Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

In one such embodiment, the lyophilized unit dose is obtained by lyophilizing 0.5 mL of a dengue vaccine composition comprising a dengue serotype 1 (e.g. chimeric dengue serotype 2/1 strain) in a concentration of 3.3 log 10 pfu/dose to 5.0 log 10 pfu/0.5 mL, a dengue serotype 2 (e.g. dengue serotype 2 strain) in a concentration of 2.7 log 10 pfu/dose to 4.9 log 10 pfu/0.5 mL, a dengue serotype 3 (e.g. chimeric dengue serotype 2/3 strain) in a concentration of 4.0 log 10 pfu/dose to 5.7 log 10 pfu/0.5 mL, and a dengue serotype 4 (e.g. chimeric dengue serotype 2/4 strain) in a concentration of 4.5 log 10 pfu/dose to 5.5 log 10 pfu/0.5 mL and pharmaceutically acceptable excipients as described herein. Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4.

In one such embodiment, the lyophilized unit dose is obtained by lyophilizing 0.5 mL of a dengue vaccine composition comprising a dengue serotype 1 (e.g. chimeric dengue serotype 2/1 strain) in a concentration of 3.3 log 10 pfu/0.5 mL to 3.6 log 10 pfu/0.5 mL, a dengue serotype 2 (e.g. dengue serotype 2 strain) in a concentration of 2.7 log 10 pfu/0.5 mL to 4.0 log 10 pfu/0.5 mL, a dengue serotype 3 (e.g. chimeric dengue serotype 2/3 strain) in a concentration of 4.0 log 10 pfu/0.5 mL to 4.6 log 10 pfu/0.5 mL, and a dengue serotype 4 (e.g. chimeric dengue serotype 2/4 strain) in a concentration of 4.5 log 10 pfu/0.5 mL or 4.6 log 10 pfu/0.5 mL to 5.1 log 10 pfu/0.5 mL and pharmaceutically acceptable excipients as described herein. Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4.

In certain embodiments, the lyophilized unit dose refers to 0.5 mL before lyophilization, wherein TDV-2 and TDV-4 are present in certain relative amounts, based on the total concentration of TDV-1, TDV-2, TDV-3 and TDV-4 in pfu/0.5 mL, and the concentration of TDV-2 measured in pfu/0.5 mL is less than 10% or less than 8% or less than 6%, and the concentration of TDV-4 measured in pfu/0.5 mL is at least 50% or at least 65%. In some of these embodiments, the concentration of TDV-1 measured in pfu/0.5 mL is at least 1% and/or the concentration of TDV-3 measured in pfu/0.5 mL is at least 6%, 7%, 8%, 10%, 12%, 14%, 16% or at least 18%.

In certain embodiments, the reconstituted unit dose has a volume of 0.5 mL and TDV-2 and TDV-4 are present in certain relative amounts, based on the total concentration of TDV-1, TDV-2, TDV-3 and TDV-4 in pfu/0.5 mL, and the concentration of TDV-2 measured in pfu/0.5 mL is less than 10% or less than 8% or less than 6%, and the concentration of TDV-4 measured in pfu/0.5 mL is at least 50% or at least 65%. In some of these embodiments, the concentration of TDV-1 measured in pfu/0.5 mL is at least 1% and/or the concentration of TDV-3 measured in pfu/0.5 mL is at least 6%, 7%, 8%, 10%, 12%, 14%, 16% or at least 18%.

In a further preferred embodiment, the reconstituted unit dose has a volume of 0.5 mL and comprises a tetravalent dengue virus composition including four live attenuated dengue virus strains, wherein the concentration of the dengue serotype 1 (e.g. dengue serotype 2/1 strain) measured in pfu/0.5 mL is 1% to 7% of the total concentration, the concentration of the dengue serotype 2 (e.g. dengue serotype 2 strain) measured in pfu/0.5 mL is less than 8% of the total concentration, such as in the range of 1% to 8% of the total concentration, the concentration of the dengue serotype 3 (e.g. dengue serotype 2/3 strain) measured in pfu/0.5 mL is at least 10% of the total concentration, and the concentration of the dengue serotype 4 (e.g. dengue serotype 2/4 strain) measured in pfu/0.5 mL is at least 65% of the total concentration, such as in the range of 65% to 80%. In certain such embodiments, the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL.

In a further preferred embodiment, the reconstituted unit dose has a volume of 0.5 mL and comprises a tetravalent dengue virus composition including four live attenuated dengue virus strains, wherein the dengue serotype 1 (e.g. chimeric dengue serotype 2/1 strain) such as TDV-1 and the dengue serotype 2 (e.g. dengue serotype 2 strain) such as TDV-2 are present each in a concentration based on the total concentration in pfu/0.5 mL which is within 5%-points of each other and/or are together less than about 10% of the total concentration in pfu/0.5 mL. In certain such embodiments the dengue serotype 3 (e.g. chimeric dengue serotype 2/3 strain) such as TDV-3 is preferably at least about 10% of the total concentration in pfu/0.5 mL and more preferably the dengue serotype 4 (e.g. chimeric dengue serotype 2/4 strain) such as TDV-4 is at least about 70% of the total concentration in pfu/0.5 mL. In certain such embodiments the dengue serotype 4 (e.g. chimeric dengue serotype 2/4 strain) such as TDV-4 represents the highest concentration in the composition of all four serotypes, preferably with at least about 70% of the total concentration in pfu/0.5 mL, dengue serotype 3 (e.g. chimeric dengue serotype 2/3 strain) such as TDV-3 represents the second highest concentration in the composition of all four serotypes, preferably with at least about 10% of the total concentration in pfu/0.5 mL, and dengue serotype 1 (e.g. chimeric dengue serotype 2/1 strain) such as TDV-1 and dengue serotype 2 (e.g. dengue serotype 2 strain) such as TDV-2 each represent lower concentrations than the concentration of serotype 3 (e.g. chimeric dengue serotype 2/3 strain) such as TDV-3, and optionally together represent less than about 10% of the total concentration in pfu/0.5 mL.

The lyophilized unit dose reconstituted in 0.5 mL will provide the above concentrations for the four dengue serotypes. While the unit dose of a dengue vaccine composition as described herein refers to the concentrations of the dengue serotypes in 0.5 mL, the lyophilized unit dose can be reconstituted with other volumes of a pharmaceutically acceptable diluent, such as an aqueous sodium chloride solution, without changing the absolute virus amount administered or the ratios of the viruses to one another.

In certain embodiments, the lyophilized unit dose of the invention is prepared from a solution comprising a non-reducing sugar, a surfactant, a protein and an inorganic salt.

In certain embodiments, the lyophilized unit dose of the invention is prepared from a solution comprising trehalose, poloxamer 407, human serum albumin and sodium chloride.

In certain embodiments, the lyophilized unit dose of the invention is prepared from a solution comprising about 10% w/v to about 20% w/v α,α-trehalose dihydrate or an equimolar amount of other forms of α,α-trehalose, from about 0.5% w/v to about 1.5% w/v poloxamer 407, from about 0.05% w/v to about 2% w/v human serum albumin, and about 70 mM to about 120 mM sodium chloride.

In preferred embodiments, the lyophilized unit dose of the invention as described herein is prepared from a solution comprising about 15% w/v α,α-trehalose dihydrate, about 1% w/v poloxamer 407, about 0.1% w/v human serum albumin and about 100 mM sodium chloride.

In one embodiment, the solution from which the lyophilized unit dose is prepared further comprises a buffer. The buffer may be phosphate buffered saline (PBS). The buffer may include at least one of sodium chloride (NaCl), monosodium dihydrogen phosphate ($NaH_2PO_4$), disodium hydrogen phosphate ($Na_2HPO_4$), potassium chloride (KCl), and potassium dihydrogen phosphate ($KH_2PO_4$). In a preferred embodiment, the buffer may include disodium hydrogen phosphate ($Na_2HPO_4$), potassium chloride (KCl), and potassium dihydrogen phosphate ($KH_2PO_4$). The buffer may have a pH in the range of about 7.0 to about 8.5 at 25° C. or a pH of about 6.8 to about 7.6 at 25° C., preferably a pH of about 7.2 at 25° C.

In preferred embodiments, the reconstituted unit dose of the invention as described herein comprising about 15% w/v α,α-trehalose dihydrate, about 1% w/v poloxamer 407, about 0.1% w/v human serum albumin and about 137 mM sodium chloride. The reconstituted unit dose may have a pH of about 7.0 to about 8.5 at 25° C., preferably a pH of about 7.2 at 25° C.

The unit dose of the invention as described herein activates multiple arms of the immune system—neutralizing antibodies, cellular immunity and anti-NS1 antibodies—in both seronegative and seropositive subject populations or in both seronegative and seropositive subjects. Thus, the unit dose of the invention as described herein protects both dengue seronegative and dengue seropositive subject populations or subjects against dengue disease.

In one embodiment, one unit dose is present in a container, preferably a vial, and said unit dose is administered to a subject after reconstitution. In one embodiment, more than one unit dose of the dengue vaccine composition may be present in a container, preferably a vial, so that with the content of one container, preferably a vial, more than one subject can be vaccinated. In one embodiment, the container comprising more than one unit doses of the invention as described herein is used for providing the reconstituted unit dose to be used in the methods of the invention as described herein.

The certain embodiments, the container comprising the unit dose of the invention is part of a kit. Thus, the invention is directed in part to a kit for preparing a reconstituted unit dose comprising a lyophilized unit dose of the present invention as described herein, and a pharmaceutically acceptable diluent for reconstitution.

In certain embodiments, the diluent for reconstitution provided in a container, preferably a vial, or a pre-filled syringe. In some embodiments, the diluent for reconstitution is selected from water for injection, phosphate buffered saline or an aqueous sodium chloride solution. In a preferred embodiment, the diluent for reconstitution is 30 to 40 mM sodium chloride, such as 37 mM sodium chloride.

In certain embodiments, the kit may further comprise a hepatitis A vaccine, such as HAVRIX® or VAQTA®. In some embodiments, the hepatitis A vaccine may be in a separate container, such as a vial. In another embodiment, the hepatitis A vaccine and the unit dose of the invention may be in the same container. Thus, the invention is directed in part to a combined dengue/hepatitis A vaccine, wherein the unit dose of the invention as described herein is combined with a hepatitis A vaccine. Such a combined dengue/hepatitis A vaccine comprises the unit dose of the invention as described herein and a hepatitis A vaccine, such as HAVRIX® or VAQTA®, in the same formulation. In certain embodiments, the invention is directed to a kit comprising such a combined dengue/hepatitis A vaccine and a unit dose of the invention as described herein.

Hepatitis A Vaccine

In certain embodiments, the hepatitis A vaccine is an inactivated hepatitis A vaccine.

In certain embodiments, the hepatitis A vaccine comprises a hepatitis A virus derived from a hepatitis A virus strain HM-175.

In certain embodiments, wherein the hepatitis A vaccine comprises an inactivated hepatitis A virus and the inactivated hepatitis A virus is derived from a wild-type hepatitis A virus strain HM-175.

In certain embodiments, the inactivated hepatitis A virus is adsorbed on a carrier aluminum. In some of these embodiments, the aluminum is aluminum hydroxide or aluminum hydroxyphosphate sulfate.

In certain embodiments, wherein the hepatitis A vaccine comprises a phosphate-buffered saline solution and excipients dissolved therein in the form of an amino acid and in the form of polysorbate. In such embodiments, the amino acid is present at a concentration of 0.2 to 0.8% w/v and/or the polysorbate is present at a concentration of 0.01 to 0.09 mg/ml.

In certain embodiments, the hepatitis A vaccine includes a hepatitis A virus expressing a viral antigen in a concentration ranging from 500 ELISA Units (EL.U.) to 2000 ELISA Units (EL.U.), preferably from 700 EL.U. to 1600 EL.U., most preferably from 1300 to 1550 EL.U. Alternatively, the concentration ranges from 500 EL.U. to 900 EL.U. In a further embodiment, the concentration ranges from 200 to 400 EL.U.

In certain embodiments, the hepatitis A vaccine is included in a liquid 1 ml dose or in a 0.5 ml dose.

An example of such an hepatitis A vaccine is HAVRIX®, from GlaxoSmithKline, which is a sterile suspension of inactivated virus for intramuscular administration. HAVRIX® makes use of the hepatitis A virus strain HM-175 which is derived from a wild-type hepatitis A virus (HAV) HM-175 of which the complete nucleotide sequence is disclosed in Cohen et al., Journal of Virology, Vol. 61, No. 1, published January 1987, p. 50 to 59 (in particular, the entire sequence of the wild-type hepatitis A virus HM-175 is provided in FIG. 1 of said publication).

The virus (strain HM175) is propagated in MRC-5 human diploid cells. After removal of the cell culture medium, the cells are lysed to form a suspension. This suspension is purified through ultrafiltration and gel permeation chromatography procedures. Treatment of this lysate with formalin ensures viral inactivation. Viral antigen activity is referenced to a standard using an enzyme linked immunosorbent assay (ELISA), and is therefore expressed in terms of ELISA Units (EL.U.). Each 1-mL dose for adults (≥18 years of age) of vaccine contains 1440 EL.U. of viral antigen, adsorbed on 0.5 mg of aluminum as aluminum hydroxide. Each 0.5-mL dose for children and adolescents (12 months through 18 years of age) of vaccine contains 720 EL.U. of viral antigen, adsorbed onto 0.25 mg of aluminum as aluminum hydroxide. HAVRIX® contains the following excipients: Amino acid supplement (0.3% w/v) in a phosphate-buffered saline solution and polysorbate 20 (0.05 mg/mL). From the manufacturing process, HAVRIX® also contains residual MRC-5 cellular proteins (not more than 5 μg/mL), formalin (not more than 0.1 mg/mL), and neomycin sulfate (not more than 40 ng/mL), an aminoglycoside antibiotic included in the cell growth media. HAVRIX® is formulated without preservatives.

Another useful hepatitis A vaccine is VAQTA® from Merck Sharp & Dohme Corp., which is an inactivated whole virus vaccine derived from hepatitis A virus grown in cell culture in human MRC-5 diploid fibroblasts. It contains inactivated virus of a strain, which was originally derived by further serial passage of a proven attenuated strain. The virus is grown, harvested, purified by a combination of physical and high performance liquid chromatographic techniques developed at the Merck Research Laboratories, formalin inactivated, and then adsorbed onto amorphous aluminum hydroxyphosphate sulfate. VAQTA® is a sterile suspension for intramuscular injection. One milliliter of the vaccine contains approximately 50 U of hepatitis A virus antigen, which is purified and formulated without a preservative. Within the limits of current assay variability, the 50 U dose of VAQTA® contains less than 0.1 µg of non-viral protein, less than $4 \times 10^{-6}$ µg of DNA, less than $10^{-4}$ µg of bovine albumin, and less than 0.8 µg of formaldehyde. Other process chemical residuals are less than 10 parts per billion (ppb), including neomycin. Each 0.5-mL pediatric dose contains 25 U of hepatitis A virus antigen and adsorbed onto approximately 0.225 mg of aluminum provided as amorphous aluminum hydroxyphosphate sulfate, and 35 µg of sodium borate as a pH stabilizer, in 0.9% sodium chloride. Each 1-mL adult dose contains 50 U of hepatitis A virus antigen and adsorbed onto approximately 0.45 mg of aluminum provided as amorphous aluminum hydroxyphosphate sulfate, and 70 µg of sodium borate as a pH stabilizer, in 0.9% sodium chloride.

Yellow Fever Vaccine

YF-VAX®, a yellow fever vaccine from Sanofi, for subcutaneous use, is prepared by culturing the YF-17D strain of yellow fever virus in living avian leukosis virus-free (ALV-free) chicken embryos. The vaccine contains sorbitol and gelatin as a stabilizer and is lyophilized. No preservative is added. YF-VAX is formulated to contain not less than 4.74 $\log_{10}$ pfu per 0.5 mL dose throughout the life of the product.

Combined Vaccine Composition

The present invention is also directed in part to a combined vaccine composition comprising a hepatitis A antigen as in HAVRIX® or VAQTA®, and a dengue antigen such as the tetravalent dengue vaccine, TDV, as disclosed herein or any other suitable tetravalent live attenuated dengue virus vaccine.

In certain embodiments, the invention is directed to the combined vaccine composition, wherein the dengue vaccine composition comprises a tetravalent dengue virus composition including four live attenuated dengue virus strains:
(i) a dengue serotype 1 preferably in a concentration of at least 3.3 log 10 pfu/0.5 mL,
(ii) a dengue serotype 2 preferably in a concentration of at least 2.7 log 10 pfu/0.5 mL,
(iii) a dengue serotype3 preferably in a concentration of at least 4.0 log 10 pfu/0.5 mL, and
(iv) a dengue serotype 4 preferably strain in a concentration of at least 4.5 log 10 pfu/0.5 mL.

In certain embodiments, the invention is directed to the combined vaccine composition, wherein the dengue vaccine composition comprises a tetravalent dengue virus composition including four live attenuated dengue virus strains:
(i) a chimeric dengue serotype 2/1 strain in a concentration of at least 3.3 log 10 pfu/0.5 mL to 3.8 log 10 pfu/0.5 ml,
(ii) a dengue serotype 2 strain in a concentration of at least 2.7 log 10 pfu/0.5 mL,
(iii) a chimeric dengue serotype 2/3 strain in a concentration of at least 4.0 log 10 pfu/0.5 mL, and
(iv) a chimeric dengue serotype 2/4 strain in a concentration of at least 4.5 log 10 pfu/0.5 mL or at least 4.6 log 10 pfu/0.5 mL to optionally 6.2 log 10 pfu/0.5 ml.

Preferably, in said embodiments the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

In certain embodiments, the invention is directed to the combined vaccine composition, wherein upon reconstitution of the dengue vaccine composition with a pharmaceutically acceptable diluent (i), (ii), (iii), and (iv) provide a total concentration of pfu/0.5 mL and based on said total concentration of pfu/0.5 ml the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 6%, at least 8%, or at least 10%, or at least 12%, or at least 14%, or at least 16%, or at least 18%.

In certain embodiments, the invention is directed to the combined vaccine composition, wherein the dengue vaccine composition comprises one or more pharmaceutically acceptable excipients. In one embodiment, the dengue vaccine composition comprises a non-reducing sugar, a surfactant, a protein and an inorganic salt. Preferably, the non-reducing sugar is trehalose, the surfactant is poloxamer 407, the protein is human serum albumin and the inorganic salt is sodium chloride.

Furthermore, any vaccine excipients or combinations thereof known to the person skilled in the art, e.g. disclosed in WO 2018/027075 A1, can be used for the combined vaccine composition.

In one embodiment, the unit dose of a dengue vaccine composition comprises the following pharmaceutically acceptable excipients:
from about 10% w/v to about 20% w/v α,α-trehalose dihydrate or an equimolar amount of other forms of α,α-trehalose,
from about 0.5% w/v to about 1.5% w/v poloxamer 407,
from about 0.05% w/v to about 2% w/v human serum albumin, and
from about 70 mM to 140 mM sodium chloride.

In certain embodiments, the invention is directed to the combined vaccine composition, wherein the dengue vaccine composition comprises other dengue vaccines such as Dengvaxia®. Dengvaxia® is a tetravalent dengue vaccine with mixed chimeric dengue viruses based on a yellow fever backbone, CYD-TDV (Dengvaxia®, Sanofi Pasteur, Lyon, France), and has been licensed in several countries based on the clinical demonstration of an overall vaccine efficacy (VE) against virologically-confirmed dengue (VCD) of 56-61% in children in Asia and Latin America (Capeding M R et al. Clinical efficacy and safety of a novel tetravalent dengue vaccine in healthy children in Asia: a phase 3, randomised, observer-masked, placebo-controlled trial. Lancet 2014, 384:1358-65; Villar L A et al. Safety and immunogenicity of a recombinant tetravalent dengue vaccine in 9-16 year olds: a randomized, controlled, phase II trial in Latin America. Pediatr Infect Dis J 2013, 32:1102-9). The preparation of these particular strains CYD1, CYD2, CYD3 and CYD4 has been described in detail in international patent applications WO 98/37911, WO 03/101397, WO07/021672, WO 08/007021, WO 08/047023 and WO 08/065315, to which reference may be made for a precise description of the processes for their preparation. The corresponding nucleotide sequences of the prM-E regions of CYD1, CYD2, CYD3 and CYD4 are provided in WO2016034629 and SEQ ID NOs are set out in Table 16 of this reference.

In certain embodiments, the invention is directed to the combined vaccine composition, wherein the quantity of a chimeric dengue virus within CYD-TDV comprised in a vaccine composition of the present invention lies within a range of about $10^5$ CCID50 to about $10^6$ CCID50. The quantity of a live attenuated chimeric dengue virus of each of serotypes 1 to 4 comprised in the CYD dosage form, e.g. Dengvaxia®, is preferably equal.

In such embodiments, the CYD-TDV is dissolved/dissolvable in a solution containing 0.4% NaCl.

In certain embodiments, the invention is directed to the combined vaccine composition, wherein the dengue vaccine composition comprises other dengue vaccines such as TV003 or TV005. TV003, developed by the U.S. National Institute of Allergy and Infectious Diseases, comprises vaccine components rDEN1Δ30, rDEN2/4Δ30, rDEN3Δ30/31 and rDEN4Δ30, wherein each of these components is present at a concentration of 3 $\log_{10}$ PFU. TV005 is similar to TV003 with the difference that the concentration of rDEN2/4Δ30 in TV005 is 4 $\log_{10}$ PFU. The vaccines TV003 and TV005 and their vaccine components as well as their production are described in more detail in WO 2008/022196 A2 and S. S. Whitehead, Expert Rev Vaccines, 2016, 15(4): 509 to 517. Using recombinant DNA technology, two attenuation strategies were utilized for the vaccine components of TV003 or TV005: deletions in the 3' untranslated region and structural gene chimerization. For example, the component rDEN4Δ30 contains all the structural and non-structural proteins of a wild type DENV-4, but is attenuated by a 30-nucleotide deletion in the 3' untranslated region (denoted "Δ30"). The other vaccine components are also attenuated due to the 30-nucleotide deletion in the 3' untranslated region. In addition, rDEN3Δ30/31 includes a 31 nucleotide deletion in the 3' untranslated region (shown in detail in FIG. 1c and FIG. 13 of WO 2008/022196 A2). The rDEN2/4Δ30 component was created by substituting the prM and E genes of DENV-2 into the rDEN4Δ30 genome. The complete genomic sequences of dengue strains which can be used to produce TV003 or TV005 are available under the Genbank accession numbers in Table A of WO 2008/022196 A1.

In certain embodiments, the invention is directed to the combined vaccine composition, wherein the hepatitis A vaccine is an inactivated hepatitis A vaccine.

In certain embodiments, wherein the hepatitis A vaccine comprises a hepatitis A virus derived from a hepatitis A virus strain HM-175.

In certain embodiments, the invention is directed to the combined vaccine composition, wherein the hepatitis A vaccine comprises an inactivated hepatitis A virus and the inactivated hepatitis A virus is derived from a wild-type hepatitis A virus strain HM-175.

In certain embodiments, the invention is directed to the combined vaccine composition, the inactivated hepatitis A virus is adsorbed on a carrier aluminum. In some of these embodiments, the aluminum is aluminum hydroxide or aluminum hydroxyphosphate sulfate.

In certain embodiments, the invention is directed to the combined vaccine composition, wherein the hepatitis A vaccine comprises a phosphate-buffered saline solution and excipients dissolved therein in the form of an amino acid and in and in the form of polysorbate. In such embodiments, the amino acid is present at a concentration of 0.2 to 0.8% w/v and/or the polysorbate is present at a concentration of 0.01 to 0.09 mg/ml.

In certain embodiments, the invention is directed to the combined vaccine composition, wherein the hepatitis A vaccine includes a hepatitis A virus expressing a viral antigen in a concentration ranging from 500 ELISA Units (EL.U.) to 2000 ELISA Units (EL.U.), preferably from 700 EL.U. to 1600 EL.U., most preferably from 1300 to 1550 EL.U. Alternatively, the concentration ranges from 500 EL.U. to 900 EL.U. In a further embodiment, the concentration ranges from 200 to 400 EL.U.

In certain embodiments, the invention is directed to the combined vaccine composition, wherein the combined vaccine is included in a dose comprising a liquid, wherein the liquid has a volume of 0.5 ml, 1 ml, or 1.5 ml.

In certain embodiments, the combined vaccine composition is provided in one single vial in a liquid form or in a dehydrated form, such as a lyophilized form.

In certain embodiments, the combined vaccine composition is obtained from mixing a unit dose of a dengue vaccine composition and a dose of a hepatitis A vaccine in a syringe.

The invention is also directed in part to a method of administering any of the above combined vaccine compositions to a subject or subject population.

In certain embodiments, the invention is directed to said methods, wherein the combined vaccine composition is administered subcutaneously or intramuscularly.

Method of Preventing Dengue Disease and Hepatitis A, Corresponding Uses, and Corresponding Kit The present invention is directed to a method of preventing hepatitis A and dengue disease.

The present invention is directed in part to a method of preventing hepatitis A and dengue disease in a subject or subject population, the method comprising simultaneously on the same day administering a hepatitis A vaccine, such as HAVRIX® or VAQTA®, and a unit dose of a dengue vaccine composition, wherein said unit dose comprises a tetravalent dengue virus composition including four live, attenuated dengue virus strains.

In certain embodiments, the invention is directed to said method, wherein the hepatitis A vaccine, such as HAVRIX®, comprises an inactivated virus. Preferably, the hepatitis A vaccine comprises an inactivated hepatitis A virus and the inactivated hepatitis A virus is derived from a hepatitis A virus strain HM-175.

In certain embodiments, the hepatitis A vaccine, such as HAVRIX®, is derived from a hepatitis A virus strain HM-175.

In certain embodiments, the invention is directed to said methods, wherein the hepatitis A vaccine, such as HAVRIX®, which is preferably a virus derived from a hepatitis A virus strain HM-175, is adsorbed on aluminum. According to some of these embodiments, the aluminum is aluminum hydroxide or aluminum hydroxyphosphate sulfate.

In certain embodiments, the invention is directed to said method, wherein the hepatitis A vaccine, such as HAVRIX®, which is preferably derived from a hepatitis A virus strain HM-175, comprises a phosphate-buffered saline solution and excipients dissolved therein in the form of an amino acid and in and in the form of polysorbate.

In certain embodiments, the invention is directed to said method, wherein the hepatitis A vaccine, such as HAVRIX®, includes a hepatitis A virus expressing a viral antigen in a concentration ranging from 500 ELISA Units (EL.U.) to 2000 ELISA Units (EL.U.), preferably from 700 EL.U. to 1600 EL.U., most preferably from 1300 to 1550 EL.U. Alternatively, the concentration ranges from 500 EL.U. to 900 EL.U. In a further embodiment, the concentration ranges from 200 to 400 EL.U.

For example, viral antigen activity of a hepatitis A vaccine can be measured according to a method disclosed in Andre F E., Hepburn A., D'Hondt E., "Inactivated candidate vaccines for hepatitis", A. Prog Med Virol 1990; 37:72-95.

In certain embodiments, the invention is directed to said method, wherein the dengue vaccine composition upon reconstitution with 0.5 mL of a pharmaceutically acceptable diluent comprises
  (i) a chimeric dengue serotype 2/1 strain in a concentration of at least 3.3 log 10 pfu/0.5 mL,
  (ii) a dengue serotype 2 strain in a concentration of at least 2.7 log 10 pfu/0.5 mL,
  (iii) a chimeric dengue serotype 2/3 strain in a concentration of at least 4.0 log 10 pfu/0.5 mL, and
  (iv) a chimeric dengue serotype 2/4 strain in a concentration of at least 4.5 log 10 pfu/0.5 mL.

According to some of these embodiments, upon reconstitution of the dengue vaccine composition with a pharmaceutically acceptable diluent, (i), (ii), (iii), and (iv) provide a total concentration of pfu/0.5 mL and based on said total concentration of pfu/0.5 ml the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 6%, at least 8%, or at least 10%, or at least 12%, or at least 14%, or at least 16%, or at least 18%.

In certain embodiments, the invention is directed to said methods, wherein the subject population or subject is seronegative with respect to all dengue serotypes. According to some of these embodiments, the subject population or subject is seronegative with respect to hepatitis A at baseline.

In certain embodiments the invention is directed to said methods, wherein the unit dose of the invention as described herein and the hepatitis A vaccine, such as HAVRIX® or VAQTA®, are administered on day 0/1.

In certain embodiments, the invention is directed to said methods, wherein the unit dose of the invention as described herein is administered by subcutaneous injection and wherein the hepatitis A vaccine, such as HAVRIX® or VAQTA®, is administered by intramuscular injection. According to some embodiments, the injections are administered to the arm, preferably to the deltoid region of the arm. According to some of these embodiments, the subcutaneous injection of the unit dose of the invention as described herein and the intramuscular injection of the hepatitis A vaccine, such as HAVRIX® or VAQTA®, are administered to different anatomical sites, such as to opposite arms.

In certain embodiments, the invention is directed to said methods, wherein two unit doses of the dengue vaccine composition of the invention as described herein are administered. In some embodiments, the two unit doses of the invention as described herein are administered within 12 month or more, or within 6 month, or within three months, such as at day 0/1 and day 90. According to some of these embodiments, a further third unit dose of the invention as described herein is administered after the second administration. Such a third administration may be administered between 6 to 12 months after the first administration, such as 12 months after the first administration, or later than 12 month after the first administration, such as 12 months (1 year) after the second administration or even 5 years or longer after the first or second administration and may act as a booster.

In certain embodiments, the invention is directed to said methods, wherein two unit doses of the invention as described herein and one dose of a hepatitis A vaccine, such as HAVRIX® or VAQTA®, are administered, in particular according to the following schedule
  a first simultaneous administration of the first unit dose and said hepatitis A vaccine on day 0/1, and
  a second administration of the second unit dose after said first simultaneous administration, such as about 3 months later such as on day 90.

In certain embodiments, the invention is directed to said method, wherein the unit dose of the invention as described herein is administered subcutaneously to a subject or subject population and the hepatitis A vaccine, such as HAVRIX® or VAQTA®, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said method, wherein the unit dose of the invention as described herein and the hepatitis A vaccine, such as HAVRIX® or VAQTA®, are administered to a subject or subject population from a dengue endemic region. In certain embodiments, the unit dose of the invention as described herein is administered subcutaneously and the hepatitis A vaccine, such as HAVRIX® or VAQTA®, is administered intramuscularly to a subject or subject population from a dengue endemic region.

In certain embodiments, the invention is directed to said method, wherein the subject or subject population is from a dengue non-endemic region, preferably from a dengue non-endemic and a hepatitis A non-endemic region.

According to some embodiments, a second dose of a hepatitis A vaccine, such as HAVRIX® or VAQTA®, is administered. The second dose of the hepatitis A vaccine may be administered after the first administration of the hepatitis A vaccine. Such a second administration may act as a booster and may be administered 6 to 12 months or 6 to 18 months, such as 9 months after the first administration of the hepatitis A vaccine, such as on day 270.

In certain embodiments, the invention is directed to said method, wherein the unit dose of the invention as described herein is administered subcutaneously and wherein the hepatitis A vaccine, such as HAVRIX® or VAQTA®, is administered intramuscularly to a subject or subject population of more than 17 years, or more than 18 years, or 18 to 60 years of age. In further embodiments, the subjects or subject population are adults of more than 21 years, or 21 to 60 years, or 21 to 45 years of age. In some embodiments, the subject or subject population is from a dengue endemic region. In another embodiment, the subject or subject population is from a dengue non-endemic region, preferably from a dengue non-endemic and a hepatitis A non-endemic region. According to certain embodiments, the subject or subject population is seronegative for all four dengue serotypes.

In certain embodiments, the invention is directed to said method, wherein the method does not include a step of determination whether there was a previous dengue infection and/or a previous hepatitis A infection in the subject population or in the subject before the administration of the hepatitis A vaccine and before the administration of the unit dose of the dengue vaccine composition or wherein the hepatitis A serostatus and/or the dengue serostatus of the subject population or of the subject is unknown before the administration of the hepatitis A vaccine and before the administration of the unit dose of the dengue vaccine composition. According to certain embodiments, the method does not include a step of determination whether there was a previous dengue infection and/or a previous hepatitis A infection in the subject population or in the subject at any time before, during and after the steps of administration of the hepatitis A vaccine and of the unit dose of the dengue vaccine composition or wherein the hepatitis A serostatus and/or the dengue serostatus of the subject population or of the subject is unknown at any time before, during or after the steps of administration of the hepatitis A vaccine and of the unit dose of the dengue vaccine composition.

In certain embodiments, the invention is directed to said method, wherein the method comprises a primary vaccination consisting of the steps of:
(A) selecting a subject for administration of the unit doses of the tetravalent dengue virus composition and the hepatitis A vaccine in need for protection against dengue infection and hepatitis A infection without determination whether there was a previous dengue infection and/or a previous hepatitis A infection, and
(B) administering simultaneously on the same day a first unit dose of the tetravalent dengue virus composition and a hepatitis A vaccine to the subject, and optionally
(C) administering at least one further unit dose of the tetravalent dengue virus composition to the subject within 3 to 12 months of administration of the first unit dose and optionally
(D) administering at least one further dose of the hepatitis A vaccine to the subject within 6 to 18 months of administration of the first unit dose.

In certain embodiments, the invention is directed to said method, the method comprises a primary vaccination consisting of the steps of:
(A) selecting a subject for administration of the unit doses of the tetravalent dengue virus composition and the hepatitis A vaccine in need for protection against dengue infection and hepatitis A infection, and
(B) administering simultaneously on the same day a first unit dose of the tetravalent dengue virus composition and a hepatitis A vaccine to the subject, and
(C) administering two further unit doses of the tetravalent dengue virus composition to the subject at about 6 and about 12 months of administration of the first unit dose and administering a further hepatitis A vaccine to the subject at either about 6 or about 12 months of administration of the first unit dose. In some of these embodiments, step (A), the selecting of the subject, is carried out without determination whether there was a previous hepatitis A infection.

In certain embodiments, the invention is directed to said method, wherein upon reconstitution of the unit dose with a pharmaceutically acceptable diluent (i), (ii), (iii), and (iv) provide a total concentration of pfu/0.5 mL and based on said total concentration of pfu/0.5 ml the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 6%, at least 8%, or at least 10%, or at least 12%, or at least 14%, or at least 16%, or at least 18%.

In certain embodiments, the method provides compatibility between the dengue vaccine composition and the hepatitis A vaccine. Compatibility means in particular that the immune response after simultaneous administration is not inferior in comparison with a mono-administration of these vaccines.

In certain embodiments, the method provides synergy between the dengue vaccine composition and the hepatitis A vaccine. Synergy means in particular that the immune response after simultaneous administration is better for one or both vaccines in comparison with a mono administration of these vaccines.

In certain embodiments, the invention is directed to said method, wherein the method provides non-inferiority in a non-inferiority clinical study including at least 60 or at least 120 healthy subjects divided into one subject population and into one control subject population, wherein the subject population receives simultaneously on the same day the hepatitis A vaccine and the unit dose of the dengue vaccine composition and the control subject population receives simultaneously on the same day a hepatitis A vaccine and a placebo administration In certain embodiments, the invention is directed to said methods, wherein the hepatitis A vaccine provides a hepatitis A seroprotection rate of at least 95% or of at least 98% on day 30 after an administration (on day 0/1) to a subject population of at least 30 or at least 50 healthy subjects receiving simultaneously on the same day the hepatitis A vaccine and the unit dose of the dengue vaccine composition and being seronegative with respect to hepatitis A at baseline and being seronegative with respect to all dengue virus serotypes at baseline.

In certain embodiments, the invention is directed to said method, wherein the method provides a hepatitis A seroprotection rate difference with respect to a hepatitis A mono-administration, the difference being determined in a non-inferiority clinical study including at least 60 or at least 120 healthy subjects being seronegative with respect to hepatitis A at baseline and seronegative with respect to all dengue virus serotypes at baseline,
   the healthy subjects being divided into
      a) a subject population of at least 30 or at least 50 healthy subjects receiving simultaneously on the same day an administration (on day 0/1) of the hepatitis A vaccine and the unit dose of the dengue vaccine composition, and
      b) a control subject population of at least 30 or at least 50 healthy subjects receiving simultaneously on the same day an administration (on day 0/1) of a hepatitis A vaccine and a placebo,
   wherein the difference is determined between the hepatitis A seroprotection rate of the control subject population on day 30 after the administration (on day 0/1) and the hepatitis A seroprotection rate of the subject population on day 30 after the administration (on day 0/1), and wherein the difference has an upper bound within a two-sided 95% confidence interval which is lower than 10%.

In certain embodiments, the invention is directed to said method, wherein the hepatitis A vaccine provides a hepatitis A seroprotection rate of at least 95% or of at least 98% or of at least 99% on day 30 after an administration (on day 0/1) to a subject population of at least 30 or at least 50 healthy subjects receiving simultaneously on the same day the hepatitis A vaccine and the unit dose of the dengue vaccine composition and being seronegative with respect to hepatitis A at baseline, wherein the healthy subjects include healthy subject(s) which are seropositive with respect to at least one dengue virus serotype at baseline and healthy subject(s) which are seronegative with respect to all dengue virus serotypes at baseline.

In certain embodiments, the invention is directed to said method, wherein the method provides a hepatitis A seroprotection rate difference with respect to a hepatitis A mono-administration, the difference being determined in a non-inferiority clinical study including at least 60 or at least 120 healthy subjects being seronegative with respect to hepatitis A at baseline, wherein the healthy subjects include healthy subject(s) which are seropositive with respect to at least one dengue virus serotype at baseline and healthy subject(s) which are seronegative with respect to all dengue virus serotypes at baseline, the healthy subjects being divided into
a) a subject population of at least 30 or at least 50 healthy subjects receiving simultaneously on the same day an administration (on day 0/1) of the hepatitis A vaccine and the unit dose of the dengue vaccine composition, wherein the subject population includes healthy subject(s) which are seropositive with respect to at least one dengue virus serotype at baseline and healthy subject(s) which are seronegative with respect to all dengue virus serotypes at baseline, and
b) a control subject population of at least 30 or at least 50 healthy subjects receiving simultaneously on the same day an administration (on day 0/1) of a hepatitis A vaccine and a placebo, wherein the control subject population includes healthy subject(s) which are seropositive with respect to at least one dengue virus serotype at baseline and healthy subject(s) which are seronegative with respect to all dengue virus serotypes at baseline, wherein the difference is determined between the hepatitis A seroprotection rate of the control subject population on day 30 after the administration (on day 0/1) and the hepatitis A seroprotection rate of the subject population on day 30 after the administration (on day 0/1), and wherein the difference has an upper bound within a two-sided 95% confidence interval which is lower than 10%.

In certain embodiments, the invention is directed to said method, wherein the subject or subject population is exposed to a hepatitis A virus outbreak and/or a dengue virus outbreak.

In certain embodiments, the invention is directed to said method, wherein the method provides an anti-hepatitis A virus antibody Geometric Mean Concentration (GMC) of at least 70 mIU/ml or at least 80 mIU/ml or at least 90 mIU/ml on day 30 after an administration (on day 0/1) to a subject population of at least 30 or at least 50 healthy subjects receiving simultaneously on the same day the hepatitis A vaccine and the unit dose of the dengue vaccine composition and being seronegative with respect to hepatitis A at baseline and being seronegative with respect to all dengue virus serotypes at baseline.

An ELISA for determining the anti-hepatitis A antibodies is for example disclosed in Beck et al. J Travel Med 2004; 11:201-207.

In certain embodiments, the invention is directed to said method, wherein the simultaneous administration of the hepatitis A vaccine and the unit dose of the dengue vaccine composition to the subject or the subject population does not provide serious adverse events related to the simultaneous administration. Additionally, there are no deaths related to the simultaneous administration.

In certain embodiments, the invention is directed to said methods, wherein the method provides the Geometric Mean Titer (GMT) of neutralizing antibodies measured by MNT50 of
at least 110 or at least 140 or at least 150 for dengue serotype 1,
at least 3000 or at least 3500 or at least 3900 for dengue serotype 2,
at least 100 or at least 120 or at least 140 for dengue serotype 3, and/or
at least 80 or at least 110 or at least 140 for dengue serotype 4,
on day 30 after an administration (on day 0/1) to a subject population of at least 30 or at least 50 healthy subjects receiving simultaneously on the same day the hepatitis A vaccine and the unit dose of the dengue vaccine composition and being seronegative with respect to hepatitis A at baseline and being seronegative with respect to all dengue virus serotypes at baseline.

In some embodiments, the geometric mean neutralizing antibody titers (GMTs) of a subject population or the neutralizing antibody titers of a subject are determined in accordance with a microneutralization test, for example according to the method described in Example 2.

The present invention is directed in part to a method of preventing hepatitis A and dengue disease in a subject or subject population, the method comprising simultaneously on the same day administering a hepatitis A vaccine, and a unit dose of a dengue vaccine composition, wherein said unit dose comprises a tetravalent dengue virus composition including four live, attenuated dengue virus strains, wherein the four live, attenuated dengue virus strains are different from the ones used in the unit dose as defined above.

In one embodiment of the invention, the method is directed to a simultaneous on the same day administration of a hepatitis A vaccine with other dengue vaccines such as Dengvaxia®. Dengvaxia® is a tetravalent dengue vaccine based on a yellow fever backbone, CYD-TDV (Dengvaxia®, Sanofi Pasteur, Lyon, France), and has been licensed in several countries based on the clinical demonstration of an overall vaccine efficacy (VE) against virologically-confirmed dengue (VCD) of 56-61% in children in Asia and Latin America (Capeding M R et al. Clinical efficacy and safety of a novel tetravalent dengue vaccine in healthy children in Asia: a phase 3, randomised, observer-masked, placebo-controlled trial. Lancet 2014, 384:1358-65; Villar L A et al. Safety and immunogenicity of a recombinant tetravalent dengue vaccine in 9-16 year olds: a randomized, controlled, phase II trial in Latin America. Pediatr Infect Dis J 2013, 32:1102-9). The preparation of these particular strains CYD1, CYD2, CYD3 and CYD4 has been described in detail in international patent applications WO 98/37911, WO 03/101397, WO07/021672, WO 08/007021, WO 08/047023 and WO 08/065315, to which reference may be made for a precise description of the processes for their preparation. The corresponding nucleotide sequences of the prM-E regions of CYD1, CYD2, CYD3 and CYD4 are provided in WO2016034629 and SEQ ID NOs are set out in Table 16 of this reference.

In one such embodiment, the method comprises a vaccination consisting of the steps of:
(A) selecting a subject for administration of the equal doses of the CYD-TDV composition, such as Dengvaxia®, and the hepatitis A vaccine, such as HAVRIX® or VAQTA®, in need for protection against dengue infection and hepatitis A infection, and
(B) administering a first dose of the CYD-TDV composition, such as Dengvaxia®, and the hepatitis A vaccine, such as HAVRIX® or VAQTA® to the subject at month 0,
(C) administering a further dose of the CYD-TDV composition, such as Dengvaxia®, and optionally the hepatitis A vaccine, such as HAVRIX® or VAQTA® to the subject within 3 to 11 months, in particular at about month 6 of the administration of the first CYD-TDV dose, and
(D) administering a final dose of the CYD-TDV, such as Dengvaxia®, and optionally the hepatitis A vaccine, such as HAVRIX® or VAQTA® to the subject at about month 12.

In certain embodiments, the subject is from 2 to 60 years of age.

In particular embodiments, the subject is 2 to 18 years of age, or 4 to 16 years of age, or 18 to 60 years of age.

Preferably, the exact quantity of each component of the CYD-TDV to be administered may vary according to the age and the weight of the subject being vaccinated, the frequency of administration as well as the other ingredients in the composition. The quantity of a chimeric dengue virus within CYD-TDV comprised in a dose of a vaccine composition lies within a range of about $10^5$ CCID50 to about $10^6$ CCID50. The quantity of a live attenuated chimeric dengue virus of each of serotypes 1 to 4 comprised in the CYD dosage form, e.g. Dengvaxia®, is preferably equal. Advantageously, a vaccine composition, as described in this section, comprises an effective amount of a dengue antigen as defined herein.

In certain embodiments, the invention is directed to said method, wherein the dengue vaccine composition comprises other dengue vaccines such as TV003 or TV005. TV003, developed by the U.S. National Institute of Allergy and Infectious Diseases, comprises vaccine components rDEN1Δ30, rDEN2/4Δ30, rDEN3Δ30/31 and rDEN4Δ30, wherein each of these components is present at a concentration of 3 $\log_{10}$ PFU. TV005 is similar to TV003 with the difference that the concentration of rDEN2/4Δ30 in TV005 is 4 $\log_{10}$ PFU. The vaccines TV003 and TV005 and their vaccine components as well as their production are described in more detail in WO 2008/022196 A2 and S. S. Whitehead, Expert Rev Vaccines, 2016, 15(4): 509 to 517. Using recombinant DNA technology, two attenuation strategies were utilized for the vaccine components of TV003 or TV005: deletions in the 3' untranslated region and structural gene chimerization. For example, the component rDEN4Δ30 contains all the structural and non-structural proteins of a wild type DENV-4, but is attenuated by a 30-nucleotide deletion in the 3' untranslated region (denoted "Δ30"). The other vaccine components are also attenuated due to the 30-nucleotide deletion in the 3' untranslated region. In addition, rDEN3Δ30/31 includes a 31 nucleotide deletion in the 3' untranslated region (shown in detail in FIG. 1c and FIG. 13 of WO 2008/022196 A2). The rDEN2/4Δ30 component was created by substituting the prM and E genes of DENV-2 into the rDEN4Δ30 genome. The complete genomic sequences of dengue strains which can be used to produce TV003 or TV005 are available under the Genbank accession numbers in Table A of WO 2008/022196 A1.

In certain embodiments, the invention is directed to said methods, wherein the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, and Dengvaxia® disclosed herein and the hepatitis A vaccine disclosed herein are simultaneously on the same day administered to the subject or to the subject population.

In certain embodiments, the invention is directed to said methods, wherein the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, and the hepatitis A vaccine disclosed herein are simultaneously on the same day administered to the subject or to the subject population on day 0/1 as a first administration and Dengvaxia® disclosed herein is subsequently administered to the subject or to the subject population within three months from the first administration, such as on day 90 from the first administration, as a second administration. Alternatively, Dengvaxia® disclosed herein and the hepatitis A vaccine disclosed herein are simultaneously on the same day administered to the subject or to subject population on day 0/1 as a first administration and the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, is administered subsequently to the subject or to the subject population within three months from the first administration, such as on day 90 from the first administration, as a second administration.

In certain embodiments, the invention is directed to said methods, wherein the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, and TV003 or TV005 disclosed herein and the hepatitis A vaccine disclosed herein are simultaneously on the same day administered to the subject or to the subject population.

In certain embodiments, the invention is directed to said methods, wherein the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, and the hepatitis A vaccine disclosed herein are simultaneously on the same day administered to the subject or the subject population on day 0/1 as a first administration and wherein TV003 or TV005 disclosed herein is subsequently administered to the subject or to the subject population within three months from the first administration, such as on day 90 from the first administration, as a second administration. Alternatively, TV003 or TV005 disclosed herein and the hepatitis A vaccine disclosed herein are simultaneously on the same day administered to the subject or to the subject population on day 0/1 as a first administration and the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, is administered subsequently to the subject or to the subject population within three months from the first administration, such as on day 90 from the first administration, as the second administration.

The above method is also to be considered in the context of a use of the unit dose of dengue vaccine as disclosed herein for such methods of preventing dengue disease and hepatitis A or in the context of the use of the unit dose of dengue vaccine for the manufacture of a medicament for such methods of preventing dengue disease and hepatitis A.

Furthermore, the present invention is directed to a kit against hepatitis A and dengue disease comprising
a box containing at least
(a) a first container holding a hepatitis A vaccine, as defined above such as HAVRIX®, and
(b) a second container holding a unit dose of a dengue vaccine composition as defined above, wherein said unit dose comprises a tetravalent dengue virus composition including four live, attenuated dengue virus strains.

Method of Preventing Dengue Disease and Yellow Fever and Uses

The present invention is directed in part to a method of preventing dengue disease as well as yellow fever in a subject. Thus, in certain embodiments the invention is directed to a method of preventing dengue disease in a subject, comprising administering to the subject a reconstituted unit dose of the invention as described herein, wherein the method further comprises preventing yellow fever in the subject by concomitant administration of a yellow fever vaccine, in particular YF-17D, to the subject.

The present invention is directed in part to a method of preventing dengue disease as well as yellow fever in a subject population. Thus, in certain embodiments the invention is directed to a method of preventing dengue disease in a subject population, comprising administering to the subject population a reconstituted unit dose of the invention as described herein, wherein the method further comprises preventing yellow fever in the subject population by concomitant administration of a yellow fever vaccine, in particular YF-17D, to the subject population.

In certain embodiments the invention is directed to said methods, wherein the unit dose of the invention as described herein and the yellow fever vaccine, in particular YF-17D, are administered simultaneously. In some of these embodiments the simultaneous administration is on day 0 or day 90, preferably on day 0. In other embodiments the administration of the unit dose of the invention as described herein and the yellow fever vaccine, in particular YF-17D, are done sequentially such as wherein the yellow fever vaccine is administered before or after the unit dose of dengue vaccine as described herein, such as within about 6 weeks, or such as within about 4 weeks, or such as within about 2 weeks, or such as about within 1 week.

In certain embodiments the invention is directed to said methods, wherein the reconstituted unit dose of the invention as described herein is administered and the yellow fever vaccine, in particular YF-17D, are administered by subcutaneous injection. According to some embodiments, the subcutaneous injections are administered to the arm, preferably to the deltoid region of the arm. According to some of these embodiments the subcutaneous injections of the unit dose of the invention as described herein and yellow fever vaccine, in particular YF-17D, are administered to different anatomical sites, such as to opposite arms, in particular when the vaccines are administered simultaneously.

In certain embodiments the invention is directed to said methods, wherein two unit doses of the invention as described herein are administered. In some embodiments the two unit doses of the invention as described herein are administered within 12 month or more, or within 6 month, or within three months, such as at day 0/1 and day 90. According to some of these embodiments a further third unit dose of the invention as described herein is administered after the second. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said methods, wherein two reconstituted unit doses of the invention as described herein and one dose of a yellow fever vaccine, in particular YF-17D, are administered, in particular according to the following schedule
an administration of said yellow fever vaccine on day 0,
a first administration of the first reconstituted unit dose after said yellow fever vaccine administration, such as 3 months later and preferably on day 90, and
a second administration of the second reconstituted unit dose after said first administration of the reconstituted unit dose, such as 3 months later and preferably on day 180.

In certain embodiments the invention is directed to said methods, wherein two reconstituted unit doses of the invention as described herein and one dose of a yellow fever vaccine, in particular YF-17D, are administered, in particular according to the following schedule
a first administration of the first reconstituted unit dose on day 0,
a second administration of the second reconstituted unit dose after said first administration of the reconstituted unit dose, such as 3 months later and preferably on day 90, and
an administration of said yellow fever vaccine after said second administration of the reconstituted unit dose, such as 3 months later and preferably on day 180.

In certain embodiments the invention is directed to said methods, wherein two reconstituted unit doses of the invention as described herein and one dose of a yellow fever vaccine, in particular YF-17D, are administered, in particular according to the following schedule
a simultaneous administration of the first reconstituted unit dose and said yellow fever vaccine on day 0, and
a second administration of the second reconstituted unit dose after said simultaneous administration, such as 3 months later and preferably on day 90.

In a preferred embodiment, the yellow fever vaccine and unit dose of the invention as described herein are administered simultaneously on day 0 or simultaneously on day 90.

In certain embodiments, the invention is directed to said methods, wherein the subject or subject population is seronegative to all dengue serotypes. In certain embodiments, the invention is directed to said methods, wherein the reconstituted unit dose of the invention as described herein is administered subcutaneously to a subject or subject population and the yellow fever vaccine, in particular YF-17D vaccine, is administered subcutaneously to a subject or subject population, and wherein the subject or the subject population is seronegative with respect to all dengue serotypes. In other embodiments, the subject or subject population is seropositive with respect to at least one dengue serotype.

In certain embodiments, the invention is directed to said methods, wherein the unit dose of the invention as described herein and the yellow fever vaccine, in particular YF-17D, are administered to a subject or subject population from a dengue endemic region. In certain embodiments, the reconstituted unit dose of the invention as described herein and the yellow fever vaccine, in particular YF-17D, are administered subcutaneously to a subject or subject population from a dengue endemic region. In other embodiments, the subject or subject population is from a dengue non-endemic region. Such a subject population or such a subject may be vaccinated according to the present invention in the context of traveling to a dengue endemic region and yellow fever endemic region.

In certain embodiments the invention is directed to said methods, wherein the reconstituted unit dose of the invention as described herein and of the yellow fever vaccine, in particular YF-17D, are administered subcutaneously to a subject or subject population of more than 17 years, or more than 18 years, or 18 to 60 years of age. In further embodiments, the subjects or subject population are adults of more than 21 years, or 21 to 60 years, or 21 to 45 years of age. In some embodiments, the subject or subject population is from a dengue endemic region. In another embodiment, the subject or subject population is from a dengue non-endemic region, preferably from a dengue non-endemic and yellow fever non-endemic region. According to some of these embodiments, the subject or subject population are seronegative for all four dengue serotypes.

The above method is also to be considered in the context of a use of the unit dose of dengue vaccine as disclosed herein for such methods or in the context of the use of the unit dose of dengue vaccine for the manufacture of a medicament for such methods.

Method of Preventing and Uses, Method of Inoculating Against Dengue Disease and Uses The present invention is directed in part to a method of preventing dengue disease (in particular virologically confirmable dengue, VCD) in a subject. Thus, in certain embodiments the invention is directed to a method of preventing dengue disease in a subject, comprising administering to the subject, a unit dose/tetravalent dengue virus composition, in particular a reconstituted unit dose of the invention as described herein.

The present invention is directed in part to a method of preventing dengue hemorrhagic fever (DHF) and dengue shock syndrome (DSS). Thus, in certain embodiments the invention is directed to a method of preventing dengue hemorrhagic fever (DHF) and dengue shock syndrome (DSS), comprising administering to the subject a reconstituted unit dose/tetravalent dengue virus composition of the invention as described herein.

The present invention is therefore directed to a method of inoculating a subject against virologically confirmable dengue disease with a tetravalent dengue virus composition including four live attenuated dengue virus strains representing serotype 1, serotype 2, serotype 3 and serotype 4, wherein in particular the tetravalent dengue virus composition includes a chimeric dengue serotype 2/1 strain and a dengue serotype 2 strain and a chimeric dengue serotype 2/3 strain and a chimeric dengue serotype 2/4 strain, wherein in particular the dengue serotype 2 strain is derived from the wild type virus strain DEN-2 16681 (SEQ ID NO 11) and differs in at least three nucleotides from the wild type as follows:
  a) 5-noncoding region (NCR)-57 (nt-57 C-to-T): major attenuation locus
  b) NS1-53 Gly-to-Asp (nt-2579 G-to-A): major attenuation locus
  c) NS3-250 Glu-to-Val (nt-5270 A-to-T): major attenuation locus; and
wherein the three chimeric dengue strains are derived from the serotype 2 strain by replacing the structural proteins prM and E from serotype 2 strain with the corresponding structural proteins from the other dengue serotypes, resulting in the following chimeric dengue strains:
  a DENV-2/1 chimera,
  a DENV-2/3 chimera and
  a DENV-2/4 chimera.

Further information regarding the serotypes of the tetravalent composition can be derived from section "Dengue virus strains" above.

The tetravalent dengue virus composition for such a method may be in the form of a unit dose comprising:
(i) a dengue serotype 1 in a concentration of at least 3.3 log 10 pfu/0.5 ml,
(ii) a dengue serotype 2 in a concentration of at least 2.7 log 10 pfu/0.5 ml,
(iii) a dengue serotype 3 in a concentration of at least 4.0 log 10 pfu/0.5 ml, and
(iv) a dengue serotype 4 in a concentration of at least 4.5 log 10 pfu/0.5 ml.

The present invention is in particular directed to such a method wherein the unit dose is lyophilized and upon reconstitution with 0.5 mL of a pharmaceutically acceptable diluent comprises:
(i) a dengue serotype 1 in a concentration of at least 3.3 log 10 pfu/0.5 ml,
(ii) a dengue serotype 2 in a concentration of at least 2.7 log 10 pfu/0.5 ml,
(iii) a dengue serotype 3 in a concentration of at least 4.0 log 10 pfu/0.5 ml, and
(iv) a dengue serotype 4 in a concentration of at least 4.5 log 10 pfu/0.5 ml.

Further information regarding the tetravalent composition or the unit dose can be derived from section "Dengue vaccine composition" and "Unit dose" above.

The present invention is therefore directed to a method and corresponding use, the method comprising a primary vaccination with only two administrations of the unit dose comprising the steps of:
(A) administering a first unit dose of the tetravalent dengue virus composition to the subject, and
(B) administering a second unit does of the tetravalent dengue virus composition to the subject within 3 months of administration of the first unit dose.
According to this embodiment the administration of only two doses within 3 months is sufficient to provide effective protection against a subsequent dengue infection.

Such method preferably provides a combined vaccine efficacy against all four serotypes in preventing virologically confirmable dengue disease with a 2-sided 95% confidence interval, wherein the lower bound is more than 60%, when measured against placebo in a subject population of at least 5,000 healthy subjects irrespective of serostatus at baseline and 14 to 16 years of age, from the first administration of the administration schedule until 18 months after the second administration of the administration schedule.

Such method also preferably provides a combined vaccine efficacy against all four serotypes, in preventing virologically confirmable dengue disease with a 2-sided 95% confidence interval, wherein the lower bound is more than 45%, when measured against placebo in a subject population of at least 1,500 or at least 2,000 healthy subjects seronegative against all serotypes at baseline and 14 to 16 years of age, from 30 days after the second administration of the administration schedule until 18 months after the second administration of the administration schedule.

According to certain embodiments the method of inoculation against the virologically confirmable dengue disease is due to a dengue serotype 2, and/or due to a dengue serotype 1. The method has very high efficacy against dengue serotype 2 and dengue serotype 1 and the highest efficacy against dengue serotype 2.

In certain embodiments, the invention is directed to said methods having a vaccine efficacy against serotype 1, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the lower bound is more than 30%, is more than 35% is more than 40%, is more than 45%, is more than 50%, or is more than 54%. In certain such embodiments the subject population of at least 1,500 is seronegative against all serotypes at base line and the lower bound is more than 35%. In certain such embodiments the seronegative and seropositive population each provide a vaccine efficacy against serotype 1 with a 2-sided 95% confidence interval, wherein the lower bounds are within 10%-points.

In certain embodiments, the invention is directed to said methods having a vaccine efficacy against serotype 1, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the vaccine efficacy is more than 40%, is more than 50%, is more than 60%, or is more than 65%. In certain such embodiments the subject population of at least 1,500 is seronegative against all serotypes at base line. In certain such embodiments the seronegative and seropositive population each provide a vaccine efficacy against serotype 1 which are within 5%-points.

In certain embodiments, the invention is directed to said methods having a vaccine efficacy against serotype 2, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the lower bound is more than 50%, is more than 60%, is more than 70%, is more than 80%, or is more than 85%. In certain such embodiments the subject population of at least 1,500, is seronegative against all serotypes. In certain such embodiments the seronegative and seropositive population each provide a vaccine efficacy against serotype 2 with a 2-sided 95% confidence interval, wherein the lower bounds are within 5%-points.

In certain embodiments, the invention is directed to said methods having a vaccine efficacy against serotype 2, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the vaccine efficacy is more than 60%, is more than 70%, is more than 80%, or is more than 90%. In certain such embodiments the subject population of at least 1,500 is seronegative against all serotypes at base line. In certain such embodiments the seronegative and seropositive population each provide a vaccine efficacy against serotype 2 which are within 5%-points.

The efficacy of the method is further described in more detail below in this the section.

In certain embodiments the unit dose is reconstituted and administered by subcutaneous injection. According to some of these embodiments, the subcutaneous injection is administered to the arm, preferably to the deltoid region of the arm.

According to one embodiment such a method does not include a step of determination whether there was a previous dengue infection in the subject before administration of the unit dose or wherein the serostatus of the subject is unknown before administration of the unit dose.

According to one embodiment such a method does not include a step of determination of a previous dengue infection in the subjects preferably at any time before, during or after the steps of administration or wherein the serostatus of the subject is unknown preferably at any time before, during or after the steps of administration.

The method according to the invention does not require the testing of the serostatus before vaccination and thus allows immediate treatment and outbreak control. According to certain embodiments the use is for a method wherein the subject is exposed to a dengue outbreak. In certain such embodiments the outbreak is due to a dengue serotype 2, and/or due to a serotype 1.

According to one embodiment such a method the subject is from a region wherein the seroprevalence rate is unknown and/or wherein the seroprevalence rate is below 80%, or below 70%, or below 60%.

According to one embodiment of such a method the subject is seronegative at baseline and is from a region or travels to a region wherein the seroprevalence rate is high with respect to serotype 1 and/or serotype 2 i.e. 80%, or 90% or above.

According this embodiment the vaccine and corresponding method is safe for seronegative and seropositive subjects and thus does not require an analysis of the serostatus or a determination of a previous dengue infection or a high seroprevalence rate in the region. Such a method preferably provides a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline, preferably in at least 1,500 healthy 4 to 16 year old subjects seronegative at baseline, from first administration of the administration schedule until 12 to 18 months after the second administration of the administration schedule. Preferably, the 2-sided 95% confidence interval of the combined vaccine efficacy against virologically-confirmed dengue with hospitalization against all four serotypes when comparing seropositive and seronegative subjects provides for lower bounds of the 2-sided confidence interval which are within 10% points or within 15% points or within 20% points. The method is preferably safe with respect to serotype 1 and serotype 2 which may therefore be used in outbreak situations due to serotype 1 and/or serotype 2 or even for seronegative subjects (e.g. travelers) or subjects with unknown serostatus in regions with very high seroprevalence rates (>80%) due to serotype 1 and/or serotype 2.

The safety of the method is further described in more detail in the section "method of preventing, method of inoculating".

According to one embodiment such a method does not include the active surveillance with respect to febrile illness of the subject after the administration of the first- and second-unit dose. During active surveillance any subject with febrile illness (defined as fever ≥38° C. on any 2 of 3 consecutive days) will be asked to return to the site for dengue fever evaluation by the Investigator. Subjects/guardians will be contacted at least weekly to ensure robust identification of febrile illness by reminding subjects/guardians of their obligation to return to the site in case of febrile illness. This contact will be implemented through appropriate methods that may differ in each trial site (eg, phone calls, text messaging, home visits, school-based surveillance).

According to one embodiment such a method does not include vaccine immunogenicity analysis including GMTs for dengue neutralizing antibodies.

According to one embodiment such a method does not include a reactogenicity analysis. Such a reactogenicity analysis relates to solicited local AEs (injection site pain, injection site erythema, and injection site swelling) and solicited systemic AEs (child <6 years: fever, irritability/fussiness, drowsiness and loss of appetite; child ≥6 years: asthenia, fever, headache, malaise and myalgia) which will e.g. be assessed for 7 days and 14 days, respectively, following each vaccination (vaccination day included) via collection of diary cards.

According to one embodiment the method does not include an active surveillance, an immunogenicity analysis and a reactogenicity analysis.

According to such embodiments the vaccine and the corresponding method of inoculation are safe and therefore do not require further steps of surveillance or analysis.

In view of the above the method according to one embodiment comprises a primary vaccination consisting of the steps of:
(A) selecting a subject for administration of the unit doses of the tetravalent dengue virus composition in need for protection against dengue infection without determination of a previous dengue infection, and
(B) administering a first unit dose of the tetravalent dengue virus composition to the subject, and
(C) administering a second unit dose of the tetravalent dengue virus composition to the subject within 3 months of administration of the first unit dose.
Therefore the method of inoculating is finalized without determination of a previous dengue infection. The method further optionally comprises at least 1 years after the administration of the second unit dose a booster dose of the unit dose.

Selecting the subject may include all types of considerations but preferably not the determination of a previous dengue infection. The selection may include consideration of the age, health conditions, and threat of infection. The threat of infection includes consideration of the seroprevalence rate in the region in which the subject normally lives or intends to travel, the serotype specific seroprevalence rate and an outbreak situation or serotype specific outbreak situations. The subject may be selected due to its exposure to serotype 1 and/or serotype 2 or due to the fact it requires protection against a specific dengue serotype, i.e. serotype 1 and/or serotype 2.

According to the invention the method is applicable to subjects of all kinds of ages. According to one embodiment the subject is under 9 years of age, or 4 to 5 years of age, or 6 to 11 years of age or 12 to 16 years, or 6 to 16 years of age or 4 to 16 years of age, or 2 to 17 years of age, or 9 years of age, or over 9 years of age, or 9 to 17 years of age, or 18 to 45 years of age, or 46 to 60 years of age, or over 60 years of age.

In particular the present invention is directed to such a method wherein the method which is safe.

In particular the present invention is directed to such a method providing a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline from first administration of the administration schedule until 12 to 18 months after the last administration of the administration schedule.

In particular the present invention is directed to such a method wherein the method which is effective.

In particular the present invention is directed to such a method providing a combined vaccine efficacy against all four serotypes, in preventing virologically confirmable dengue disease with a 2-sided 95% confidence interval, wherein the lower bound is more than 60%, when measured against placebo in a subject population of at least 5,000 healthy subjects irrespective of serostatus at baseline and 14 to 16 years of age, from the first administration of the administration schedule until 18 months after the last administration of the administration schedule.

In certain embodiments, the invention is directed to said methods, wherein the subject is seronegative to all dengue serotypes.

The present invention is directed in part to a method of preventing dengue disease (in particular virologically confirmable dengue, VCD) in a subject population. Thus, in certain embodiments the invention is directed to a method of preventing dengue disease in a subject population, comprising administering to the subject population a unit dose, in particular a reconstituted unit dose of the invention as described herein.

The present invention is in part directed to said method for preventing dengue disease (in particular virologically confirmable dengue, VCD) in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to said method for preventing dengue disease (in particular virologically confirmable dengue, VCD) in a subject comprising administering to the subject at least a first reconstituted unit dose of the invention as described herein, wherein certain ratios of neutralizing antibody titers at day 180 or 365 after administration of said first unit dose to the subject are achieved. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for GMT DENV-4 of not more than 50, or not more than 40, or not more than 30, or not more than 20. In some of these embodiments, the ratio of the neutralizing antibody titers of DENV-2: DENV-1 is not more than 20, or not more than 18, or not more than 15 at day 180 or 365 after administration of said first reconstituted unit dose, and/or the ratio of the neutralizing antibody titers of DENV-2: DENV-3 is not more than 20, or not more than 18, or not more than 15 at day 180 or 365 after administration of said first reconstituted unit dose.

The geometric mean neutralizing antibody titers (GMTs) of a subject population or the neutralizing antibody titers of a subject are determined in accordance with the microneutralization test disclosed herein, for example according to the method described in Example 2. Without wishing to be bound to any theory, it is presently understood that a method inducing a more balanced immune response due to the administration of the reconstituted unit dose of the invention as described herein, in terms of less differences between the geometric mean neutralizing antibody titers (GMTs) against the four dengue serotypes or the neutralizing antibody titers against the four dengue serotypes, is beneficial to the subject or subject population to be vaccinated. In particular, it is understood that a much greater response to any one of the four serotypes, such as to DENV-2 in comparison to the other serotypes, is less beneficial.

The present invention is in part directed to said method for preventing dengue disease (in particular virologically confirmable dengue, VCD) in a subject or subject population wherein the method provides a seropositivity rate in a subject population of at least 50 subjects including the administration of two unit doses subcutaneously at day 1 and at day 90, wherein the subjects of the subject population are seronegative to all dengue serotypes at baseline. In certain such embodiments, at least 80% of the subject population are seropositive for all four dengue serotypes at least one month after administration of the first unit dose, such as at day 30, and/or at least 80% of the subject population are seropositive for all four dengue serotypes before or at the time of the administration of the second unit dose, such as at day 90, and/or at least 80%, or at least 85%, or at least 90%, or at least 95% of the subject population are seropositive for all four dengue serotypes after the administration of the second unit dose, such as at day 120, and/or at least 80%, or at least 85%, or at least 90% of the subject population are seropositive for all four dengue serotypes after the administration of the second unit dose, such as at day 270.

The present invention is in part directed to said method for preventing dengue disease (in particular virologically confirmable dengue, VCD) in a subject or subject population wherein the method provides a seropositivity rate in a subject population of at least 100 subjects including administration of two unit doses subcutaneously at day 1 and at day 90, wherein the subjects of the subject population comprises from 20% to 40% subjects who are seronegative to all dengue serotypes and from 60% to 80% subjects who are seropositive to at least one dengue serotype at base line, wherein at day 120 and/or day 270 the seropositivity rate for all four dengue serotypes in the seronegative part of the subject population and the seropositivity rate for all four dengue serotypes in the seropositive part of the subject population do not deviate more than 10%-points and/or wherein at day 120 the seropositivity rate for all four dengue serotypes in the seronegative part of the subject population and the seropositivity rate for all four dengue serotypes in the seropositive part of the subject population do not deviate more than 5%-points.

The present invention is in part directed to a method of preventing virologically confirmable dengue disease in a subject or subject population comprising administering to the subject or subject population a reconstituted unit dose of a tetravalent dengue virus composition including four live, attenuated dengue serotypes, in particular the virus strains as described herein.

The present invention is in part directed to a method of preventing virologically confirmable dengue disease with hospitalization in a subject or subject population comprising administering to the subject or subject population a reconstituted unit dose of a tetravalent dengue virus composition including four live, attenuated dengue serotypes, in particular the virus strains as described herein.

In certain embodiments, the method includes a reconstituted unit dose/tetravalent dengue virus composition of a dengue vaccine composition administered for preventing dengue disease in a subject or a subject population, the reconstituted unit dose comprising: a tetravalent virus composition including four live attenuated dengue virus strains, wherein a unit dose is lyophilized and upon reconstitution with 0.5 mL of a pharmaceutically acceptable diluent the reconstituted unit dose is obtained which comprises:

(i) a dengue serotype 1, such as a chimeric dengue serotype 2/1 strain, in a concentration of at least 3.3 log 10 pfu/0.5 ml, (ii) a dengue serotype 2, such as a dengue serotype 2 strain, in a concentration of at least 2.7 log 10 pfu/0.5 ml, (iii) a dengue serotype 3, such as a chimeric dengue serotype 2/3 strain, in a concentration of at least 4.0 log 10 pfu/0.5 ml, and (vi) a dengue serotype 4, such as a chimeric dengue serotype 2/4 strain, in a concentration of at least 4.5 log 10 pfu/0.5 ml.

It is preferred that the reconstituted unit dose/tetravalent dengue virus composition is used in the method of preventing dengue disease of the present invention, wherein upon reconstitution of the unit dose with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6% and wherein the subject or subject population is of 18 to 60 years of age.

In another preferred embodiment, the reconstituted unit dose/tetravalent dengue virus composition is used in the method of preventing dengue disease of the present invention, wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8% and wherein the subject or subject population is of 2 to 17 years of age.

In certain embodiments, the invention is directed to said methods, wherein said unit dose comprises a tetravalent dengue virus composition including four live attenuated dengue serotypes, in particular the virus strains described herein wherein the serotypes have certain concentrations as described herein with respect to the virus composition and unit dose such as:
  (i) a dengue serotype 1 (e.g. chimeric dengue serotype 2/1 strain) has a concentration of 3.3 log 10 pfu/dose to 5.0 log 10 pfu/dose, or 3.3 log 10 pfu/0.5 mL to 5.0 log 10 pfu/0.5 mL
  (ii) a dengue serotype 2 (e.g. dengue serotype 2 strain) has a concentration of 2.7 log 10 pfu/dose to 4.9 log 10 pfu/0.5 dose, or 2.7 log 10 pfu/0.5 ml to 4.9 log 10 pfu/0.5 ml
  (iii) a dengue serotype 3 (e.g. chimeric dengue serotype 2/3 strain) has a concentration of 4.0 log 10 pfu/dose to 5.7 log 10 pfu/0.5 dose, or 4.0 log 10 pfu/0.5 mL to 5.7 log 10 pfu/0.5 mL and
  (iv) a dengue serotype 4 (e.g. chimeric dengue serotype 2/4 strain) has a concentration of 4.5 log 10 pfu/dose to 5.5 log 10 pfu/0.5 dose, or 4.5 log 10 pfu/0.5 mL to 5.5 log 10 pfu/0.5 mL.

In preferred such embodiments, the subject or subject population is of 2 to 17 years of age, such as 4 to 16 years of age, and preferably less than 9 years of age. In other preferred embodiments, the subject or subject population is 4-5 years of age, 6-11 years of age or 12-16 years of age.

In certain embodiments, the invention is directed to said methods, wherein said unit dose upon reconstitution with 0.5 mL of a pharmaceutically acceptable diluent has a concentration of 3.3 log 10 pfu/0.5 mL to 3.6 log 10 pfu/0.5 mL for dengue serotype 1 (e.g. chimeric dengue serotype 2/1 strain), has a concentration of 2.7 log 10 pfu/0.5 mL to 4.0 log 10 pfu/0.5 mL for dengue serotype 2 (e.g. dengue serotype 2 strain), has a concentration of 4.0 log 10 pfu/0.5 mL to 4.6 log 10 pfu/0.5 mL for dengue serotype 3 (e.g. chimeric dengue serotype 2/3 strain) and has a concentration of 4.5 log 10 pfu/0.5 mL or 4.6 log 10 pfu/0.5 mL to 5.1 log 10 pfu/0.5 mL for dengue serotype 4 (e.g. chimeric dengue serotype 2/4 strain). In preferred such embodiments, the subject or subject population is of 2 to 17 years of age, such as 4 to 16 years of age, and preferably less than 9 years of age. In other preferred embodiments, the subject or subject population is 4-5 years of age, 6-11 years of age or 12-16 years of age.

In certain embodiments, the invention is directed to said methods, wherein the concentration of the dengue serotype 1 (e.g. chimeric dengue serotype 2/1 strain) measured in pfu/0.5 mL is 1% to 7% of the total concentration, the concentration of the dengue serotype 2 (e.g. dengue serotype 2 strain) measured in pfu/0.5 mL is less than 8% of the total concentration, such as in the range of 1% to 8% of the total concentration, the concentration of the dengue serotype 3 (e.g. chimeric dengue serotype 2/3 strain) measured in pfu/0.5 mL is at least 10% of the total concentration, and the concentration of the dengue serotype 4 (e.g. chimeric dengue serotype 2/4 strain) measured in pfu/0.5 mL is at least 65% of the total concentration, such as in the range of 65% to 80%. In certain such embodiments, the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL Preferably, in said embodiments the subject or subject population is of 2 to 17 years of age, such as 4 to 16 years of age, and even more preferably less than 9 years of age. In other preferred embodiments, the subject or subject population is 4-5 years of age, 6-11 years of age or 12-16 years of age.

In a further preferred embodiment, the invention is directed to said methods, wherein the dengue serotype 1 (e.g. chimeric dengue serotype 2/1 strain) such as TDV-1 and the dengue serotype 2 (e.g. dengue serotype 2 strain) such as TDV-2 are present each in a concentration based on the total concentration in pfu/0.5 mL which is within 5%-points of each other and/or are together less than about 10% of the total concentration in pfu/0.5 mL. In certain such embodiments the dengue serotype 3 (e.g. chimeric dengue serotype 2/3 strain) such as TDV-3 is preferably at least about 10% of the total concentration in pfu/0.5 mL and more preferably the dengue serotype 4 (e.g. chimeric dengue serotype 2/4 strain) such as TDV-4 is at least about 70% of the total concentration in pfu/0.5 mL. In certain such embodiments the dengue serotype 4 (e.g. chimeric dengue serotype 2/4 strain) such as TDV-4 represents the highest concentration in the composition of all four serotypes, preferably with at least about 70% of the total concentration in pfu/0.5 mL, dengue serotype 3 (e.g. chimeric dengue serotype 2/3 strain) such as TDV-3 represents the second highest concentration in the composition of all four serotypes, preferably with at least about 10% of the total concentration in pfu/0.5 mL, and dengue serotype 1 (e.g. chimeric dengue serotype 2/1 strain) such as TDV-1 and dengue serotype 2 (e.g. dengue serotype 2 strain) such as TDV-2 each represent lower concentrations than the concentration of serotype 3 (e.g. chimeric dengue serotype 2/3 strain) such as TDV-3, and optionally together represent less than about 10% of the total concentration in pfu/0.5 mL.

Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

In certain embodiments, the invention is directed to said methods, wherein the reconstituted unit dose of the invention as described herein is administered by subcutaneous injection. According to some of these embodiments, the subcutaneous injection is administered to the arm, preferably to the deltoid region of the arm.

In certain embodiments, the invention is directed to said methods, wherein the reconstituted unit dose is administered to a subject of unknown serostatus and/or wherein no test has been carried out to determine whether the subject is seropositive or seronegative (before) the unit dose as described herein is administered. In certain embodiments, the invention is directed to said methods which do not include a step of determination of a previous dengue infection in the subject or subjects. In certain embodiments, the invention is directed to said methods which do not include the analysis of the seroprevalence rate in the region or is conducted in a region with a seroprevalence of below 80%, below 70% or below 60%. In certain embodiments the invention is directed to a method wherein the serostatus of the subject is unknown. In such embodiments the serostatus is not determined at any time before and after administration in relation to this method. In certain embodiments of the invention the method is used in an outbreak situation. In certain embodiments, the invention is directed to said methods being conducted outside a clinical trial In certain embodiments, the invention is directed to said methods, wherein the subject, or subject population is seronegative to all dengue serotypes.

In certain embodiments, the invention is directed to said methods, wherein two unit doses of the invention as described herein are administered. In some embodiments the two unit doses are administered within 12 months or more, or within six months, or within three months, and optionally at least 4 weeks apart such as at day 0 and day 90 or at day 1 and day 90. According to some of these embodiments, a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments, the method of the invention comprises or consists of a single unit dose of the invention being administered.

In certain embodiments, the invention is directed to said methods, wherein the reconstituted unit dose of the invention as described herein is administered subcutaneously to a subject or subject population that is seronegative with respect to all dengue serotypes. In other embodiments, the subject or subject population is seropositive with respect to at least one dengue serotype.

In certain embodiments, the invention is directed to said methods, wherein the unit dose of the invention as described herein is administered to a subject or subject population from a dengue endemic region. In some of these embodiments, the subject or subject population is from Singapore, Dominican Republic, Panama, Philippines, Colombia, Puerto Rico or Thailand, in particular from Singapore, Dominican Republic, Panama, or Philippines. In a preferred embodiment, the subject or subject population is from Asia Pacific or from Latin America. In some other of these embodiments, the subject or subject population is from Thailand, Sri Lanka, Philippines, Panama, Nicaragua, Dominican Republic, Colombia or Brazil. In other embodiments, the subject, or subject population is from a dengue non-endemic region. Such a subject population or such a subject may be vaccinated according to the present invention in the context of traveling to a dengue endemic region. In certain embodiments, the reconstituted unit dose of the invention as described herein is administered subcutaneously to a subject, or subject population that is from a dengue endemic region or a dengue non-endemic region.

In certain embodiments, the invention is directed to said methods, wherein the reconstituted unit dose of the invention as described herein is administered subcutaneously to a subject or subject population of 2 to 60 years of age. In some embodiments, the subjects or subject population are adults of more than 17 years, or more than 18 years, or 18 to 60 years. In further specific embodiments, the subjects or subject population are adults of more than 21 years, or 21 to 60 years, or 21 to 45 years of age.

In certain embodiments, the invention is directed to said methods, wherein the reconstituted unit dose of the invention as described herein is administered subcutaneously to children and adolescents of 2 to 17 years of age. In some embodiments, the subjects or subject population are less than 9 years of age, or less than 4 years of age. In some embodiments, the subjects or subject population are from 2 to 9 years of age, or from 2 to 5 years of age, or from 4 to 9 years of age or from 6 to 9 years of age. In other embodiment, the subject or subject population is 4 to 16 years of age. In some such embodiments, the subject or subject population is 4-5 years of age, 6-11 years of age or 12-16 years of age. Optionally, the subject or subject population is seronegative with respect to all dengue serotypes.

In certain embodiments, the invention is directed to said methods, wherein the unit dose of the invention as described herein is administered to a pediatric subject or pediatric subject population of less than 2 years of age, preferably of 2 months to 2 years or 2 months to 1.5 years or 2 months to 1 year. According to some of these embodiments, the pediatric subject or pediatric subject population is seronegative and from a dengue endemic region.

In certain embodiments, the invention is directed to said methods, wherein the reconstituted unit dose of the invention as described herein is administered to a pediatric subject or pediatric subject population of less than 2 years of age, preferably of 2 months to 2 years or 2 months to 1.5 years or 2 months to 1 year, preferably by subcutaneous injection. According to some of these embodiments, the pediatric subject or pediatric subject population is seronegative and from a dengue endemic region.

In a certain embodiments, the invention is directed to said methods, wherein the subject or subject population is 4-5 years of age and from Asia Pacific, 6-11 years of age and from Asia Pacific, or 12-16 years of age and from Asia Pacific. In other embodiments, the subject or subject population is 4-5 years of age and from Latin America, 6-11 years of age and from Latin America, or 12-16 years of age and from Latin America.

In a certain embodiments, the invention is directed to said methods, wherein the subject or subject population is 4-5 years of age and seropositive for at least 1 dengue serotype, 6-11 years of age and seropositive for at least 1 dengue serotype, or 12-16 years of age and seropositive for at least 1 dengue serotype. In other embodiments, the subject or subject population is 4-5 years of age and seronegative for all dengue serotypes, 6-11 years of age and seronegative for all dengue serotypes, or 12-16 years of age and seronegative for all dengue serotypes.

In a certain embodiments, the invention is directed to said methods, wherein the subject or subject population is from Asia Pacific or Latin America and seropositive for at least one dengue serotype at baseline. In other embodiments, the subject or subject population is from Asia Pacific or Latin America and seronegative for at all dengue serotype at baseline.

In certain embodiments, the invention is directed to said methods, wherein the subject or subject population is from Asia Pacific, seropositive for at least one dengue serotype at baseline and 4-5 years of age, 6-11 years of age, or 12-16 years of age. In other embodiments, the subject or subject population is from Asia Pacific, seronegative for all dengue serotypes at baseline and 4-5 years of age, 6-11 years of age, or 12-16 years of age. In yet other embodiments, the subject or subject population is from Latin America, seropositive for at least one dengue serotype at baseline and 4-5 years of age, 6-11 years of age, or 12-16 years of age. In other embodiments, the subject or subject population is from America, seronegative for all dengue serotypes at baseline and 4-5 years of age, 6-11 years of age, or 12-16 years of age.

In certain embodiments, the invention is directed to said methods, wherein the subject or subject population had prior vaccination against Yellow Fever. In other embodiments, the subject or subject population had prior vaccination against Japanese Encephalitis. In yet other embodiments, the subject or subject population had no prior vaccination against Yellow Fever. In other embodiments, the subject or subject population had no prior vaccination against Japanese Encephalitis. Prior vaccination indicates a vaccination prior to 30 days after a second administration, such as within 4 months after the first administration, with the reconstituted unit dose as described herein. For example for vaccine efficacy (VE) as determined in Example 6 from 30 days post-second vaccination, a prior vaccination of Yellow Fever is defined as a Yellow Fever vaccination occurring before 30 days post-second vaccination. In certain embodiments, the subject or subject population received Dengvaxia® within the administration regimen as described herein or within 4.5 years after administration of the first dose.

Particularly unbalanced titers of neutralizing antibodies against the four dengue serotypes are observed in seronegative populations or subjects after administration of the commercially available dengue vaccine. The present invention shows that in particular seronegative subjects show a more balanced immune response to the four dengue serotypes after administration of the reconstituted unit dose of the invention as described herein. It is therefore contemplated that the unit dose of the invention as described herein and methods of the present invention as described herein may provide a more robust immune response in a subject population including both seropositive and seronegative subjects. This balanced response and balanced efficacy and safety is required to allow inoculation without prior serostatus analysis which is a major advantage in vaccination programs and in particular in outbreak situations.

The present invention is directed in part to a method of preventing virologically confirmable dengue disease in a subject comprising administering to the subject a tetravalent dengue virus composition including four dengue virus strains representing serotype 1, serotype 2, serotype 3 and serotype 4, wherein the virus strains are optionally live, attenuated dengue virus strains.

The present invention is directed in part to a method of preventing virologically confirmable dengue disease in a subject consisting of administering to the subject a tetravalent dengue virus composition including four dengue virus strains representing serotype 1, serotype 2, serotype 3 and serotype 4, wherein the virus strains are optionally live, attenuated dengue virus strains.

In certain embodiments, the invention is directed to said methods, wherein there is no step of determining the serostatus of the subject at baseline, in other words, said methods do not comprise a determination of a previous dengue infection of the subject at baseline before the administration of the tetravalent dengue virus composition. In particular, such methods are safe and effective. Thus, in certain such embodiments, the subject has not been tested for the presence a previous dengue infection.

In certain embodiments, the invention is directed to said methods, wherein the vaccine administration is safe irrespective of whether there is a determination that the subject had a previous dengue infection before the administration of the tetravalent dengue virus composition. In particular, such methods are also effective.

In certain embodiments, the invention is directed to said methods, wherein the method is safe and/or effective.

In certain embodiments, the invention is directed to said methods, wherein the composition includes at least one chimeric dengue virus. In certain such embodiments, the invention is directed to said methods, wherein the composition includes at least one non-chimeric dengue virus and at least one chimeric dengue virus, in particular a chimeric dengue serotype 2/1 strain and a dengue serotype 2 strain and a chimeric dengue serotype 2/3 strain and a chimeric dengue serotype 2/4 strain. The details of the composition are described above.

Therefore, in certain embodiments, the invention is directed to said methods having a vaccine efficacy, preferably a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) irrespective of serostatus at baseline and e.g. 14 to 16 years of age, wherein a reconstituted unit dose/tetravalent dengue virus composition as described herein or placebo is administered e.g. at least twice within less than 6 months, such as within 3 months, after first administration or 30 days after the second/last administration until at least 12 to 18 months (e.g. at 12 or at 18 months) after the second/last administration. In embodiments, the invention is directed to said methods having a vaccine efficacy, preferably a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) irrespective of serostatus at baseline, wherein a reconstituted unit dose or tetravalent dengue virus composition as described herein or placebo is administered at least once, until 15 to 21 months (e.g. 15 or 21 months) after the first administration of the administration schedule. In certain such embodiments, the lower bound is more than 30%, more than 40%, more than 50%, more than 55%, more than 60%, more than 65%, more than 70% or more than 72%. Preferably said reconstituted unit dose or placebo is administered subcutaneously within about 3 months, such as on days 0 and 90.

Therefore, in certain embodiments, the invention is directed to said methods having a combined vaccine efficacy against all four serotypes, in preventing virologically confirmable dengue disease with a 2-sided 95% confidence interval, wherein the lower bound is more than 60%, when measured against placebo in a subject population of at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is administered e.g. at least twice within less than 6 months, such as within 3 months, after the first administration until 18 months after the last administration. In these embodiments, the lower bound is e.g. more than 62%, more than 64%, more than 66%, more than 68%, or more than 69%.

In certain embodiments, the invention is directed to said methods having a vaccine efficacy, preferably a combined vaccine efficacy against all four serotypes, in preventing virologically confirmable dengue disease of more than 30%, when measured against placebo in a subject population of at least 5,000 healthy subjects (or at least 10,000, or at least 15,000 healthy subjects) irrespective of serostatus at baseline and e.g. 14 to 16 years of age, wherein a reconstituted unit dose or tetravalent dengue virus composition as described herein or placebo is administered at least twice within less than 6 months, such as within 3 months, after first administration or 30 days after the second administration/last administration until at least 12 months or until 12 to 18 months (e.g. at 12 or at 18 months) after the second administration/last administration. In certain embodiments, the invention is directed to said methods having a vaccine efficacy, preferably a combined vaccine efficacy against all four serotypes, in preventing virologically confirmable dengue disease of more than 30%, when measured against placebo in a subject population of at least 5,000 healthy subjects (or at least 10,000, or at least 15,000 healthy subjects) irrespective of serostatus at baseline, wherein a reconstituted unit dose or tetravalent dengue virus composition as described herein or placebo is administered at least once, until 15 months after the first administration of the administration schedule. In certain such embodiments, the vaccine efficacy is more than 40%, more than 50%, more than 55%, more than 60%, more than 65%, more than 70%, more than 75%, more than 78%, more than 79% or about 80%. Preferably said reconstituted unit dose or placebo is administered subcutaneously within about 3 month, such as on days 0 and 90.

Therefore, in certain embodiments, the invention is directed to said methods having a combined vaccine efficacy against all four serotypes, in preventing virologically confirmable dengue disease of more than 66%, when measured against placebo in a subject population of at least 5,000 healthy subjects (or at least 10,000, or at least 15,000 healthy subjects) irrespective of serostatus at baseline and 14 to 16 years of age, wherein a reconstituted unit dose/tetravalent dengue virus composition as described herein or placebo is administered e.g. at least twice within less than 6 months, such as within 3 months, after the first administration until 18 months after the last administration. In these embodiments, the vaccine efficacy is e.g. more than 68%, more than 70%, more than 72%, or more than 74%.

In certain embodiments, the invention is directed to said methods having a vaccine efficacy, preferably a combined vaccine efficacy against all four serotypes, in preventing virologically confirmable dengue disease with hospitalization with a 2-sided 95% confidence interval, wherein the lower bound is more than 0%, when measured against placebo in a subject population of at least 5,000 healthy subjects (or at least 10,000, or at least 15,000 healthy subjects) irrespective of serostatus at baseline, wherein a reconstituted unit dose or tetravalent dengue virus composition as described herein or placebo is administered at least twice within less than 6 months, such as within 3 months, 30 days after the second administration until at least 18 months after the second administration. In certain such embodiments, the lower bound is more than 10%, is more than 20%, is more than 30%, is more than 40%, is more than 50%, is more than 55%, is more than 60%, is more than 65%, is more than 70% or is more than 80%, or more than 90%.

In certain embodiments, the invention is directed to said methods having a combined vaccine efficacy against all four dengue serotypes in seronegative subjects with a 2-sided 95% confidence interval, wherein the lower bound is more than 25%, when measured against placebo in a subject population of at least 1,500 or at least 2,000 healthy subjects being seronegative against all serotypes at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, or is more than 55%.

In certain embodiments, the invention is directed to said methods having a combined vaccine efficacy against all four serotypes, in preventing virologically confirmable dengue disease with a 2-sided 95% confidence interval, wherein the lower bound is more than 25%, when measured against placebo in a subject population of at least 1,500 or at least 2,000 or at least 5,000 healthy subjects (or at least 10,000, or at least 15,000 healthy subjects) being seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the lower bound is more than 30%, is more than 35%, is more than 40%, or is more than 45%.

In certain embodiments, the invention is directed to said methods having a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the lower bound is more than 40%, is more than 45%, is more than 50%, is more than 60%, or is more than 65%.

In certain embodiments, the invention is directed to said methods having a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline being or seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the difference between the lower bound provided by the seropositive subjects at baseline and the subjects seronegative against all serotypes at baseline is no more than 15%-points.

In certain embodiments, the invention is directed to said methods having a combined vaccine efficacy against all four dengue serotypes in seronegative subjects of more than 30%, when measured against placebo in a subject population of at least 1,500 or at least 2,000 healthy subjects being seronegative against all serotypes at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against all four dengue serotypes in seronegative subjects is more than 40%, is more than 50%, is more than 60%, is more than 65%, or is more than 70%.

In certain embodiments, the invention is directed to said methods having a combined vaccine efficacy against all four serotypes, in preventing virologically confirmable dengue disease, when measured against placebo in a subject population of at least 1,500 or at least 2,000 or at least 5,000 healthy subjects (or at least 10,000, or at least 15,000 healthy subjects) being seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments the said vaccine efficacy is more than 30%, is more than 40%, is more than 50%, is more than 55%, is more than 60%, or is more than 65%.

In certain embodiments, the invention is directed to said methods having a combined vaccine efficacy against all four serotypes, in preventing virologically confirmable dengue disease, when measured against placebo in a subject population of at least 5,000 healthy subjects (or at least 10,000, or at least 15,000 healthy subjects) being seropositive at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments the said vaccine efficacy is more than 40%, is more than 50%, is more than 60%, is more than 65%, or is more than 70%, or is more than 75%.

In certain embodiments, the invention is directed to said methods having a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline being or seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the difference between the lower bound provided by the seropositive subjects at baseline and the subjects seronegative against all serotypes at baseline is no more than 15%-points, or is no more than 10%-points.

In certain embodiments, the invention is directed to said methods having a combined vaccine efficacy against all four dengue serotypes with a 2-sided 95% confidence interval, wherein the lower bound is more than 25%, when measured against placebo in a subject population of at least 1,000 healthy subjects 4 to 5 years of age at the time of randomization and irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 45%.

In certain embodiments, the invention is directed to said methods having a combined vaccine efficacy against all four dengue serotypes of more than 30%, when measured against placebo in a subject population of at least 1,000 healthy subjects 4 to 5 years of age at the time of randomization and irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against all four dengue serotypes is more than 40%, is more than 50%, is more than 60%, is more than 65%, or is more than 70%.

In certain embodiments, the invention is directed to said methods having a combined vaccine efficacy against all four dengue serotypes with a 2-sided 95% confidence interval, wherein the lower bound is more than 25%, when measured against placebo in a subject population of at least 1,000 healthy subjects 6 to 11 years of age at the time of randomization and irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, is more than 60%, or is more than 70%.

In certain embodiments, the invention is directed to said methods having a combined vaccine efficacy against all four dengue serotypes of more than 30%, when measured against placebo in a subject population of at least 1,000 healthy subjects 6 to 11 years of age at the time of randomization and irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against all four dengue serotypes is more than 40%, is more than 50%, is more than 60%, is more than 70%, is more than 75%, or is more than 80%.

In certain embodiments, the invention is directed to said methods having a combined vaccine efficacy against all four dengue serotypes with a 2-sided 95% confidence interval, wherein the lower bound is more than 25%, when measured against placebo in a subject population of at least 1,000 healthy subjects 12 to 16 years of age at the time of randomization and irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, is more than 60%, is more than 65%, or is more than 68%.

In certain embodiments, the invention is directed to said methods having a combined vaccine efficacy against all four dengue serotypes of more than 30%, when measured against placebo in a subject population of at least 1,000 healthy subjects 12 to 16 years of age at the time of randomization and irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against all four dengue serotypes is more than 40%, is more than 50%, is more than 60%, is more than 70%, is more than 75%, or is more than 80%.

In certain embodiments, the invention is directed to said methods having a vaccine efficacy against dengue serotype 1 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, or is more than 50%.

In certain embodiments, the invention is directed to said methods having a vaccine efficacy against serotype 1, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 or at 18 months) after the last administration. In certain such embodiments, the lower bound is more than 30%, is more than 35% is more than 40%, is more than 45%, is more than 50%, or is more than 54%. In certain such embodiments the subject population of at least 1,500 is seronegative against all serotypes at base line and the lower bound is more than 35%. In certain such embodiments the seronegative and seropositive population each provide a vaccine efficacy against serotype 1 with a 2-sided 95% confidence interval, wherein the lower bounds are within 10%-points.

In certain embodiments, the invention is directed to said methods having a vaccine efficacy against dengue serotype 1 of more than 30%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the vaccine efficacy against dengue serotype 1 is more than 40%, is more than 50%, is more than 60%, is more than 65%, or is more than 70%.

In certain embodiments, the invention is directed to said methods having a vaccine efficacy against serotype 1, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 or at 18 months) after the last administration. In certain such embodiments, the vaccine efficacy is more than 40%, is more than 50%, is more than 60%, or is more than 65%. In certain such embodiments the subject population of at least 1,500 is seronegative against all serotypes at base line. In certain such embodiments the seronegative and seropositive population each provide a vaccine efficacy against serotype 1 which are within 5%-points.

In certain embodiments, the invention is directed to said methods having a vaccine efficacy against dengue serotype 2 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50, is more than 60, is more than 70, is more than 80, or is more than 90%.

In certain embodiments, the invention is directed to said methods having a vaccine efficacy against serotype 2, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 or at 18 months) after the last administration. In certain such embodiments, the lower bound is more than 50%, is more than 60%, is more than 70%, is more than 80%, or is more than 85%. In certain such embodiments the subject population of at least 1,500, is seronegative against all serotypes. In certain such embodiments the seronegative and seropositive population each provide a vaccine efficacy against serotype 2 with a 2-sided 95% confidence interval, wherein the lower bounds are within 5%-points.

In certain embodiments, the invention is directed to said methods having a vaccine efficacy against dengue serotype 2 of more than 30%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the vaccine efficacy against dengue serotype 2 is more than 40%, is more than 50%, is more than 60%, is more than 70%, is more than 80, or is more than 90%.

In certain embodiments, the invention is directed to said methods having a vaccine efficacy against serotype 2, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 or at 18 months) after the last administration. In certain such embodiments, the vaccine efficacy is more than 60%, is more than 70%, is more than 80%, or is more than 90%. In certain such embodiments the subject population of at least 1,500 is seronegative against all serotypes at base line. In certain such embodiments the seronegative and seropositive population each provide a vaccine efficacy against serotype 2 which are within 5%-points.

In certain embodiments, the invention is directed to said methods having a vaccine efficacy against dengue serotype 3 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, about 30 days after the second administration of the administration schedule until at least 12 months after the second administration of the administration schedule. In certain such embodiments, the lower bound is more than 30%, is more than 40%.

In certain embodiments, the invention is directed to said methods having a vaccine efficacy against dengue serotype 3 of more than 30%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, 30 days after the second administration until at least 12 months after the second administration. In certain such embodiments, the vaccine efficacy against dengue serotype 3 is more than 40%, is more than 50%, is more than 55%, or is more than 60%.

In certain embodiments, the invention is directed to said methods having a combined vaccine efficacy against all four serotypes, in preventing virologically confirmable dengue disease with hospitalization with a 2-sided 95% confidence interval, wherein the lower bound is more than 25%, when measured against placebo in a subject population of at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from first administration until 12 to 18 months (e.g. at 12 months or at 18 months) after the last administration, or from 30 days post last administration until 12 to 18 months (e.g. at 12 or at 18 months) after the last administration. In certain such embodiments, the lower bound is more than 10%, is more than 20%, is more than 30%, is more than 40%, is more than 50%, is more than 55%, is more than 60%, is more than 65%, is more than 66%, is more than 67%, is more than 70%, is more than 75%, is more than 77%, or is more than 80%.

In certain embodiments, the invention is directed to said methods having a combined vaccine efficacy against all four serotypes, in preventing virologically confirmable dengue disease with hospitalization, when measured against placebo in a subject population of at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from first administration until 12 to 18 months (e.g. at 12 months or at 18 months) after the last administration, or from 30 days post last administration until 12 to 18 months (e.g. at 12 or at 18 months) after the last administration. In certain such embodiments, the vaccine efficacy is more than is more than 70%, is more than 75%, is more than 80%, or is more than 82%, or is more than 85%, more than 88%.

In certain embodiments, the invention is directed to said methods having a combined vaccine efficacy against virologically-confirmed dengue with hospitalization against all four serotypes with a 2-sided 95% confidence interval, wherein the lower bound is more than 25%, when measured against placebo in a subject population of at least 1,500 or at least 2,000 healthy subjects being seronegative against all serotypes at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, is more than 60%, is more than 70%, or is more than 75%.

In certain embodiments, the invention is directed to said methods having a combined vaccine efficacy against all four serotypes, in preventing virologically confirmable dengue disease with hospitalization with a 2-sided 95% confidence interval, wherein the lower bound is more than 25%, when measured against placebo in a subject population of at least 5,000 healthy subjects (or at least 10,000, or at least 15,000 healthy subjects) being seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the lower bound is more than 60%, is more than 65%, is more than 66%, is more than 67%, is more than 70%, is more than 75%, is more than 77% or is more than 80%.

In certain embodiments, the invention is directed to said methods having a combined vaccine efficacy against virologically-confirmed dengue with hospitalization against all four serotypes of more than 30%, when measured against placebo in a subject population of at least 1,500 or at least 2,000 healthy subjects, healthy subjects being seronegative against all serotypes at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against virologically-confirmed dengue with hospitalization against all four serotypes is more than 40%, is more than 50%, is more than 60%, is more than 70%, is more than 80%, or is more than 90%.

In certain embodiments, the invention is directed to said methods having a combined vaccine efficacy against all four serotypes, in preventing virologically confirmable dengue disease with hospitalization, when measured against placebo in a subject population of at least 5,000 healthy subjects (or at least 10,000, or at least 15,000 healthy subjects) being seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the said vaccine efficacy is more than 60%, is more than 65%, is more than 66%, is more than 67%, is more than 70%, is more than 75%, is more than 77%, is more than 80, or is more than 85%.

In certain embodiments, the invention is directed to said methods having a combined vaccine efficacy against virologically-confirmed dengue with hospitalization against all four serotypes with a 2-sided 95% confidence interval, wherein the lower bound is more than 25%, when measured against placebo in a subject population of at least 1,500 or at least 2,000 healthy subjects being seropositive at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, is more than 60%, is more than 70%, or is more than 80%.

In certain embodiments, the invention is directed to said methods having a combined vaccine efficacy against all four serotypes, in preventing virologically confirmable dengue disease with hospitalization with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the lower bound is more than 60%, is more than 65%, is more than 70%, is more than 75%, or is more than 80%.

In certain embodiments, the invention is directed to said methods having a combined vaccine efficacy against virologically-confirmed dengue with hospitalization against all four serotypes of more than 30%, when measured against placebo in a subject population at least 1,500 or of at least 2,000 healthy subjects, healthy subjects being seropositive at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against virologically-confirmed dengue with hospitalization against all four serotypes is more than 40%, is more than 50%, is more than 60%, is more than 70%, is more than 80%, or is more than 90%.

In certain embodiments, the invention is directed to said methods having a combined vaccine efficacy against all four serotypes, in preventing virologically confirmable dengue disease with hospitalization, when measured against placebo in a subject population of at least 5,000 healthy subjects (or at least 10,000, or at least 15,000 healthy subjects) being seropositive at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the vaccine efficacy is more than 75%, is more than 70%, is more than 80%, is more than 85%, or is more than 90%.

In certain embodiments, the invention is directed to said methods having a combined vaccine efficacy against all four serotypes, in preventing virologically confirmable dengue disease with hospitalization with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline being or seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the difference between the lower bound provided by the seropositive subjects at baseline and the subjects seronegative against all serotypes at baseline is no more than 15%-points.

In certain embodiments, the invention is directed to said methods having a combined vaccine efficacy against all four serotypes, in preventing virologically confirmable dengue disease with hospitalization, when measured against placebo in a subject population of at least 5,000 healthy subjects (or at least 10,000, or at least 15,000 healthy subjects) being seropositive at baseline being or seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the difference between the vaccine efficacy provided by the seropositive subjects at baseline and the subjects seronegative against all serotypes at baseline is no more than 10%-points or no more than 5%-points.

In certain embodiments, the invention is directed to said methods having a relative risk, preferably a combined relative risk against all four serotypes, with a 2-sided 95% confidence interval, wherein the upper bound is less than 0.75, when measured against placebo in a subject population of at least 5,000 healthy subjects (or at least 10,000, or at least 15,000 healthy subjects) irrespective of serostatus at baseline, wherein a reconstituted unit dose/tetravalent dengue virus composition as described herein or placebo is administered at least twice within less than 6 months, such as within 3 months, 30 days after the second administration until at least 12 months after the second administration. In certain such embodiments, the upper bound is less than 0.70, less than 0.65, less than 0.60, less than 0.55, less than 0.50, less than 0.45, less than 0.40, less than 0.35, less than 0.30 or less than 0.28. Preferably said reconstituted unit dose or placebo is administered subcutaneously within about 3 month, such as on days 0 and 90.

In certain embodiments, the invention is directed to said methods having a relative risk, preferably a combined relative risk against all four serotypes, of less than 0.70, when measured against placebo in a subject population of at least 5,000 healthy subjects (or at least 10,000, or at least 15,000 healthy subjects) irrespective of serostatus at baseline, wherein a reconstituted unit dose/tetravalent dengue virus composition as described herein or placebo is administered at least twice within less than 6 months, such as within 3 months, 30 days after the second administration until at least 12 months after the second administration. In certain such embodiments, the relative risk is less than 0.65, less than 0.60, less than 0.55, less than 0.50, less than 0.45, less than 0.40, less than 0.35, less than 0.30, less than 0.25 or less than 0.23. Preferably said reconstituted unit dose or placebo is administered subcutaneously within about 3 month, such as on days 0 and 90.

In certain embodiments, the invention is directed to said methods, wherein virologically confirmable dengue disease occurs in less than 2.5% of the subjects, when measured against placebo in a subject population of at least 5,000 healthy subjects (or at least 10,000, or at least 15,000 healthy subjects) irrespective of serostatus at baseline, wherein a reconstituted unit dose/tetravalent dengue virus composition as described herein or placebo is administered at least twice within less than 6 months, such as within 3 months, 30 days after the second administration until at least 12 months or at least 18 months after the second administration. In certain such embodiments, virologically confirmable dengue disease occurs in less than 2.0% of the subjects, less than 1.5% of the subjects, less than 1.0% of the subjects, less than 0.8% of the subjects, or less than 0.6% of the subjects. Preferably said reconstituted unit dose or placebo is administered subcutaneously within about 3 month, such as on days 0 and 90.

In certain embodiments, the invention is directed to said methods having a combined vaccine efficacy against all four serotypes with a 2-sided 95% confidence interval, wherein the lower bound is more than 61.0%, or more than 65.0 or more than 70.0% or more than 72.0% when measured against placebo in a subject population of at least 5,000 healthy subjects (or at least 10,000, or at least 15,000 healthy subjects) from endemic irrespective of serostatus at baseline and being selected from the group consisting of 4 to 16 year old subjects at the time of randomization, wherein said unit dose/tetravalent dengue virus composition or said placebo is administered at least twice within 6 months or less, about 30 days after the last administration of the administration schedule until at least 12 or 13 months after the last administration of the administration schedule.

In certain embodiments, the invention is directed to said methods having a combined vaccine efficacy against all four serotypes of more than 66%, or of more than 70%, or of more than 75%, or of more than 77%, or of more than 80.0%, when measured against placebo in a subject population of at least 5,000 healthy subjects (or at least 10,000, or at least 15,000 healthy subjects) from endemic areas irrespective of serostatus at baseline and being selected from the group consisting of 4 to 16 year old subjects at the time of randomization, wherein said unit dose/tetravalent dengue virus composition or said placebo is administered at least twice within 6 months or less, about 30 days after the last administration of the administration schedule until at least 12 months or 13 month after the last administration of the administration schedule.

In certain embodiments, the invention is directed to said methods, wherein the combined vaccine efficacy against all four serotypes is measured about 30 days after the last administration of the administration schedule until 12 or 13 months after the last administration of the administration schedule.

In certain embodiments, the invention is directed to said methods, wherein said unit dose or said placebo is administered at least twice within three months, in particular at about day 1 and about day 90, and wherein the combined vaccine efficacy against all four serotypes is measured 30 days after the second administration until 12 or 13 months after the second administration of the administration schedule.

In certain embodiments, the invention is directed to said methods, wherein said methods are effective and safe. In some of these embodiments, the subject or subject population is under 9 years of age, under 4 years of age, or under 2 years of age or from 2 to 9 years of age, or from 2 to 5 years of age, or from 4 to 9 years of age or from 6 to 9 years of age. Optionally the subject is seronegative with respect to all dengue serotypes.

In certain embodiments, the invention is directed to said methods, wherein said methods having a relative risk for virologically confirmed dengue with hospitalization of 1 or less, or 0.8 or less, or 0.6 or less, when measured against placebo in a subject population of at least 5,000 healthy subjects (or at least 10,000, or at least 15,000 healthy subjects). In some of these embodiments, the subject or subject population is under 9 years of age, under 4 years of age, or under 2 years of age or from 2 to 9 years of age, or from 2 to 5 years of age, or from 4 to 9 years of age or from 6 to 9 years of age. Optionally the subject is seronegative with respect to all dengue serotypes.

In certain embodiments, the invention is directed to said methods, wherein the healthy subjects of the subject population are 4 to 16 years of age. In some of such embodiments, the healthy subjects of the subject population are 4 to 5 years of age, 6 to 11 years of age, or 12 to 16 years of age.

In certain embodiments, the invention is directed to said methods, wherein the healthy subjects of the subject population are defined as being healthy in view of the exclusion criteria specified in Example 6.

In certain embodiments, the invention is directed to said methods, wherein the healthy subjects of the subject population are from Asia Pacific or Latin America.

In certain embodiments, the invention is directed to said methods, wherein the healthy subjects of the subject population are seropositive with respect to at least one serotype. In other embodiments, the healthy subjects of the subject population are seronegative with respect to all serotypes.

In certain embodiments, the invention is directed to said methods, wherein the healthy subjects of the subject population are 4-5 years of age and from Asia Pacific, 6-11 years of age and from Asia Pacific, or 12-16 years of age and from Asia Pacific. In other embodiments, the healthy subjects of the subject population are 4-5 years of age and from Latin America, 6-11 years of age and from Latin America, or 12-16 years of age and from Latin America.

In certain embodiments, the invention is directed to said methods, wherein the healthy subjects of the subject population are 4-5 years of age and seropositive for at least 1 dengue serotype, 6-11 years of age and seropositive for at least 1 dengue serotype, or 12-16 years of age and seropositive for at least 1 dengue serotype. In other embodiments, the healthy subjects of the subject population are 4-5 years of age and seronegative for all dengue serotypes, 6-11 years of age and seronegative for all dengue serotypes, or 12-16 years of age and seronegative for all dengue serotypes.

In certain embodiments, the invention is directed to said methods, wherein the healthy subjects of the subject population are from Asia Pacific or Latin America and seropositive for at least one dengue serotype at baseline. In other embodiments, the healthy subjects of the subject population are from Asia Pacific or Latin America and seronegative for at all dengue serotype at baseline.

In certain embodiments, the invention is directed to said methods, wherein the healthy subjects of the subject population are from Asia Pacific, seropositive for at least one dengue serotype at baseline and 4-5 years of age, 6-11 years of age, or 12-16 years of age. In other embodiments, the healthy subjects of the subject population are from Asia Pacific, seronegative for all dengue serotypes at baseline and 4-5 years of age, 6-11 years of age, or 12-16 years of age. In yet other embodiments, the healthy subjects of the subject population are from Latin America, seropositive for at least one dengue serotype at baseline and 4-5 years of age, 6-11 years of age, or 12-16 years of age. In other embodiments, the healthy subjects of the subject population are from America, seronegative for all dengue serotypes at baseline and 4-5 years of age, 6-11 years of age, or 12-16 years of age.

In certain embodiments, the invention is directed to said methods, wherein the healthy subjects of the subject population had prior vaccination against Yellow Fever. In other embodiments, the healthy subjects of the subject population had no prior vaccination against Yellow Fever. Prior vaccination indicates a vaccination prior to the first vaccination with the reconstituted unit dose as described herein. For example for vaccine efficacy (VE) as determined in Example 6 from 30 days post-second vaccination, a prior vaccination of Yellow Fever is defined as a Yellow Fever vaccination occurring before 30 days post-second vaccination.

In certain embodiments, the invention is directed to said methods, wherein the healthy subjects of the subject population had prior vaccination against Japanese Encephalitis.

In other embodiments, the healthy subjects of the subject population had no prior vaccination against Japanese Encephalitis.

In certain embodiments, the invention is directed to said methods, wherein the healthy subjects of the subject population received Dengvaxia® within the administration regimen as described herein or within 4.5 years after administration of the first dose. In certain embodiments, the invention is directed to said methods, wherein the occurrence of vaccine related serious adverse events is less than 0.1%.

In certain embodiments, the invention is directed to said methods, wherein the occurrence of vaccine related unsolicited adverse events occurring within 4 weeks of administration is less than 2%.

In certain embodiments, the invention is directed to said methods, wherein the occurrence of vaccine related solicited adverse events occurring within 2 weeks of administration is less than 35%.

In certain embodiments, the invention is directed to said methods, wherein the occurrence of vaccine related solicited local reactions occurring within 1 weeks of administration is less than 40%.

In certain embodiments, the invention is directed to said methods, wherein the method does not increase the risk of virologically-confirmed dengue with hospitalization in the individual, such as in a seronegative individual.

The above methods are also to be considered in the context of a unit dose for use in such methods or in the context of a use of such a unit dose for use in the manufacture of a medicament for such methods.

In certain embodiments, a tetravalent dengue vaccine such as Dengvaxia® is used for inoculating against dengue disease. Dengvaxia® is a tetravalent dengue vaccine based on a yellow fever backbone, CYD-TDV (Dengvaxia®, Sanofi Pasteur, Lyon, France), and has been licensed in several countries based on the clinical demonstration of an overall vaccine efficacy (VE) against virologically-confirmed dengue (VCD) of 56-61% in children in Asia and Latin America (Capeding M R et al. Clinical efficacy and safety of a novel tetravalent dengue vaccine in healthy children in Asia: a phase 3, randomised, observer-masked, placebo-controlled trial. Lancet 2014, 384:1358-65; Villar L A et al. Safety and immunogenicity of a recombinant tetravalent dengue vaccine in 9-16 year olds: a randomized, controlled, phase II trial in Latin America. Pediatr Infect Dis J 2013, 32:1102-9). The preparation of these particular strains CYD1, CYD2, CYD3 and CYD4 has been described in detail in international patent applications WO 98/37911, WO 03/101397, WO07/021672, WO 08/007021, WO 08/047023 and WO 08/065315, to which reference may be made for a precise description of the processes for their preparation. The corresponding nucleotide sequences of the prM-E regions of CYD1, CYD2, CYD3 and CYD4 are provided in WO2016034629 and SEQ ID NOs are set out in Table 16 of this reference.

In certain embodiments, the invention is directed to said methods, wherein the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, and Dengvaxia® disclosed herein are administered simultaneously on the same day to the subject or to the subject population.

In certain embodiments, the invention is directed to said methods, wherein the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, is administered to the subject or to the subject population on day 0/1 as a first administration and Dengvaxia® disclosed herein is subsequently administered to the subject or to the subject population within three months from the first administration, such as on day 90 from the first administration, as a second administration. Alternatively, Dengvaxia® disclosed herein is administered to the subject or to the subject population on day 0/1 as a first administration and the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, is administered subsequently to the subject or the subject population within three months from the first administration, such as on day 90 from the first administration, as a second administration.

In certain embodiments, the invention is directed to said method, wherein the dengue vaccine composition comprises other dengue vaccines such as TV003 or TV005. TV003, developed by the U.S. National Institute of Allergy and Infectious Diseases, comprises vaccine components rDEN1Δ30, rDEN2/4Δ30, rDEN3Δ30/31 and rDEN4Δ30, wherein each of these components is present at a concentration of 3 $\log_{10}$ PFU. TV005 is similar to TV003 with the difference that the concentration of rDEN2/4Δ30 in TV005 is 4 $\log_{10}$ PFU. The vaccines TV003 and TV005 and their vaccine components as well as their production are described in more detail in WO 2008/022196 A2 and S. S. Whitehead, Expert Rev Vaccines, 2016, 15(4): 509 to 517. Using recombinant DNA technology, two attenuation strategies were utilized for the vaccine components of TV003 or TV005: deletions in the 3' untranslated region and structural gene chimerization. For example, the component rDEN4Δ30 contains all the structural and non-structural proteins of a wild type DENV-4, but is attenuated by a 30-nucleotide deletion in the 3' untranslated region (denoted "Δ30"). The other vaccine components are also attenuated due to the 30-nucleotide deletion in the 3' untranslated region. In addition, rDEN3Δ30/31 includes a 31 nucleotide deletion in the 3' untranslated region (shown in detail in FIG. 1c and FIG. 13 of WO 2008/022196 A2). The rDEN2/4Δ30 component was created by substituting the prM and E genes of DENV-2 into the rDEN4Δ30 genome. The complete genomic sequences of dengue strains which can be used to produce TV003 or TV005 are available under the Genbank accession numbers in Table A of WO 2008/022196 A1.

In certain embodiments, the invention is directed to said methods, wherein the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, and TV003 or TV005 disclosed herein are administered simultaneously on the same day to the subject or to the subject population.

In certain embodiments, the invention is directed to said methods, wherein the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, is administered to the subject or the subject population on day 0/1 as a first administration and wherein TV003 or TV005 disclosed herein is subsequently administered to the subject or to the subject population within three months from the first administration, such as on day 90 from the first administration, as a second administration. Alternatively, TV003 or TV005 disclosed herein is administered to the subject or to subject population on day 0/1 as a first administration and the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, is administered subsequently to the subject or to the subject population within three months from the first administration, such as on day 90 from the first administration, as a second administration.

EXAMPLES

The following Examples are included to demonstrate certain aspects and embodiments of the invention as described in the claims. It should be appreciated by those of skill in the art, however, that the following description is illustrative only and should not be taken in any way as a restriction of the invention.

Example 1: Preparation of the Dengue Virus Strains

The methods used to generate the chimeric dengue strains TDV-1, -3 and -4 were standard molecular cloning and DNA engineering methods and are describe et al. (2003) J. Virology 77(21): 11436-11447. The following well-known methods were used to construct and introduce the prM-E genes of dengue serotypes 1, 3 and 4 into the TDV-2 backbone: Reverse-transcriptase PCR (RT-PCR), PCR, restriction enzyme digestion, DNA fragment ligation, bacterial transformations by electroporation, plasmid DNA preparations, in vitro transcription by T7 RNA polymerase, and transfection of Vero cells by electroporation.

After growing and purifying the different dengue serotypes separately as described in Huang et al. (2013) PLOS Neglected Dis, 7(5):e2243, they are mixed in certain concentrations provided in Example 4. The mixture of dengue serotypes is present in a dengue vaccine composition and combined with a composition of pharmaceutically acceptable excipients resulting in a dengue vaccine composition comprising 15% w/v α,α trehalose dihydrate, 1% w/v poloxamer 407, 0.1% w/v human serum albumin and 100 mM sodium chloride. The dengue vaccine composition is lyophilized and represents a lyophilized unit dose of TDV. The lyophilized unit dose is reconstituted with 37 mM aqueous sodium chloride solution and the reconstituted unit dose comprises 15% w/v α,α trehalose dihydrate, 1% w/v poloxamer 407, 0.1% w/v human serum albumin and 137 mM sodium chloride.

Example 2: Microneutralization Test

Immunogenicity was measured by a microneutralization assay to each one of the four dengue serotypes with titers defined as the dilution resulting in a 50% reduction in plaque values (MNT50). Briefly, on day 1 Vero cells were seeded on 96-well assay plates in DMEM and 10% FBS at a density of $2.5 \times 10^5$ cells/ml and incubated at 37° C. for 24 hours. On day 2 serial dilutions of the heat-inactivated antibody-containing test and control sera samples (dilutions range 1:10 to 1:20480) were prepared and mixed with a constant concentration of dengue viruses, in particular DENV-1 strain 16007, DENV-2 strain 16681, DENV-3 strain 16562 and DENV-4 strain 1036, (target 60-80 pfu/well) in a 96 well microtiter plate and incubated overnight at 2-8° C. to enable the neutralization of the virus by the antibodies present in the sera. After the incubation the mixture of virus and antibodies was transferred onto the 96 well plates with Vero cells and the plates were incubated at 37° C. for 90-120 minutes to infect the Vero cells. A 1% methylcellulose overlay in DMEM was applied to the plate to restrict spread of progeny virus and the plate was incubated for 46-70 hours at 34° C. depending on the Dengue serotype:

DENV1—66±2 hours
DENV2—70±2 hours
DENV3—66±2 hours
DENV4—46±2 hours

After the incubation the cells were washed twice with PBS and fixed by adding cold methanol and incubating for 60 minutes at a temperature of −20° C. After fixing the plates were dried and washed three times with washing buffer (1×PBS, pH 7.4 with 0.5% Tween), before 50 µl of serotype-specific anti-dengue monoclonal antibodies in blocking solution (2.5% nonfat dry milk in PBST) per well were added and incubated with the cells for 18±4 hours at 2-8° C.

The monoclonal antibodies were made as described in Gentry et al. (1982) Am. J. Trop. Med. Hyg. 31, 548-555; Henchal et al. (1985) Am. J. Trop. Med. Hyg. 34, 162-169; and Henchal et al. (1982) Am. J. Trop. Med. Hyg. 31(4): 830-6). Briefly, the anti-DENV-1 HBD was made against dengue 1 strain Hawaii, Envelope, the anti-DENV-2 was made against dengue 2 strain New Guinea C, Envelope, isotype 1, the anti-DENV-3 HBD was made against dengue 3 strain H87, Envelope, isotype 2A, and the anti-DENV-4 HBD was made against dengue 4 strain H241, Envelope, isotype 2A.

After incubation, the plates were washed three times with washing buffer and 50 µl of a secondary peroxidase labelled goat anti-mouse IgG (H+L) (KPL Cat #074-1806) in blocking solution was added and incubated for 90 to 120 minutes at 37° C. Then the plates were washed three times with washing buffer and 50 µl of precipitant substrate (2-amino-9-ethyl carbazole (AEC) tablet in 2.5 ml DMSO, 47.5 ml 50 mM acetate buffer and 250 µl hydrogen peroxide) were added and the mixture was incubated for 20 minutes at room temperature. Finally, the substrate was removed, the plates were rinsed with dH$_2$O and dried.

Sample titers are calculated using the linear regression method and reported as MNT50 titers for each sample. Clinical data are reported as a geometric mean titer for all the individual MNT50 titers in each treatment group. Briefly, the number of infectious foci in each well was counted and the titer of neutralizing antibodies was determined by comparing the percent reduction of infectious foci centers in wells containing antibody (test samples) in comparison to wells containing virus alone. The MNT50 was calculated using the following linear regression equation:

$$MNT50=10^{[(50-c)/m]} \text{ where } c=y \text{ intercept of regression line and } m=\text{slope of regression line}$$

Each test sample was tested in triplicates and the titer was calculated from the average of the triplicates. A schematic drawing of the steps performed in this test is provided in FIG. 2.

Example 3: Phase III Clinical Trial in Children

A Phase III, double-blind, randomized, and placebo-controlled trial in 20100 subjects aged 4 to 16 years living in Thailand, Sri Lanka, Philippines, Panama, Nicaragua, Dominican Republic, Colombia or Brazil was performed evaluating the efficacy, safety and immunogenicity of a tetravalent dengue vaccine referred to hereinafter as TDV (TDV-1, TDV-2, TDV-3 and TDV-4 as described herein). The trial includes 3 parts. Part 1 evaluates vaccine efficacy (VE) and lasts until both of the following 2 criteria are fulfilled: (i) 120 cases of dengue fever are confirmed and (ii) minimum duration of subject follow-up of 12 months post-second vaccination. Part 2 is for an additional 6 months to evaluate VE and for secondary efficacy analyses. Part 3 will evaluate long-term safety by following participants for side effects and will last an additional 3 years.

Part 1: Active surveillance for the primary assessment of efficacy in all subjects. During this time subjects were contacted at least weekly to ensure identification of febrile illness that could potentially be due to dengue. This part commenced on the day of vaccination and finished once both of the following 2 criteria were fulfilled: (i) 120 cases of dengue fever are confirmed and (ii) minimum duration of subject follow-up of 12 months post-second vaccination. The end of Part 1 was defined for each subject so that the duration of follow up after the second vaccination was approximately the same for all subjects. Virologically-confirmed cases in Part 1 count towards the primary efficacy objective if occurring at least 30 days post-second vaccination. Part 1 was finished 12 months post-second vaccination Part 2: Active surveillance for an additional 6 months for each subject following the completion of Part 1, I, i.e. 18 month post second vaccination. During this time subjects were contacted at least weekly to ensure identification of febrile illness that could potentially be due to dengue. Virologically-confirmed cases in Parts 1 and 2 contribute towards the secondary efficacy objectives.

Part 3: Modified active surveillance for the assessment of safety in all subjects following the completion of Part 2 and lasting 3 years for each subject. The modified surveillance during Part 3 will maintain at least weekly contacts through Part 3 of the trial, but the intensity of investigation will be modified based on the need for hospitalization. Surveillance will identify febrile illness of any severity that could potentially be due to dengue.

Criteria for Inclusion include:
- The subject was aged 4 to 16 years inclusive, at the time of randomization.
- Individuals who were in good health at the time of entry into the trial as determined by medical history, physical examination (including vital signs) and clinical judgment of the Investigator.
- The subject and/or the subject's parent/guardian signed and dated an assent/written informed consent form where applicable, and any required privacy authorization prior to the initiation of any trial procedures, after the nature of the trial has been explained according to local regulatory requirements.
- Individuals who can comply with trial procedures and are available for the duration of follow-up.

Exclusion criteria include:
1. Febrile illness (temperature ≥38° C.) or moderate or severe acute illness or infection at the time of randomization.
2. History or any illness that, in the opinion of the Investigator, might interfere with the results of the trial or pose an additional risk to the subject due to participation in the trial, including but not limited to:
   a. Known hypersensitivity or allergy to any of the vaccine components.
   b. Female subjects (post-menarche) who are pregnant or breastfeeding.
   c. Individuals with any serious chronic or progressive disease according to judgment of the Investigator (e.g., neoplasm, insulin-dependent diabetes, cardiac, renal or hepatic disease, neurologic or seizure disorder or Guillain-Barre syndrome).
d. Known or suspected impairment/alteration of immune function, including:
i. Chronic use of oral steroids (equivalent to 20 mg/day prednisone 12 weeks/2 mg/kg body weight/day prednisone 2 weeks) within 60 days prior to Day 1 (Month 0) (use of inhaled, intranasal, or topical corticosteroids is allowed).
ii. Receipt of parenteral steroids (equivalent to 20 mg/day prednisone 12 weeks/2 mg/kg body weight/day prednisone 2 weeks) within 60 days prior to Day 1 (Month 0).
iii. Administration of immunoglobulins and/or any blood products within the 3 months prior to Day 1 (Month 0) or planned administration during the trial.
iv. Receipt of immunostimulants within 60 days prior to Day 1 (Month 0).
v. Immunosuppressive therapy such as anti-cancer chemotherapy or radiation therapy within 6 months prior to Day 1 (Month 0).
vi. Human Immunodeficiency Virus (HIV) infection or HIV-related disease.
vii. Genetic immunodeficiency.
3. Receipt of any other vaccine within 14 days (for inactivated vaccines) or 28 days (for live vaccines) prior to Day 1 (Month 0) or planning to receive any vaccine within 28 days after Day 1 (Month 0).
4. Participation in any clinical trial with another investigational product 30 days prior to Day 1 (Month 0) or intent to participate in another clinical trial at any time during the conduct of this trial.
5. Previous participation in any clinical trial of a dengue candidate vaccine, or previous receipt of a dengue vaccine.
6. First degree relatives of individuals involved in trial conduct.
7. Females of childbearing potential who are sexually active, and who have not used any of the acceptable contraceptive method for at least 2 months prior to Day 1 (Month 0).
8. Females of childbearing potential who are sexually active, and who refuse to use an acceptable contraceptive method up to 6 weeks post-second vaccination.
9. Deprived of freedom by administrative or court order, or in an emergency setting, or hospitalized involuntarily.
10. Current alcohol abuse or drug addiction that may interfere with the subject's ability to comply with trial procedures.
11. Identified as an employee of the Investigator or trial center, with direct involvement in the proposed trial or other trials under the direction of that Investigator or trial center.

Eligible subjects were randomized (2:1) into two treatment groups: groups 1 received one subcutaneous (SC) dose of TDV in the upper arm on Day 1 and on Day 90, and group 2 received one subcutaneous dose of placebo in the upper arm on Day 1 and on Day 90. Randomization was stratified by region (Asia Pacific and Latin America) and age range (children aged 4-5 years, 6-11 years, and 12-16 years) to ensure each age range has the appropriate ratio of TDV to placebo in each region. After randomization dropouts were not replaced. Study Day 1 is defined to be the date of the first dose administration of TDV or placebo. The TDV was prepared as described in Example 1. Each subcutaneous dose of TDV was 0.5 mL and the concentration of the four dengue serotypes in the TDV vaccine in each dose was 3.6 $\log_{10}$ PFU/dose, 4.0 $\log_{10}$ PFU/dose, 4.6 $\log_{10}$ PFU/dose and 5.1 $\log_{10}$ PFU/dose of TDV-1, TDV-2, TDV-3 and TDV-4, respectively.

The "total concentration in pfu/0.5 ml" which serves as a base value for the calculation of the percentage concentration for each individual component of a tetravalent dengue vaccine is shown for one exemplary tetravalent vaccine composition comprising dengue serotype 1 in a concentration of 3.60 $\log_{10}$ pfu/0.5 ml, a dengue serotype 2 concentration of 4.00 $\log_{10}$ pfu/0.5 ml, a dengue serotype 3 concentration of 4.60 log 10 pfu/0.5 ml and a dengue serotype 4 concentration of 5.11 $\log_{10}$ pfu/0.5 ml. Primarily, the logarithmic values of the concentrations are converted into numerical values. The results of this conversion are $4\times10^3$ pfu/0.5 ml for serotype 1, $1\times10^4$ pfu/0.5 ml for serotype 2, $4\times10^4$ pfu/0.5 ml for serotype 3 and $1.3\times10^5$ pfu/0.5 ml for serotype 4. The total concentration in pfu/0.5 ml is the sum of the preceding numerical values resulting in $1.84\times10^5$ pfu/0.5 ml.

The "percentage concentration" for each of the serotypes 1, 2, 3 and 4 is obtained by dividing the numerical concentration value (expressed as pfu/0.5 ml) of an individual serotype by the total concentration (expressed in pfu/0.5 ml) and multiplying the result by 100 i.e.:

$$\text{Percentage concentration of serotype } 1 = (4\times10^3 \text{ pfu}/0.5 \text{ ml} \pm 1.84\times10^5 \text{ pfu}/0.5 \text{ ml})\times100 = 2\%$$

$$\text{Percentage concentration of serotype } 2 = (1\times10^4 \text{ pfu}/0.5 \text{ ml} \pm 1.84\times10^5 \text{ pfu}/0.5 \text{ ml})\times100 = 5\%$$

$$\text{Percentage concentration of serotype } 3 = (4\times10^4 \text{ pfu}/0.5 \text{ ml} \pm 1.84\times10^5 \text{ pfu}/0.5 \text{ ml})\times100 = 22\%$$

$$\text{Percentage concentration of serotype } 4 = (1.3\times10^5 \text{ pfu}/0.5 \text{ ml} \pm 1.84\times10^5 \text{ pfu}/0.5 \text{ ml})\times100 = 71\%.$$

The percentage concentrations are rounded to whole numbers.

Primary Outcome Measures included the vaccine efficacy (VE) of two doses of TDV in preventing virologically-confirmed dengue (VCD) fever induced by any dengue serotype [time frame: 30 days post-second vaccination (Day 120) until the end of Part 1]. VE is defined as $1-(\lambda v/\lambda c)$, wherein $\lambda v$ and $\lambda c$ denote the hazard rates for the TDV and placebo groups, respectively. A virologically-confirmed dengue case is defined as febrile illness (defined as temperature ≥38° C. on any 2 of 3 consecutive days) or illness clinically suspected to be dengue by the Investigator with a positive serotype-specific reverse transcriptase polymerase chain reaction (RT-PCR). A febrile illness will require an interval of at least 14 days from a previous febrile illness to avoid overlap of acute and convalescent visits from one episode with those from a second episode.

Secondary Outcome Measures Include:
1) VE of two doses of TDV in preventing virologically-confirmed dengue fever induced by each dengue serotype [time frame: from 30 days post-second vaccination (Day 120) until the end of Part 2].
2) VE of two doses of TDV in preventing virologically-confirmed dengue fever induced by any dengue serotype in participants dengue seronegative at baseline [time frame: from 30 days post-second vaccination (Day 120) until the end of Part 2 (up to 21 months)].
3) VE of two doses of TDV in preventing virologically-confirmed dengue fever induced by any dengue serotype in participants dengue seropositive at baseline [time frame: from 30 days post-second vaccination (Day 120) until the end of Part 2].

4) VE of two doses of TDV in preventing hospitalization due to virologically-confirmed dengue fever induced by any dengue serotype [time frame: from 30 days post-second vaccination (Day 120) until the end of Part 2].

5) VE of two doses of TDV in preventing virologically-confirmed severe dengue fever induced by any dengue serotype [time frame: from 30 days post-second vaccination (Day 120) until the end of Part 2].

6) Percentage of participants with solicited local injection site adverse events (AEs) in the safety subset [time frame: Days 1 through 7 after each vaccination] and severity of solicited local injection AEs. Solicited local AEs at injection site are defined as pain, erythema and swelling that occurred within 7 days after each vaccination.

7) Percentage of participants with solicited systemic adverse events (AEs) in the safety subset [time frame: Days 1 through 14 after each vaccination] and severity of solicited systemic AEs. Solicited systemic AEs in children (<6 years) are defined as fever, irritability/fussiness, drowsiness and loss of appetite that occurred within 14 days after each vaccination. Solicited systemic AEs in children (≥6 years) are defined as fever, headache, asthenia, malaise and myalgia that occurred within 14 days after each vaccination.

8) Percentage of participants with any unsolicited adverse events (AEs) in the safety subset [time frame: Days 1 through 28 after each vaccination]. Unsolicited AEs are any AEs that are not solicited local or systemic AEs, as defined above.

9) Percentage of participants with serious adverse events (SAEs) during Parts 1 and 2 [time frame: from Day 1 until the end of Parts 1 and 2]. A serious adverse event (SAE) is any untoward medical occurrence or effect that at any dose results in death, is life-threatening, requires inpatient hospitalization or prolongation of existing hospitalization, results in persistent or significant disability/incapacity, is a congenital anomaly/birth defect or is medically important due to other reasons than the above mentioned criteria.

10) Percentage of participants with fatal SAEs and SAEs related to study drug during the first and second half of Part 3 [time frame: for 3 years (18 month halves) beginning at the end of Part 2 (approximately 21 months after the first vaccination)].

11) Percentage of participants with a seropositive response for each of the four dengue serotypes in the immunogenicity subset [time frame: Day 1 and months 1, 3, 4, 9, 15 and then annually (up to 3 years)]. Seropositive response is defined as a reciprocal neutralizing titer ≥10. The four DENV serotypes are DEN-1, DEN-2, DEN-3 and DEN-4.

12) Percentage of participants with a seropositive response for multiple dengue serotypes in the immunogenicity subset [time frame: Day 1 and months 1, 3, 4, 9, 15 and then annually (up to 3 years)].

13) Geometric Mean Titers (GMTs) of neutralizing antibodies for each of the four dengue serotypes in the immunogenicity subset [time frame: Day 1 and months 1, 3, 4, 9, 15 and then annually (up to 3 years)]. GMTs of neutralizing antibodies will be measured via microneutralization test (MNT) as described in Example 2.

a) Study Population

Figure 3:
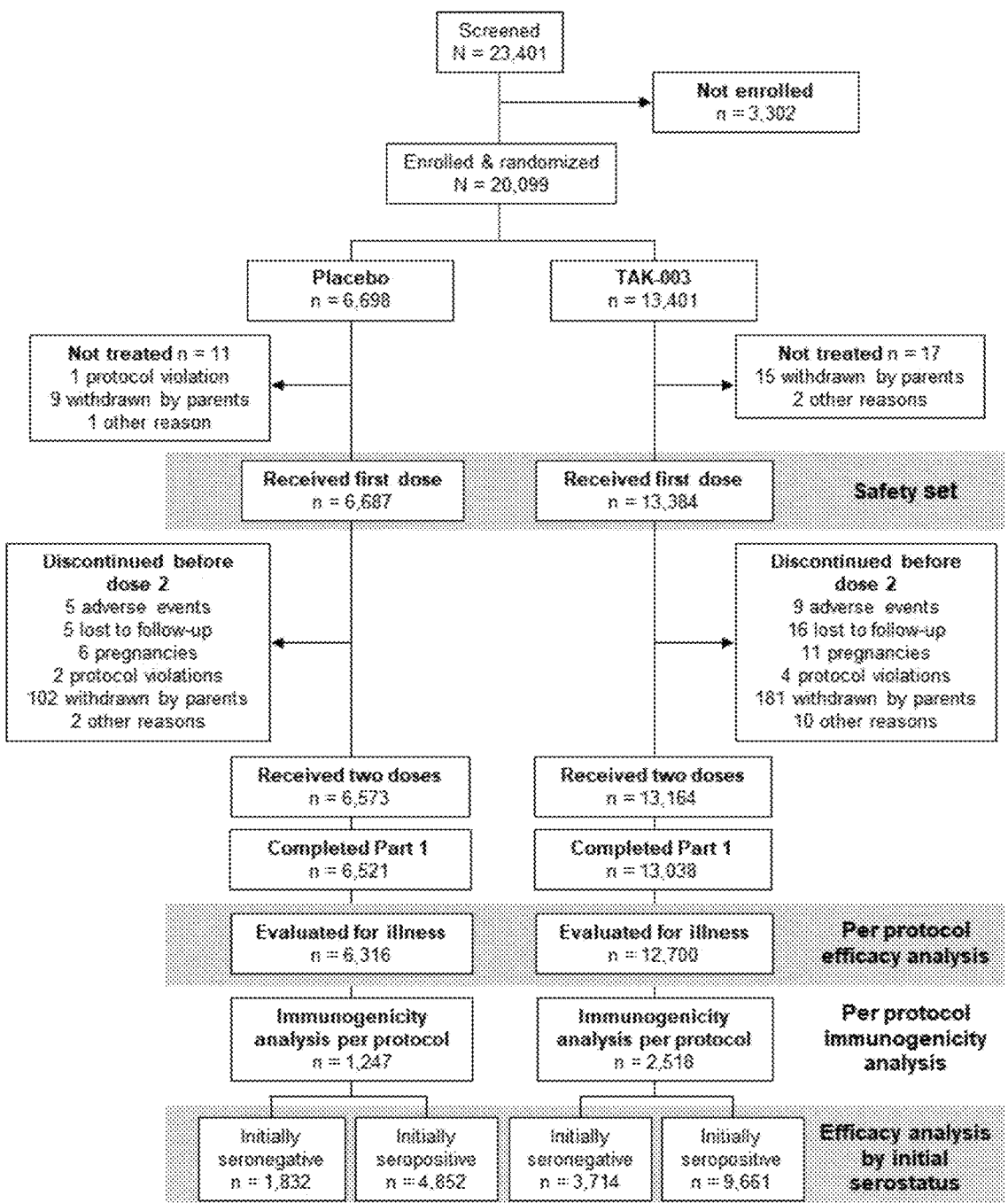
FIG. 3: Flow diagram of the clinical trial of Example 3.

After screening, 20,099 participants were randomized, and 20,071 received at least one injection. In total, 97.4% of placebo participants (n/N: 6,521/6,698) and 97.3% of vaccines (n/N: 13,038/13,401) completed Part 1 of the study (FIG. 3). Reasons for study withdrawals included AEs, participants lost to follow-up, pregnancy, protocol violations, and withdrawal by participants (or parents/guardians). Baseline characteristics were similar across both treatment groups (Table 5). Mean age of study participants was 9.6 years, with baseline seronegativity of 27.7%, and enrollment was broadly balanced across regions (46.5% in Asia, 53.5% in Latin America). The highest seronegative rate was in Panama (62.2%), followed by Sri Lanka (38.5%), Thailand (34.4%), Brazil (28.8%), Nicaragua (22.3%), Colombia (15.4%), the Philippines (12.4%), and the Dominican Republic (2.8%).

TABLE 5

Baseline characteristics of study population (number, %)

| | TDV | Placebo | Total |
|---|---|---|---|
| Per Protocol Set | | | |
| Number of Participants | 12,704 | 6,317 | 19,021 |
| Mean Age (Years, SD) | 9.6 (3.35) | 9.6 (3.34) | 9.6 (3.35) |
| Baseline Seronegative[a] | 3,533 (27.8) | 1,726 (27.3) | 5,259 (27.7) |
| Female | 6,314 (49.7) | 3,098 (49.0) | 9,412 (49.5) |
| Male | 6,390 (50.3) | 3,219 (51.0) | 9,609 (50.5) |
| Asia Pacific | 5,896 (46.4) | 2,942 (46.6) | 8,838 (46.5) |
| Baseline Seronegative[a] | 1,503 (25.5) | 773 (26.3) | 2,276 (25.8) |
| Latin America | 6,808 (53.6) | 3,375 (53.4) | 10,183 (53.5) |
| Baseline Seronegative[a] | 2,030 (29.8) | 953 (28.2) | 2,983 (29.3) |
| Safety Set[b] | | | |
| Number of Participants | 13,380 | 6,687 | 20,071 |
| Mean Age (Years, SD) | 9.6 (3.36) | 9.6 (3.34) | 9.6 (3.35) |
| Baseline Seronegative[a] | 3,714 (27.8) | 1,832 (27.4) | 5,547 (27.6) |
| Female | 6,651 (49.7) | 3,276 (49.0) | 9,929 (49.5) |
| Male | 6,729 (50.3) | 3,411 (51.0) | 10,142 (50.5) |
| Safety Set of Subset[b] | | | |
| Number of Participants | 2,663 | 1,329 | 3,993 |
| Baseline Seronegative[a] | 740 (27.8) | 369 (27.8) | 1,109 (27.8) |

[a] Seronegative for all serotypes; seropositive defined as reciprocal neutralizing antibody titer ≥10; SD, standard deviation.
[b] numbers of participants in TVD plus placebo groups are not equal to total numbers shown because misallocated participants (i.e. those who received both TVD and placebo due to an administrative error) are not included in the TDV and placebo group data.

b) Febrile Illnesses and VCD

During Part 1, 5,754 and 4,663 episodes of febrile illness were reported in Asian and Latin American sites, respectively. Acute samples were obtained in 99.5% and 96.6% of these cases, with 98.3% and 85.1% of samples taken within five days, in Asia and Latin America, respectively. There were 278 VCD cases (76 hospitalized) in the safety set during the entire Part 1 period, of which 210 (58 hospitalized) were 30 days post-second vaccination in the PPS (Table 6; Table 8) and were included in primary endpoint analysis.

c) Distribution of VCD Included in Primary Endpoint Analysis

DENV-1 was reported in all countries with VCD and included all the 21 cases in Panama. In Sri Lanka, 54 of 60 VCD were DENV-2, and 87 of 109 VCD in the Philippines were DENV-3. All seven DENV-4 VCD were reported in the Philippines. No VCD were reported in Nicaragua or the Dominican Republic. Of the associated 58 hospitalized VCD, 43 were reported in Sri Lanka. A total of two severe dengue (both DENV-3) and five dengue hemorrhagic fever (DHF; three DENV-2; two DENV-3) cases were reported (Table 7). These seven were also the only such cases in the entire part 1 safety set.

d) Vaccine Efficacy

Figure 4:
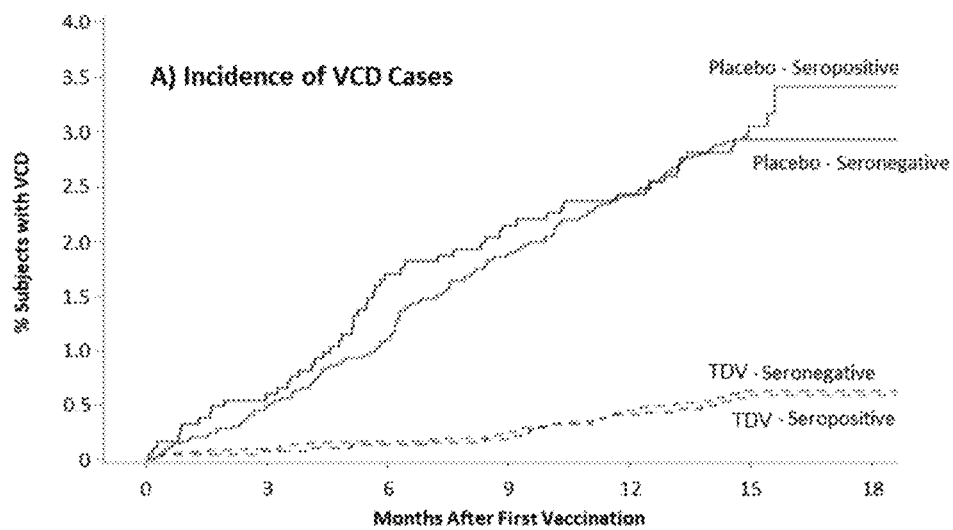
FIG. 4: Cumulative incidence of A) virologically-confirmed dengue cases and B) hospitalized virologically-confirmed dengue cases over time during Part 1 study period by baseline serostatus (safety set data; data presented truncated at Month 18). Tables show numbers of participants under follow-up at various time points to end of Part 1 study period.
Figure 4:
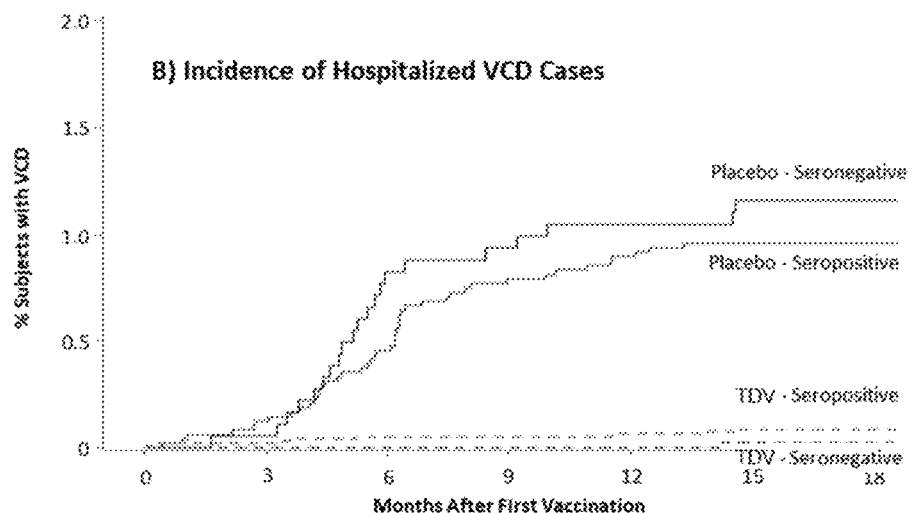
Figure 5:
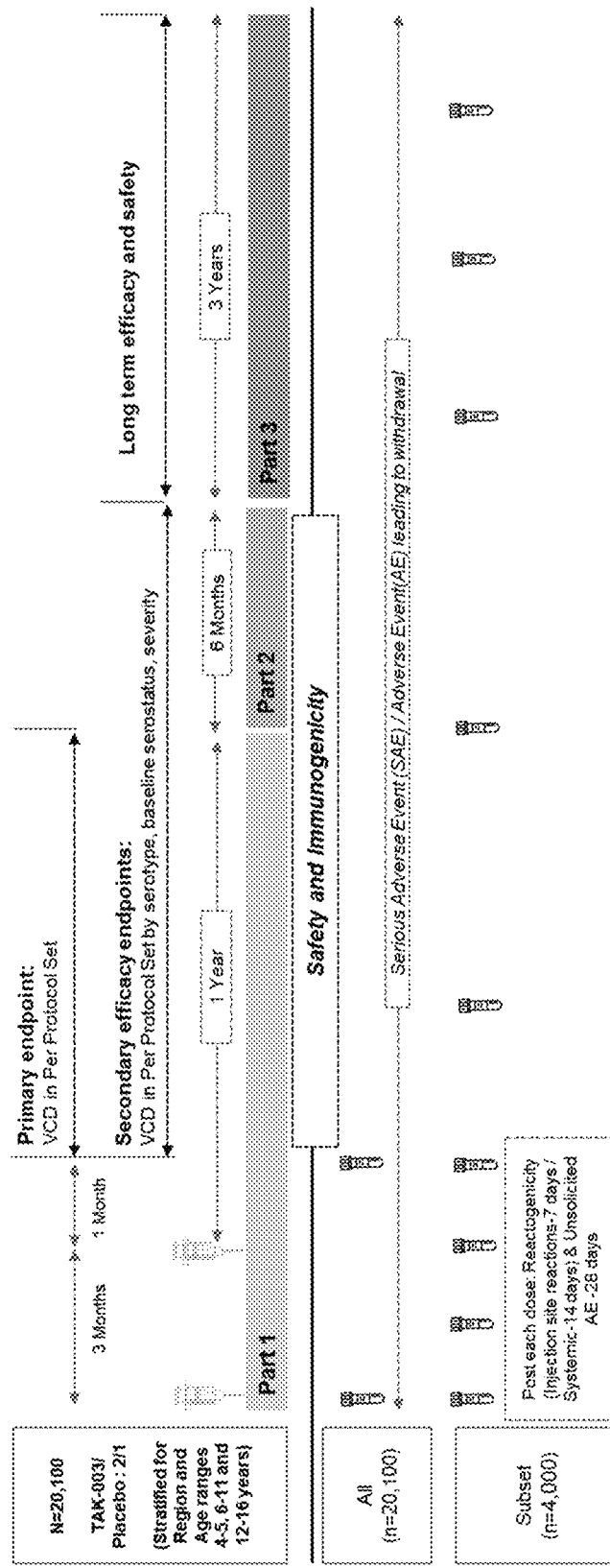
FIG. 5: Study design of phase III study described in example 3.

VE against VCD of any serotype was 80.2% (95% CI: 73.3-85.3; P<0.001). A similar efficacy of 81% (95% CI: 64.1-90.0) between the doses and from first dose onwards in the safety set (Table 6) suggests that the vaccine was efficacious after the first dose. Exploratory analysis of the secondary efficacy endpoints showed a trend of differential efficacy by serotype, with the highest efficacy against DENV-2 (97.7%), followed by DENV-1 (73.7%), DENV-4 (63.2% with CI containing zero), and DENV-3 (62.6%; Table 7). Overall, efficacy was similar in baseline seronegatives (74.9%) and seropositives (82.2%; FIG. 4 above); however, this varied by serotype. Efficacy against DENV-2 was not impacted by serostatus; efficacy against DENV-1 was slightly higher in baseline seropositives (79.8%; 95% CI: 51.3-91.6) than baseline seronegatives (67.2%; 95% CI: 23.2-86.0). No efficacy was observed against DENV-3 in baseline seronegatives (−38.7%; 95% CI: −335.7-55.8) compared to baseline seropositives (71.3%; 95% CI: 54.2-82.0). Efficacy by serostatus could not be calculated for DENV-4 because no cases were observed in baseline seronegatives. In the primary endpoint timeframe of the PPS, only five VCD requiring hospitalization were reported in the vaccine group compared with 53 cases in the placebo group, with a VE of 95.4% (95% CI: 88.4-98.2; 97.2% for baseline seronegatives and 94.4% for baseline seropositives; Table 7; FIG. 4 below), consistent with a VE of 93.3% (95% CI: 86.7-96.7) in the safety set from first dose onwards.

The primary vaccine efficacy (VE) of two doses of TDV in preventing virologically-confirmed dengue (VCD) fever induced by any dengue serotype is shown in Table 6.

TABLE 6

Vaccine efficacy of TDV in preventing virologically-confirmed dengue (VCD) fever against any serotype from 30 days post-second vaccination until end of part 1 Per Protocol Set (PPS), i.e. 12 months post-second vaccination. Safety set analysis from first dose to end of Part 1 study period, i.e. 12 months post-second vaccination

|  | Placebo<br>n = 6317 | TDV (PPS)<br>n = 12,704 |
|---|---|---|
| number of subject evaluated | 6,316 | 12,700 |
| number of subjects with febrile illness | 1,712 | 3,195 |
| number of febrile illness cases | 2,591 | 4,692 |
| virologically confirmed dengue fever (n [%]) | 149 [2.4] | 61 [0.5] |
| Person-years at risk | 5,670.1 | 11,578.7 |
| incident density | 2.6 | 0.5 |
| relative risk | | 0.20 |
| 95% CI of relative risk | | (0.15, 0.27) |
| vaccine efficacy (%) | | 80.2 |
| 95% CI of vaccine efficacy | | (73.3, 85.3) |
| p-value for vaccine efficacy | | <0.001 |

|  | Placebo | TDV (Safety Set)* |
|---|---|---|
| number of subject evaluated | 6,687 | 13,380 |
| virologically confirmed dengue fever (n [%]) | 199 [3.0] | 78 [0.6] |
| Person-years at risk | 8,072.0 | 16,351.5 |
| incident density | 2.5 | 0.5 |

TABLE 6-continued

Vaccine efficacy of TDV in preventing virologically-confirmed dengue (VCD) fever against any serotype from 30 days post-second vaccination until end of part 1 Per Protocol Set (PPS), i.e. 12 months post-second vaccination. Safety set analysis from first dose to end of Part 1 study period, i.e. 12 months post-second vaccination

| vaccine efficacy (%) | 80.9 |
|---|---|
| 95% CI of vaccine efficacy | (75.2, 85.3) |

Note 1:
Percentage of virologically confirmed dengue (VCD) fever are based on number of subjects evaluated.

Note 2:
Person-years at risks is defined as cumulative time in years until start of VCD fever or until end of Part 1 study period or discontinuation date, whichever comes first. Incident density is defined as the number of cases per 100 person-years at risk. Percentages are based on total number (denominator) of analysis set participants evaluated and may not be equal to the total number of participants in the per protocol analysis set.
*One participant had two instances of VCD during Part 1, only the first VCD was included in efficacy calculation Note 3:
Vaccine efficacy (VE) and 2-sided 95% CIs are estimated from a Cox proportional hazard model with TDV as a factor, adjusted for age and stratified by region.

Note 4:
Statistical significance will be concluded if the lower bound of the 95% CI for VE is above 25%. Since the hypotheses will be tested in a confirmatory manner at a 2-sided significance level of 5%, the calculated p-value should be compared with 0.025.

Note 5:
Relative risk is calculated as the number of events divided by the number of subjects evaluated in the TDV group, over the number of events divided by the number of subjects evaluated in the placebo group.

For the efficacy evaluation shown in Table 6, a case of VCD was defined as febrile illness (defined as fever ≥38° C. on any 2 of 3 consecutive days) with a positive serotype-specific RT-PCR (i.e., positive dengue detection RT-PCR) and occurring at any time starting from 30 days post-second vaccination (Day 120 [Month 4]) through the end of Part 1. The analysis was performed on the Per-Protocol Set (PPS) and Safety Set.

As used herein, the "Per-Protocol Set (PPS)" consist of all subjects in the Full Analysis Set (FAS) consisting of all randomized subjects who received at least one dose of TDV or placebo who had no major protocol violations. Major protocol violations are not receiving both doses of TDV or placebo administration, not receiving both doses in the correct interval, not having the correct administration of TDV or placebo, use of prohibited medications/vaccines by the subject, the subject meets any of the exclusion criteria of 2d, 3, 4 or 5 defined above or product preparation error.

The p-value is obtained by solving the critical value Z in the following equation:

Upper bound of 1-sided (1−$p$%) CI of HR=0.75, wherein HR is the hazard ratio and defined as HR=$\lambda V/\lambda C$.

$e^{\hat{}}[\hat{\beta}+Z^*SE]=0.75$, wherein $\hat{\beta}$ defines the treatment and SE the related standard error.

The 1-sided p-value is 1−(area to the left of the critical value Z from a standard normal distribution). Since the hypotheses will be tested in a confirmatory manner 2-sided at a significance level of 5%, the calculated 1-sided p-value should be compared with 0.025.

In summary in Part 1 of this study, a high vaccine efficacy of 80.2% against virologically-confirmed dengue of any serotype in children 4-16 years of age was found. It included an efficacy of 74.9% in baseline seronegatives and a robust 95.4% reduction in hospitalizations. Onset of protection could be seen after the first dose with 81% efficacy between doses. Overall, these results suggest a potential benefit for each vaccine recipient regardless of prior dengue exposure or age. This finding is significant because vaccine development against dengue has been challenging, especially for dengue naïve individuals, and dengue remains one of the WHO's top ten threats to global health in 2019.19 Furthermore, the onset of protection after the first dose has potential utility in the context of outbreak control or travel vaccination, offering a reduction in the risk of dengue after only one dose.

Severe forms of dengue were assessed as follows: Dengue Hemorrhagic Fever (DHF) as defined by the 1997 WHO definition. Severe Dengue through the Dengue Case Adjudication Committee. The Dengue Case Adjudication Committee (DCAC) consisted of four members: a voting chairperson, two voting members, and an independent non-voting statistician. The three DCAC voting members are all physicians and clinical dengue experts. DCAC members are not study investigators and do not have any conflict of interest that would bias their review of the trial data. All non-hospitalized cases were considered non-severe. The DCAC severe dengue case criteria applied in a blinded manner to virologically-confirmed hospitalized dengue cases are as follows: 1) bleeding abnormality, for a case to be considered severe there needs to be a significant intervention required in response to the bleeding episode such as blood transfusion, nasal packing, hormonal therapy, or, bleeding occurred into critical organs such as the brain; 2) plasma leakage, for a case to be considered severe there needs to be evidence of both plasma leakage and functional impairment (plasma leakage includes clinical evidence, radiological evidence, or hematocrit elevated >20% above normal levels or baseline; functional impairment defined as shock or respiratory distress); 3) liver, for a case to be considered severe there needs to be evidence of both hepatitis and functional impairment (hepatitis defined as an aspartate aminotransferase [AST] or alanine aminotransferase [ALT]>10 upper limit of normal range [ULN]; functional impairment defined as prothrombin [PT]>1.5 ULN or hypoalbuminemia); 4) renal, serum creatinine >2.5 times ULN or requiring dialysis; 5) cardiac, abnormalities intrinsic to the heart (i.e. not resulting from intravascular volume depletion) and with evidence of functional impairment (examples of intrinsic abnormality: myocarditis, pericarditis, and myopericarditis; example of functional impairment: new conduction abnormality resulting in irregular heart rhythm [i.e. not transient first-degree heart block]); 6) central nervous system, any abnormality with the exception of a simple febrile convulsion or a brief delirium; 7) shock, all shock cases considered severe. At least 1 functional impairment (of criterion 3,4,5,6), needs to be present but the totality of data were considered by the members in their assessment.

Further results of part 1 and part 2 are presented in Tables 7a to c.

TABLE 7a

Distribution of cases contributing to primary endpoint by per protocol set subgroup (30 days after second vaccination until end of Part 1, i.e. 12 months after second vaccination)

| | TDV Dengue Cases | TDV Incidence Density | Placebo Dengue Cases | Placebo Incidence Density | Vaccine Efficacy (95% CI) |
|---|---|---|---|---|---|
| VCD cases | | | | | |
| Baseline Seropositive[a] | 41/9,165 (0.4%) | 0.5 | 110/4,587 (2.4%) | 2.7 | 82.2% (74.5%-87.6%) |
| Baseline Seronegative[a] | 20/3,531 (0.6%) | 0.6 | 39/1,726 (2.3%) | 2.5 | 74.9% (57.0%-85.4%) |
| DENV-1 | 16/12,700 (0.1%) | 0.1 | 30/6,316 (0.5%) | 0.5 | 73.7% (51.7%-85.7%) |
| DENV-2 | 3/12,700 (<0.1%) | <0.1 | 64/6,316 (1.0%) | 1.1 | 97.7% (92.7%-99.3%) |
| DENV-3 | 39/12,700 (0.3%) | 0.3 | 51/6,316 (0.8%) | 0.9 | 62.6% (43.3%-75.4%) |
| DENV-4[d] | 3/12,700 (<0.1%) | <0.1 | 4/6,316 (<0.1%) | <0.1 | 63.2% (-64.6%-91.8%) |
| 4-5 Years Old | 13/1,619 (0.8%) | 0.9 | 23/801 (2.9%) | 3.2 | 72.8% (46.2%-86.2%) |
| 6-11 Years Old | 34/7,009 (0.5%) | 0.5 | 85/3,491 (2.4%) | 2.7 | 80.7% (71.3%-87.0%) |
| 12-16 Years Old | 14/4,072 (0.3%) | 0.4 | 41/2,024 (2.0%) | 2.2 | 83.3% (69.3%-90.9%) |
| Asia | 54/5,894 (0.9%) | 1.0 | 127/2,942 (4.3%) | 4.9 | 79.5% (71.8%-85.1%) |
| Latin America | 7/6,806 (0.1%) | 0.1 | 22/3,374 (0.7%) | 0.7 | 84.3% (63.1%-93.3%) |
| Hospitalized VCD cases | | | | | |
| Baseline Seropositive[a] | 4/9,165 (<0.1%) | <0.1 | 35/4,587 (0.8%) | 0.8 | 94.4% (84.3%-98.0%) |
| Baseline Seronegative[a] | 1/3,531 (<0.1%) | <0.1 | 18/1,726 (1.0%) | 1.2 | 97.2% (79.1%-99.6%) |
| Cases of DHF[b] | | | | | |
| All participants | 1/12,700 (<0.1%) | <0.1 | 4/6,316 (<0.1%) | <0.1 | 87.3% (-13.5%-98.6%) |
| Severe VCD Cases[c] | | | | | |
| All participants | 1/12,700 (<0.1%) | <0.1 | 1/6,316 (<0.1%) | <0.1 | 50.8% (-686.9%-96.9%) |

VCD, virologically-confirmed dengue;
DHF, dengue hemorrhagic fever
[a]Seronegative for all serotypes; baseline seropositive defined as reciprocal neutralizing antibody titer ≥10 to one or more serotypes.
[b]VCD cases meeting WHO 1997 DHF criteria; incidence density defined as the number of cases per 100 person-years at risk; percentages are based on total number (denominator) of per protocol set participants evaluated.
[c]two severe VCD were not classified as DHF.
[d]The number of cases identified was sufficient to provide reasonably precise estimates of vaccine efficacy against all individual serotypes, except DENV-4.

TABLE 7b

Distribution of cases contributing to secondary endpoint by per protocol set subgroup (30 days after second vaccination until end of Part 2, i.e. 18 months after second vaccination)

| | TDV Dengue Cases | TDV Incidence Density | Placebo Dengue Cases | Placebo Incidence Density | Vaccine Efficacy (95% CI) |
|---|---|---|---|---|---|
| VCD cases | | | | | |
| Overall | | | | | 73.3% (66.5%-78.8%) |
| Baseline Seropositive[a] | 75 | 0.6 | 150 | 2.4 | 76.1% (68.5%-81.9%) |
| Baseline Seronegative[a] | 39 | 0.8 | 56 | 2.4 | 66.2% (49.1%-77.5%) |
| DENV-1 | 38 | 0.2 | 62 | 0.7 | 69.8% (54.8%-79.9%) |
| Baseline Seropositive[a] | 21 | 0.2 | 37 | 0.6 | 72.0 (52.2%-83.6%) |
| Baseline Seronegative[a] | 17 | 0.3 | 25 | 1 | 67.8 (40.3%-82.6%) |
| DENV-2 | 8 | <0.1 | 80 | 0.9 | 95.1% (89.9%-97.6%) |
| Baseline Seropositive[a] | 7 | <0.1 | 54 | 0.9 | 93.7 (86.1%-97.1%) |
| Baseline Seronegative[a] | 1 | <0.1 | 26 | 1.1 | 98.1 (85.8%-99.7%) |
| Hospitalized VCD cases | | | | | |
| Overall | 13 | <0.1 | 66 | 0.8 | 90.4% (82.6%-94.7%) |
| Baseline Seropositive[a] | 8 | <0.1 | 45 | 0.7 | 91.4% (81.7%-95.9%) |
| Baseline Seronegative[a] | 5 | 0.1 | 21 | 0.9 | 88.1% (68.5%-95.5%) |

VCD, virologically-confirmed dengue;
[a]Seronegative for all serotypes; baseline seropositive defined as reciprocal neutralizing antibody titer ≥10 to one or more serotypes.

TABLE 7c

Distribution of cases contributing to secondary endpoint by safety set (first vaccination until end of Part 2, i.e. 21 months after first vaccination)

| | TDV Dengue Cases | TDV Incidence Density | Placebo Dengue Cases | Placebo Incidence Density | Vaccine Efficacy (95% CI) |
|---|---|---|---|---|---|
| VCD cases | | | | | |
| Overall | | | | | 75.3% (69.5%-80.0%) |
| Overall in between[a] | | | | | 81.0% (64.1%-90.0%) |
| Baseline Seropositive[b] | 89 | 0.5 | 187 | 2.3 | 77.2% (70.6%-82.3%) |
| Baseline Seronegative[b] | 42 | 0.7 | 70 | 2.3 | 70.6% (56.9%-79.9%) |
| DENV-1 | 41 | 0.2 | 78 | 0.7 | 73.9% (61.9%-82.1%) |
| DENV-2 | 14 | <0.1 | 109 | 1.0 | 93.7% (89.0%-96.4%) |
| Hospitalized VCD cases | | | | | |
| Overall | 17 | <0.1 | 81 | 0.7 | 89.7% (82.6%-93.9%) |

VCD, virologically-confirmed dengue;
[a]In between: VCD after first vaccination and before second vaccination.
[b]Seronegative for all serotypes; baseline seropositive defined as reciprocal neutralizing antibody titer ≥10 to one or more serotypes.

TABLE 7d

Dengvaxia ® VCD (first vaccination until 25 months after first vaccination (i.e. 13 month after third vaccination), ITT from CYD15, 9 to 16 years of age)[a]

| | Vaccine Efficacy (95% CI) |
|---|---|
| Overall VCD | 64.7% (58.7%-69.8%) |
| Baseline Seropositive[b] | 83.7% (62.2%-93.7%) |
| Baseline Seronegative[b] | 43.2% (-61.5%-80.0%) |
| DENV-1 | 58.8% (40.2%-65.9%) |
| DENV-2 | 50.2% (31.8%-63.6%) |
| Overall Hospitalized VCD | 80.3% (64.7%-89.5%) |

[a]Luis Villar et al. Efficacy of a tetravalent dengue vaccine in Children in Latin America: N Engl J of Med 2015 Vol. 372 No2, 113-123

Clinical signs and symptoms of virologically-confirmed dengue cases during Part 1 study period in safety set data are shown in Table 8.

TABLE 8

Clinical signs and symptoms of virologically-confirmed dengue cases during Part 1 study period (safety set data)

|  | TDV (N = 13,380) | Placebo (N = 6,687) | Relative Risk |
|---|---|---|---|
| Number of VCD Cases | 78 | 200 | — |
| Median Duration of Febrile Illness (days; 95% CI)[a] | 6.0 (5.7-7.4) | 6.0 (5.9-6.8) | — |
| Median Duration of Fever (days; 95% CI) | 4.0 (3.9-4.6) | 5.0 (4.5-5.0) | — |
| Number of Hospitalized VCD Cases | 9 | 67 | — |
| Median Duration of Hospitalization (days; 95% CI) | 5.0 (2.8-5.4) | 5.0 (4.6-5.4) | — |
| Evidence of Bleeding (%, n/N) | 3.8% (3/78) | 3.5% (7/200) | 1.10 |
| Plasma Leakage (%, n/N) | 2.6% (2/78) | 6.5% (13/200) | 0.39 |
| Plasma Leakage - Pleural Effusion (%, n/N) | 1.3% (1/78) | 1.5% (3/200) | — |
| Plasma Leakage - Ascites (%, n/N) | 1.3% (1/78) | 3.0% (6/200) | — |
| Plasma Leakage - Radiological Signs (%, n/N) | 40.0% (2/5) | 19.6% (10/51) | — |
| Plasma Leakage - Hematocrit Increase ≥20% (%, n/N)[b] | 3.8% (2/53) | 9.5% (13/137) | — |
| Platelet Count ≤100 × $10^9$ (%, n/N)[c] | 6.4% (5/78) | 22.0% (44/200) | 0.29 |
| Platelet Count ≤50 × $10^9$ (%, n/N)[c] | 3.8% (3/78) | 11.0% (22/200) | 0.35 |
| ALT or AST ≥1000 U/L (%, n/N)[c] | 0% (0/78) | 0% (0/200) | — |

VCD, virologically-confirmed dengue;
ALT, alanine aminotransferase;
AST, aspartate aminotransferase
[a]Duration of febrile illness defined as start date of earliest symptom to end date of latest symptom plus one day (symptoms considered include fever and any general symptoms).
[b]Hematocrit increase defined as maximum hematocrit between Day 3 and Day 7 inclusive, from onset of fever ≥20% increase over minimum hematocrit before Day 3 or after Day 7 from onset of fever.
[c]For platelet, ALT, and AST data, assessments within 14 days of onset of febrile illness have been considered.
N refers to number of VCD cases with available data for the specific parameter e) Immunogenicity The highest geometric mean titers (GMTs) were observed against DENV-2 regardless of baseline serostatus (Table 10). A very high tetravalent seropositivity rate (99.5%) in baseline seronegatives one month after the second dose (Tables 9 and 10) was observed.

Seropositivity rate (% of seropositive subjects) for each of the four dengue serotypes is determined at prevaccination on Day 1 (Month 0), post-first vaccination on Day 30 (Month 1), prevaccination on Day 90 (Month 3), post-second vaccination on Day 120 (Month 4), Day 270 (Month 9), Day 450 (Month 15), and then annually. Seropositivity rates (% participants, 95% CI) by dengue serotype per protocol set for immunogenicity data for Day 0, Day 30, Day 90, Day 120, and Day 270 are shown in Table 9.

Seropositivity rates (% participants, 95% CI) by dengue serotype against three or more serotypes (trivalent) and against all four serotypes (tetravalent) per protocol set for immunogenicity data for Day 0, Day 30, Day 90, Day 120, and Day 270 are shown in Table 9. The tetravalent seropositivity rates were high (>91%) in baseline seronegatives six months after second dose.

TABLE 9

Seropositivity rates (% participants, 95% CI) by dengue serotype (per protocol set for immunogenicity data)

| BASELINE SEROPOSITIVE | | BASELINE SERONEGATIVE | |
|---|---|---|---|
| TDV N = 1,816 | Placebo N = 902 | TDV N = 702 | Placebo N = 345 |
| DENV-1 | | | |
| 89.1 (87.6-90.5) | 90.6 (88.5-92.4) | 0 (0-0.5) | 0 (0-1.1) |
| 99.5 (99.1-99.8) | 88.6 (86.3-90.7) | 94.1 (92.0-95.8) | 4.9 (2.8-7.8) |
| 99.3 (98.8-99.6) | 90.2 (88.1-92.1) | 91.6 (89.3-93.5) | 6.1 (3.8-9.2) |
| >99.9 (99.7-100) | 90.3 (88.1-92.3) | 99.5 (98.6-99.9) | 8.3 (5.5-11.9) |
| 99.6 (99.1-99.8) | 89.8 (87.5-91.8) | 95.1 (93.0-96.6) | 9.0 (6.0-12.8) |
| DENV-2 | | | |
| 96.5 (95.6-97.3) | 97.2 (95.9-98.2) | 0 (0-0.5) | 0 (0-1.1) |
| 99.9 (99.6-100) | 93.3 (91.4-94.9) | 98.6 (97.4-99.4) | 10.7 (7.5-14.5) |
| >99.9 (99.7-100) | 94.0 (92.2-95.5) | 99.0 (98.0-99.6) | 12.2 (8.9-16.1) |
| 99.9 (99.6-100) | 93.6 (91.7-95.2) | 100 (99.4-100) | 14.7 (11.0-19.1) |
| 100 (99.8-100) | 94.6 (92.8-96.1) | 100 (99.4-100) | 18.3 (14.1-23.2) |
| DENV-3 | | | |
| 88.1 (86.5-89.6) | 88.0 (85.7-90.1) | 0 (0-0.5) | 0 (0-1.1) |
| 99.8 (99.4-99.9) | 87.6 (85.1-89.7) | 96.1 (94.3-97.4) | 4.0 (2.1-6.7) |
| 99.5 (99.1-99.8) | 87.3 (84.9-89.4) | 94.4 (92.5-96.0) | 2.0 (0.8-4.1) |
| 99.8 (99.5-100) | 87.9 (85.5-90.1) | 100 (99.4-100) | 5.1 (2.9-8.2) |
| 99.7 (99.4-99.9) | 87.1 (84.6-89.4) | 96.4 (94.6-97.7) | 7.7 (4.9-11.3) |

TABLE 9-continued

Seropositivity rates (% participants, 95% CI) by dengue serotype (per protocol set for immunogenicity data)

| BASELINE SEROPOSITIVE | | BASELINE SERONEGATIVE | |
|---|---|---|---|
| TDV<br>N = 1,816 | Placebo<br>N = 902 | TDV<br>N = 702 | Placebo<br>N = 345 |
| DENV-4 | | | |
| 88.1 (86.5-89.6) | 87.4 (85.0-89.5) | 0 (0-0.5) | 0 (0-1.1) |
| 99.6 (99.2-99.9) | 86.6 (84.1-88.8) | 90.5 (88.0-92.6) | 1.8 (0.7-3.9) |
| 99.3 (98.8-99.7) | 86.9 (84.5-89.0) | 92.0 (89.8-93.9) | 2.9 (1.4-5.3) |
| >99.9 (99.7-100) | 88.3 (85.9-90.4) | 99.8 (99.1-100) | 4.8 (2.7-7.8) |
| 99.7 (99.3-99.9) | 87.6 (85.1-89.9) | 97.0 (95.4-98.2) | 6.3 (3.9-9.7) |
| Three or More Serotypes | | | |
| 87.5 (85.9-89.0) | 87.3 (84.9-89.4) | 0 (0-0.5) | 0 (0-1.1) |
| 99.8 (99.5-100) | 87.2 (84.7-89.4) | 96.5 (94.8-97.8) | 1.2 (0.3-3.1) |
| 99.7 (99.3-99.9) | 87.7 (85.3-89.7) | 94.9 (93.0-96.4) | 1.7 (0.6-3.7) |
| 99.9 (99.6-100) | 88.4 (86.0-90.5) | 99.8 (99.1-100) | 4.2 (2.2-7.0) |
| 99.7 (99.4-99.9) | 87.3 (84.7-89.5) | 97.5 (96.0-98.6) | 5.7 (3.3-8.9) |
| All Four Serotypes | | | |
| 83.5 (81.7-85.2) | 83.5 (80.9-85.8) | 0 (0-0.5) | 0 (0-1.1) |
| 99.1 (98.5-99.5) | 82.9 (80.2-85.4) | 85.3 (82.4-87.9) | 0.9 (0.2-2.6) |
| 98.6 (97.9-99.1) | 83.6 (81.0-86.0) | 84.3 (81.4-86.9) | 1.4 (0.5-3.3) |
| 99.8 (99.5-100) | 85.2 (82.6-87.6) | 99.5 (98.6-99.9) | 3.5 (1.8-6.2) |
| 99.2 (98.7-99.6) | 84.6 (81.9-87.0) | 91.3 (88.7-93.4) | 5.3 (3.1-8.5) |

Seropositivity rates (% participants, 95% CI) by dengue serotype (per protocol set for immunogenicity data; seropositive defined as a reciprocal neutralizing antibody titer ≥10; baseline seronegative defined as seronegative to all serotypes; baseline seropositive defined as seropositive to one or more serotypes; N refers to number of participants in the analysis set; number of participants evaluated at each time point may vary)

Seropositivity rates (% participants, 95% CI) by dengue serotype (per protocol set for immunogenicity data; seropositive defined as a reciprocal neutralizing antibody titer ≥10; baseline seronegative defined as seronegative to all serotype; baseline seropositive defined as seropositive to one or more serotypes; N refers to number of participants in the analysis set; number of participants evaluated at each time point may vary)

Geometric mean titers (GMTs) of neutralizing antibodies (microneutralization test [MNT]) for each dengue serotype are determined at pre-vaccination on Day 1 (Month 0), post-first vaccination on Day 30 (Month 1), pre-vaccination on Day 90 (Month 3), post-second vaccination on Day 120 (Month 4), Day 270 (Month 9), Day 450 (Month 15), and then annually. Geometric mean titers (95% CI) by dengue serotype per protocol set for immunogenicity data for Day 0, Day 30, Day 90, Day 120, and Day 270 are shown in Table 10.

TABLE 10

Geometric mean titers (95% CI) by dengue serotype (per protocol set for immunogenicity data)

| | BASELINE SEROPOSITIVE | | BASELINE SERONEGATIVE | |
|---|---|---|---|---|
| | TDV<br>N = 1,816 | Placebo<br>N-902 | TDV<br>N = 702 | Placebo<br>N = 345 |
| | DENV-1 | | | |
| Day 1 | 410 (365-461) | 445 (377-524) | 5.0 (5.0-5.0) | 5.0 (5.0-5.0) |
| Day 30 | 2,404 (2,204-2,622) | 430 (361-512) | 118 (106-131) | 5.8 (5.3-6.3) |
| Day 90 | 1,945 (1,791-2,112) | 410 (349-481) | 91 (82-102) | 5.9 (5.4-6.3) |
| Day 120 | 2,115 (1,957-2,286) | 451 (381-534) | 184 (169-201) | 6.3 (5.7-7.0) |
| Day 270 | 1,447 (1,329-1,574) | 415 (350-492) | 87 (79-97) | 6.3 (5.7-6.9) |
| | DENV-2 | | | |
| Day 1 | 745 (674-825) | 802 (697-924) | 5.0 (5.0-5.0) | 5.0 (5.0-5.0) |
| Day 30 | 6,697 (6,301-7,117) | 744 (635-870) | 6,277 (5,648-6,977) | 6.6 (6.0-7.3) |
| Day 90 | 4,826 (4,571-5,096) | 729 (629-845) | 1,682 (1,544-1,834) | 7.0 (6.3-7.9) |
| Day 120 | 4,897 (4,646-5,163) | 766 (655-896) | 1,730 (1,614-1,855) | 7.7 (6.7-8.8) |
| Day 270 | 3,692 (3,496-3,898) | 776 (665-906) | 929 (856-1,010) | 8.7 (7.4-10.2) |
| | DENV-3 | | | |
| Day 1 | 357 (321-398) | 356 (305-415) | 5.0 (5.0-5.0) | 5.0 (5.0-5.0) |
| Day 30 | 2,255 (2,094-2,428) | 349 (298-409) | 194 (173-218) | 5.5 (5.2-5.9) |
| Day 90 | 1,563 (1,453-1,682) | 321 (277-374) | 94 (85-104) | 5.5 (5.1-5.9) |
| Day 120 | 1,761 (1,646-1,885) | 353 (301-414) | 228 (212-246) | 6.0 (5.4-6.6) |
| Day 270 | 1,089 (1,009-1,175) | 307 (261-360) | 72 (66-78) | 6.3 (5.7-7.0) |

TABLE 10-continued

Geometric mean titers (95% CI) by dengue serotype
(per protocol set for immunogenicity data)

| | BASELINE SEROPOSITIVE | | BASELINE SERONEGATIVE | |
|---|---|---|---|---|
| | TDV<br>N = 1,816 | Placebo<br>N-902 | TDV<br>N = 702 | Placebo<br>N = 345 |
| | DENV-4 | | | |
| Day 1 | 218 (198-241) | 234 (203-270) | 5.0 (5.0-5.0) | 5.0 (5.0-5.0) |
| Day 30 | 1,303 (1,221-1,391) | 222 (191-258) | 111 (98-125) | 5.4 (5.0-5.7) |
| Day 90 | 1,002 (940-1,069) | 215 (187-248) | 63 (57-70) | 5.5 (5.1-5.9) |
| Day 120 | 1,129 (1,066-1,196) | 241 (208-280) | 144 (134-155) | 5.8 (5.3-6.4) |
| Day 270 | 778 (730-830) | 229 (197-266) | 64 (59-70) | 6.2 (5.6-6.9) |

Vaccine viremia is assessed by three PCRs: dengue detection RT-PCR, vaccine screening PCR and TDV sequencing in subjects with febrile illness within 30 days after each vaccination.

f) Safety

Rates of serious adverse events (SAEs) were similar in the vaccine and placebo groups (3.1% and 3.8% of participants, respectively; Table 11). One vaccine and four placebo recipients experienced SAEs considered to be related to receiving blinded investigational product by the investigator (two experienced hypersensitivity, two were diagnosed with dengue, and one with DHF). There were five deaths during Part 1, and all were considered unrelated to the investigational product or study procedures. Total rates of unsolicited AEs were similar between the vaccine and placebo groups. The most commonly (≥1% of vaccine-recipients) reported unsolicited AEs within four weeks of any dose by preferred term were pyrexia (vaccine group 1.5%; placebo 1.4%), nasopharyngitis (vaccine 2.7%; placebo 3.0%), upper respiratory tract infection (vaccine 2.6%; placebo 2.9%), and viral infection (vaccine 1.1%; placebo 0.9%). Solicited local reactions were reported more frequently in the vaccine group.

TABLE 11a

Overview of safety data. Subjects with at least one adverse event after any vaccine dose. Data presented as number of events (percentage of subjects; number [n] of subjects/total [N] subjects) unless otherwise stated (safety set data)

| | TDV | Placebo |
|---|---|---|
| Safety Set | N = 13,380 | N = 6,687 |
| SAEs | 3.1% (409/13,380) | 3.8% (255/6,687) |
| Non-IP-Related[a] SAEs | 3.0% (408/13,380) | 3.8% (251/6,687) |
| IP-Related[a] SAEs | <0.1% (1/13,380) | <0.1% (4/6,687) |
| SAEs Leading to IP Withdrawal and/or Trial Discontinuation | 0.1% (18/13,380) | 0.1% (8/6,687) |
| Deaths | <0.1% (4/13,380) | <0.1% (1/6,687) |
| IP-Related Deaths | 0% (0/13,380) | 0% (0/6,687) |
| Safety Subset | N = 2,663 | N = 1,329 |
| Unsolicited AEs Occurring Within 4 Weeks of Any Dose | 18.4% (490/2,663) | 18.8% (250/1,329) |
| IP-Related[a] Unsolicited AEs Occurring Within 4 Weeks of Any Dose | 1.0% (27/2,663) | 1.6% (21/1,329) |
| Solicited Systemic AEs Occurring Within 2 Weeks of Any Dose[b] | 42.0% (1,107/2,635) | 38.0% (501/1,317) |
| IP-Related[a] Solicited Systemic AEs Occurring Within 2 Weeks of Any Dose | 31.2% (821/2,635) | 28.2% (371/1,317) |
| Solicited Local Reactions Occurring Within 1 Week of Any Dose[c] | 36.7% (967/2,633) | 25.7% (338/1,317) |

AE, adverse event;

SAE, serious adverse event;

IP, investigational product/TDV

[a]IP-related, defined as related to the investigational product as assessed by investigator

[b]only participants with diary data available were evaluated

[c]all injection site (solicited local) reactions considered to be IP-related

TABLE 11b

Number of participants (%) with serious adverse events after any vaccination during Part 1 by MedDRA (Medical Dictionary for Regulatory Activities) System Organ Class in the order of decreasing frequency (safety set data presented by TDV and placebo group for events that occurred in >3 participants due to risk of unblinding).

| MedDRA System Organ Class | TDV N = 13,380 | Placebo N = 6,687 | Total* N = 20,071 |
|---|---|---|---|
| Any Serious Adverse Events | 409 (3.1) | 255 (3.8) | 664 (3.3) |
| Infections and infestations | 235 (1.8) | 179 (2.7) | 414 (2.1) |
| Injury, poisoning and procedural complications | 87 (0.7) | 37 (0.6) | 124 (0.6) |
| Gastrointestinal disorders | 23 (0.2) | 9 (0.1) | 32 (0.2) |
| Nervous system disorders | 14 (0.1) | 6 (<0.1) | 20 (<0.1) |
| Respiratory, thoracic and mediastinal disorders | 14 (0.1) | 6 (<0.1) | 20 (<0.1) |
| Renal and urinary disorders | 15 (0.1) | 3 (<0.1) | 18 (<0.1) |
| Blood and lymphatic system disorders | 8 (<0.1) | 2 (<0.1) | 10 (<0.1) |
| Pregnancy, puerperium and perinatal conditions | 8 (<0.1) | 2 (<0.1) | 10 (<0.1) |
| Skin and subcutaneous tissue disorders | 7 (<0.1) | 3 (<0.1) | 10 (<0.1) |
| Psychiatric disorders | 7 (<0.1) | 2 (<0.1) | 9 (<0.1) |
| General disorders and administration site conditions | 5 (<0.1) | 3 (<0.1) | 8 (<0.1) |
| Immune system disorders | 3 (<0.1) | 4 (<0.1) | 7 (<0.1) |
| Metabolism and nutrition disorders | 6 (<0.1) | 1 (<0.1) | 7 (<0.1) |
| Musculoskeletal and connective tissue | 1 (<0.1) | 5 (<0.1) | 6 (<0.1) |
| Social circumstances | 2 (<0.1) | 4 (<0.1) | 6 (<0.1) |
| Congenital, familial and genetic disorders | 3 (<0.1) | 2 (<0.1) | 5 (<0.1) |
| Neoplasms benign, malignant and unspecified (including cysts and polyps) | 3 (<0.1) | 1 (<0.1) | 4 (<0.1) |
| Endocrine disorders | — | — | 3 (<0.1) |
| Hepatobiliary disorders | — | — | 3 (<0.1) |
| Reproductive system and breast disorders | — | — | 3 (<0.1) |
| Vascular disorders | — | — | 3 (<0.1) |
| Cardiac disorders | — | — | 2 (<0.1) |
| Eye disorders | — | — | 2 (<0.1) |
| Investigations | — | — | 1 (<0.1) |
| Product issues | — | — | 1 (<0.1) |
| Surgical and medical procedures | — | — | 1 (<0.1) |

*Total column includes participants who received both TAK-003 and placebo due to administration error and are excluded from the TAK-003 and placebo groups.
N in column header refers to number of participants in the safety set TABLE 11c Number of participants (%) with unsolicited adverse events of any severity up to 28-days after any vaccination by MedDRA System Organ Class in the order of decreasing frequency (Subset of safety set data presented by TDV and placebo group for events that occurred in >6 participants due to risk of unblinding).

| MedDRA System Organ Class | TDV N = 2,663 | Placebo N = 1,329 | Total N = 3,993 |
|---|---|---|---|
| Any Unsolicited Adverse Events | 487 (18.3) | 249 (18.7) | 736 (18.4) |
| Infections and infestations | 368 (13.8) | 190 (14.3) | 558 (14.0) |
| Injury, poisoning and procedural complications | 21 (0.8) | 22 (1.7) | 43 (1.1) |
| Gastrointestinal disorders | 33 (1.2) | 9 (0.7) | 42 (1.1) |
| General disorders and administration site conditions | 30 (1.1) | 11 (0.8) | 41 (1.0) |
| Skin and subcutaneous tissue disorders | 27 (1.0) | 7 (0.5) | 34 (0.9) |
| Nervous system disorders | 18 (0.7) | 13 (1.0) | 31 (0.8) |
| Respiratory, thoracic and mediastinal disorders | 18 (0.7) | 10 (0.8) | 28 (0.7) |
| Blood and lymphatic system disorders | 6 (0.2) | 5 (0.4) | 11 (0.3) |
| Musculoskeletal and connective tissue disorders | 6 (0.2) | 5 (0.4) | 11 (0.3) |
| Immune system disorders | — | — | 6 (0.2) |
| Psychiatric disorders | — | — | 3 (<0.1) |
| Reproductive system and breast disorders | — | — | 3 (<0.1) |
| Ear and labyrinth disorders | — | — | 2 (<0.1) |
| Cardiac disorders | — | — | 1 (<0.1) |
| Congenital, familial and genetic disorders | — | — | 1 (<0.1) |
| Eye disorders | — | — | 1 (<0.1) |
| Renal and urinary disorders | — | — | 1 (<0.1) |
| Social circumstances | — | — | 1 (<0.1) |

*Total column includes participants who received both TAK-003 and placebo due to administration error and are excluded from the TAK-003 and placebo groups. N in column header refers to number of participants in the subset of safety set.

TABLE 11d

Summary of diary reported injection site reactions up to 7 days and systemic adverse events up to 14 days after any vaccination (Subset of safety set data). Data presented as number of participants with events/number of evaluated participants in the analysis set (% of evaluated participants with events).

| Solicited Events | TDV | Placebo |
|---|---|---|
| Injection site reactions (Age <6 years) | | |
| Any | 106/331 (32.0) | 43/169 (25.4) |
| Pain | 104/331 (31.4) | 43/169 (25.4) |
| Erythema | 5/331 (1.5) | 1/169 (0.6) |
| Swelling | 11/331 (3.3) | 2/169 (1.2) |
| Injection site reactions (Age ≥6 years) | | |
| Any | 861/2302 (37.4) | 295/1148 (25.7) |
| Pain | 853/2302 (37.1) | 293/1148 (25.5) |
| Erythema | 33/2301 (1.4) | 1/1147 (<0.1) |
| Swelling | 33/2300 (1.4) | 6/1147 (0.5) |
| Systemic adverse events (Age <6 years) | | |
| Any | 88/331 (26.6) | 35/169 (20.7) |
| Irritability/Fussiness | 41/331 (12.4) | 16/169 (9.5) |
| Drowsiness | 45/331 (13.6) | 21/169 (12.4) |
| Loss of Appetite | 57/331 (17.2) | 22/169 (13.0) |
| Fever (Body temperature >= 38° C. or 100.4° F.) | 45/327 (13.8) | 23/169 (13.6) |
| Systemic adverse events (Age ≥6 years) | | |
| Any | 941/2302 (40.9) | 422/1147 (36.8) |
| Headache | 715/2302 (31.1) | 326/1147 (28.4) |
| Asthenia | 404/2302 (17.5) | 187/1147 (16.3) |
| Malaise | 510/2301 (22.2) | 226/1147 (19.7) |
| Myalgia | 554/2302 (24.1) | 216/1147 (18.8) |
| Fever (Body temperature >= 38° C. or 100.4° F.) | 221/2279 (9.7) | 124/1134 (10.9) |

Additionally, a study to assess the efficacy of a booster dose as a follow-on study of the above-described phase III study, such that booster will be given at 4 to 4.5 years post the second dose in a large enough subset of the above-described phase III study, wherein said subset e.g. includes at least 20 subjects or at least 200 subjects, is possible.

Example 4: Concomitant Administration of a Hepatitis a Vaccine and a Dengue Vaccine 4.1 Introduction, Purpose and Objectives of the Study A randomized, observer blind, phase 3 trial was conducted in 900 healthy adult subjects aged 18 to 60 years (distributed across the entire age range) in non-endemic countries for dengue disease and hepatitis A virus (HAV) to investigate the immunogenicity and safety of two doses of tetravalent dengue vaccine TDV (subcutaneous (SC) injection), and of the simultaneous on the same day administration of a single dose of HAV vaccine (containing an inactivated HAV; intramuscular (IM) injection) and TDV (SC injection).

A purpose of the study was to assess whether HAV vaccine can be safely administered simultaneously on the same day with TDV as travel vaccines before an international travel of a subject to HAV and dengue (DENV)-endemic countries.

The primary objective of this study was demonstrate non-inferiority (NI) of the immune response to one dose of HAV vaccine simultaneously administered on the same day with one dose TDV on the same day, compared to one dose HAV vaccine simultaneously on the same day administered with placebo on the same day, in DENV/HAV-naïve subjects one month after vaccination.

The secondary objectives of this study were to describe TDV-induced immunogenicity after a single dose of TDV in DENV/HAV-naïve subjects; to describe TDV-induced immunogenicity after two doses of TDV administered 90 days apart in DENV/HAV-naïve subjects; to describe HAV vaccine-induced immunogenicity in DENV/HAV-naïve subjects; and to assess the safety profile after each vaccine injection in all trial groups.

4.2 Eligibility Criteria

Criteria for inclusion include:
1. The participant is aged 18 to 60 years, inclusive.
2. Participants who are in good health at the time of entry into the trial as determined by medical history, physical examination (including vital signs) and the clinical judgment of the Investigator.
3. The participant signs and dates a written informed consent form and any required privacy authorization prior to the initiation of any trial procedures, after the nature of the trial has been explained according to local regulatory requirements.
4. Participants who can comply with trial procedures and are available for the duration of follow-up.

Exclusion criteria include:
1. Participants with an elevated oral temperature (≥38° C. or 100.4° F.) within 3 days of the intended date of vaccination.
2. Known hypersensitivity or allergy to any of the vaccine components (including excipients of the investigational vaccines or placebo).
3. Participants with behavioral or cognitive impairment or psychiatric disease that, in the opinion of the Investigator, may interfere with the participant's ability to participate in the trial.
4. Participants with any history of progressive or severe neurologic disorder, seizure disorder or neuro-inflammatory disease (e.g., Guillain-Barre syndrome).
5. Participants with history or any illness that, in the opinion of the Investigator, might interfere with the results of the trial or pose additional risk to the participant due to participation in the trial.
6. Known or suspected impairment/alteration of immune function, including:
   1. Chronic use of oral steroids (equivalent to 20 mg/day prednisone 12 weeks/≥2 mg/kg body weight/day prednisone 2 weeks) within 60 days prior to Day 1 (M0) (use of inhaled, intranasal, or topical corticosteroids is allowed).
   2. Receipt of parenteral steroids (equivalent to 20 mg/day prednisone 12 weeks/2 mg/kg body weight/day prednisone 2 weeks) within 60 days prior to Day 1 (M0).
   3. Administration of immunoglobulins and/or any blood products within the 3 months prior to Day 1 (M0) or planned administration during the trial.
   4. Receipt of immunostimulants within 60 days prior to Day 1 (M0).
   5. Immunosuppressive therapy such as anti-cancer chemotherapy or radiation therapy within 6 months prior to Day 1 (M0).
   6. Human immunodeficiency virus (HIV) infection or HIV-related disease.
   7. Hepatitis A virus (HAV) infection.
   8. Hepatitis C virus infection.
   9. Genetic immunodeficiency.

7. Abnormalities of splenic or thymic function.
8. Participants with a known bleeding diathesis, or any condition that may be associated with a prolonged bleeding time.
9. Participants with any serious chronic or progressive disease according to judgment of the Investigator (e.g., neoplasm, insulin dependent diabetes, cardiac, renal or hepatic disease).
10. Participants with body mass index (BMI) greater than or equal to 35 kg/m^2(=weight in kg/[height in meters$^2$]).
11. Participants participating in any clinical trial with another investigational product 30 days prior to Day 1 (M0) or intent to participate in another clinical trial at any time during the conduct of this trial.
12. Participants who received any other vaccine within 14 days (for inactivated vaccines) or 28 days (for live vaccines) prior to enrollment in this trial or who are planning to receive any vaccine within 28 days of trial vaccine administration.
13. Previous HAV vaccination (in a clinical trial or with an approved product).
14. Participants involved in the trial conduct or their first degree relatives.
15. Participants with history of substance or alcohol abuse within the past 2 years.
16. Female participants who are pregnant or breastfeeding.
17. Females of childbearing potential who are sexually active, and who have not used any of the acceptable contraceptive methods for at least 2 months prior to Day 1 (M0).
    1. Of childbearing potential is defined as status post onset of menarche and not meeting any of the following conditions: bilateral tubal ligation (at least 1 year previously), bilateral oophorectomy (at least 1 year previously) or hysterectomy
    2. Acceptable birth control methods are defined as one or more of the following:
        i. Hormonal contraceptive (such as oral, injection, transdermal patch, implant, cervical ring).
        ii. Barrier method (condom with spermicide or diaphragm with spermicide) each and every time during intercourse.
        iii. Intrauterine device (IUD). iv. Monogamous relationship with vasectomized partner (partner must have been vasectomized for at least 6 months prior to Day 1 [M0]).
    Other contraceptive methods may be considered in agreement with the Sponsor and implemented only after approval of a substantial amendment by the regulatory authorities and by the appropriate ethics committee.
18. Females of childbearing potential who are sexually active, and who refuse to use an acceptable contraceptive method up to 6 weeks after the last dose of trial vaccine (Day 90 [M3]). In addition, they must be advised not to donate ova during this period.
19. Any positive or indeterminate pregnancy test.
20. Previous and planned vaccination (during the trial conduct) against any flaviviruses including dengue, yellow fever (YF), Japanese Encephalitis (JE) viruses or tick-borne encephalitis.
21. Previous participation in any clinical trial of a dengue or other flavivirus (e.g., West Nile [WN] virus) candidate vaccine, except for participants who received placebo in those trials.
22. Participants with a current or previous infection with a flavivirus such as dengue, Zika, YF, JE, WN fever, tick-borne encephalitis or Murray Valley encephalitis and participants with a history of prolonged (≥1 year) habitation in a dengue endemic area.
23. Participants with contraindications, warnings and/or precautions to vaccination with the HAV vaccine as specified within the product information.

4.3 Study Design & Vaccinations

Eligible subjects were randomized equally (1:1:1 ratio) to one of the following 3 trial groups (300 subjects per group):
Group 1: HAV vaccine (IM) and placebo (SC), simultaneously on the same day administered on day 1 (month 0); placebo (SC) administered at day 90 (month 3).
Group 2: TDV (SC) and placebo (IM), simultaneously on the same day administered on day 1 (month 0); TDV (SC) administered at day 90 (month 3).
Group 3: TDV (SC) and HAV vaccine (IM), simultaneously on the same day administered on day 1 (month 0); TDV (SC) administered at day 90 (month 3).

A more detailed scheme of the study design is shown in FIG. 6. Up to 28 days prior to the first vaccination, enrolment was carried out and blood samples were taken for screening anti-HAV antibodies. On day 1, pre-vaccination blood samples were taken. On day 30 (after the first vaccination on day 1) post-vaccination blood samples were taken. On day 120 (after the first vaccination on day 1) another blood sample was taken. Safety follow-up took place on day 270 (after the first vaccination on day 1).

The TDV was prepared as described in Example 1. Each subcutaneous dose of the TDV had a volume of 0.5 ml and the concentration of the four dengue serotypes in the TDV in each dose was 5.1 $\log_{10}$ pfu/0.5 ml, 4.5 $\log_{10}$ pfu/0.5 ml, 5.4 $\log_{10}$ pfu/0.5 ml and 5.9 $\log_{10}$ pfu/0.5 ml of TDV-1, TDV-2, TDV-3 and TDV-4, respectively. Each subcutaneous dose comprises the TDV dispersed in 0.5 ml of an aqueous solution containing Pluronic F127 (10.6 mg/ml), trehalose dihydrate (170 mg/ml) and human serum albumin (1.08 mg/ml).

The HAV vaccine includes an inactivated hepatitis A virus, derived from a hepatitis A virus strain HM-175 (see definitions above), and is commercially available under the tradename HAVRIX® as described above. The intramuscular dose of the HAV vaccine administered to groups 1) and 3) was 1 ml and each 1 ml dose has a viral antigen activity of about 1440 EL.U., wherein the viral antigen is adsorbed on 0.5 mg of aluminum in the form of aluminum hydroxide. The hepatitis A vaccine contains excipients in the form of an amino acid supplement (about 0.3% w/v) and in the form of polysorbate (about 0.05 mg/ml) dissolved in a phosphate-buffered saline solution.

Simultaneously on the same day administered trial vaccines were injected to opposite arms. Normal saline solution for injection (0.9% NaCl) was used as placebo. A blood sample for an anti-HAV antibody test were collected at screening from all subjects to exclude subjects who are positive for anti-HAV antibodies up to 28 days prior to vaccination (see FIG. 6). All subjects were followed-up for 6 months after the second vaccination at day 90 (month 3), so the trial duration was 270 days or 9 months for each subject (not including the screening period). Outside the context of this trial, subjects in Groups 1 and 3 will be offered a HAV vaccine booster dose after the completion of trial procedures at day 270 (month 9).

Dengue neutralizing antibodies (microneutralization test (MNT50)) were measured using blood samples collected at pre-first trial vaccination (day 1 (month 0)), 1 month post first trial vaccination (day (month 1)), and 1 month post second trial vaccination (day 120 (month 4)). Blood samples for the measurement of anti-HAV antibodies (enzyme-linked immunosorbent assay (ELISA)) were collected at pre-first trial vaccination (day 1 (month 0)) and 1 month post first trial vaccination (day 30 (month 1)).

4.4 Primary Endpoint

The primary endpoint included the proportion of HAV/DENV-naïve subjects at baseline who are seroprotected against HAV at day 30 (month 1) as measured by enzyme-linked immunosorbent assay (ELISA)). In other words, the primary endpoint includes the seroprotection rates (SPRs). Seroprotection is defined as serum anti-HAV antibody levels 10 mIU/mL. Immunological naivety to HAV/DENV is defined as anti-HAV antibody levels <10 mIU/mL and reciprocal neutralizing titers for all 4 dengue serotypes <10.

4.5 Secondary Endpoints a) Secondary Immunogenicity Endpoints

The secondary endpoints included the geometric mean titers of neutralizing antibodies (GMTs) (microneutralization test (MNT50)) for each of the 4 dengue serotypes at day 30 (month 1) and day 120 (month 4) which were determined in HAV/DENV-naïve subjects at baseline; the proportion of HAV/DENV-naive subjects at baseline who are seropositive for each of the 4 dengue serotypes at day 30 (month 1) and day 120 (month 4) (seroprotection rate); and geometric mean concentrations (GMC) of anti-HAV antibodies at day 30 (month 1) in subjects HAV/DENV-naive at baseline.

Seropositivity for dengue virus is defined as a reciprocal neutralizing titer 10 for any of the four dengue serotypes within the secondary immunogenicity endpoints.

b) Secondary Safety Endpoints

Secondary safety endpoints included the frequency and severity of solicited local adverse events (AE) for 7 days after each trial vaccination; the frequency and severity of solicited systemic AEs for 14 days after each trial vaccination; the percentage of subjects with any unsolicited AEs for 28 days after each trial vaccination; the percentage of subjects with serious adverse events (SAE) throughout the trial; and the percentage of subjects with medically attended adverse events (MAAE) throughout the trial.

4.6 Analysis Sets of the Study

Table 12 below displays each analysis set of the present study. In total, 1199 subjects belonging to the group "all screened" included all subjects who signed the informed consent, regardless of whether the subjects were screen failures. After initial screening, 900 subjects were included into the "randomized set" which includes all randomized subjects, regardless of whether any dose of the IPs was received. The safety set, consisting of 897 subjects, includes all randomized subjects who received 1 dose of the IPs. The immunogenicity subjects included a total of 359 subjects and is subdivided into the following four subsets. The HAV-full analysis set (HAV-FAS) includes all randomized subjects in the immunogenicity subset who received 1 dose of the trial vaccine with available day 1 and day 30 anti-HAV antibody measurements. The HAV-per-protocol set (HAV-PPS) includes all HAV- and DENV-naive subjects from the HAV-FAS who have no major protocol violations. The TDV-full analysis set (TDV-FAS) includes all randomized subjects in the immunogenicity subset who received 1 dose of trial vaccine and with available day 1 and ≥1 post-dose measurements. The TDV-per-protocol set (TDV-PPS), consisting of 197 subjects, includes all HAV- and DENV-naïve subjects from the TDV-FAS who have no major protocol violations.

TABLE 12

Analysis sets of the study.

| | HAV/Pbo | TDV/Pbo | HAV/TDV | Total |
|---|---|---|---|---|
| All Screened[1] | NA | NA | NA | 1199 |
| Randomized Set[2] | 300 | 300 | 300 | 900 |
| Safety Set (SS)[3] | 299 | 300 | 298 | 897 |
| Immunogenicity Subset | 119 | 120 | 120 | 359 |
| HAV Full Analysis Set (HAV-FAS)[4] | 115 | 117 | 114 | 346 |
| HAV Per-Protocol Set (HAV-PPS)[5] | 75 | 71 | 81 | 227 |
| TDV-FAS[6] | 116 | 117 | 115 | 348 |
| TDV-PPS[7] | 67 | 63 | 67 | 197 |
| Subjects analyzed for primary non-inferiority objective[8] | 69/115 | NA | 79/114 | 148/227 |

[1]All Screened: All subjects who signed the informed consent, regardless of whether subjects were screen failures
[2]Randomized Set: All randomized subjects, regardless of whether any dose of the trial vaccines was received.
[3]Safety Set: All randomized subjects who received ≥1 dose of trial vaccines.
[4]HAV-FAS: All randomized subjects in the immunogenicity subset who received ≥1 dose of trial vaccine, with available Day 1 and Day 30 HAV measurements.
[5]HAV-PPS: All HAV & DENV-naïve subjects from the HAV-FAS who have no major protocol violations.
[6]TDV-FAS: All randomized subjects in the immunogenicity subset who received ≥1 dose of trial vaccine and available Day 1 and ≥1 post-dose measurement.
[7]TDV-PPS: All HAV & DENV-naïve subjects from the TDV-FAS who have no major protocol violations.
[8] Subject excluded from TDV-PPS but included into analysis for primary non-inferiority objective had their Day 30 measurement outside the protocol defined visit window.

From a total number of 359 subjects in the immunogenicity subset (including all subjects which received ≥1 vaccination), 13 subjects have been excluded from HAV-FAS because of not providing a valid baseline and post-dosing measurement (on day 30) for HAV. Furthermore, HAV-PPS includes all HAV- and DENV-naïve subjects of HAV-FAS who had no major protocol violations. The subjects analyzed for primary non-inferiority objective are based on the HAV-PPS subjects of the HAV/Pbo and HAV/TDV group, wherein based on HAV-PPS of these two groups (HAV/Pbo and HAV//TDV), some subjects were not included in the 30 days analysis (6 subjects of the HAV/Pbo group and 2 Subjects of the HAV/TDV group), since these subjects had their day 30 measurement outside the visit window defined in the protocol. Therefore, a total of 69 subjects was included into the TDV/Pbo group and a total of 79 subjects was included in the HAV/TDV group for analyzing the primary non-inferiority objective.

From a total number of 359 subjects in the immunogenicity subset (including all subjects which received ≥1 vaccination), a total of 11 subjects have been excluded from TDV-FAS, because they did not provide a valid baseline and at least one post-dosing measurement (day 30 and/or day 120) for TDV. Furthermore, a total number of 151 subjects had been excluded from the TDV-PPS for not being HAV & DENV-naïve at baseline or for not receiving both vaccinations 1 and 2 or if vaccination 2 (usually on day 90) is outside the window −15/+25 days or if major protocol violations occur.

4.7 HAV Baseline Serostatus and Demographic & Baseline Characteristics

The safety set evaluated for baseline HAV antibody levels included a total of 362 subjects of which 27.3% were HAV seropositive at baseline (see Table 13).

HAS-FAS included a total of 346 subjects evaluated for baseline HAV antibody levels (see Table 13). HAV-naivety was defined as anti-HAV antibody (ab) level of <10 mIU/ml. However, the ELISA used for serological analysis could not be validated below levels of 12.5 mIU/ml. The qualitative screening test had a specification that effectively amounted to a lower limit of quantification of 70 mIU/ml. In view of these criteria, 72.5% of the subjects of said HAS-FAS evaluated for baseline HAV antibody levels were HAV naive at baseline (see Table 13).

TABLE 13

HAV baseline serostatus in the safety set and in the HAV-FAS

|  | HAV/Pbo | TDV/Pbo | HAV/TDV | Total |
| --- | --- | --- | --- | --- |
| Safety set evaluated for baseline HAV antibody levels | 119 | 121 | 122 | 362 |
| HAV seropositive at baseline | 31 (26.1%) | 38 (31.4%) | 30 (24.6%) | 99 (27.3%) |
| HAV-FAS Evaluated For Baseline HAV antibody levels | 115 (100%) | 117 (100%) | 114 (100%) | 346 (100%) |
| HAV seronegative at baseline <12.5 mIU/ml (a) | 86 (74.8%) | 79 (67.5%) | 86 (74.4%) | 251 (72.5%) |
| HAV seropositive at baseline (b) | 29 (25.2%) | 38 (32.5%) | 28 (24.6%) | 95 (27.5%) |
| baseline 12.5-70 mIU/ml | 18 | 23 | 13 | 54 |
| baseline 70-1000 mIU/ml | 11 | 14 | 14 | 39 |
| baseline >1000 | 0 | 1 | 1 | 2 |

(a) HAV-naivety was defined as anti-HAV ab level of <10 mIU/ml; The ELISA used for serological analysis could not be validated below levels of 12.5 mIU/ml.
(b) The qualitative screening test had a specification that effectively amounted to a lower limit of quantification of 70 mIU/ml The HAV-PPS includes a total number of 227 subjects (see Table 14). The mean age of the total number of subjects of the HAV-PPS, which are DENV- and HAV-naïve was 34.8. 31.3% of the total number of subjects of the HAV-PPS were female (see Table 14). In total, 97.8% of the total subjects of the HAV-PPS were of an ethnicity which is NOT Hispanic or Latino, and, in particular, 89.9% of the HAV-PPS participants were of race "white European", especially in order to reflect the situation of travelers of HAV- and dengue non-endemic countries (see Table 14).

The safety set includes a total number of 897 subjects (see Table 14). The mean age of the total number of subjects of the safety set was 35.4 years of which 31.3% were female. In total, 97.7% of the total subjects of the HAV-PPS were of an ethnicity which is NOT Hispanic or Latino, and, in particular, 87.1% of the HAV-PPS participants were of race "white European", especially in order to reflect the situation of travelers of HAV- and dengue non-endemic countries (see Table 14).

TABLE 14

Demographic and baseline characteristics (HAV-PPS and Safety Set)

|  |  | HAV/Pbo | TDV/Pbo | HAV/TDV | Total |
| --- | --- | --- | --- | --- | --- |
| HAV-PPS (DENV/HAV-naïve) | N | 75 | 71 | 81 | 227 |
| Age Years | Mean (SD) | 34.3 (11.68) | 35.5 (11.24) | 34.8 (11.70) | 34.8 (11.51) |
| Gender | Female n (%) | 24 (32.0%) | 30 (42.3%) | 17 (21.0%) | 71 (31.3%) |
| Ethnicity NOT Hispanic or | n (%) | 72 (96.0%) | 71 (100.0%) | 79 (97.5%) | 222 (97.8%) |

TABLE 14-continued

Demographic and baseline characteristics (HAV-PPS and Safety Set)

|  |  | HAV/Pbo | TDV/Pbo | HAV/TDV | Total |
|---|---|---|---|---|---|
| Latino |  |  |  |  |  |
| Race White European | n (%) | 64 (85.3%) | 64 (90.1%) | 76 (93.8%) | 204 (89.9%) |
| Safety set | N | 299 | 300 | 298 | 897 |
| Age Years | Mean (SD) | 34.7 (12.04) | 36.0 (11.88) | 35.5 (11.96%) | 35.4 (11.96) |
| Gender | Female n (%) | 107 (35.8%) | 120 (40.0%) | 90 (30.2%) | 317 (35.3%) |
| Ethnicity NOT Hispanic or Latino | n (%) | 289 (96.7%) | 293 (97.7%) | 294 (98.7%) | 876 (97.7%) |
| Race White European | n (%) | 255 (85.3%) | 265 (88.3%) | 261 (87.6%) | 781 (87.1%) |

4.8 Study Results a) Primary Endpoint and Sensitivity Analyses

The present study was successful in meeting the primary objective of non-inferiority for the simultaneous on the same day administration of HAV and TDV. Table 15 displays the seroprotection rates (SPRs) of groups 1 (received HAV/Pbo) and 3 (received HAV/TDV) on day 30 after the first vaccination (on day 1), the SPR differences between the HAV/Pbo group and the HAV/TDV group on day 30, and the confidence intervals (CIs) of these SPR differences for HAV and DENV-baseline naïve subjects. These values (SPRs, SPR differences; CIs) were used for the primary endpoint evaluation of the study. Table 15 further shows these values for the results of three sensitivity analyses (also used for non-inferiority assessments), wherein the subjects had different, i.e. mixed, HAV/TDV serostatuses at baseline. Non-inferiority between the hepatitis A vaccine and the tetravalent dengue vaccine, when simultaneously on the same day administered, in the present study is concluded, if the seroprotection rate (SPR) difference between group 1 (received HAV and placebo on the same day 1) and group 3 (received HAV and TDV on the same day 1) has an upper bound of a two-sided 95% confidence interval, calculated using the Newcombe score method, which is lower than the 10% non-inferiority margin. This criterion is fulfilled for each of the groups in Table 15. In the primary endpoint group, the upper bound of the 95% CI of the SPR difference is 4.31% which is less than the non-inferiority margin of 10% (see second line from above in Table 15).

As mentioned above, sensitivity analyses 1 to 3 were used to evaluate populations that included subjects who were seropositive for dengue and/or for hepatitis A at baseline, in particular reflecting "real life" travel clinic settings in non-endemic countries in which subjects, i.e. travelers who plan to go to dengue and HAV endemic countries, are not always aware of their HAV and/or dengue serostatus before requesting pre-travel vaccinations.

The object of non-inferiority of the simultaneous on the same day administration was also met in sensitivity analyses 1 to 3 (upper bounds of the 95% CI of the SPR differences: 3.21%; 2.93%; and 2.55% which are each less than the non-inferiority margin of 10%). Furthermore, the SPRs of the HAV/TDV groups (98.8%; 99.0%; 99.1%, respectively, see Table 15) were respectively higher than the SPRs of the HAV/Pbo group (96.2%; 96.9%; 97.2%, respectively, see Table 15).

Therefore, due to the non-inferiority of the simultaneous on the same day administration of the HAV vaccine and TDV to subjects with mixed baseline serostatus (and baseline naivety) with respect to HAV and all dengue serotypes, there is no need for determining or knowing the subject's baseline serostatus with respect to each of the two diseases, prior to simultaneously on the same day administering the HAV vaccine and TDV.

TABLE 15

Primary endpoint: Non-inferiority (NI) assessments & sensitivity analysis

| Analysis | Analysis Set | HAV/Pbo (Group 1) SPR % (n/n) | HAV/TDV (Group3) SPR % (n/n) | SPR difference | 95% CI[1] (of SPR difference) |
|---|---|---|---|---|---|
| Primary endpoint | HAV PPS - includes baseline HAV- and DENV- subjects | 97.1% (67/69) | 98.7% (78/79) | −1.63 | (−8.78, 4.31) |
| Sensitivity Analysis 1 | HAV PPS - includes baseline HAV-, DENV-, and DENV+ subjects | 96.2% (76/79) | 98.8% (83/84) | −2.61 | (−9.46, 3.21) |
| Sensitivity Analysis 2 | HAV PPS - includes baseline HAV-; HAV+ (12.5-70 mIU/ml); DENV-; DENV+ | 96.9% (93/96) | 99.0% (96/97) | −2.09 | (−7.82, 2.93) |
| Sensitivity Analysis 3 | HAV PPS - includes baseline HAV-; HAV+; DENV-; DENV+ | 97.2% (103/106) | 99.1% (109/110) | −1.92 | (−7.14, 2.55) |

[1]CI = Confidence Interval
Non-inferiority Assessment: Seroprotection Rates (SPRs) for HAV Group 1 (HAV + placebo simultaneous on the same day administration) vs Group 3 (HAV + TDV simultaneous on the same day administration)
Rates difference for primary comparison (Group 1-Group 3) are presented together with 95% CI calculated using Newcombe score method
NI of simultaneous on the same day administration of HAV and TDV to HAV alone will be concluded if the upper bound of the 95% CI is less than NI margin of 10%.

b) Secondary Immunogenicity Endpoints

Table 16 shows GMTs (with respect to each of the four dengue virus serotypes DENV-1 to DENV-4) when measured on day 1 pre-first vaccination, on day 30 after the first vaccination (on day 1), and on day 120 after the first vaccination of the subjects (on day 1) of the DENV-PPS including the groups receiving HAV/TDV, TDV and placebo, as well as HAV and placebo (Pbo), respectively. Table 16 shows positive trends in favor of the simultaneous on the same day administration group (received HAV/TDV) with respect to all dengue GMTs.

Said positive trend in favor of the simultaneous on the same day administration and the day 30 synergism of the simultaneously on the same day administered vaccines is also confirmed in Table 17.

TABLE 18a

Frequency of Solicited Local AEs and Solicited Systemic AEs after first vaccination - Safety Set

|  | HAV/Pbo (N = 270) | TDV/Pbo (N = 271) | HAV/TDV (N = 257) |
|---|---|---|---|
| Solicited Local (within 7 days) | 141/289 (48.8) | 152/292 (52.1) | 196/285 (68.8) |
| Solicited Systemic (within 14 days) | 139/289 (48.1) | 132/292 (45.2) | 141/285 (49.5) |

TABLE 16

Immunogenicity of DENV-PPS: GMTs of DENV MNT50. In particular, DENV GMTs against each serotype with respect to mean titers of neutralizing antibodies measured by MNT50 for each dengue serotype by trial visit are shown.

|  |  | DENV-1 | | | DENV-2 | | | DENV-3 | | | DENV-4 | | |
|---|---|---|---|---|---|---|---|---|---|---|---|---|---|
|  |  | HAV/p | TDV/p | HAV/TDV | HAV/p | TDV/p | HAV/TDV | HAV/p | TDV/p | HAV/TDV | HAV/p | TDV/p | HAV/TDV |
| Day 1 | n | 67 | 63 | 67 | 67 | 63 | 67 | 67 | 63 | 67 | 67 | 63 | 67 |
|  | GMT | 5.0 | 5.0 | 5.0 | 5.0 | 5.0 | 5.0 | 5.0 | 5.0 | 5.0 | 5.0 | 5.0 | 5.0 |
|  | (SD[1]) | (1.00) | (1.00) | (1.00) | (1.00) | (1.00) | (1.00) | (1.00) | (1.00) | (1.00) | (1.00) | (1.00) | (1.00) |
| Day 30 | n | 62 | 60 | 65 | 62 | 60 | 65 | 62 | 60 | 65 | 62 | 60 | 65 |
|  | GMT | 5.0 | 108.2 | 152.5 | 6.0 | 2897.9 | 3960.0 | 5.3 | 95.4 | 140.5 | 5.0 | 74.3 | 142.1 |
|  | (SD) | (1.00) | (5.64) | (4.62) | (1.87) | (13.86) | (8.79) | (1.49) | (6.24) | (4.50) | (1.00) | (5.03) | (6.19) |
| Day 120 | n | 50 | 55 | 62 | 50 | 55 | 62 | 50 | 55 | 62 | 50 | 55 | 62 |
|  | GMT | 5.0 | 171.3 | 173.7 | 5.7 | 2064.1 | 1764.3 | 5.0 | 83.8 | 92.6 | 5.0 | 56.1 | 81.4 |
|  | (SD) | (1.00) | (6.23) | (4.28) | (1.72) | (3.60) | (4.03) | (1.00) | (3.66) | (2.80) | (1.00) | (3.19) | (3.49) |

[1]SD = standard deviation.

TABLE 17

Secondary endpoint: HAV Geometric Mean Concentrations (GMCs)

|  | HAV/Pbo | TDV/Pbo | HAV/TDV | Total |
|---|---|---|---|---|
| Baseline |  |  |  |  |
| n | 75 | 71 | 81 | 227 |
| Geometric Mean (SD[1]) | 6.3 (1.00) | 6.3 (1.00) | 6.3 (1.00) | 6.3 (1.00) |
| 95% CI[2] | (NE, NE) | (NE, NE) | (NE, NE) | (NE, NE) |
| Median | 6.3 | 6.3 | 6.3 | 6.3 |
| Min-max | 6, 6 | 6, 6 | 6, 6 | 6, 6 |
| Day 30 |  |  |  |  |
| n | 69 | 66 | 79 | 214 |
| Geometric Mean (SD) | 80.5 (3.01) | 6.7 (1.27) | 93.0 (2.44) | 39.5 (4.27) |
| 95% CI | (61.8, 105.0) | (6.4, 7.2) | (76.1, 113.6) | (32.5, 48.0) |
| Median | 81.5 | 6.3 | 94.5 | 52.4 |
| Min-max | 6, 1044 | 6, 16 | 6, 1859 | 6, 1859 |

[1]SD = standard deviation.
[2]CI = confidence interval.

c) Secondary Safety Endpoints

The safety set was investigated for solicited adverse events, solicited systemic adverse events, unsolicited adverse events and serious adverse events throughout the study. Tables 18a to 21c show the study results of the safety set with respect to each secondary safety endpoint.

TABLE 18a-continued

Frequency of Solicited Local AEs and Solicited Systemic AEs after first vaccination - Safety Set

|  | HAV/Pbo (N = 270) | TDV/Pbo (N = 271) | HAV/TDV (N = 257) |
|---|---|---|---|
| Related to IP | 98/289 (33.9) | 106/292 (36.3) | 117/285 (41.1) |
| Not related to IP | 41/289 (14.2) | 26/292 (8.9) | 24/285 (8.4) |

Note:
For solicited AEs, excluding prolonged solicited AEs, percentages are calculated based on number of subjects with non-missing data (n) evaluated in each trial group. Subjects with 1 or more AEs for a particular category of AEs are counted only once using the most related event.

TABLE 18b

Frequency of Solicited Local AEs and Solicited Systemic AEs after second vaccination - Saftey Set

|  | Pbo (N = 270) | TDV (N = 271) | TDV (N = 257) |
|---|---|---|---|
| Solicited Local (within 7 days) | 28/255 (11.0) | 100/264 (37.9) | 103/251 (41.0) |
| Solicited Systemic (within 14 days) | 73/254 (28.7) | 82/263 (31.2) | 85/251 (33.9) |
| Related to IP | 49/254 (19.3) | 60/263 (22.8) | 61/251 (24.3) |
| Not related to IP | 24/254 (9.4) | 22/263 (8.4) | 24/251 (9.6) |

Note:
For solicited AEs, excluding prolonged solicited AEs, percentages are calculated based on number of subjects with non-missing data (n) evaluated in each trial group. Subjects with 1 or more AEs for a particular category of AEs are counted only once using the most related event.

TABLE 18c

Frequency of Solicited Local AEs and Solicited Systemic AEs after any vaccination - Safety Set

|  | HAV/Pbo (n = 299) | TDV/Pbo (n = 300) | HAV/TDV (n = 298) |
|---|---|---|---|
| Solicited Local (within 7 days) | 151/289 (52.2) | 175/292 (59.9) | 216/285 (75.8) |
| Solicited Systemic (within 14 days) | 161/289 (55.7) | 167/292 (57.2) | 167/285 (58.6) |
| Related to IP | 121/289 (41.9) | 133/292 (45.5) | 141/285 (49.5) |
| Not related to IP | 40/289 (13.8) | 34/292 (11.6) | 26/285 (9.1) |

Note:
For solicited AEs, excluding prolonged solicited AEs, percentages are calculated based on number of subjects with non-missing data (n) evaluated in each trial group. Subjects with 1 or more AEs for a particular category of AEs are counted only once using the most related event.

TABLE 19a

Overview of Unsolicited AE up to 28 Days Post-vaccination (after first vaccination) - Safety Set

|  | HAV/Pbo N = 299 | TDV/Pbo N = 300 | HAV/TDV N = 298 |
|---|---|---|---|
| [Any AE], n (%) | 43 (14.4%) | 51 (17.0%) | 56 (18.8%) |
| Mild | 32 (10.7%) | 32 (10.7%) | 43 (14.4%) |
| Moderate | 11 (3.7%) | 18 (6.0%) | 12 (4.0%) |
| Severe | 0 | 1 (0.3%) | 1 (0.3%) |

Notes:
This summary includes all unsolicited AEs with a date of onset within 28 days after each trial vaccination.
N is the number of subjects who received the specific vaccination. Percentages are calculated based on N for corresponding column.
Table shows the number of subjects that reported unsolicited AE
Subjects with 1 or more AEs for a particular category of adverse event are counted only once using the most related/most severe/most serious event.

TABLE 19b

Overview of Unsolicited AE up to 28 Days Post-vaccination (after second vaccination) - Safety Set

|  | Pbo N = 270 | TDV N = 271 | TDV N = 257 |
|---|---|---|---|
| Any AE, n (%) | 39 (14.4%) | 27 (10.0%) | 30 (11.7%) |
| Mild | 17 (6.3%) | 14 (5.2%) | 15 (5.8%) |
| Moderate | 22 (8.1%) | 13 (4.8%) | 13 (5.1%) |
| Severe | 0 | 0 | 2 (0.8%) |

Notes:
This summary includes all unsolicited AEs with a date of onset within 28 days after each trial vaccination.
N is the number of subjects who received the specific vaccination. Percentages are calculated based on N for corresponding column.
Table shows the totals of AE that were experienced by the number of subjects that reported unsolicited AE
Subjects with 1 or more AEs for a particular category of adverse event are counted only once using the most related/most severe/most serious event.

TABLE 20

Most Common Unsolicited AEs Up to 28 Days Post-Vaccination (after Any Vaccination)* - Safety Set

| AE, n (%) | HAV/Pbo N = 299 | TDV/Pbo N = 300 | HAV/TDV N = 298 |
|---|---|---|---|
| Nasopharyngitis | 9 (3.0%) | 8 (2.7%) | 11 (3.7%) |

*Reported by ≥2.0% of subjects

TABLE 21a

Safety: Overview of Serious Adverse Events (SAEs) After any dose - Safety Set

| Number of events, number (%) subjects with SAE | HAV/Pbo (n = 299) Events | HAV/Pbo (n = 299) Subjects | TDV/Pbo (n = 300) Events | TDV/Pbo (n = 300) Subjects | HAV/TDV (n = 298) Events | HAV/TDV (n = 298) Subjects | Total (N = 597) Events | Total (N = 597) Subjects |
|---|---|---|---|---|---|---|---|---|
| SAEs - any | 3 | 2 (0.7%) | 10 | 8 (2.7%) | 10 | 7 (2.3%) | 23 | 17 (2.8%) |
| After 1st dose up to 2nd dose | 0 | 0 | 3 | 3 (1.0%) | 3 | 2 (0.7%) | 6 | 5 (0.8%) |
| After 2nd dose up to trial end | 3 | 2 (0.7%) | 7 | 5 (1.8%) | 7 | 5 (1.9%) | 17 | 12 (2.0%) |
| SAEs - related | 0 | 0 | 0 | 0 | 0 | 0 | 0 | 0 |
| SAE - premature vaccine and/or trial discontinuation | 0 | 0 | 1 | 1 (0.3%) | 0 | 0 | 1 | 1 (0.2%) |
| Deaths | 0 | 0 | 0 | 0 | 0 | 0 | 0 | 0 | p = Placebo

TABLE 21b

Safety: Serious Adverse Events by System Organ Class and Preferred Term after first and after second dose - Safety Set

| Number (%) subjects with SAE | | HAV/Pbo (N = 299) | TDV/Pbo (N = 300) | HAV/TDV (N = 298) |
|---|---|---|---|---|
| SOC | PT | | | |
| After 1st dose up to 2nd dose - any SAE | | 0 | 3 (1.0) | 2 (0.7) |

TABLE 21b-continued

Safety: Serious Adverse Events by System Organ Class and Preferred Term after first and after second dose - Safety Set

| Number (%) subjects with SAE | | HAV/Pbo | TDV/Pbo | HAV/TDV |
|---|---|---|---|---|
| SOC | PT | (N = 299) | (N = 300) | (N = 298) |
| Gastrointestinal disorders | Crohn's disease* | 0 | 1 (0.3) | 0 |
| Injury, poisoning and procedural complications | Intentional overdose | 0 | 0 | 1 (0.3) |
| Neoplasms benign, malignant and unspecified | Bladder cancer stage II | 0 | 1 (0.3) | 0 |
| Nervous system disorders | Loss of consciousness** | 0 | 1 (0.3) | 0 |
| Psychiatric disorders | Intentional self-injury | 0 | 0 | 1 (0.3) |
| | | Pbo (N = 270) | TDV (N = 271) | TDV (N = 257) |
| After 2$^{nd}$ dose up to end of trial - any SAE | | 2 (0.7) | 5 (1.8) | 5 (7.9) |
| Cardiac disorders | Supraventricular tachycardia | 0 | 0 | 1 (0.4) |
| Gastrointestinal disorders | Abdominal pain | 0 | 1 (0.4) | 0 |
| | Abdominal strangulated hernia | 1 (0.4) | 0 | 0 |
| | Intestinal ischaemia | 0 | 0 | 1 (0.4) |
| | Mesenteric vein thrombosis | 0 | 0 | 1 (0.4) |
| | Oesophagitis | 0 | 1 (0.4) | 0 |

*Subject had a history of irritable bowel syndrome
**Occurred >2 months after vaccination

TABLE 21c

Safety: Serious Adverse Events by System Organ Class and Preferred Term After first and after second dose - Safety Set - Continued

| Number (%) subjects with SAE | | Pbo | TDV | TDV |
|---|---|---|---|---|
| SOC | PT | (N = 270) | (N = 271) | (N = 257) |
| Infections and infestations | Appendicitis | 0 | 1 (0.4) | 0 |
| | Wound infection | 1 (0.4) | 0 | 0 |
| Injury, poisoning and procedural complications | Abdominal injury | 0 | 1 (0.4) | 0 |
| | Cervical vertebral fracture | 0 | 0 | 1 (0.4) |
| | Fractured coccyx | 1 (0.4) | 0 | 0 |
| | Joint dislocation | 0 | 1 (0.4) | 0 |
| | Lower limb fracture | 0 | 0 | 1 (0.4) |
| | Thermal burn | 0 | 1 (0.4) | 0 |
| Neoplasms benign, malignant and unspecified | Invasive ductal breast carcinoma | 0 | 1 (0.4) | 0 |
| | Prostate cancer | 0 | 0 | 1 (0.4) |
| Respiratory, thoracic and mediastinal disorders | Acute respiratory distress syndrome | 0 | 0 | 1 (0.4) |

The invention claimed is:

1. A method of effective vaccination against hepatitis A and dengue disease in a subject or subject population, the method comprising, simultaneously on the same day administering a hepatitis A vaccine and a unit dose of a tetravalent dengue virus composition to the subject or the subject population, wherein the unit dose comprises four live attenuated dengue virus serotypes
wherein the unit dose is lyophilized and upon reconstitution with 0.5 mL of a pharmaceutically acceptable diluent comprises:
(i) a chimeric dengue serotype 2/1 strain, in a concentration of at least 3.3 log 10 pfu/0.5 ml,
(ii) a dengue serotype 2 strain, in a concentration of at least 2.7 log 10 pfu/0.5 ml,
(iii) a chimeric dengue serotype 2/3 strain, in a concentration of at least 4.0 log 10 pfu/0.5 ml, and
(iv) a chimeric dengue serotype 2/4 strain, in a concentration of at least 4.5 log 10 pfu/0.5 ml,
wherein the four live attenuated dengue virus serotypes are defined by at least one of the following:
(1) a dengue serotype 2 strain which is derived from the wild type virus strain DEN-2 16681 and differs in at least three nucleotides from the wild type as follows:
a) 5'-noncoding region (NCR)-57,
b) NS1-53 Gly-to-Asp, and
c) NS3-250 Glu-to-Val; and
wherein the three chimeric dengue strains are derived from the dengue serotype 2 strain by replacing the structural proteins prM and E from the dengue serotype 2 strain with the corresponding structural proteins from the other dengue serotypes, resulting in the following chimeric dengue strains:
the chimeric dengue serotype 2/1 strain,
the chimeric dengue serotype 2/3 strain, and
the chimeric dengue serotype 2/4 strain;
(2) the chimeric dengue serotype 2/1 strain comprising a nucleotide sequence according to SEQ ID NO: 1,
the dengue serotype 2 strain comprising a nucleotide sequence according to SEQ ID NO: 3,
the chimeric dengue serotype 2/3 strain comprising a nucleotide sequence according to SEQ ID NO: 5, and
the chimeric dengue serotype 2/4 strain comprising a nucleotide sequence according to SEQ ID NO: 7;
(3) the chimeric dengue serotype 2/1 strain comprising the structural proteins provided in the amino acid sequence of SEQ ID NO: 2,
the dengue serotype 2 strain comprising the structural proteins provided in the amino acid sequence of SEQ ID NO: 4,
the chimeric dengue serotype 2/3 strain comprising the structural proteins provided in the amino acid sequence of SEQ ID NO: 6, and
the chimeric dengue serotype 2/4 strain comprising the structural proteins provided in the amino acid sequence of SEQ ID NO: 8, and
(4) the chimeric dengue serotype 2/1 strain comprising a nucleotide sequence encoding the amino acid sequence SEQ ID NO: 2,
the dengue serotype 2 strain comprising a nucleotide sequence encoding the amino acid sequence SEQ ID NO: 4,
the chimeric dengue serotype 2/3 strain comprising a nucleotide sequence encoding the amino acid sequence SEQ ID NO: 6, and
the chimeric dengue serotype 2/4 strain comprising a nucleotide sequence encoding the amino acid sequence SEQ ID NO: 8.

2. The method according to claim 1, wherein the hepatitis A vaccine is an inactivated virus vaccine.

3. The method according to claim 1, wherein the subject population or subject is seronegative to all dengue serotypes.

4. The method according to claim 1, wherein the unit dose of the dengue vaccine composition is administered by subcutaneous injection and the hepatitis A vaccine is administered by intramuscular injection.

5. The method according to claim 4, wherein the unit dose of the dengue vaccine composition and the hepatitis A vaccine are administered to different anatomical sites.

6. The method according to claim 4, wherein the unit dose of the dengue vaccine composition and the hepatitis A vaccine are both administered to the arm.

7. The method according to claim 6, wherein the unit dose of the dengue vaccine composition and the hepatitis A vaccine are both administered to the deltoid region of the arm.

8. The method according to claim 1, wherein two of the unit doses of the dengue vaccine composition are administered within 12 months or more, or within six months, or within three months.

9. The method according to claim 8, comprising the administration of the first and second unit doses of the dengue vaccine composition and one dose of the hepatitis A vaccine, according to the following schedule:
   simultaneous administration of the first unit dose of the dengue vaccine composition and the hepatitis A vaccine on day 0, and
   administration of the second unit dose of the dengue vaccine composition after the first simultaneous administration, about 3 months after.

10. The method according to claim 1, wherein the subject population or subject is of 2 to 60 years of age.

11. The method according to claim 1, wherein the subject population or subject is from a dengue endemic region.

12. The method according to claim 1, wherein the subject population or subject is from a dengue non-endemic region.

13. The method according to claim 12, wherein the subject population or subject is from a dengue non-endemic region and a hepatitis A non-endemic region.

14. The method according to claim 1, wherein the hepatitis A vaccine comprises a hepatitis A virus derived from a hepatitis A virus strain HM-175.

15. The method according to claim 1, wherein the hepatitis A vaccine comprises an inactivated hepatitis A virus.

16. The method according to claim 15, wherein the inactivated hepatitis A virus is derived from a hepatitis A virus strain HM-175.

17. The method according to claim 1, wherein the hepatitis A vaccine comprises an inactivated hepatitis A virus and wherein the inactivated hepatitis A virus is adsorbed on aluminum.

18. The method according to claim 17, wherein the aluminum is aluminum hydroxide or aluminum hydroxyphosphate sulfate.

19. The method according to claim 1, wherein the hepatitis A vaccine comprises an inactivated hepatitis A virus and wherein the hepatitis A vaccine comprises a phosphate-buffered saline solution and excipients dissolved therein in the form of an amino acid and in and in the form of polysorbate.

20. The method according to claim 1, wherein the hepatitis A vaccine includes a hepatitis A virus expressing a viral antigen in a concentration ranging from 500 ELISA Units (EL.U.) to 2000 ELISA Units (EL.U.).

21. The method according to claim 1, wherein the method:
   does not include a step of determination whether there was a previous dengue infection and/or a previous hepatitis A infection in the subject population or in the subject before the administration of the hepatitis A vaccine and before the administration of the unit dose of the dengue vaccine composition; or
   wherein the hepatitis A serostatus and/or the dengue serostatus of the subject population or of the subject is unknown before the administration of the hepatitis A vaccine and before the administration of the unit dose of the dengue vaccine composition.

22. The method according to claim 1, wherein the method does not include a step of determination whether there was a previous dengue infection and/or a previous hepatitis A infection in the subject population or in the subject at any time before, during and after the steps of administration of the hepatitis A vaccine and of the unit dose of the dengue vaccine composition; or
   wherein the hepatitis A serostatus and/or the dengue serostatus of the subject population or of the subject is unknown at any time before, during or after the steps of administration of the hepatitis A vaccine and of the unit dose of the dengue vaccine composition.

23. The method according to claim 1, wherein the method comprises a primary vaccination consisting of the steps of:
   (A) selecting a subject for administration of the unit doses of the tetravalent dengue virus composition and the hepatitis A vaccine in need for protection against dengue infection and hepatitis A infection without determination whether there was a previous dengue infection and/or a previous hepatitis A infection, and
   (B) administering a first unit dose of the tetravalent dengue virus composition and a hepatitis A vaccine to the subject, and optionally
   (C) administering at least one further unit dose of the tetravalent dengue virus composition to the subject within 3 to 12 months of administration of the first unit dose, and optionally
   (D) administering at least one further dose of the hepatitis A vaccine to the subject within 6 to 18 months of administration of the first unit dose.

24. The method according to claim 1, wherein the method comprises a primary vaccination consisting of the steps of:
   (A) selecting a subject for administration of the unit doses of the tetravalent dengue virus composition and the hepatitis A vaccine in need for protection against dengue infection and hepatitis A infection, and
   (B) administering a first unit dose of the tetravalent dengue virus composition and a hepatitis A vaccine to the subject, and
   (C) administering two further unit doses of the tetravalent dengue virus composition to the subject at about 6 and about 12 months of administration of the first unit dose and administering a hepatitis A vaccine to the subject at either about 6 or about 12 months of administration of the first unit dose.

25. The method according to claim 24, wherein step (A) is carried out without determination whether there was a previous hepatitis A infection.

26. The method according to claim 1, wherein upon reconstitution of the dengue vaccine composition with a pharmaceutically acceptable diluent (i), (ii), (iii), and (iv) provide a total concentration of pfu/0.5 mL and based on the total concentration of pfu/0.5 ml
   the concentration of (i) in pfu/0.5 ml is at least 1%,
   the concentration of (ii) in pfu/0.5 ml is less than 10%,
   the concentration of (iii) in pfu/0.5 ml is at least 10%, and
   the concentration of (iv) in pfu/0.5 ml is at least 50%.

27. The method according to claim 1, wherein the method provides compatibility between the dengue vaccine composition and the hepatitis A vaccine.

28. The method according to claim 1, wherein the method provides synergy between the dengue vaccine composition and the hepatitis A vaccine.

29. The method according to claim 1, wherein the method provides non-inferiority in a non-inferiority clinical study including at least 60 or at least 120 healthy subjects divided into one subject population and into one control subject population, wherein the subject population receives simultaneously on the same day the hepatitis A vaccine and the unit dose of the dengue vaccine composition and the control subject population receives simultaneously on the same day a hepatitis A vaccine and a placebo administration.

30. The method according to claim 1, wherein the hepatitis A vaccine provides a hepatitis A seroprotection rate of at least 95% or of at least 98% on day 30 after an administration (on day 0/1) to a subject population of at least 30 or at least 50 healthy subjects receiving simultaneously on the same day the hepatitis A vaccine and the unit dose of the dengue vaccine composition and being seronegative with respect to hepatitis A at baseline and being seronegative with respect to all dengue virus serotypes at baseline.

31. The method according to claim 1, wherein the method provides a hepatitis A seroprotection rate difference with respect to a hepatitis A mono-administration, the difference being determined in a non-inferiority clinical study including at least 60 or at least 120 healthy subjects being seronegative with respect to hepatitis A at baseline and seronegative with respect to all dengue virus serotypes at baseline,
the healthy subjects being divided into
a) a subject population of at least 30 or at least 50 healthy subjects receiving simultaneously on the same day an administration (on day 0/1) of the hepatitis A vaccine and the unit dose of the dengue vaccine composition, and
b) a control subject population of at least 30 or at least 50 healthy subjects receiving simultaneously on the same day an administration (on day 0/1) of a hepatitis A vaccine and a placebo,
wherein the difference is determined between the hepatitis A seroprotection rate of the control subject population on day 30 after the administration (on day 0/1) and the hepatitis A seroprotection rate of the subject population on day 30 after the administration (on day 0/1), and
wherein the difference has an upper bound within a two-sided 95% confidence interval which is lower than 10%.

32. The method according to claim 1, wherein the hepatitis A vaccine provides a hepatitis A seroprotection rate of at least 95% or of at least 98% or of at least 99% on day 30 after an administration (on day 0/1) to a subject population of at least 30 or at least 50 healthy subjects receiving simultaneously on the same day the hepatitis A vaccine and the unit dose of the dengue vaccine composition and being seronegative with respect to hepatitis A at baseline, wherein the healthy subjects include healthy subject(s) which are seropositive with respect to at least one dengue virus serotype at baseline and healthy subject(s) which are seronegative with respect to all dengue virus serotypes at baseline.

33. The method according to claim 1, wherein the method provides a hepatitis A seroprotection rate difference with respect to a hepatitis A mono-administration, the difference being determined in a non-inferiority clinical study including at least 60 or at least 120 healthy subjects being seronegative with respect to hepatitis A at baseline, wherein the healthy subjects include healthy subject(s) which are seropositive with respect to at least one dengue virus serotype at baseline and healthy subject(s) which are seronegative with respect to all dengue virus serotypes at baseline,
the healthy subjects being divided into
a subject population of at least 30 or at least 50 healthy subjects receiving simultaneously on the same day an administration (on day 0/1) of the hepatitis A vaccine and the unit dose of the dengue vaccine composition, wherein the subject population includes healthy subject(s) which are seropositive with respect to at least one dengue virus serotype at baseline and healthy subject(s) which are seronegative with respect to all dengue virus serotypes at baseline, and
a control subject population of at least 30 or at least 50 healthy subjects receiving simultaneously on the same day an administration (on day 0/1) of a hepatitis A vaccine and a placebo, wherein the control subject population includes healthy subject(s) which are seropositive with respect to at least one dengue virus serotype at baseline and healthy subject(s) which are seronegative with respect to all dengue virus serotypes at baseline,
wherein the difference is determined between the hepatitis A seroprotection rate of the control subject population on day 30 after the administration (on day 0/1) and the hepatitis A seroprotection rate of the subject population on day 30 after the administration (on day 0/1), and
wherein the difference has an upper bound within a two-sided 95% confidence interval which is lower than 10%.

34. The method according to claim 1, wherein the subject or subject population is exposed to at least one of a hepatitis A virus outbreak and a dengue virus outbreak.

35. The method according to claim 1, wherein the method provides an anti-hepatitis A virus antibody Geometric Mean Concentration (GMC) of at least 70 mIU/ml or at least 80 mIU/ml or at least 90 mIU/ml on day 30 after an administration (on day 0/1) to a subject population of at least 30 or at least 50 healthy subjects receiving simultaneously on the same day the hepatitis A vaccine and the unit dose of the dengue vaccine composition and being seronegative with respect to hepatitis A at baseline and being seronegative with respect to all dengue virus serotypes at baseline.

36. The method according to claim 1, wherein the simultaneous on the same day administration of the hepatitis A vaccine and the unit dose of the dengue vaccine composition to the subject or the subject population is safe.

37. The method according to claim 36, wherein there are no serious adverse events related to the simultaneous on the same day administration of the hepatitis A vaccine and the unit dose of the dengue vaccine composition.

38. The method according to claim 1, wherein the method provides the Geometric Mean Titer (GMT) of neutralizing antibodies measured by MNT50 of
at least 110 or at least 140 or at least 150 for dengue serotype 1,
at least 3000 or at least 3500 or at least 3900 for dengue serotype 2,
at least 100 or at least 120 or at least 140 for dengue serotype 3, and/or
at least 80 or at least 110 or at least 140 for dengue serotype 4,
on day 30 after an administration (on day 0/1) to a subject population of at least 30 or at least 50 healthy subjects receiving simultaneously on the same day the hepatitis A vaccine and the unit dose of the dengue vaccine composition and being seronegative with respect to hepatitis A at baseline and being seronegative with respect to all dengue virus serotypes at baseline.

39. The method according to claim 1, wherein the subject or subject population is 18 to 60 years of age.

40. A kit against hepatitis A and dengue disease infection comprising:
(a) a first container holding a hepatitis A vaccine, and
(b) a second container holding a unit dose of a dengue vaccine composition, wherein the unit dose comprises a tetravalent dengue virus composition including four live, attenuated dengue virus strains, wherein the unit dose is lyophilized and upon reconstitution with 0.5 mL of a pharmaceutically acceptable diluent comprises:
(i) a chimeric dengue serotype 2/1 strain, in a concentration of at least 3.3 log 10 pfu/0.5 ml,
(ii) a dengue serotype 2 strain, in a concentration of at least 2.7 log 10 pfu/0.5 ml,
(iii) a chimeric dengue serotype 2/3 strain, in a concentration of at least 4.0 log 10 pfu/0.5 ml, and
(iv) a chimeric dengue serotype 2/4 strain, in a concentration of at least 4.5 log 10 pfu/0.5 ml, wherein the four live attenuated dengue virus serotypes are defined by at least one of the following:
(1) a dengue serotype 2 strain which is derived from the wild type virus strain DEN-2 16681 and differs in at least three nucleotides from the wild type as follows:
   a) 5'-noncoding region (NCR)-57,
   b) NS1-53 Gly-to-Asp, and
   c) NS3-250 Glu-to-Val; and
wherein the three chimeric dengue strains are derived from the dengue serotype 2 strain by replacing the structural proteins prM and E from the dengue serotype 2 strain with the corresponding structural proteins from the other dengue serotypes, resulting in the following chimeric dengue strains:
   the chimeric dengue serotype 2/1 strain,
   the chimeric dengue serotype 2/3 strain, and
   the chimeric dengue serotype 2/4 strain;
(2) the chimeric dengue serotype 2/1 strain comprising a nucleotide sequence according to SEQ ID NO: 1,
   the dengue serotype 2 strain comprising a nucleotide sequence according to SEQ ID NO: 3,
   the chimeric dengue serotype 2/3 strain comprising a nucleotide sequence according to SEQ ID NO: 5, and
   the chimeric dengue serotype 2/4 strain comprising a nucleotide sequence according to SEQ ID NO: 7;
(3) the chimeric dengue serotype 2/1 strain comprising the structural proteins provided in the amino acid sequence of SEQ ID NO: 2,
   the dengue serotype 2 strain comprising the structural proteins provided in the amino acid sequence of SEQ ID NO: 4,
   the chimeric dengue serotype 2/3 strain comprising the structural proteins provided in the amino acid sequence of SEQ ID NO: 6, and
   the chimeric dengue serotype 2/4 strain comprising the structural proteins provided in the amino acid sequence of SEQ ID NO: 8, and
(4) the chimeric dengue serotype 2/1 strain comprising a nucleotide sequence encoding the amino acid sequence SEQ ID NO: 2,
   the dengue serotype 2 strain comprising a nucleotide sequence encoding the amino acid sequence SEQ ID NO: 4,
   the chimeric dengue serotype 2/3 strain comprising a nucleotide sequence encoding the amino acid sequence SEQ ID NO: 6, and
the chimeric dengue serotype 2/4 strain comprising a nucleotide sequence encoding the amino acid sequence SEQ ID NO: 8.

* * * * *